US012440564B2

(12) United States Patent
Friedman et al.

(10) Patent No.: US 12,440,564 B2
(45) Date of Patent: Oct. 14, 2025

(54) COMPOSITIONS FOR TREATING CANCER

(71) Applicant: Kelonia Therapeutics, Inc., Boston, MA (US)

(72) Inventors: Kevin M. Friedman, Boston, MA (US); Molly R. Perkins, Milton, MA (US); Connor S. Dobson, Washington, DC (US); Stephen L. Sazinsky, Winchester, MA (US); Shannon G. Contrastano, Auburndale, MA (US); Emily Thompson Beura, Mansfield, MA (US); Cory Ahonen, Lebanon, NH (US); Andrew Avery, Lebanon, NH (US)

(73) Assignee: Kelonia Therapeutics, Inc., Boston, MA (US)

( * ) Notice: Subject to any disclaimer, the term of this patent is extended or adjusted under 35 U.S.C. 154(b) by 0 days.

(21) Appl. No.: 18/919,082

(22) Filed: Oct. 17, 2024

(65) Prior Publication Data

US 2025/0099587 A1 Mar. 27, 2025

Related U.S. Application Data

(63) Continuation of application No. PCT/US2024/048301, filed on Sep. 25, 2024.

(60) Provisional application No. 63/618,878, filed on Jan. 8, 2024, provisional application No. 63/540,336, filed on Sep. 25, 2023.

(51) Int. Cl.

| | |
|---|---|
| ***A61K 40/00*** | (2025.01) |
| ***A61K 40/11*** | (2025.01) |
| ***A61K 40/15*** | (2025.01) |
| ***A61K 40/31*** | (2025.01) |
| ***A61K 40/42*** | (2025.01) |
| ***A61K 48/00*** | (2006.01) |
| ***A61P 35/00*** | (2006.01) |
| ***C07K 14/725*** | (2006.01) |
| ***C07K 16/28*** | (2006.01) |
| ***C12N 15/86*** | (2006.01) |

(52) U.S. Cl.

CPC .......... *A61K 40/4215* (2025.01); *A61K 40/11* (2025.01); *A61K 40/15* (2025.01); *A61K 40/31* (2025.01); *A61K 48/005* (2013.01); *A61P 35/00* (2018.01); *C07K 14/7051* (2013.01); *C07K 16/2809* (2013.01); *C07K 16/2878* (2013.01); *C12N 15/86* (2013.01); *A61K 2239/13* (2023.05); *C07K 2317/622* (2013.01); *C12N 2740/15022* (2013.01); *C12N 2740/15023* (2013.01); *C12N 2740/15043* (2013.01); *C12N 2830/48* (2013.01); *C12N 2830/50* (2013.01)

(58) Field of Classification Search

None

See application file for complete search history.

(56) References Cited

U.S. PATENT DOCUMENTS

| | | | |
|---|---|---|---|
| 7,901,671 | B2 | 3/2011 | Leboulch et al. |
| 9,994,867 | B2 | 6/2018 | Baltimore et al. |
| 11,767,366 | B1 | 9/2023 | Russell et al. |
| 12,030,915 | B2 | 7/2024 | Albertini et al. |
| 12,061,187 | B2 | 8/2024 | Birnbaum et al. |
| 12,061,188 | B2 | 8/2024 | Birnbaum et al. |
| 12,091,434 | B2 | 9/2024 | Albertini et al. |
| 12,222,347 | B2 | 2/2025 | Birnbaum et al. |
| 12,264,180 | B2 | 4/2025 | Albertini et al. |
| 12,269,848 | B2 | 4/2025 | Albertini et al. |
| 12,269,882 | B1 | 4/2025 | Friedman et al. |
| 12,291,551 | B2 | 5/2025 | Albertini et al. |
| 12,297,237 | B2 | 5/2025 | Albertini et al. |
| 12,312,593 | B2 | 5/2025 | Perkins et al. |
| 2008/0124357 | A1 | 5/2008 | Yao et al. |
| 2008/0241929 | A1 | 10/2008 | Naldini et al. |
| 2014/0017766 | A1 | 1/2014 | Chen et al. |
| 2015/0182617 | A1 | 7/2015 | Bauche et al. |
| 2015/0316511 | A1 | 11/2015 | Guo |
| 2016/0333374 | A1 | 11/2016 | Anastasov et al. |
| 2017/0051252 | A1 | 2/2017 | Morgan et al. |
| 2017/0137783 | A1 | 5/2017 | Bedoya et al. |
| 2017/0176435 | A1 | 6/2017 | Seidell, III et al. |
| 2017/0192011 | A1 | 7/2017 | Birnbaum et al. |
| 2017/0240631 | A1 | 8/2017 | Monroe et al. |
| 2017/0356010 | A1 | 12/2017 | Frost et al. |
| 2018/0155425 | A1 | 6/2018 | Ma et al. |
| 2018/0201954 | A1 | 7/2018 | Buchholz et al. |
| 2018/0362966 | A1 | 12/2018 | Flechtner et al. |

(Continued)

FOREIGN PATENT DOCUMENTS

| | | | |
|---|---|---|---|
| CA | 2344208 | A1 | 10/2002 |
| CN | 1643164 | A | 7/2005 |

(Continued)

OTHER PUBLICATIONS

Winkler, K., et al., "Changing the Antigen Binding Specificity by Single Point Mutations of an Anti-p24 (HIV-1) Antibody," J Immunol, 165(8):4505-14 (2000).

(Continued)

*Primary Examiner* — Peter J Reddig

*Assistant Examiner* — Estella M. Gustilo

(74) *Attorney, Agent, or Firm* — Morse, Barnes-Brown & Pendleton, P.C.; Lisa M. Warren, Esq.; Erin E. Bryan, Esq.

(57) ABSTRACT

The present disclosure provides compositions and methods comprising recombinant particles suitable for specifically delivering one or more chimeric antigen receptors to immune effector cells in vivo.

25 Claims, 20 Drawing Sheets

Specification includes a Sequence Listing.

(56) References Cited

U.S. PATENT DOCUMENTS

| | | | |
|---|---|---|---|
| 2019/0144885 | A1 | 5/2019 | Costa Fejoz et al. |
| 2019/0161530 | A1 | 5/2019 | Certo et al. |
| 2020/0023010 | A1 | 1/2020 | DiLillo et al. |
| 2020/0216502 | A1 | 7/2020 | Albertini et al. |
| 2020/0277629 | A1 | 9/2020 | Cawood et al. |
| 2020/0339699 | A1 | 10/2020 | Li et al. |
| 2020/0368370 | A1 | 11/2020 | Leboulch et al. |
| 2020/0371088 | A1 | 11/2020 | Birnbaum et al. |
| 2021/0128619 | A1 | 5/2021 | Campbell et al. |
| 2021/0137977 | A1 | 5/2021 | Chaudhary |
| 2021/0324100 | A1 | 10/2021 | Sather et al. |
| 2022/0204946 | A1 | 6/2022 | Antunes et al. |
| 2022/0340876 | A1 | 10/2022 | Birnbaum et al. |
| 2023/0051847 | A1 | 2/2023 | Vogelstein et al. |
| 2023/0159651 | A1 | 5/2023 | Zhao et al. |
| 2023/0167158 | A1 | 6/2023 | Najjar et al. |
| 2023/0279363 | A1 | 9/2023 | Russell et al. |
| 2024/0044873 | A1 | 2/2024 | Birnbaum et al. |
| 2024/0092839 | A1 | 3/2024 | Albertini et al. |
| 2024/0150788 | A1 | 5/2024 | Perkins et al. |
| 2024/0218390 | A1 | 7/2024 | Perkins et al. |
| 2024/0230627 | A1 | 7/2024 | Birnbaum et al. |
| 2024/0317811 | A1 | 9/2024 | Albertini et al. |
| 2024/0317812 | A1 | 9/2024 | Albertini et al. |
| 2024/0327466 | A1 | 10/2024 | Albertini et al. |
| 2024/0327467 | A1 | 10/2024 | Albertini et al. |
| 2025/0099615 | A1 | 3/2025 | Friedman et al. |
| 2025/0101106 | A1 | 3/2025 | Friedman et al. |
| 2025/0101122 | A1 | 3/2025 | Friedman et al. |
| 2025/0147007 | A1 | 5/2025 | Birnbaum et al. |
| 2025/0171504 | A1 | 5/2025 | Albertini et al. |
| 2025/0171505 | A1 | 5/2025 | Albertini et al. |
| 2025/0236672 | A1 | 7/2025 | Friedman et al. |

FOREIGN PATENT DOCUMENTS

| | | | | |
|---|---|---|---|---|
| CN | 108040484 | A | 5/2018 | |
| CN | 115322257 | A | 11/2022 | |
| EP | 2020444 | A1 | 2/2009 | |
| EP | 1461079 | B1 | 8/2011 | |
| JP | 2005/516607 | A | 6/2005 | |
| JP | 2005/247757 | A | 9/2005 | |
| JP | 2010/535495 | A | 11/2010 | |
| JP | 2016/501528 | A | 1/2016 | |
| WO | 2001/19380 | A2 | 3/2001 | |
| WO | 2008/037458 | A2 | 4/2008 | |
| WO | 2009/013324 | A1 | 1/2009 | |
| WO | 2010/040023 | A2 | 4/2010 | |
| WO | 2012/088381 | A2 | 6/2012 | |
| WO | 2015/104376 | A1 | 7/2015 | |
| WO | 2015/112541 | A2 | 7/2015 | |
| WO | 2015/117027 | A1 | 8/2015 | |
| WO | 2016/139463 | A1 | 9/2016 | |
| WO | 2017/182585 | A1 | 10/2017 | |
| WO | 2019/056015 | A2 | 3/2019 | |
| WO | 2019/057974 | A1 | 3/2019 | |
| WO | 2020/123936 | A1 | 6/2020 | |
| WO | 2020/236263 | A1 | 11/2020 | |
| WO | WO2022013872 | A1 * | 1/2022 | ........... C07K 14/005 |
| WO | 2022/183072 | A1 | 9/2022 | |
| WO | 2022/221745 | A1 | 10/2022 | |
| WO | 2025/038475 | A1 | 2/2025 | |
| WO | 2025/072253 | A1 | 4/2025 | |
| WO | 2025/072257 | A1 | 4/2025 | |

OTHER PUBLICATIONS

Yang, H., et al., "Cell Type-Specific Targeting with Surface-Engineered Lentiviral Vectors Co-displaying OKT3 Antibody and Fusogenic Molecule," Pharm Res, 26(6): 1432-45 (2009).

Yang, et al., "Targeting Lentiviral Vectors to Specific Cell Types in vivo," PNAS, 103(31 ): 114 79-84 (2006).

Yu, B., et al., "Engineered Cell Entry Links Receptor Biology with Single-cell Genomics," Cell, 185(26):4904-4920 (2022).

Zhang, et al, "Cell-specific Targeting of Lentiviral Vectors Mediated by Fusion Proteins Derived from Sindbis Virus, Vesicular Stomatitis Virus, or Avian Sarcoma/Leukosis Virus," Retrovirology, Biomed Central Ltd., 7(1):3 (2010).

Zhang, N., et al., "Leucine-rich Repeat-containing G Protein-coupled Receptor 4 Facilitates Vesicular Stomatitis Virus Infection by Binding Vesicular Stomatitis Virus Glycoprotein," J Biol Chem, 292(40):16527-16538 (2017).

International Search Report from International Application No. PCT/US2022/018027, dated mailed: Jun. 21, 2022.

International Search Report from International Application No. PCT/US2020/024175, date mailed: Sep. 14, 2020.

International Search Report in International Application No. PCT/US2022/025142, dated: Apr. 10, 2022.

International Search Report in International Application No. PCT/EP2018/075824, dated: Nov. 28, 2018.

International Search Report in International Application No. PCT/US2024/048295, dated: Jan. 10, 2025.

Baroja, et al., "Specific CD3 epsilon association of a phosphodiesterase 4B isoform determines its selective tyrosine phosphorylation after CD3 ligation," Journal of Immunology, 162(4):2016-23, 1999.

International Search Report in International Application No. PCT/US2024/048301, dated: Jan. 16, 2025.

Strausberg, et al., CD8a molecule [*Homo sapiens*], GenBank Association: AAH25715.1, Jul. 15, 2006, pp. 103, [retrieved Nov. 18, 2024]. Retrieved from the Internet <URL: https://www.ncbi.nlm.nih.gov/protein/AAH25715.1?report=genbank&log$=pros top &blast rank=6&RID=KRB38RWiJ013>. entire document.

Albertini, et al., "Molecular and Cellular Aspects of Rhabdovirus Entry," Viruses, 4:117-139 (2012).

Altschul, et al., "Basic Local Alignment Search Tool," J Mol Biol. (3):403-10 (1990).

Altschul, et al., "Gapped Blast and PSI-Blast: A New Generation of Protein Database Search Programs," Nucleic Acids Res, 25(17):3389-402 (1997).

Amirache, et al., "Mystery Solved: VSV-G-LVs Do Not Allow Efficient Gene Transfer into Unstimulated T Cells, B Cells, and HSCs Because They Lack the LDL Receptor," Blood, 123: 1422-1424 (2014).

Ammayappan, et al., "Characteristics of Oncolytic Vesicular Stomatitis Virus Displaying Tumor-Targeting Ligands," Journal of Virology vol. 87(24):13543-13555 (2013).

An, X., "Preliminary Study on HBV and HIV seudovirus Vector Systems," China Master's Thesis Full-text Database, Basic Science Collection: 1-121 (2007).

Barber, G.N., "VSV-tumor Selective Replication and Protein Translation," Oncogene 24: 7710-7719 (2005).

Bentzen, et al., "Evolution of MHC-based Technologies Used for Detection of Antigen-responsive T Cells," Cancer Immunol Immunother, 66:657-66 (2017).

Bowie, J., et al., "Deciphering the Message in Progein Sequences: Tolerance to Amino Acid Substitutions," Science, 247(4948):1306-10 (1990).

Buchholz, et al., "Retroviral Display and High Throughput Screening," Comb Chem High Throughput Screen, 11(2):99-110 (2008).

Chan, L., et al., "Conjugation of Lentivirus to Paramagnetic Particles via Nonviral Proteins Allows Efficient Concentration and Infection of Primary Acute Myeloid Leukemia Cells," J. of Virology, 79(20):13190-13194 (2005).

Chen, Z., et al., "Human Monoclonal Antibodies Targetingthe Haemagglutinin Glycoprotein can Neutralize H7N9 Influenza Virus," Nat Commun, 6:6714 (2015).

Cire, S, "Immunization of Mice with Lentiviral Vectors Targeted to MHC Class II+ Cells is Due to Preferential Transduction of Dendritic Cells in vivo," PLoS One, 9(7):e101644, (2014).

Dobson, C., et al., "Antigen Identification and High-Throughput Interaction Mapping by Reprogramming Viral Entry," Nature Methods, 19:449-460 (2022).

Dreja, H., et al., "The Effects of N-terminal Insertion into VSV-G of an scFv Peptide," Viral J, 3:69, 1186 (2006).

(56) References Cited

OTHER PUBLICATIONS

Ferlin, et al., "Characterization of pH-sensitive Molecular Switches that Trigger the Structural Transition of Vesicular Stomatitis Virus Glycoprotein from the Postfusion State Toward the Prefusion State," J Virol, 88:13396-13409 (2014).
Finkelshtein, et al., "LDL Receptor and its Family Members Serve as the Cellular Receptors for Vesicular Stomatitis Virus," PNAS, 110(18):7306-7311 (2013).
Frank, A., et al., "Surface-Engineered Lentiviral Vectors for Selective Gene Transfer into Subtypes of Lymphocytes," Mol Ther Methods Clin Dev, 12:19-31 (2018).
Froelich, et al., "Targeted Gene Delivery to CD117-expressing Cells in vivo with Lentiviral Vectors Co-displaying Stem Cell Factor and a Fusogenic Molecule,", Biotechnology and Bioengineering, 104(1):206-215 (2009).
Funke, et al., Targeted Cell Entry of Lentiviral Vectors,: Mol Ther. I6(8):1427-36 (2008).
Goyvaerts, C., et al., "Development of the Nanobody Display Technology to Target Lentiviral Vectors to Antigen-Presenting Cells," Gene Therapy, 19:1133-1140 (2012).
Grubaugh, et al., "Proteins as T Cell Antigens: Methods for High-throughput Identification," Vaccine 31(37) (2013).
Guideng, et al., "T Cell Antigen Discovery via Trogocytosis," Nature Methods, 16(2):183-90 (2019).
Hastie, E, et al., "Understanding and Altering Cell Tropism of Vesicular Stomatitis Virus," Virus Res. 176(1-2):16-32 (2013).
He, et al., "Can Immunotherapy Reinforce Chemotherapy Efficacy? A New Perspective on Colorectal Cancer Treatment," Front. Immunol. 14:1237764 (2023).
Höfig, I., et al., "Systematic Improvement of Lentivirus Transduction Protocols by Antibody Fragments Fused to VSV-G as Envelope Glycoprotein," Biomaterials, 35(13):4204-12 (2014).
Humes, D., "The Top Vector: a New High-titer Lentiviral Construct for Delivery of sgRNAs and Transgenes to Primary T Cells," Molecular Therapy Methods & Clinical Development, 20:30-38 (2021).
Joglekar, et al., "T Cell Antigen Discovery via Signaling and Antigen-presenting Bifunctional Receptors," Nature Methods, 16(2):191-8 (2019).
Kameyama, Y., et al., "Antibody-dependent Gene Transduction using Gammaretroviral and Lentiviral Vectors Pseudotyped with Chimeric Vesicular Stomatitis Virus Glycoprotein," J Viral Methods, 153(1 ):49-54 (2008).
Karlin, et al., "Applications and Statistics for Multiple High-scoring Segments in Molecular Sequences," Proc Natl Acad Sci US A, 90(12):5873-7 (1993).
Karlin, et al., "Methods for Assessing the Statistical Significance of Molecular Sequence Features by Using General Scoring Schemes," Proc Natl Acad Sci US A., 87(6):2264-8 (1998).
Kussie, P., et al., "A Single Engineered Amino Acid Substitution Changes Antibody Fine Specificity," J Immunol, 152(1):146-52. (1994).
Labbe, R., et al., "Lentiviral Vectors for T Cell Engineering: Clinical Applications, Bioprocessing and Future Perspectives," Viruses 13(1528): 1-22 (2021).
Milani, M., et al., "Genome Editing for Scalable Production of Alloantigen-free Lentiviral Vectors for in vivo Gene Therapy," EMBO Mol Med, 9(11):1558-1573 (2017).
Nikolic, J., et al., "Structural Basis for the Recognition of LDL-Receptor Family Members by VSV Glycoprotein," Nature Communications, 9(1029):1-12 (2018).
Ou, W, et al., "Specific Targeting of Human Interleukin ( I L)-13 Receptor A2-positive Cells with Lentiviral Vectors Dsplaying I L-13," Hum Gene Ther Methods, 2:137-47, (2012).
Patent Owner's Preliminary Response with Exhibit 2001, of U.S. Pat. No. 11,767,366, Before the Patent Trial and Appeal Board, *Kelonia Theraptutics, Inc.* Petitioner, v. *Interius Biotherapeutics, Inc.*, Patent Owner, Case No. PGR2024-00008, 95 Pages.
Peach, et al., "Both Extracellular Immunoglobin-like Domains of CD80 Contain Residues Critical for Binding T Cell Surface Receptors CTLA-4 and CD28," J. Biol Chem, 270(36):21181-21187 (1995).
Roche, et al., "Crystal Structure of the Low-pH Form of the Vesicular Stomatitis Virus Glycoprotein," G. Science, 313: 187-191 (2006).
Roche, et al., "Structure of the Prefusion Form of the Vesicular Stomatitis Virus Glycoprotein G," Science 315: 843-848 (2007).
Schamback, A., et al., "Biosafety Features of Lentiviral Vectors," Human Gene Therapy, 24:132-142 (2013).
Sela-Culang, I., et al., "The Structural Basis of Antibody-Antigen Recognition," Front Immunol, 4:302 (2013).
Sevier, CS, et al, "Efficient Export of the Vesicular Stomatitis Virus G Protein from the Endoplasmic Reticulum Requires a Signal in the Cytoplasmic Tail that Includes both Tyrosine-based and Di-acidic Motifs," Mol Biol Cell. 1:13-22 (2000).
Sirin, S., et al., "AB-Bind: Antibody Binding Mutational Database for Computational Affinity Predictions," Protein Sci, 25(2):393-409 (2015).
Taube, et al., "Lentivirus Display: Stable Expression of Human Antibodies on the Surface of Human Cells and Virus Particles," PLoS One, 3(9):e3181 (2008).
Urban, et al., "Retroviral Display in Gene Therapy, Protein Engineering, and Vvaccine Development," ACS Chem Biol., 6(1):61-74(2011).
Urban, et al., "Selection of Functional Human Antibodies from Retroviral Display Libraries," Nucleic Acids Res., 33(4):e35 (2005).
Agarwal, et al., "In Vivo Generation of CAR T Cells Selectively in Human CD4+ Lymphocytes," Molecular Therapy, 28(8), Aug. 2020.
Final Office Action in U.S. Appl. No. 18/919,103, dated May 21, 2025.
Mishra, et al., "CAR-T-Cell Therapy in Multiple Myeloma: B-Cell Maturation Antigen (BCMA) and Beyond," Vaccines, 11, 1721, 2023.
Non-Final Office Action in U.S. Appl. No. 19/172,374, dated: May 29, 2025.
Pinto, et al., "From ex vivo to in vivo chimeric antigen T cells manufacturing: new horizons for CAR T-cell based therapy," Journal of Translational Medicine, 23:10, 2025.
Short, et al., " Direct in vivo CAR T cell engineering," Trends in Pharmacological Sciences, 45(5), May 2024.
Bjorkman, et al., "Mutations That Affect Ligand Binding to the *Escherichia coli* Aspartate Receptor," Journal of Biological Chemistry, 276(4):2808-2815, 2001.
Burt, et al., "Blinatumomab, a bispecific B-cell and T-cell engaging antibody, in the treatment of B-cell malignancies," Human Vaccines & Immunotherapeutics, vol. 15(3), pp. 594-602, 2019.
Final Office Action in U.S. Appl. No. 18/375,868, dated Jan. 28, 2025.
International Search Report in International Application No. PCT/US2024/041779, dated: Dec. 20, 2024.
Knopp, et al., "Transient Retrovirus-Based CRISPR/Cas9 All-in-One Particles for Efficient, Targeted Gene Knockout," Molecular Therapy: Nucleic Acids, vol. 13, Dec. 2018.
Lanzavecchia, et al., "The use of hybrid hybridomas to target human cytotoxic T lymphocytes," Eur. J. Immunol., 17:105-111, 1987.
Lombardo, et al., "Gene editing in human stem cells using zinc finger nucleases and integrase-defective lentiviral vector delivery," Nature Biotechnology, vol. 25(11), Nov. 2007.
Non-Final Office Action in U.S. Appl. No. 18/269,204, dated: Aug. 19, 2024.
Non-Final Office Action in U.S. Appl. No. 18/629,097, dated: Aug. 12, 2024.
Notice of Allowance for U.S. Appl. No. 18/375,868, dated Apr. 16, 2025.
Patent Owner's Sur-Reply of U.S. Pat. No. 11,767,366, Before the Patent Trial and Appeal Board, *Kelonia Therapeutics, Inc.*, Petitioner v. *Interius Biotherapeutics, Inc.*, Patent Owner, Case No. PGR2024-0008, 6 pages, dated Mar. 29, 2024.

(56) References Cited

OTHER PUBLICATIONS

Petition for Post-Grant Review of U.S. Pat. No. 11,767,366, Before the Patent Trial and Appeal Board, *Kelonia Therapeutics, Inc*., Petitioner v. *Interius Biotherapeutics, Inc*., Patent Owner, 98 Pages, dated Oct. 31, 2023.
Petitioner's Reply to Patent Owner's Preliminary Response of U.S. Pat. No. 11,767,366 Before the Patent Trial and Appeal Board, *Kelonia Therapeutics, Inc*., Petitioner v. *Interius Biotherapeutics, Inc*, Inc., Patent Owner, Case No. PGR2024-0008, 8 pages, dated Mar. 22, 2024.
Notice of Allowance for U.S. Appl. No. 18/919,103, dated Jul. 22, 2025.
Notice of Allowance for U.S. Appl. No. 19/172,374, dated: Jul. 25, 2025.
Brown, et al., "A Receptor Mediated Pathway for Cholesterol Homeostasis," Science, vol. 232, p. 34-47, Apr. 4, 1986.
Fernandez, et al., "Genetically Engineered Vesicular Stomatitis Virus in Gene Therapy: Application for Treatment of Malignant Disease," Journal of Virology, vol. 76, No. 2, p. 895-904, Jan. 2002.
Goyvaerts, et al., "Targeting of Human Antigen-Presenting Cell Subsets," Journal of Virology, 87(20):11304-11308, 2013.
Harper, et al., "Purification of proteins fused to glutathione S-tranferase," Methods Mol Biol.; 681:259-280, 2011.
Hastie, et al., "Oncolytic Vesicular Stomatitis Virus in an Immunocompetent Model of MUC1-Positive or MUC1-Null Pancreatic Ductal Adenocarcinoma," Journal of Virology, p. 10283-10294, vol. 87, No. 18, Sep. 2013.
Ho, et al., "Decoupling the Functional Pleiotropy of Stem Cell Factor by Tuning c-Kit Signaling," Cell, 168 (6):1041-1052, 2017.
Messer, et al., "Optimizing intracellular antibodies (intrabodies/nanobodies) to treat neurodegenerative disorders," Neurobiology of Disease 134, 104619, 2020.
Nikolic, et al., "Structural basis for the recognition of LDL-receptor family members by VSV glycoprotein," Nature Communications, 9:1029, 2018 with attached Supplementary Information.
Non-Final Office Action for U.S. Appl. No. 18/279,201, dated Jun. 13, 2025.
Non-Final Office Action in U.S. Appl. No. 18/375,868, dated: Jun. 28, 2024.
Notice of Allowance from U.S. Appl. No. 18/375,868, dated Apr. 19, 2024.
Notice of Allowance in U.S. Appl. No. 18/919,069, dated: Jan. 16, 2025.
Rose, et al., "Glycoprotein Exchange Vectors Based on Vesicular Stomatitis Virus Allow Effective Boosting and Generation of Neutralizing Antibodies to a Primary Isolate of Human Immunodeficiency Virus Type 1," Journal of Virology, vol. 74, No. 23, p. 10903-10910, Dec. 2000.
Annex A—Experimental data, cited in EP Opposition for EP Application No. 18773448.8 on May 14, 2025.
Baquero, et al., "Recent mechanistic and structural insights on class III viral fusion glycoproteins," Current Opinion on Structural Biology, 33:52-60, 2015.
Beglova, et al., "The LDL receptor: how acid pulls the trigger," Trends in Biochemical Sciences, 30(6), 2005.
Beilstein, et al., "Identification of a pH-Sensitive Switch in VSV-G and a Crystal Structure of the G Pre-fusion State Highlight the VSV-G Structural Transition Pathway," Cell Reports, 32, 108042, 2020.
Bortoletto, et al., "Optimizing anti-CD3 affinity for effective T cell targeting against tumor cells," Eur. J. Immunol., 32:3102-3107, 2002.
Buchholz, et al., "Surface-Engineered Viral Vectors for Selective and Cell Type-Specific Gene Delivery," Trends in Biotechnology, 33:12, 2015.
Experimental Report cited in EP Opposition for EP Application No. 18773448.8 dated May 14, 2025.
Hwang, et al., "Engineering a serum-resistant and thermostable vesicular stomatitis virus G glycoprotein for pseudotyping retroviral and lentiviral vectors," Gene Therapy, 2013 with supplementary data.
Joglekar, et al., "Pseudotyped Lentiviral Vectors: One Vector, Many Guises," Human Gene Therapy Methods, 28(6), 2017.
Lillis, et al., "LDL Receptor-Related Protein 1: Unique Tissue-Specific Functions Revealed by Selective Gene Knockout Studies," Physiol. Rev., vol. 88, 2008.
Roche, et al., "Structures of vesicular stomatitis virus glycoprotein: membrane fusion revisited," Cell. Mol. Life Sci., 65, 1716-1728, 2008.
Rucker, et al., "pH-dependent molecular dynamics of vesicular stomatitis virus glycoprotein G," Proteins, 80:2601-2613, 2012 with supplementary data.
WO 2010/040023 figures as filed as cited in EP Opposition for EP Application No. 18773448.8 dated May 14, 2025.

* cited by examiner

SEQUENCE LISTING

```
Sequence total quantity: 374
SEQ ID NO: 1           moltype = AA  length = 495
FEATURE                Location/Qualifiers
source                 1..495
                       mol_type = protein
                       organism = synthetic construct
SEQUENCE: 1
KFTIVFPHNQ KGNWKNVPSN YHYCPSSSDL NWHNDLIGTA LQVKMPKSHK AIQADGWMCH  60
ASKWVTTCDF RWYGPKYITH SIRSFTPSVE QCKESIEQTK QGTWLNPGFP PQSCGYATVT  120
DAEAVIVQVT PHHVLVDEYT GEWVDSQFIN GKCSNYICPT VHNSTTWHSD YKVKGLCDSN  180
```

```
LISMDITFFS EDGELSSLGK EGTGFRSNYF AYETGGKACK MQYCKHWGVR LPSGVWFEMA  240
DKDLFAAARF PECPEGSSIS APSQTSVDVS LIQDVERILD YSLCQETWSK IRAGLPISPV  300
DLSYLAPKNP GTGPAFTIIN GTLKYFETRY IRVDIAAPIL SRMVGMISGT TTERELWDDW  360
APYEDVEIGP NGVLRTSSGY KFPLYMIGHG MLDSDLHLSS KAQVFEHPHI QDAASQLPDD  420
ESLFFGDTGL SKNPIELVEG WFSSWKSSIA SFFFIIGLII GLFLVLRVGI HLCIKLKHTK  480
KRQIYTDIEM NRLGK                                                  495

SEQ ID NO: 2            moltype = AA  length = 495
FEATURE                 Location/Qualifiers
source                  1..495
                        mol_type = protein
                        organism = synthetic construct
SEQUENCE: 2
KFTIVFPHNQ KGNWKNVPSN YHYCPSSSDL NWHNDLIGTA IQVKMPKSHK AIQADGWMCH  60
ASKWVTTCDF RWYGPKYITQ SIRSFTPSVE QCKESIEQTK QGTWLNPGFP PQSCGYATVT  120
DAEAVIVQVT PHHVLVDEYT GEWVDSQFIN GKCSNYICPT VHNSTTWHSD YKVKGLCDSN  180
LISMDITFFS EDGELSSLGK EGTGFRSNYF AYETGGKACK MQYCKHWGVR LPSGVWFEMA  240
DKDLFAAARF PECPEGSSIS APSQTSVDVS LIQDVERILD YSLCQETWSK IRAGLPISPV  300
DLSYLAPKNP GTGPAFTIIN GTLKYFETRY IRVDIAAPIL SRMVGMISGT TTERELWDDW  360
APYEDVEIGP NGVLRTSSGY KFPLYMIGHG MLDSDLHLSS KAQVFEHPHI QDAASQLPDD  420
ESLFFGDTGL SKNPIELVEG WFSSWKSSIA SFFFIIGLII GLFLVLRVGI HLCIKLKHTK  480
KRQIYTDIEM NRLGK                                                  495

SEQ ID NO: 3            moltype = AA  length = 495
FEATURE                 Location/Qualifiers
source                  1..495
                        mol_type = protein
                        organism = synthetic construct
SEQUENCE: 3
KFTIVFPHNQ KGNWKNVPSN YHYCPSSSDL NWHNDLIGTA IQVKMPKSHK AIQADGWMCH  60
ASKWVTTCDF RWYGPKYITH SIRSFTPSVE QCKESIEQTK QGTWLNPGFP PQSCGYATVT  120
DAEAVIVQVT PHHVLVDEYT GEWVDSQFIN GKCSNYICPT VHNSTTWHSD YKVKGLCDSN  180
LISMDITFFS EDGELSSLGK EGTGFRSNYF AYETGGKACK MQYCKHWGVR LPSGVWFEMA  240
DKDLFAAARF PECPEGSSIS APSQTSVDVS LIQDVERILD YSLCQETWSK IRAGLPISPV  300
DLSYLAPKNP GTGPAFTIIN GTLKYFETRY IRVDIAAPIL SRMVGMISGT TTERELWDDW  360
APYEDVEIGP NGVLRTSSGY KFPLYMIGHG MLDSDLHLSS KAQVFEHPHI QDAASQLPDD  420
ESLFFGDTGL SKNPIELVEG WFSSWKSSIA SFFFIIGLII GLFLVLRVGI HLCIKLKHTK  480
KRQIYTDIEM NRLGK                                                  495

SEQ ID NO: 4            moltype = AA  length = 495
FEATURE                 Location/Qualifiers
source                  1..495
                        mol_type = protein
                        organism = synthetic construct
SEQUENCE: 4
KFTIVFPHNQ KGNWKNVPSN YHYCPSSSDL NWHNDLIGTA LQVKMPKSHK AIQADGWMCH  60
ASKWVTTCDF RWYGPKYITQ SIRSFTPSVE QCKESIEQTK QGTWLNPGFP PQSCGYATVT  120
DAEAVIVQVT PHHVLVDEYT GEWVDSQFIN GKCSNYICPT VHNSTTWHSD YKVKGLCDSN  180
LISMDITFFS EDGELSSLGK EGTGFRSNYF AYETGGKACK MQYCKHWGVR LPSGVWFEMA  240
DKDLFAAARF PECPEGSSIS APSQTSVDVS LIQDVERILD YSLCQETWSK IRAGLPISPV  300
DLSYLAPKNP GTGPAFTIIN GTLKYFETRY IRVDIAAPIL SRMVGMISGT TTERELWDDW  360
APYEDVEIGP NGVLRTSSGY KFPLYMIGHG MLDSDLHLSS KAQVFEHPHI QDAASQLPDD  420
ESLFFGDTGL SKNPIELVEG WFSSWKSSIA SFFFIIGLII GLFLVLRVGI HLCIKLKHTK  480
KRQIYTDIEM NRLGK                                                  495

SEQ ID NO: 5            moltype = AA  length = 495
FEATURE                 Location/Qualifiers
source                  1..495
                        mol_type = protein
                        organism = synthetic construct
SEQUENCE: 5
KFTIVFPHNQ KGNWKNVPSN YHYCPSSSDL NWHNDLIGTA LQVKMPKSHK AIQADGWMCH  60
ASKWITTCDF RWYGPKYITH SIQSFTPSVE QCKESIEQTK QGTWLNPGFP PQSCGYATVT  120
DAEAVIVQVT PHHVLVDEYT GEWVDSQFIN GKCSNDICLT VHNSTTWHSD YKVKGLCDSN  180
LISMDITFFS EDGELSSLGK AGTGFRSNYF AYETGDKACK MQYCKHWGVR LPSGVWFEMA  240
DKDLFAAAKF PECPEGSSIS APSQTSVDVS LIQDVERILD YSLCQETWSK IRAGLPISPV  300
DLSYLAPKNP GTGPAFTIIN GTLKYFETRY IRVDIAAPIL SRMVGMISGT NTERELWEDW  360
APYEDVEIGP NGVLRTSSGY KFPLYMIGHG MLDSDLHLSS KVQVFEHPHI QDAASQLPDD  420
ETLFFGDTGL SKNPIELVEG WFSGWKSSIA SFFFIIGLII GLFLVLRVGI YLCIKLKHTR  480
KRKIYADIEM NRLGK                                                  495

SEQ ID NO: 6            moltype = AA  length = 495
FEATURE                 Location/Qualifiers
source                  1..495
                        mol_type = protein
                        organism = synthetic construct
SEQUENCE: 6
KFTTVFPHNK KGDWKNVPSN YHYCPSSSDL NWHNDLIGTA LQVKMPKSHK AIQADGWMCH  60
ASKWVTTCDF RWYGPKYITH SIRSFTPSVE QCKESIEQTK QGTWLNPGFP PQSCGYATVT  120
```

```
DAEAVIVQVT PHHVLVDEYT GEWVDSQFIN GKCSDDICPT VHNSTTWHSD YKVKGLCDSN  180
LISMDITFFS EDGELSSLGK EGTGFRSNYF AYETGDKACK MQYCKHWGVR LPSGVWFEMA  240
DKNLFAAAKF PECPEGSSIS APSQTSVDVS LIQDVERILD YSLCQETWSK IRAGLPISPV  300
DLSYLAPKNP GTGPAFTIIN GTLKYFETRY IRVDIAAPIL SRMVGMISGT TTERELWEDW  360
APYEDVEIGP NGVLRTSSGY KFPLYMIGHG MLDSDLHLSS KAQVFEHPHI PDATSQLPDD  420
ETLFFGDTGL SKDPIELVEG WFSGWKSSIA SFFFIIGLII GLFFVLRIGV YLCIKLKHTN  480
KRQIYTDIEM NRLGK                                                  495

SEQ ID NO: 7           moltype = AA  length = 495
FEATURE                Location/Qualifiers
source                 1..495
                       mol_type = protein
                       organism = synthetic construct
SEQUENCE: 7
KFTIVFPHNQ KGTWKNVPSN YHYCPSSSDL NWHNDLIGTA LQVKMPKSHK AIQADGWMCH  60
ASKWVTTCDF RWYGPKYITH SIRSFTPSVE QCRESIEQTK QGTWLNPGFP PQSCGYATVT  120
DAEAVIVQVT PHHVLVDEYT GEWVDSQFIN GKCSNDICPT VHNSTTWHSD YKVKGLCDSN  180
LISMDITFFS EDGELSSLGK EGTGFRSNHF AYETGDKACK MQYCKHWGVR LPSGVWFEMA  240
DQDLFAAARF PECPEGSSIS APSQTSVDVS LIQDVERILD YSLCQETWSK IGAGLPISPV  300
DLSYLAPKNP GTGPAFTIIN GTLKYFETRY IRVDIAAPIL SRMVGMISGT TTERELWDDW  360
APYEDVEIGP NGVLRTSSGY KFPLYMIGHG MLDSDLHLSS KAQVFEHPHI QDAASQLPDD  420
ETLFFGDTGL SKNPIELVEG WFSGWKSSIA SFFFIIGLII GLFLVLRVGI YLCIKLKHTK  480
KRQIYTDIEM NRLGK                                                  495

SEQ ID NO: 8           moltype = AA  length = 495
FEATURE                Location/Qualifiers
source                 1..495
                       mol_type = protein
                       organism = synthetic construct
SEQUENCE: 8
KFTIVFPHNQ KGNWKNVPSN YHYCPSSSDL NWHNDLIGTG LQVKMPKSHK AIQADGWMCH  60
ASKWVTTCDF RWYGPKYITH SIRSFTPSVE QCKESIEQTK QGTWLNPGFP PQSCGYATVT  120
DAEAVIVQVT PHHVLVDEYT GEWVDSQFIN GKCSNDICPT VHNSTTWHSD YKVKGLCDSN  180
LISTDITFFS EDRELSSLGK EGTGFRSNYF AYETGDKACK MQYCKHWGVR LPSGVWFEMA  240
DKDLFAAARF PECPEGSSIS APSQTSVDVS LIQDVERILD YSLCQETWSK IRAGLPISPV  300
DLSYLAPKNP GTGPAFTIIN GTLKYFETRY IRVDIAAPIL SRMVGMISGT TTERELWDDW  360
APYEDVEIGP NGVLRTSSGY KFPLYMIGHG MLDSGLHLSS KAQVFEHPHI QDAASQLPDD  420
EILFFGDTGL SKNPIDFVEG WFSSWKSSIA SFFFIIGLII GLFLVLRVGI YLYIKLKHTK  480
KRQIYTDIEM NRLGR                                                  495

SEQ ID NO: 9           moltype = AA  length = 495
FEATURE                Location/Qualifiers
source                 1..495
                       mol_type = protein
                       organism = synthetic construct
SEQUENCE: 9
KFSIVFPQSQ KGNWKNVPSS YHYCPSSSDQ NWHNDLLGIT MKVKMPKTHK AIQADGWMCH  60
AAKWITTCDF RWYGPKYITH SIHSIQPTSE QCKESIKQTK QGTWMSPGFP PQNCGYATVT  120
DSVAVVVQAT PHHVLVDEYT GEWIDSQFPN GKCETEECET VHNSTVWYSD YKVTGLCDAT  180
LVDTEITFFS EDGKKESIGK PNTGYRSNYF AYEKGDKVCK MNYCKHAGVR LPSGVWFEFV  240
DQDVYAAAKL PECPVGATIS APTQTSVDVS LILDVERILD YSLCQETWSK IRSKQPVSPV  300
DLSYLAPKNP GTGPAFTIIN GTLKYFETRY IRIDIDNPII SKMVGKISGS QTERELWTEW  360
FPYEGVEIGP NGILKTPTGY KFPLFMIGHG MLDSDLHKTS QAEVFEHPHL AEAPKQLPEE  420
ETLFFGDTGI SKNPVELIEG WFSSWKSTVV TFFFAIGVFI LLYVVARIVI AVRYRYQGSN  480
NKRIYNDIEM SRFRK                                                  495

SEQ ID NO: 10          moltype = AA  length = 184
FEATURE                Location/Qualifiers
source                 1..184
                       mol_type = protein
                       organism = Homo sapiens
SEQUENCE: 10
MLQMAGQCSQ NEYFDSLLHA CIPCQLRCSS NTPPLTCQRY CNASVTNSVK GTNAILWTCL  60
GLSLIISLAV FVLMFLLRKI NSEPLKDEFK NTGSGLLGMA NIDLEKSRTG DEIILPRGLE  120
YTVEECTCED CIKSKPKVDS DHCFPLPAME EGATILVTTK TNDYCKSLPA ALSATEIEKS  180
ISAR                                                              184

SEQ ID NO: 11          moltype = AA  length = 118
FEATURE                Location/Qualifiers
source                 1..118
                       mol_type = protein
                       organism = synthetic construct
SEQUENCE: 11
QITLKESGPT LVKPTQTLTL TCTFSGFSLS TSGVGVGWIR QPPGKALEWL ALIYWNDEKR  60
YSPSLKSRLT ITKDTSKNQV VLTMTNMDPV DTAVYYCARD EYGGFDIWGQ GTMVTVSS    118

SEQ ID NO: 12          moltype = AA  length = 7
FEATURE                Location/Qualifiers
source                 1..7
```

```
                        mol_type = protein
                        organism = synthetic construct
SEQUENCE: 12
TSGVGVG                                                               7

SEQ ID NO: 13           moltype = AA  length = 16
FEATURE                 Location/Qualifiers
source                  1..16
                        mol_type = protein
                        organism = synthetic construct
SEQUENCE: 13
LIYWNDEKRY SPSLKS                                                     16

SEQ ID NO: 14           moltype = AA  length = 8
FEATURE                 Location/Qualifiers
source                  1..8
                        mol_type = protein
                        organism = synthetic construct
SEQUENCE: 14
DEYGGFDI                                                              8

SEQ ID NO: 15           moltype = AA  length = 107
FEATURE                 Location/Qualifiers
source                  1..107
                        mol_type = protein
                        organism = synthetic construct
SEQUENCE: 15
EIVLTQSPAT LSLSPGERAT LSCRASQSVS SYLAWYQQKP GQAPRLLIYD ASNRATGIPA  60
RFSGSGSGTD FTLTISSLEP EDFAVYYCQQ RVVYPITFGG GTKVEIK                107

SEQ ID NO: 16           moltype = AA  length = 11
FEATURE                 Location/Qualifiers
source                  1..11
                        mol_type = protein
                        organism = synthetic construct
SEQUENCE: 16
RASQSVSSYL A                                                          11

SEQ ID NO: 17           moltype = AA  length = 7
FEATURE                 Location/Qualifiers
source                  1..7
                        mol_type = protein
                        organism = synthetic construct
SEQUENCE: 17
DASNRAT                                                               7

SEQ ID NO: 18           moltype = AA  length = 9
FEATURE                 Location/Qualifiers
source                  1..9
                        mol_type = protein
                        organism = synthetic construct
SEQUENCE: 18
QQRVVYPIT                                                             9

SEQ ID NO: 19           moltype = AA  length = 245
FEATURE                 Location/Qualifiers
source                  1..245
                        mol_type = protein
                        organism = synthetic construct
SEQUENCE: 19
QITLKESGPT LVKPTQTLTL TCTFSGFSLS TSGVGVGWIR QPPGKALEWL ALIYWNDEKR  60
YSPSLKSRLT ITKDTSKNQV VLTMTNMDPV DTAVYYCARD EYGGFDIWGQ GTMVTVSSGG  120
GGSGGGGSGG GGSGGGGSEI VLTQSPATLS LSPGERATLS CRASQSVSSY LAWYQQKPGQ  180
APRLLIYDAS NRATGIPARF SGSGSGTDFT LTISSLEPED FAVYYCQQRV VYPITFGGGT  240
KVEIK                                                                 245

SEQ ID NO: 20           moltype = AA  length = 245
FEATURE                 Location/Qualifiers
source                  1..245
                        mol_type = protein
                        organism = synthetic construct
SEQUENCE: 20
EIVLTQSPAT LSLSPGERAT LSCRASQSVS SYLAWYQQKP GQAPRLLIYD ASNRATGIPA  60
RFSGSGSGTD FTLTISSLEP EDFAVYYCQQ RVVYPITFGG GTKVEIKGGG GSGGGGSGGG  120
GSGGGGSQIT LKESGPTLVK PTQTLTLTCT FSGFSLSTSG VGVGWIRQPP GKALEWLALI  180
YWNDEKRYSP SLKSRLTITK DTSKNQVVLT MTNMDPVDTA VYYCARDEYG GFDIWGQGTM  240
VTVSS                                                                 245

SEQ ID NO: 21           moltype = AA  length = 118
```

```
FEATURE                Location/Qualifiers
source                 1..118
                       mol_type = protein
                       organism = synthetic construct
SEQUENCE: 21
QITLKESGPT LVKPTQTLTL TCTFSGFSLS TSGVGVGWIR QPPGKALEWL ALIYWNDDKR  60
YSPSLKSRLT ITKDTSKNQV VLTMTNMDPV DTAVYYCARD EYGGFDIWGQ GTMVTVSS    118

SEQ ID NO: 22          moltype = AA  length = 7
FEATURE                Location/Qualifiers
source                 1..7
                       mol_type = protein
                       organism = synthetic construct
SEQUENCE: 22
TSGVGVG                                                            7

SEQ ID NO: 23          moltype = AA  length = 16
FEATURE                Location/Qualifiers
source                 1..16
                       mol_type = protein
                       organism = synthetic construct
SEQUENCE: 23
LIYWNDDKRY SPSLKS                                                  16

SEQ ID NO: 24          moltype = AA  length = 8
FEATURE                Location/Qualifiers
source                 1..8
                       mol_type = protein
                       organism = synthetic construct
SEQUENCE: 24
DEYGGFDI                                                           8

SEQ ID NO: 25          moltype = AA  length = 107
FEATURE                Location/Qualifiers
source                 1..107
                       mol_type = protein
                       organism = synthetic construct
SEQUENCE: 25
EIVLTQSPAT LSLSPGERAT LSCRASQSVS SYLAWYQQKP GQAPRLLIYD ASNRATGIPA  60
RFSGSGSGTD FTLTISSLEP EDFAVYYCQQ RFDYPITFGG GTKVEIK                107

SEQ ID NO: 26          moltype = AA  length = 11
FEATURE                Location/Qualifiers
source                 1..11
                       mol_type = protein
                       organism = synthetic construct
SEQUENCE: 26
RASQSVSSYL A                                                       11

SEQ ID NO: 27          moltype = AA  length = 7
FEATURE                Location/Qualifiers
source                 1..7
                       mol_type = protein
                       organism = synthetic construct
SEQUENCE: 27
DASNRAT                                                            7

SEQ ID NO: 28          moltype = AA  length = 9
FEATURE                Location/Qualifiers
source                 1..9
                       mol_type = protein
                       organism = synthetic construct
SEQUENCE: 28
QQRFDYPIT                                                          9

SEQ ID NO: 29          moltype = AA  length = 245
FEATURE                Location/Qualifiers
source                 1..245
                       mol_type = protein
                       organism = synthetic construct
SEQUENCE: 29
QITLKESGPT LVKPTQTLTL TCTFSGFSLS TSGVGVGWIR QPPGKALEWL ALIYWNDDKR  60
YSPSLKSRLT ITKDTSKNQV VLTMTNMDPV DTAVYYCARD EYGGFDIWGQ GTMVTVSSGG  120
GGSGGGGSGG GGSGGGGSEI VLTQSPATLS LSPGERATLS CRASQSVSSY LAWYQQKPGQ  180
APRLLIYDAS NRATGIPARF SGSGSGTDFT LTISSLEPED FAVYYCQQRF DYPITFGGGT  240
KVEIK                                                              245

SEQ ID NO: 30          moltype = AA  length = 245
FEATURE                Location/Qualifiers
```

```
source                  1..245
                        mol_type = protein
                        organism = synthetic construct
SEQUENCE: 30
EIVLTQSPAT LSLSPGERAT LSCRASQSVS SYLAWYQQKP GQAPRLLIYD ASNRATGIPA  60
RFSGSGSGTD FTLTISSLEP EDFAVYYCQQ RFDYPITFGG GTKVEIKGGG GSGGGGSGGG  120
GSGGGGSQIT LKESGPTLVK PTQTLTLTCT FSGFSLSTSG VGVGWIRQPP GKALEWLALI  180
YWNDDKRYSP SLKSRLTITK DTSKNQVVLT MTNMDPVDTA VYYCARDEYG GFDIWGQGTM  240
VTVSS                                                              245

SEQ ID NO: 31           moltype = AA  length = 117
FEATURE                 Location/Qualifiers
source                  1..117
                        mol_type = protein
                        organism = synthetic construct
SEQUENCE: 31
QVQLVESGGG VVQPGRSLRL SCAASGFTFS SYGMHWVRQA PGKGLEWVAV ISYEGSNKYY  60
ADSVKGRFTI SRDNSKNTLY LQMNSLRAED TAVYYCAREL GDGMDVWGQG TTVTVSS     117

SEQ ID NO: 32           moltype = AA  length = 5
FEATURE                 Location/Qualifiers
source                  1..5
                        mol_type = protein
                        organism = synthetic construct
SEQUENCE: 32
SYGMH                                                              5

SEQ ID NO: 33           moltype = AA  length = 17
FEATURE                 Location/Qualifiers
source                  1..17
                        mol_type = protein
                        organism = synthetic construct
SEQUENCE: 33
VISYEGSNKY YADSVKG                                                 17

SEQ ID NO: 34           moltype = AA  length = 8
FEATURE                 Location/Qualifiers
source                  1..8
                        mol_type = protein
                        organism = synthetic construct
SEQUENCE: 34
ELGDGMDV                                                           8

SEQ ID NO: 35           moltype = AA  length = 106
FEATURE                 Location/Qualifiers
source                  1..106
                        mol_type = protein
                        organism = synthetic construct
SEQUENCE: 35
EIVLTQSPAT LSLSPGERAT LSCRASQSVS SYLAWFQQKP GQAPRLLIYD ASNRATGIPA  60
RFSGSGSGTD FTLTISSLEP EDFAVYYCQQ RVDLWTFGGG TKVEIK                 106

SEQ ID NO: 36           moltype = AA  length = 11
FEATURE                 Location/Qualifiers
source                  1..11
                        mol_type = protein
                        organism = synthetic construct
SEQUENCE: 36
RASQSVSSYL A                                                       11

SEQ ID NO: 37           moltype = AA  length = 7
FEATURE                 Location/Qualifiers
source                  1..7
                        mol_type = protein
                        organism = synthetic construct
SEQUENCE: 37
DASNRAT                                                            7

SEQ ID NO: 38           moltype = AA  length = 8
FEATURE                 Location/Qualifiers
source                  1..8
                        mol_type = protein
                        organism = synthetic construct
SEQUENCE: 38
QQRVDLWT                                                           8

SEQ ID NO: 39           moltype = AA  length = 243
FEATURE                 Location/Qualifiers
source                  1..243
```

```
                        mol_type = protein
                        organism = synthetic construct
SEQUENCE: 39
QVQLVESGGG VVQPGRSLRL SCAASGFTFS SYGMHWVRQA PGKGLEWVAV ISYEGSNKYY  60
ADSVKGRFTI SRDNSKNTLY LQMNSLRAED TAVYYCAREL GDGMDVWGQG TTVTVSSGGG  120
GSGGGGSGGG GSGGGGSEIV LTQSPATLSL SPGERATLSC RASQSVSSYL AWFQQKPGQA  180
PRLLIYDASN RATGIPARFS GSGSGTDFTL TISSLEPEDF AVYYCQQRVD LWTFGGGTKV  240
EIK                                                                243

SEQ ID NO: 40           moltype = AA  length = 243
FEATURE                 Location/Qualifiers
source                  1..243
                        mol_type = protein
                        organism = synthetic construct
SEQUENCE: 40
EIVLTQSPAT LSLSPGERAT LSCRASQSVS SYLAWFQQKP GQAPRLLIYD ASNRATGIPA  60
RFSGSGSGTD FTLTISSLEP EDFAVYYCQQ RVDLWTFGGG TKVEIKGGGG SGGGGSGGGG  120
SGGGGSQVQL VESGGGVVQP GRSLRLSCAA SGFTFSSYGM HWVRQAPGKG LEWVAVISYE  180
GSNKYYADSV KGRFTISRDN SKNTLYLQMN SLRAEDTAVY YCARELGDGM DVWGQGTTVT  240
VSS                                                                243

SEQ ID NO: 41           moltype = AA  length = 118
FEATURE                 Location/Qualifiers
source                  1..118
                        mol_type = protein
                        organism = synthetic construct
SEQUENCE: 41
EVQLVESGGG LVKPGGSLRL SCAASGFTFS DYYMSWIRQA PGKGLEWVSY ISSSGSTIYY  60
ADSVKGRFTI SRDNAKNSLY LQMNSLRAED TAVYYCARDQ GNYGVDVWGQ GTTVTVSS    118

SEQ ID NO: 42           moltype = AA  length = 5
FEATURE                 Location/Qualifiers
source                  1..5
                        mol_type = protein
                        organism = synthetic construct
SEQUENCE: 42
DYYMS                                                              5

SEQ ID NO: 43           moltype = AA  length = 17
FEATURE                 Location/Qualifiers
source                  1..17
                        mol_type = protein
                        organism = synthetic construct
SEQUENCE: 43
YISSSGSTIY YADSVKG                                                 17

SEQ ID NO: 44           moltype = AA  length = 9
FEATURE                 Location/Qualifiers
source                  1..9
                        mol_type = protein
                        organism = synthetic construct
SEQUENCE: 44
DQGNYGVDV                                                          9

SEQ ID NO: 45           moltype = AA  length = 107
FEATURE                 Location/Qualifiers
source                  1..107
                        mol_type = protein
                        organism = synthetic construct
SEQUENCE: 45
DIQMTQSPST LSASVGDRVT ITCRASQSIS SWLAWYQQKP GKAPKLLIYD ASSLESGVPS  60
RFSGSGSGTE FTLTISSLQP DDFATYYCQQ VSSLPPTFGG GTKVEIK                107

SEQ ID NO: 46           moltype = AA  length = 11
FEATURE                 Location/Qualifiers
source                  1..11
                        mol_type = protein
                        organism = synthetic construct
SEQUENCE: 46
RASQSISSWL A                                                       11

SEQ ID NO: 47           moltype = AA  length = 7
FEATURE                 Location/Qualifiers
source                  1..7
                        mol_type = protein
                        organism = synthetic construct
SEQUENCE: 47
DASSLES                                                            7
```

-continued

```
SEQ ID NO: 48           moltype = AA  length = 9
FEATURE                 Location/Qualifiers
source                  1..9
                        mol_type = protein
                        organism = synthetic construct
SEQUENCE: 48
QQVSSLPPT                                                          9

SEQ ID NO: 49           moltype = AA  length = 245
FEATURE                 Location/Qualifiers
source                  1..245
                        mol_type = protein
                        organism = synthetic construct
SEQUENCE: 49
EVQLVESGGG LVKPGGSLRL SCAASGFTFS DYYMSWIRQA PGKGLEWVSY ISSSGSTIYY  60
ADSVKGRFTI SRDNAKNSLY LQMNSLRAED TAVYYCARDQ GNYGVDVWGQ GTTVTVSSGG  120
GGSGGGGSGG GGSGGGGSDI QMTQSPSTLS ASVGDRVTIT CRASQSISSW LAWYQQKPGK  180
APKLLIYDAS SLESGVPSRF SGSGSGTEFT LTISSLQPDD FATYYCQQVS SLPPTFGGGT  240
KVEIK                                                              245

SEQ ID NO: 50           moltype = AA  length = 245
FEATURE                 Location/Qualifiers
source                  1..245
                        mol_type = protein
                        organism = synthetic construct
SEQUENCE: 50
DIQMTQSPST LSASVGDRVT ITCRASQSIS SWLAWYQQKP GKAPKLLIYD ASSLESGVPS  60
RFSGSGSGTE FTLTISSLQP DDFATYYCQQ VSSLPPTFGG GTKVEIKGGG GSGGGGSGGG  120
GSGGGGSEVQ LVESGGGLVK PGGSLRLSCA ASGFTFSDYY MSWIRQAPGK GLEWVSYISS  180
SGSTIYYADS VKGRFTISRD NAKNSLYLQM NSLRAEDTAV YYCARDQGNY GVDVWGQGTT  240
VTVSS                                                              245

SEQ ID NO: 51           moltype = AA  length = 118
FEATURE                 Location/Qualifiers
source                  1..118
                        mol_type = protein
                        organism = synthetic construct
SEQUENCE: 51
QVQLVESGGG LVKPGGSLRL SCAASGFTFS DYYMSWIRQA PGKGLEWVSY ISSSGSTIYY  60
ADSVKGRFTI SRDNAKNSLY LQMNSLRAED TAVYYCARDQ GNYGVDVWGQ GTTVTVSS    118

SEQ ID NO: 52           moltype = AA  length = 5
FEATURE                 Location/Qualifiers
source                  1..5
                        mol_type = protein
                        organism = synthetic construct
SEQUENCE: 52
DYYMS                                                              5

SEQ ID NO: 53           moltype = AA  length = 17
FEATURE                 Location/Qualifiers
source                  1..17
                        mol_type = protein
                        organism = synthetic construct
SEQUENCE: 53
YISSSGSTIY YADSVKG                                                 17

SEQ ID NO: 54           moltype = AA  length = 9
FEATURE                 Location/Qualifiers
source                  1..9
                        mol_type = protein
                        organism = synthetic construct
SEQUENCE: 54
DQGNYGVDV                                                          9

SEQ ID NO: 55           moltype = AA  length = 107
FEATURE                 Location/Qualifiers
source                  1..107
                        mol_type = protein
                        organism = synthetic construct
SEQUENCE: 55
DIQMTQSPST LSASVGDRVT ITCRASQSIS SWLAWYQQKP GKAPKLLIYE ASSLESGVPS  60
RFSGSGSGTE FTLTISSLQP DDFATYYCQQ SDSHPITFGG GTKVEIK                107

SEQ ID NO: 56           moltype = AA  length = 11
FEATURE                 Location/Qualifiers
source                  1..11
                        mol_type = protein
                        organism = synthetic construct
```

```
SEQUENCE: 56
RASQSISSWL A                                                       11

SEQ ID NO: 57           moltype = AA  length = 7
FEATURE                 Location/Qualifiers
source                  1..7
                        mol_type = protein
                        organism = synthetic construct
SEQUENCE: 57
EASSLES                                                            7

SEQ ID NO: 58           moltype = AA  length = 9
FEATURE                 Location/Qualifiers
source                  1..9
                        mol_type = protein
                        organism = synthetic construct
SEQUENCE: 58
QQSDSHPIT                                                          9

SEQ ID NO: 59           moltype = AA  length = 245
FEATURE                 Location/Qualifiers
source                  1..245
                        mol_type = protein
                        organism = synthetic construct
SEQUENCE: 59
QVQLVESGGG LVKPGGSLRL SCAASGFTFS DYYMSWIRQA PGKGLEWVSY ISSSGSTIYY  60
ADSVKGRFTI SRDNAKNSLY LQMNSLRAED TAVYYCARDQ GNYGVDVWGQ GTTVTVSSGG  120
GGSGGGGSGG GGSGGGGSDI QMTQSPSTLS ASVGDRVTIT CRASQSISSW LAWYQQKPGK  180
APKLLIYEAS SLESGVPSRF SGSGSGTEFT LTISSLQPDD FATYYCQQSD SHPITFGGGT  240
KVEIK                                                              245

SEQ ID NO: 60           moltype = AA  length = 245
FEATURE                 Location/Qualifiers
source                  1..245
                        mol_type = protein
                        organism = synthetic construct
SEQUENCE: 60
DIQMTQSPST LSASVGDRVT ITCRASQSIS SWLAWYQQKP GKAPKLLIYE ASSLESGVPS  60
RFSGSGSGTE FTLTISSLQP DDFATYYCQQ SDSHPITFGG GTKVEIKGGG GSGGGGSGGG  120
GSGGGGSQVQ LVESGGGLVK PGGSLRLSCA ASGFTFSDYY MSWIRQAPGK GLEWVSYISS  180
SGSTIYYADS VKGRFTISRD NAKNSLYLQM NSLRAEDTAV YYCARDQGNY GVDVWGQGTT  240
VTVSS                                                              245

SEQ ID NO: 61           moltype = AA  length = 118
FEATURE                 Location/Qualifiers
source                  1..118
                        mol_type = protein
                        organism = synthetic construct
SEQUENCE: 61
EVQLVESGGG LVKPGGSLRL SCAASGFTFS DYYMSWIRQA PGKGLEWVSY ISSSGSTIYY  60
ADSVKGRFTI SRDNAKNSLY LQMNSLRAED TAVYYCARDQ GNYGVDVWGQ GTTVTVSS    118

SEQ ID NO: 62           moltype = AA  length = 5
FEATURE                 Location/Qualifiers
source                  1..5
                        mol_type = protein
                        organism = synthetic construct
SEQUENCE: 62
DYYMS                                                              5

SEQ ID NO: 63           moltype = AA  length = 17
FEATURE                 Location/Qualifiers
source                  1..17
                        mol_type = protein
                        organism = synthetic construct
SEQUENCE: 63
YISSSGSTIY YADSVKG                                                 17

SEQ ID NO: 64           moltype = AA  length = 9
FEATURE                 Location/Qualifiers
source                  1..9
                        mol_type = protein
                        organism = synthetic construct
SEQUENCE: 64
DQGNYGVDV                                                          9

SEQ ID NO: 65           moltype = AA  length = 107
FEATURE                 Location/Qualifiers
source                  1..107
```

```
                        mol_type = protein
                        organism = synthetic construct
SEQUENCE: 65
DIQMTQSPST LSASVGDRVT ITCRASQSIS SWLAWYQQKP GKAPKLLIYE ASSLESGVPS  60
RFSGSGSGTE FTLTISSLQP DDFATYYCQQ ANSHPITFGG GTKVEIK               107

SEQ ID NO: 66           moltype = AA  length = 11
FEATURE                 Location/Qualifiers
source                  1..11
                        mol_type = protein
                        organism = synthetic construct
SEQUENCE: 66
RASQSISSWL A                                                      11

SEQ ID NO: 67           moltype = AA  length = 7
FEATURE                 Location/Qualifiers
source                  1..7
                        mol_type = protein
                        organism = synthetic construct
SEQUENCE: 67
EASSLES                                                           7

SEQ ID NO: 68           moltype = AA  length = 9
FEATURE                 Location/Qualifiers
source                  1..9
                        mol_type = protein
                        organism = synthetic construct
SEQUENCE: 68
QQANSHPIT                                                         9

SEQ ID NO: 69           moltype = AA  length = 245
FEATURE                 Location/Qualifiers
source                  1..245
                        mol_type = protein
                        organism = synthetic construct
SEQUENCE: 69
EVQLVESGGG LVKPGGSLRL SCAASGFTFS DYYMSWIRQA PGKGLEWVSY ISSSGSTIYY  60
ADSVKGRFTI SRDNAKNSLY LQMNSLRAED TAVYYCARDQ GNYGVDVWGQ GTTVTVSSGG  120
GGSGGGGSGG GGSGGGGSDI QMTQSPSTLS ASVGDRVTIT CRASQSISSW LAWYQQKPGK  180
APKLLIYEAS SLESGVPSRF SGSGSGTEFT LTISSLQPDD FATYYCQQAN SHPITFGGGT  240
KVEIK                                                             245

SEQ ID NO: 70           moltype = AA  length = 245
FEATURE                 Location/Qualifiers
source                  1..245
                        mol_type = protein
                        organism = synthetic construct
SEQUENCE: 70
DIQMTQSPST LSASVGDRVT ITCRASQSIS SWLAWYQQKP GKAPKLLIYE ASSLESGVPS  60
RFSGSGSGTE FTLTISSLQP DDFATYYCQQ ANSHPITFGG GTKVEIKGGG GSGGGGSGGG  120
GSGGGGSEVQ LVESGGGLVK PGGSLRLSCA ASGFTFSDYY MSWIRQAPGK GLEWVSYISS  180
SGSTIYYADS VKGRFTISRD NAKNSLYLQM NSLRAEDTAV YYCARDQGNY GVDVWGQGTT  240
VTVSS                                                             245

SEQ ID NO: 71           moltype = AA  length = 122
FEATURE                 Location/Qualifiers
source                  1..122
                        mol_type = protein
                        organism = synthetic construct
SEQUENCE: 71
EVQLLESGGG LVQPGGSLRL SCAASGFTFS NYAMSWVRQA PGKGLEWVSA ISGSGGSTYY  60
ADSVKGRFTI SRDNSKNTLY LQMNSLRAED TAVYYCARPG DGYYEGVYFD YWGQGTLVTV  120
SS                                                                122

SEQ ID NO: 72           moltype = AA  length = 5
FEATURE                 Location/Qualifiers
source                  1..5
                        mol_type = protein
                        organism = synthetic construct
SEQUENCE: 72
NYAMS                                                             5

SEQ ID NO: 73           moltype = AA  length = 17
FEATURE                 Location/Qualifiers
source                  1..17
                        mol_type = protein
                        organism = synthetic construct
SEQUENCE: 73
AISGSGGSTY YADSVKG                                                17
```

```
SEQ ID NO: 74          moltype = AA  length = 13
FEATURE                Location/Qualifiers
source                 1..13
                       mol_type = protein
                       organism = synthetic construct
SEQUENCE: 74
PGDGYYEGVY FDY                                                      13

SEQ ID NO: 75          moltype = AA  length = 107
FEATURE                Location/Qualifiers
source                 1..107
                       mol_type = protein
                       organism = synthetic construct
SEQUENCE: 75
DIQMTQSPSS LSASVGDRVT ITCRASQSIS SYLNWYQQKP GKAPKLLIYA ASSLQSGVPS  60
RFSGSGSGTD FTLTISSLQP EDFATYYCQQ AHSSPITFGG GTKVEIK                107

SEQ ID NO: 76          moltype = AA  length = 11
FEATURE                Location/Qualifiers
source                 1..11
                       mol_type = protein
                       organism = synthetic construct
SEQUENCE: 76
RASQSISSYL N                                                        11

SEQ ID NO: 77          moltype = AA  length = 7
FEATURE                Location/Qualifiers
source                 1..7
                       mol_type = protein
                       organism = synthetic construct
SEQUENCE: 77
AASSLQS                                                             7

SEQ ID NO: 78          moltype = AA  length = 9
FEATURE                Location/Qualifiers
source                 1..9
                       mol_type = protein
                       organism = synthetic construct
SEQUENCE: 78
QQAHSSPIT                                                           9

SEQ ID NO: 79          moltype = AA  length = 249
FEATURE                Location/Qualifiers
source                 1..249
                       mol_type = protein
                       organism = synthetic construct
SEQUENCE: 79
EVQLLESGGG LVQPGGSLRL SCAASGFTFS NYAMSWVRQA PGKGLEWVSA ISGSGGSTYY  60
ADSVKGRFTI SRDNSKNTLY LQMNSLRAED TAVYYCARPG DGYYEGVYFD YWGQGTLVTV  120
SSGGGGSGGG GSGGGGSGGG GSDIQMTQSP SSLSASVGDR VTITCRASQS ISSYLNWYQQ  180
KPGKAPKLLI YAASSLQSGV PSRFSGSGSG TDFTLTISSL QPEDFATYYC QQAHSSPITF  240
GGGTKVEIK                                                           249

SEQ ID NO: 80          moltype = AA  length = 249
FEATURE                Location/Qualifiers
source                 1..249
                       mol_type = protein
                       organism = synthetic construct
SEQUENCE: 80
DIQMTQSPSS LSASVGDRVT ITCRASQSIS SYLNWYQQKP GKAPKLLIYA ASSLQSGVPS  60
RFSGSGSGTD FTLTISSLQP EDFATYYCQQ AHSSPITFGG GTKVEIKGGG GSGGGGSGGG  120
GSGGGGSEVQ LLESGGGLVQ PGGSLRLSCA ASGFTFSNYA MSWVRQAPGK GLEWVSAISG  180
SGGSTYYADS VKGRFTISRD NSKNTLYLQM NSLRAEDTAV YYCARPGDGY YEGVYFDYWG  240
QGTLVTVSS                                                           249

SEQ ID NO: 81          moltype = AA  length = 124
FEATURE                Location/Qualifiers
source                 1..124
                       mol_type = protein
                       organism = synthetic construct
SEQUENCE: 81
QITLKESGPT LVKPTQTLTL TCTFSGFSLS TSGVGVGWIR QPPGKALEWL ALIYWNDEKR  60
YSPSLKSRLT ITKDTSKNQV VLTMTNMDPV DTAVYYCARE GSHDYKSSNW FDPWGQGTLV  120
TVSS                                                                124

SEQ ID NO: 82          moltype = AA  length = 7
FEATURE                Location/Qualifiers
source                 1..7
```

```
                       mol_type = protein
                       organism = synthetic construct
SEQUENCE: 82
TSGVGVG                                                            7

SEQ ID NO: 83          moltype = AA  length = 16
FEATURE                Location/Qualifiers
source                 1..16
                       mol_type = protein
                       organism = synthetic construct
SEQUENCE: 83
LIYWNDEKRY SPSLKS                                                  16

SEQ ID NO: 84          moltype = AA  length = 14
FEATURE                Location/Qualifiers
source                 1..14
                       mol_type = protein
                       organism = synthetic construct
SEQUENCE: 84
EGSHDYKSSN WFDP                                                    14

SEQ ID NO: 85          moltype = AA  length = 107
FEATURE                Location/Qualifiers
source                 1..107
                       mol_type = protein
                       organism = synthetic construct
SEQUENCE: 85
DIQMTQSPSS LSASVGDRVT ITCQASQDIA NYLNWYQQKP GKAPKLLIYD ASNLETGVPS  60
RFSGSGSGTD FTFTISSLQP EDIATYYCQQ HFNLPLTFGG GTKVEIK                107

SEQ ID NO: 86          moltype = AA  length = 11
FEATURE                Location/Qualifiers
source                 1..11
                       mol_type = protein
                       organism = synthetic construct
SEQUENCE: 86
QASQDIANYL N                                                       11

SEQ ID NO: 87          moltype = AA  length = 7
FEATURE                Location/Qualifiers
source                 1..7
                       mol_type = protein
                       organism = synthetic construct
SEQUENCE: 87
DASNLET                                                            7

SEQ ID NO: 88          moltype = AA  length = 10
FEATURE                Location/Qualifiers
source                 1..10
                       mol_type = protein
                       organism = synthetic construct
SEQUENCE: 88
QQHFNLPLTF                                                         10

SEQ ID NO: 89          moltype = AA  length = 251
FEATURE                Location/Qualifiers
source                 1..251
                       mol_type = protein
                       organism = synthetic construct
SEQUENCE: 89
QITLKESGPT LVKPTQTLTL TCTFSGFSLS TSGVGVGWIR QPPGKALEWL ALIYWNDEKR  60
YSPSLKSRLT ITKDTSKNQV VLTMTNMDPV DTAVYYCARE GSHDYKSSNW FDPWGQGTLV  120
TVSSGGGGSG GGGSGGGGSG GGGSDIQMTQ SPSSLSASVG DRVTITCQAS QDIANYLNWY  180
QQKPGKAPKL LIYDASNLET GVPSRFSGSG SGTDFTFTIS SLQPEDIATY YCQQHFNLPL  240
TFGGGTKVEI K                                                       251

SEQ ID NO: 90          moltype = AA  length = 251
FEATURE                Location/Qualifiers
source                 1..251
                       mol_type = protein
                       organism = synthetic construct
SEQUENCE: 90
DIQMTQSPSS LSASVGDRVT ITCQASQDIA NYLNWYQQKP GKAPKLLIYD ASNLETGVPS  60
RFSGSGSGTD FTFTISSLQP EDIATYYCQQ HFNLPLTFGG GTKVEIKGGG GSGGGGSGGG  120
GSGGGGSQIT LKESGPTLVK PTQTLTLTCT FSGFSLSTSG VGVGWIRQPP GKALEWLALI  180
YWNDEKRYSP SLKSRLTITK DTSKNQVVLT MTNMDPVDTA VYYCAREGSH DYKSSNWFDP  240
WGQGTLVTVS S                                                       251

SEQ ID NO: 91          moltype = AA  length = 124
```

```
FEATURE                Location/Qualifiers
source                 1..124
                       mol_type = protein
                       organism = synthetic construct
SEQUENCE: 91
EVQLVESGGG LVKPGGSLRL SCAASGFTFS SYSMNWVRQA PGKGLEWVSS ISSSSSYIYY  60
ADSVKGRFTI SRDNAKNSLY LQMNSLRAED TAVYYCARAG DTYSAADYYY MDVWGKGTTV  120
TVSS                                                               124

SEQ ID NO: 92          moltype = AA  length = 5
FEATURE                Location/Qualifiers
source                 1..5
                       mol_type = protein
                       organism = synthetic construct
SEQUENCE: 92
SYSMN                                                              5

SEQ ID NO: 93          moltype = AA  length = 17
FEATURE                Location/Qualifiers
source                 1..17
                       mol_type = protein
                       organism = synthetic construct
SEQUENCE: 93
SISSSSSYIY YADSVKG                                                 17

SEQ ID NO: 94          moltype = AA  length = 15
FEATURE                Location/Qualifiers
source                 1..15
                       mol_type = protein
                       organism = synthetic construct
SEQUENCE: 94
AGDTYSAADY YYMDV                                                   15

SEQ ID NO: 95          moltype = AA  length = 111
FEATURE                Location/Qualifiers
source                 1..111
                       mol_type = protein
                       organism = synthetic construct
SEQUENCE: 95
DIVMTQSPLS LPVTPGEPAS ISCRSSQSLL HSNGYNYLDW YLQKPGQSPQ LLIYLGSNRA  60
SGVPDRFSGS GSGTDFTLKI SRVEAEDVGV YYCMQALGLI TFGGGTKVEI K           111

SEQ ID NO: 96          moltype = AA  length = 16
FEATURE                Location/Qualifiers
source                 1..16
                       mol_type = protein
                       organism = synthetic construct
SEQUENCE: 96
RSSQSLLHSN GYNYLD                                                  16

SEQ ID NO: 97          moltype = AA  length = 7
FEATURE                Location/Qualifiers
source                 1..7
                       mol_type = protein
                       organism = synthetic construct
SEQUENCE: 97
LGSNRAS                                                            7

SEQ ID NO: 98          moltype = AA  length = 8
FEATURE                Location/Qualifiers
source                 1..8
                       mol_type = protein
                       organism = synthetic construct
SEQUENCE: 98
MQALGLIT                                                           8

SEQ ID NO: 99          moltype = AA  length = 255
FEATURE                Location/Qualifiers
source                 1..255
                       mol_type = protein
                       organism = synthetic construct
SEQUENCE: 99
EVQLVESGGG LVKPGGSLRL SCAASGFTFS SYSMNWVRQA PGKGLEWVSS ISSSSSYIYY  60
ADSVKGRFTI SRDNAKNSLY LQMNSLRAED TAVYYCARAG DTYSAADYYY MDVWGKGTTV  120
TVSSGGGGSG GGGSGGGGSG GGGSDIVMTQ SPLSLPVTPG EPASISCRSS QSLLHSNGYN  180
YLDWYLQKPG QSPQLLIYLG SNRASGVPDR FSGSGSGTDF TLKISRVEAE DVGVYYCMQA  240
LGLITFGGGT KVEIK                                                   255

SEQ ID NO: 100         moltype = AA  length = 255
```

```
FEATURE                Location/Qualifiers
source                 1..255
                       mol_type = protein
                       organism = synthetic construct
SEQUENCE: 100
DIVMTQSPLS LPVTPGEPAS ISCRSSQSLL HSNGYNYLDW YLQKPGQSPQ LLIYLGSNRA  60
SGVPDRFSGS GSGTDFTLKI SRVEAEDVGV YYCMQALGLI TFGGGTKVEI KGGGGSGGGG  120
SGGGGSGGGG SEVQLVESGG GLVKPGGSLR LSCAASGFTF SSYSMNWVRQ APGKGLEWVS  180
SISSSSSYIY YADSVKGRFT ISRDNAKNSL YLQMNSLRAE DTAVYYCARA GDTYSAADYY  240
YMDVWGKGTT VTVSS                                                   255

SEQ ID NO: 101         moltype = AA  length = 116
FEATURE                Location/Qualifiers
source                 1..116
                       mol_type = protein
                       organism = synthetic construct
SEQUENCE: 101
EVQLLESGGG LVQPGGSLRL SCAASGFTFG SEAMSWVRQA PGKERELVSA ISGSGEVTYY  60
ADSVKGRFTI SRDNSKNTLY LQMNSLRAED TAVYYCQRLV EAKRHWGQGT QVTVSS      116

SEQ ID NO: 102         moltype = AA  length = 5
FEATURE                Location/Qualifiers
source                 1..5
                       mol_type = protein
                       organism = synthetic construct
SEQUENCE: 102
SEAMS                                                              5

SEQ ID NO: 103         moltype = AA  length = 17
FEATURE                Location/Qualifiers
source                 1..17
                       mol_type = protein
                       organism = synthetic construct
SEQUENCE: 103
AISGSGEVTY YADSVKG                                                 17

SEQ ID NO: 104         moltype = AA  length = 7
FEATURE                Location/Qualifiers
source                 1..7
                       mol_type = protein
                       organism = synthetic construct
SEQUENCE: 104
LVEAKRH                                                            7

SEQ ID NO: 105         moltype = AA  length = 116
FEATURE                Location/Qualifiers
source                 1..116
                       mol_type = protein
                       organism = synthetic construct
SEQUENCE: 105
EVQLLESGGG LVQPGGSLRL SCAASGFTFE SEAMSWYRQA PGKERELVSV ITSEGSTYYA  60
DSVKGRFTIS RDNSKNTLYL QMNSLRAEDT AVYYCAHIEW ETRLNWGQGT QVTVSS      116

SEQ ID NO: 106         moltype = AA  length = 5
FEATURE                Location/Qualifiers
source                 1..5
                       mol_type = protein
                       organism = synthetic construct
SEQUENCE: 106
SEAMS                                                              5

SEQ ID NO: 107         moltype = AA  length = 16
FEATURE                Location/Qualifiers
source                 1..16
                       mol_type = protein
                       organism = synthetic construct
SEQUENCE: 107
VITSEGSTYY ADSVKG                                                  16

SEQ ID NO: 108         moltype = AA  length = 8
FEATURE                Location/Qualifiers
source                 1..8
                       mol_type = protein
                       organism = synthetic construct
SEQUENCE: 108
IEWETRLN                                                           8

SEQ ID NO: 109         moltype = AA  length = 118
FEATURE                Location/Qualifiers
```

```
source                 1..118
                       mol_type = protein
                       organism = synthetic construct
SEQUENCE: 109
EVQLLESGGG LVQPGGSLRL SCAASGFTFD EYTMHWFRQA PGKEREFVSA ISGGGSETYY  60
ADSVKGRFTI SRDNSKNTLY LQMNSLRAED TAVYYCAAGG EEAGVGYWGQ GTQVTVSS    118

SEQ ID NO: 110         moltype = AA  length = 5
FEATURE                Location/Qualifiers
source                 1..5
                       mol_type = protein
                       organism = synthetic construct
SEQUENCE: 110
EYTMH                                                              5

SEQ ID NO: 111         moltype = AA  length = 17
FEATURE                Location/Qualifiers
source                 1..17
                       mol_type = protein
                       organism = synthetic construct
SEQUENCE: 111
AISGGGSETY YADSVKG                                                 17

SEQ ID NO: 112         moltype = AA  length = 9
FEATURE                Location/Qualifiers
source                 1..9
                       mol_type = protein
                       organism = synthetic construct
SEQUENCE: 112
GGEEAGVGY                                                          9

SEQ ID NO: 113         moltype = AA  length = 120
FEATURE                Location/Qualifiers
source                 1..120
                       mol_type = protein
                       organism = synthetic construct
SEQUENCE: 113
EVQLLESGGG LVQPGGSLRL SCAASGFTFE DYAMSWFRQA PGKEREGVSA ISGKGGSTYY  60
ADSVKGRFTI SRDNSKNTLY LQMNSLRAED TAVYYCAVLD EEAGAEGGYW GQGTQVTVSS  120

SEQ ID NO: 114         moltype = AA  length = 5
FEATURE                Location/Qualifiers
source                 1..5
                       mol_type = protein
                       organism = synthetic construct
SEQUENCE: 114
DYAMS                                                              5

SEQ ID NO: 115         moltype = AA  length = 17
FEATURE                Location/Qualifiers
source                 1..17
                       mol_type = protein
                       organism = synthetic construct
SEQUENCE: 115
AISGKGGSTY YADSVKG                                                 17

SEQ ID NO: 116         moltype = AA  length = 11
FEATURE                Location/Qualifiers
source                 1..11
                       mol_type = protein
                       organism = synthetic construct
SEQUENCE: 116
LDEEAGAEGG Y                                                       11

SEQ ID NO: 117         moltype = AA  length = 120
FEATURE                Location/Qualifiers
source                 1..120
                       mol_type = protein
                       organism = synthetic construct
SEQUENCE: 117
EVQLLESGGG LVQPGGSLRL SCAASGFTFD RYAMSWFRQA PGKEREGVSA ISTSGDSTYY  60
ADSVKGRFTI SRDNSKNTLY LQMNSLRAED TAVYYCAVLD EEAGAEGGYW GQGTQVTVSS  120

SEQ ID NO: 118         moltype = AA  length = 5
FEATURE                Location/Qualifiers
source                 1..5
                       mol_type = protein
                       organism = synthetic construct
SEQUENCE: 118
```

```
RYAMS                                                            5

SEQ ID NO: 119          moltype = AA  length = 17
FEATURE                 Location/Qualifiers
source                  1..17
                        mol_type = protein
                        organism = synthetic construct
SEQUENCE: 119
AISTSGDSTY YADSVKG                                               17

SEQ ID NO: 120          moltype = AA  length = 11
FEATURE                 Location/Qualifiers
source                  1..11
                        mol_type = protein
                        organism = synthetic construct
SEQUENCE: 120
LDEEAGAEGG Y                                                     11

SEQ ID NO: 121          moltype = AA  length = 121
FEATURE                 Location/Qualifiers
source                  1..121
                        mol_type = protein
                        organism = synthetic construct
SEQUENCE: 121
EVQLLESGGG LVQPGGSLRL SCAASGFTFA SDAMSWYRQA PGKERELVSA ISGSGGSTYY  60
ADSVKGRFTI SRDNSKNTLY LQMNSLRAED TAVYYCAAHD SGEAYLAFDY WGQGTQVTVS  120
S                                                                121

SEQ ID NO: 122          moltype = AA  length = 5
FEATURE                 Location/Qualifiers
source                  1..5
                        mol_type = protein
                        organism = synthetic construct
SEQUENCE: 122
SDAMS                                                            5

SEQ ID NO: 123          moltype = AA  length = 17
FEATURE                 Location/Qualifiers
source                  1..17
                        mol_type = protein
                        organism = synthetic construct
SEQUENCE: 123
AISGSGGSTY YADSVKG                                               17

SEQ ID NO: 124          moltype = AA  length = 12
FEATURE                 Location/Qualifiers
source                  1..12
                        mol_type = protein
                        organism = synthetic construct
SEQUENCE: 124
HDSGEAYLAF DY                                                    12

SEQ ID NO: 125          moltype = AA  length = 121
FEATURE                 Location/Qualifiers
source                  1..121
                        mol_type = protein
                        organism = synthetic construct
SEQUENCE: 125
EVQLLESGGG LVQPGGSLRL SCAASGFTFD SYTMSWYRQA PGKERELVSA ISGHGDSTYY  60
ADSVKGRFTI SRDNSKNTLY LQMNSLRAED TAVYYCTRIS ITTEWLAGDY WGQGTQVTVS  120
S                                                                121

SEQ ID NO: 126          moltype = AA  length = 5
FEATURE                 Location/Qualifiers
source                  1..5
                        mol_type = protein
                        organism = synthetic construct
SEQUENCE: 126
SYTMS                                                            5

SEQ ID NO: 127          moltype = AA  length = 17
FEATURE                 Location/Qualifiers
source                  1..17
                        mol_type = protein
                        organism = synthetic construct
SEQUENCE: 127
AISGHGDSTY YADSVKG                                               17

SEQ ID NO: 128          moltype = AA  length = 12
```

```
FEATURE                Location/Qualifiers
source                 1..12
                       mol_type = protein
                       organism = synthetic construct
SEQUENCE: 128
ISITTEWLAG DY                                                        12

SEQ ID NO: 129         moltype = AA  length = 123
FEATURE                Location/Qualifiers
source                 1..123
                       mol_type = protein
                       organism = synthetic construct
SEQUENCE: 129
EVQLLESGGG LVQPGGSLRL SCAASGFTFS SYAMSWFRQA PGKEREFVSF ISGSGDSTYY  60
ADSVKGRFTI SRDNSKNTLY LQMNSLRAED TAVYYCTRWP YDFEEPSEPG VYWGQGTQVT  120
VSS                                                                123

SEQ ID NO: 130         moltype = AA  length = 5
FEATURE                Location/Qualifiers
source                 1..5
                       mol_type = protein
                       organism = synthetic construct
SEQUENCE: 130
SYAMS                                                              5

SEQ ID NO: 131         moltype = AA  length = 17
FEATURE                Location/Qualifiers
source                 1..17
                       mol_type = protein
                       organism = synthetic construct
SEQUENCE: 131
FISGSGDSTY YADSVKG                                                 17

SEQ ID NO: 132         moltype = AA  length = 14
FEATURE                Location/Qualifiers
source                 1..14
                       mol_type = protein
                       organism = synthetic construct
SEQUENCE: 132
WPYDFEEPSE PGVY                                                    14

SEQ ID NO: 133         moltype = AA  length = 123
FEATURE                Location/Qualifiers
source                 1..123
                       mol_type = protein
                       organism = synthetic construct
SEQUENCE: 133
EVQLLESGGG LVQPGGSLRL SCAASGFTFT DYDMSWYRQA PGKERELVSV IHSGGSTYYA  60
DSVKGRFTIS RDNSKNTLYL QMNSLRAEDT AVYYCAPGYY SDLSFDYYNF DYWGQGTQVT  120
VSS                                                                123

SEQ ID NO: 134         moltype = AA  length = 5
FEATURE                Location/Qualifiers
source                 1..5
                       mol_type = protein
                       organism = synthetic construct
SEQUENCE: 134
DYDMS                                                              5

SEQ ID NO: 135         moltype = AA  length = 16
FEATURE                Location/Qualifiers
source                 1..16
                       mol_type = protein
                       organism = synthetic construct
SEQUENCE: 135
VIHSGGSTYY ADSVKG                                                  16

SEQ ID NO: 136         moltype = AA  length = 15
FEATURE                Location/Qualifiers
source                 1..15
                       mol_type = protein
                       organism = synthetic construct
SEQUENCE: 136
GYYSDLSFDY YNFDY                                                   15

SEQ ID NO: 137         moltype = AA  length = 123
FEATURE                Location/Qualifiers
source                 1..123
                       mol_type = protein
```

```
                        organism = synthetic construct
SEQUENCE: 137
EVQLLESGGG LVQPGGSLRL SCAASGFTFS DYAMHWFRQA PGKERVLVSS IDSGGSTYYA  60
DSVKGRFTIS RDNSKNTLYL QMNSLRAEDT AVYYCNAGFK GDHPHPKDAF DIWGQGTQVT  120
VSS                                                               123

SEQ ID NO: 138          moltype = AA  length = 5
FEATURE                 Location/Qualifiers
source                  1..5
                        mol_type = protein
                        organism = synthetic construct
SEQUENCE: 138
DYAMH                                                             5

SEQ ID NO: 139          moltype = AA  length = 16
FEATURE                 Location/Qualifiers
source                  1..16
                        mol_type = protein
                        organism = synthetic construct
SEQUENCE: 139
SIDSGGSTYY ADSVKG                                                 16

SEQ ID NO: 140          moltype = AA  length = 15
FEATURE                 Location/Qualifiers
source                  1..15
                        mol_type = protein
                        organism = synthetic construct
SEQUENCE: 140
GFKGDHPHPK DAFDI                                                  15

SEQ ID NO: 141          moltype = AA  length = 125
FEATURE                 Location/Qualifiers
source                  1..125
                        mol_type = protein
                        organism = synthetic construct
SEQUENCE: 141
EVQLLESGGG LVQPGGSLRL SCAASGFTFS SEGMSWVRQA PGKERELVSA ISGSGDHTYY  60
ADSVRGRFTI SRDNSKNTLY LQMNSLRAED TAVYYCNALE GGPTTAIQPG GPDYWGQGTQ  120
VTVSS                                                             125

SEQ ID NO: 142          moltype = AA  length = 5
FEATURE                 Location/Qualifiers
source                  1..5
                        mol_type = protein
                        organism = synthetic construct
SEQUENCE: 142
SEGMS                                                             5

SEQ ID NO: 143          moltype = AA  length = 17
FEATURE                 Location/Qualifiers
source                  1..17
                        mol_type = protein
                        organism = synthetic construct
SEQUENCE: 143
AISGSGDHTY YADSVRG                                                17

SEQ ID NO: 144          moltype = AA  length = 16
FEATURE                 Location/Qualifiers
source                  1..16
                        mol_type = protein
                        organism = synthetic construct
SEQUENCE: 144
LEGGPTTAIQ PGGPDY                                                 16

SEQ ID NO: 145          moltype = AA  length = 119
FEATURE                 Location/Qualifiers
source                  1..119
                        mol_type = protein
                        organism = synthetic construct
SEQUENCE: 145
DVQLVQSGAE VKKPGASVKV SCKASGYTFT RYTMHWVRQA PGQGLEWIGY INPSRGYTNY  60
ADSVKGRFTI TTDKSTSTAY MELSSLRSED TATYYCARYY DDHYCLDYWG QGTTVTVSS   119

SEQ ID NO: 146          moltype = AA  length = 5
FEATURE                 Location/Qualifiers
source                  1..5
                        mol_type = protein
                        organism = synthetic construct
SEQUENCE: 146
```

```
RYTMH                                                      5

SEQ ID NO: 147          moltype = AA  length = 17
FEATURE                 Location/Qualifiers
source                  1..17
                        mol_type = protein
                        organism = synthetic construct
SEQUENCE: 147
YINPSRGYTN YADSVKG                                         17

SEQ ID NO: 148          moltype = AA  length = 10
FEATURE                 Location/Qualifiers
source                  1..10
                        mol_type = protein
                        organism = synthetic construct
SEQUENCE: 148
YYDDHYCLDY                                                 10

SEQ ID NO: 149          moltype = AA  length = 106
FEATURE                 Location/Qualifiers
source                  1..106
                        mol_type = protein
                        organism = synthetic construct
SEQUENCE: 149
DIVLTQSPAT LSLSPGERAT LSCRASQSVS YMNWYQQKPG KAPKRWIYDT SKVASGVPAR  60
FSGSGSGTDY SLTINSLEAE DAATYYCQQW SSNPLTFGGG TKVEIK                 106

SEQ ID NO: 150          moltype = AA  length = 10
FEATURE                 Location/Qualifiers
source                  1..10
                        mol_type = protein
                        organism = synthetic construct
SEQUENCE: 150
RASQSVSYMN                                                 10

SEQ ID NO: 151          moltype = AA  length = 7
FEATURE                 Location/Qualifiers
source                  1..7
                        mol_type = protein
                        organism = synthetic construct
SEQUENCE: 151
DTSKVAS                                                    7

SEQ ID NO: 152          moltype = AA  length = 9
FEATURE                 Location/Qualifiers
source                  1..9
                        mol_type = protein
                        organism = synthetic construct
SEQUENCE: 152
QQWSSNPLT                                                  9

SEQ ID NO: 153          moltype = AA  length = 241
FEATURE                 Location/Qualifiers
source                  1..241
                        mol_type = protein
                        organism = synthetic construct
SEQUENCE: 153
DVQLVQSGAE VKKPGASVKV SCKASGYTFT RYTMHWVRQA PGQGLEWIGY INPSRGYTNY  60
ADSVKGRFTI TTDKSTSTAY MELSSLRSED TATYYCARYY DDHYCLDYWG QGTTVTVSSS  120
GGGGSGGGGS GGGGSDIVLT QSPATLSLSP GERATLSCRA SQSVSYMNWY QQKPGKAPKR  180
WIYDTSKVAS GVPARFSGSG SGTDYSLTIN SLEAEDAATY YCQQWSSNPL TFGGGTKVEI  240
K                                                                  241

SEQ ID NO: 154          moltype = AA  length = 241
FEATURE                 Location/Qualifiers
source                  1..241
                        mol_type = protein
                        organism = synthetic construct
SEQUENCE: 154
DIVLTQSPAT LSLSPGERAT LSCRASQSVS YMNWYQQKPG KAPKRWIYDT SKVASGVPAR  60
FSGSGSGTDY SLTINSLEAE DAATYYCQQW SSNPLTFGGG TKVEIKSGGG GSGGGGSGGG  120
GSDVQLVQSG AEVKKPGASV KVSCKASGYT FTRYTMHWVR QAPGQGLEWI GYINPSRGYT  180
NYADSVKGRF TITTDKSTST AYMELSSLRS EDTATYYCAR YYDDHYCLDY WGQGTTVTVS  240
S                                                                  241

SEQ ID NO: 155          moltype = AA  length = 119
FEATURE                 Location/Qualifiers
source                  1..119
                        mol_type = protein
```

```
                        organism = synthetic construct
SEQUENCE: 155
DVQLVQSGAE VKKPGASVKV SCKASGYTFT RYTMHWVRQA PGQGLEWIGY INPSRGYTNY  60
ADSVKGRFTI TTDKSTSTAY MELSSLRSED TATYYCARYY DDPYCLDYWG QGTTVTVSS   119

SEQ ID NO: 156          moltype = AA  length = 5
FEATURE                 Location/Qualifiers
source                  1..5
                        mol_type = protein
                        organism = synthetic construct
SEQUENCE: 156
RYTMH                                                              5

SEQ ID NO: 157          moltype = AA  length = 17
FEATURE                 Location/Qualifiers
source                  1..17
                        mol_type = protein
                        organism = synthetic construct
SEQUENCE: 157
YINPSRGYTN YADSVKG                                                 17

SEQ ID NO: 158          moltype = AA  length = 10
FEATURE                 Location/Qualifiers
source                  1..10
                        mol_type = protein
                        organism = synthetic construct
SEQUENCE: 158
YYDDPYCLDY                                                         10

SEQ ID NO: 159          moltype = AA  length = 106
FEATURE                 Location/Qualifiers
source                  1..106
                        mol_type = protein
                        organism = synthetic construct
SEQUENCE: 159
DIVLTQSPAT LSLSPGERAT LSCRASQSVS YMNWYQQKPG KAPKRWIYDT SKVASGVPAR  60
FSGSGSGTDY SLTINSLEAE DAATYYCQQW SSNPLTFGGG TKVEIK                 106

SEQ ID NO: 160          moltype = AA  length = 10
FEATURE                 Location/Qualifiers
source                  1..10
                        mol_type = protein
                        organism = synthetic construct
SEQUENCE: 160
RASQSVSYMN                                                         10

SEQ ID NO: 161          moltype = AA  length = 7
FEATURE                 Location/Qualifiers
source                  1..7
                        mol_type = protein
                        organism = synthetic construct
SEQUENCE: 161
DTSKVAS                                                            7

SEQ ID NO: 162          moltype = AA  length = 9
FEATURE                 Location/Qualifiers
source                  1..9
                        mol_type = protein
                        organism = synthetic construct
SEQUENCE: 162
QQWSSNPLT                                                          9

SEQ ID NO: 163          moltype = AA  length = 241
FEATURE                 Location/Qualifiers
source                  1..241
                        mol_type = protein
                        organism = synthetic construct
SEQUENCE: 163
DVQLVQSGAE VKKPGASVKV SCKASGYTFT RYTMHWVRQA PGQGLEWIGY INPSRGYTNY  60
ADSVKGRFTI TTDKSTSTAY MELSSLRSED TATYYCARYY DDPYCLDYWG QGTTVTVSSS  120
GGGGSGGGGS GGGGSDIVLT QSPATLSLSP GERATLSCRA SQSVSYMNWY QQKPGKAPKR  180
WIYDTSKVAS GVPARFSGSG SGTDYSLTIN SLEAEDAATY YCQQWSSNPL TFGGGTKVEI  240
K                                                                  241

SEQ ID NO: 164          moltype = AA  length = 241
FEATURE                 Location/Qualifiers
source                  1..241
                        mol_type = protein
                        organism = synthetic construct
```

SEQUENCE: 164
DIVLTQSPAT LSLSPGERAT LSCRASQSVS YMNWYQQKPG KAPKRWIYDT SKVASGVPAR 60
FSGSGSGTDY SLTINSLEAE DAATYYCQQW SSNPLTFGGG TKVEIKSGGG GSGGGGSGGG 120
GSDVQLVQSG AEVKKPGASV KVSCKASGYT FTRYTMHWVR QAPGQGLEWI GYINPSRGYT 180
NYADSVKGRF TITTDKSTST AYMELSSLRS EDTATYYCAR YYDDPYCLDY WGQGTTVTVS 240
S 241

SEQ ID NO: 165 moltype = AA length = 120
FEATURE Location/Qualifiers
source 1..120
mol_type = protein
organism = synthetic construct
SEQUENCE: 165
DVQLVQSGAE VKKPGASVKV SCKASGYTFT RYTMHWVRQA PGQGLEWIGY INPSRGYTNY 60
ADSVKGRFTI TTDKSTSTAY MELSSLRSED TATYYCARYY NDQYCLDYWG QGTTVTVSSS 120

SEQ ID NO: 166 moltype = AA length = 5
FEATURE Location/Qualifiers
source 1..5
mol_type = protein
organism = synthetic construct
SEQUENCE: 166
RYTMH 5

SEQ ID NO: 167 moltype = AA length = 17
FEATURE Location/Qualifiers
source 1..17
mol_type = protein
organism = synthetic construct
SEQUENCE: 167
YINPSRGYTN YADSVKG 17

SEQ ID NO: 168 moltype = AA length = 10
FEATURE Location/Qualifiers
source 1..10
mol_type = protein
organism = synthetic construct
SEQUENCE: 168
YYNDQYCLDY 10

SEQ ID NO: 169 moltype = AA length = 106
FEATURE Location/Qualifiers
source 1..106
mol_type = protein
organism = synthetic construct
SEQUENCE: 169
DIVLTQSPAT LSLSPGERAT LSCRASQSVS YMNWYQQKPG KAPKRWIYDT SKVASGVPAR 60
FSGSGSGTDY SLTINSLEAE DAATYYCQQW SSNPLTFGGG TKVEIK 106

SEQ ID NO: 170 moltype = AA length = 10
FEATURE Location/Qualifiers
source 1..10
mol_type = protein
organism = synthetic construct
SEQUENCE: 170
RASQSVSYMN 10

SEQ ID NO: 171 moltype = AA length = 7
FEATURE Location/Qualifiers
source 1..7
mol_type = protein
organism = synthetic construct
SEQUENCE: 171
DTSKVAS 7

SEQ ID NO: 172 moltype = AA length = 9
FEATURE Location/Qualifiers
source 1..9
mol_type = protein
organism = synthetic construct
SEQUENCE: 172
QQWSSNPLT 9

SEQ ID NO: 173 moltype = AA length = 242
FEATURE Location/Qualifiers
source 1..242
mol_type = protein
organism = synthetic construct
SEQUENCE: 173

```
DVQLVQSGAE VKKPGASVKV SCKASGYTFT RYTMHWVRQA PGQGLEWIGY INPSRGYTNY  60
ADSVKGRFTI TTDKSTSTAY MELSSLRSED TATYYCARYY NDQYCLDYWG QGTTVTVSSS  120
SGGGGSGGGG SGGGGSDIVL TQSPATLSLS PGERATLSCR ASQSVSYMNW YQQKPGKAPK  180
RWIYDTSKVA SGVPARFSGS GSGTDYSLTI NSLEAEDAAT YYCQQWSSNP LTFGGGTKVE  240
IK                                                                 242

SEQ ID NO: 174          moltype = AA  length = 242
FEATURE                 Location/Qualifiers
source                  1..242
                        mol_type = protein
                        organism = synthetic construct
SEQUENCE: 174
DIVLTQSPAT LSLSPGERAT LSCRASQSVS YMNWYQQKPG KAPKRWIYDT SKVASGVPAR  60
FSGSGSGTDY SLTINSLEAE DAATYYCQQW SSNPLTFGGG TKVEIKSGGG GSGGGGSGGG  120
GSDVQLVQSG AEVKKPGASV KVSCKASGYT FTRYTMHWVR QAPGQGLEWI GYINPSRGYT  180
NYADSVKGRF TITTDKSTST AYMELSSLRS EDTATYYCAR YYNDQYCLDY WGQGTTVTVS  240
SS                                                                 242

SEQ ID NO: 175          moltype = AA  length = 119
FEATURE                 Location/Qualifiers
source                  1..119
                        mol_type = protein
                        organism = synthetic construct
SEQUENCE: 175
DVQLVQSGAE VKKPGASVKV SCKASGYTFT RYTMHWVRQA PGQGLEWIGY INPSRGYTNY  60
ADSVKGRFTI TTDKSTSTAY MELSSLRSED TATYYCARYY DAHNCLDYWG QGTTVTVSS   119

SEQ ID NO: 176          moltype = AA  length = 5
FEATURE                 Location/Qualifiers
source                  1..5
                        mol_type = protein
                        organism = synthetic construct
SEQUENCE: 176
RYTMH                                                              5

SEQ ID NO: 177          moltype = AA  length = 17
FEATURE                 Location/Qualifiers
source                  1..17
                        mol_type = protein
                        organism = synthetic construct
SEQUENCE: 177
YINPSRGYTN YADSVKG                                                 17

SEQ ID NO: 178          moltype = AA  length = 10
FEATURE                 Location/Qualifiers
source                  1..10
                        mol_type = protein
                        organism = synthetic construct
SEQUENCE: 178
YYDAHNCLDY                                                         10

SEQ ID NO: 179          moltype = AA  length = 106
FEATURE                 Location/Qualifiers
source                  1..106
                        mol_type = protein
                        organism = synthetic construct
SEQUENCE: 179
DIVLTQSPAT LSLSPGERAT LSCRASQSVS YMNWYQQKPG KAPKRWIYDT SKVASGVPAR  60
FSGSGSGTDY SLTINSLEAE DAATYYCQQW SSNPLTFGGG TKVEIK                 106

SEQ ID NO: 180          moltype = AA  length = 10
FEATURE                 Location/Qualifiers
source                  1..10
                        mol_type = protein
                        organism = synthetic construct
SEQUENCE: 180
RASQSVSYMN                                                         10

SEQ ID NO: 181          moltype = AA  length = 7
FEATURE                 Location/Qualifiers
source                  1..7
                        mol_type = protein
                        organism = synthetic construct
SEQUENCE: 181
DTSKVAS                                                            7

SEQ ID NO: 182          moltype = AA  length = 9
FEATURE                 Location/Qualifiers
source                  1..9
```

```
                        mol_type = protein
                        organism = synthetic construct
SEQUENCE: 182
QQWSSNPLT                                                                9

SEQ ID NO: 183          moltype = AA  length = 241
FEATURE                 Location/Qualifiers
source                  1..241
                        mol_type = protein
                        organism = synthetic construct
SEQUENCE: 183
DVQLVQSGAE VKKPGASVKV SCKASGYTFT RYTMHWVRQA PGQGLEWIGY INPSRGYTNY  60
ADSVKGRFTI TTDKSTSTAY MELSSLRSED TATYYCARYY DAHNCLDYWG QGTTVTVSSS  120
GGGGSGGGGS GGGGSDIVLT QSPATLSLSP GERATLSCRA SQSVSYMNWY QQKPGKAPKR  180
WIYDTSKVAS GVPARFSGSG SGTDYSLTIN SLEAEDAATY YCQQWSSNPL TFGGGTKVEI  240
K                                                                  241

SEQ ID NO: 184          moltype = AA  length = 241
FEATURE                 Location/Qualifiers
source                  1..241
                        mol_type = protein
                        organism = synthetic construct
SEQUENCE: 184
DIVLTQSPAT LSLSPGERAT LSCRASQSVS YMNWYQQKPG KAPKRWIYDT SKVASGVPAR  60
FSGSGSGTDY SLTINSLEAE DAATYYCQQW SSNPLTFGGG TKVEIKSGGG GSGGGGSGGG  120
GSDVQLVQSG AEVKKPGASV KVSCKASGYT FTRYTMHWVR QAPGQGLEWI GYINPSRGYT  180
NYADSVKGRF TITTDKSTST AYMELSSLRS EDTATYYCAR YYDAHNCLDY WGQGTTVTVS  240
S                                                                  241

SEQ ID NO: 185          moltype = AA  length = 119
FEATURE                 Location/Qualifiers
source                  1..119
                        mol_type = protein
                        organism = synthetic construct
SEQUENCE: 185
DVQLVQSGAE VKKPGASVKV SCKASGYTFT RYTMHWVRQA PGQGLEWIGY INPSRGYTNY  60
ADSVKGRFTI TTDKSTSTAY MELSSLRSED TATYYCARYS DDHYCLDYWG QGTTVTVSS   119

SEQ ID NO: 186          moltype = AA  length = 5
FEATURE                 Location/Qualifiers
source                  1..5
                        mol_type = protein
                        organism = synthetic construct
SEQUENCE: 186
RYTMH                                                              5

SEQ ID NO: 187          moltype = AA  length = 17
FEATURE                 Location/Qualifiers
source                  1..17
                        mol_type = protein
                        organism = synthetic construct
SEQUENCE: 187
YINPSRGYTN YADSVKG                                                 17

SEQ ID NO: 188          moltype = AA  length = 10
FEATURE                 Location/Qualifiers
source                  1..10
                        mol_type = protein
                        organism = synthetic construct
SEQUENCE: 188
YSDDHYCLDY                                                         10

SEQ ID NO: 189          moltype = AA  length = 106
FEATURE                 Location/Qualifiers
source                  1..106
                        mol_type = protein
                        organism = synthetic construct
SEQUENCE: 189
DIVLTQSPAT LSLSPGERAT LSCRASQSVS YMNWYQQKPG KAPKRWIYDT SKVASGVPAR  60
FSGSGSGTDY SLTINSLEAE DAATYYCQQW SSNPLTFGGG TKVEIK                 106

SEQ ID NO: 190          moltype = AA  length = 10
FEATURE                 Location/Qualifiers
source                  1..10
                        mol_type = protein
                        organism = synthetic construct
SEQUENCE: 190
RASQSVSYMN                                                         10
```

```
SEQ ID NO: 191          moltype = AA  length = 7
FEATURE                 Location/Qualifiers
source                  1..7
                        mol_type = protein
                        organism = synthetic construct
SEQUENCE: 191
DTSKVAS                                                            7

SEQ ID NO: 192          moltype = AA  length = 9
FEATURE                 Location/Qualifiers
source                  1..9
                        mol_type = protein
                        organism = synthetic construct
SEQUENCE: 192
QQWSSNPLT                                                          9

SEQ ID NO: 193          moltype = AA  length = 241
FEATURE                 Location/Qualifiers
source                  1..241
                        mol_type = protein
                        organism = synthetic construct
SEQUENCE: 193
DVQLVQSGAE VKKPGASVKV SCKASGYTFT RYTMHWVRQA PGQGLEWIGY INPSRGYTNY  60
ADSVKGRFTI TTDKSTSTAY MELSSLRSED TATYYCARYS DDHYCLDYWG QGTTVTVSSS  120
GGGGSGGGGS GGGGSDIVLT QSPATLSLSP GERATLSCRA SQSVSYMNWY QQKPGKAPKR  180
WIYDTSKVAS GVPARFSGSG SGTDYSLTIN SLEAEDAATY YCQQWSSNPL TFGGGTKVEI  240
K                                                                  241

SEQ ID NO: 194          moltype = AA  length = 241
FEATURE                 Location/Qualifiers
source                  1..241
                        mol_type = protein
                        organism = synthetic construct
SEQUENCE: 194
DIVLTQSPAT LSLSPGERAT LSCRASQSVS YMNWYQQKPG KAPKRWIYDT SKVASGVPAR  60
FSGSGSGTDY SLTINSLEAE DAATYYCQQW SSNPLTFGGG TKVEIKSGGG GSGGGGSGGG  120
GSDVQLVQSG AEVKKPGASV KVSCKASGYT FTRYTMHWVR QAPGQGLEWI GYINPSRGYT  180
NYADSVKGRF TITTDKSTST AYMELSSLRS EDTATYYCAR YSDDHYCLDY WGQGTTVTVS  240
S                                                                  241

SEQ ID NO: 195          moltype = AA  length = 119
FEATURE                 Location/Qualifiers
source                  1..119
                        mol_type = protein
                        organism = synthetic construct
SEQUENCE: 195
DVQLVQSGAE VKKPGASVKV SCKASGYTFT RYTMHWVRQA PGQGLEWIGY INPSRGYTNY  60
ADSVKGRFTI TTDKSTSTAY MELSSLRSED TATYYCARYS DDRYCLDYWG QGTTVTVSS   119

SEQ ID NO: 196          moltype = AA  length = 5
FEATURE                 Location/Qualifiers
source                  1..5
                        mol_type = protein
                        organism = synthetic construct
SEQUENCE: 196
RYTMH                                                              5

SEQ ID NO: 197          moltype = AA  length = 17
FEATURE                 Location/Qualifiers
source                  1..17
                        mol_type = protein
                        organism = synthetic construct
SEQUENCE: 197
YINPSRGYTN YADSVKG                                                 17

SEQ ID NO: 198          moltype = AA  length = 10
FEATURE                 Location/Qualifiers
source                  1..10
                        mol_type = protein
                        organism = synthetic construct
SEQUENCE: 198
YSDDRYCLDY                                                         10

SEQ ID NO: 199          moltype = AA  length = 106
FEATURE                 Location/Qualifiers
source                  1..106
                        mol_type = protein
                        organism = synthetic construct
SEQUENCE: 199
```

```
DIVLTQSPAT LSLSPGERAT LSCRASQSVS YMNWYQQKPG KAPKRWIYDT SKVASGVPAR  60
FSGSGSGTDY SLTINSLEAE DAATYYCQQW SSNPLTFGGG TKVEIK                 106

SEQ ID NO: 200          moltype = AA  length = 10
FEATURE                 Location/Qualifiers
source                  1..10
                        mol_type = protein
                        organism = synthetic construct
SEQUENCE: 200
RASQSVSYMN                                                         10

SEQ ID NO: 201          moltype = AA  length = 7
FEATURE                 Location/Qualifiers
source                  1..7
                        mol_type = protein
                        organism = synthetic construct
SEQUENCE: 201
DTSKVAS                                                            7

SEQ ID NO: 202          moltype = AA  length = 9
FEATURE                 Location/Qualifiers
source                  1..9
                        mol_type = protein
                        organism = synthetic construct
SEQUENCE: 202
QQWSSNPLT                                                          9

SEQ ID NO: 203          moltype = AA  length = 241
FEATURE                 Location/Qualifiers
source                  1..241
                        mol_type = protein
                        organism = synthetic construct
SEQUENCE: 203
DVQLVQSGAE VKKPGASVKV SCKASGYTFT RYTMHWVRQA PGQGLEWIGY INPSRGYTNY  60
ADSVKGRFTI TTDKSTSTAY MELSSLRSED TATYYCARYS DDRYCLDYWG QGTTVTVSSS  120
GGGGSGGGGS GGGGSDIVLT QSPATLSLSP GERATLSCRA SQSVSYMNWY QQKPGKAPKR  180
WIYDTSKVAS GVPARFSGSG SGTDYSLTIN SLEAEDAATY YCQQWSSNPL TFGGGTKVEI  240
K                                                                  241

SEQ ID NO: 204          moltype = AA  length = 241
FEATURE                 Location/Qualifiers
source                  1..241
                        mol_type = protein
                        organism = synthetic construct
SEQUENCE: 204
DIVLTQSPAT LSLSPGERAT LSCRASQSVS YMNWYQQKPG KAPKRWIYDT SKVASGVPAR  60
FSGSGSGTDY SLTINSLEAE DAATYYCQQW SSNPLTFGGG TKVEIKSGGG GSGGGGSGGG  120
GSDVQLVQSG AEVKKPGASV KVSCKASGYT FTRYTMHWVR QAPGQGLEWI GYINPSRGYT  180
NYADSVKGRF TITTDKSTST AYMELSSLRS EDTATYYCAR YSDDRYCLDY WGQGTTVTVS  240
S                                                                  241

SEQ ID NO: 205          moltype = AA  length = 120
FEATURE                 Location/Qualifiers
source                  1..120
                        mol_type = protein
                        organism = synthetic construct
SEQUENCE: 205
DVQLVQSGAE VKKPGASVKV SCKASGYTFT RYTMHWVRQA PGQGLEWIGY INPSRGYTNY  60
ADSVKGRFTI TTDKSTSTAY MELSSLRSED TATYYCARYY DDNYCLDYWG QGTTVTVSSS  120

SEQ ID NO: 206          moltype = AA  length = 5
FEATURE                 Location/Qualifiers
source                  1..5
                        mol_type = protein
                        organism = synthetic construct
SEQUENCE: 206
RYTMH                                                              5

SEQ ID NO: 207          moltype = AA  length = 17
FEATURE                 Location/Qualifiers
source                  1..17
                        mol_type = protein
                        organism = synthetic construct
SEQUENCE: 207
YINPSRGYTN YADSVKG                                                 17

SEQ ID NO: 208          moltype = AA  length = 10
FEATURE                 Location/Qualifiers
source                  1..10
```

```
                      mol_type = protein
                      organism = synthetic construct
SEQUENCE: 208
YYDDNYCLDY                                                        10

SEQ ID NO: 209        moltype = AA  length = 106
FEATURE               Location/Qualifiers
source                1..106
                      mol_type = protein
                      organism = synthetic construct
SEQUENCE: 209
DIVLTQSPAT LSLSPGERAT LSCRASQSVS YMNWYQQKPG KAPKRWIYDT SKVASGVPAR  60
FSGSGSGTDY SLTINSLEAE DAATYYCQQW SSNPLTFGGG TKVEIK                106

SEQ ID NO: 210        moltype = AA  length = 10
FEATURE               Location/Qualifiers
source                1..10
                      mol_type = protein
                      organism = synthetic construct
SEQUENCE: 210
RASQSVSYMN                                                        10

SEQ ID NO: 211        moltype = AA  length = 7
FEATURE               Location/Qualifiers
source                1..7
                      mol_type = protein
                      organism = synthetic construct
SEQUENCE: 211
DTSKVAS                                                           7

SEQ ID NO: 212        moltype = AA  length = 9
FEATURE               Location/Qualifiers
source                1..9
                      mol_type = protein
                      organism = synthetic construct
SEQUENCE: 212
QQWSSNPLT                                                         9

SEQ ID NO: 213        moltype = AA  length = 242
FEATURE               Location/Qualifiers
source                1..242
                      mol_type = protein
                      organism = synthetic construct
SEQUENCE: 213
DVQLVQSGAE VKKPGASVKV SCKASGYTFT RYTMHWVRQA PGQGLEWIGY INPSRGYTNY  60
ADSVKGRFTI TTDKSTSTAY MELSSLRSED TATYYCARYY DDNYCLDYWG QGTTVTVSSS  120
SGGGGSGGGG SGGGGSDIVL TQSPATLSLS PGERATLSCR ASQSVSYMNW YQQKPGKAPK  180
RWIYDTSKVA SGVPARFSGS GSGTDYSLTI NSLEAEDAAT YYCQQWSSNP LTFGGGTKVE  240
IK                                                                242

SEQ ID NO: 214        moltype = AA  length = 242
FEATURE               Location/Qualifiers
source                1..242
                      mol_type = protein
                      organism = synthetic construct
SEQUENCE: 214
DIVLTQSPAT LSLSPGERAT LSCRASQSVS YMNWYQQKPG KAPKRWIYDT SKVASGVPAR  60
FSGSGSGTDY SLTINSLEAE DAATYYCQQW SSNPLTFGGG TKVEIKSGGG GSGGGGSGGG  120
GSDVQLVQSG AEVKKPGASV KVSCKASGYT FTRYTMHWVR QAPGQGLEWI GYINPSRGYT  180
NYADSVKGRF TITTDKSTST AYMELSSLRS EDTATYYCAR YYDDNYCLDY WGQGTTVTVS  240
SS                                                                242

SEQ ID NO: 215        moltype = AA  length = 119
FEATURE               Location/Qualifiers
source                1..119
                      mol_type = protein
                      organism = synthetic construct
SEQUENCE: 215
DVQLVQSGAE VKKPGASVKV SCKASGYTFT RYTMHWVRQA PGQGLEWIGY INPSRGYTNY  60
ADSVKGRFTI TTDKSTSTAY MELSSLRSED TATYYCARYY DDQYCLDYWG QGTTVTVSS   119

SEQ ID NO: 216        moltype = AA  length = 5
FEATURE               Location/Qualifiers
source                1..5
                      mol_type = protein
                      organism = synthetic construct
SEQUENCE: 216
RYTMH                                                             5
```

```
SEQ ID NO: 217          moltype = AA  length = 17
FEATURE                 Location/Qualifiers
source                  1..17
                        mol_type = protein
                        organism = synthetic construct
SEQUENCE: 217
YINPSRGYTN YADSVKG                                                17

SEQ ID NO: 218          moltype = AA  length = 10
FEATURE                 Location/Qualifiers
source                  1..10
                        mol_type = protein
                        organism = synthetic construct
SEQUENCE: 218
YYDDQYCLDY                                                        10

SEQ ID NO: 219          moltype = AA  length = 106
FEATURE                 Location/Qualifiers
source                  1..106
                        mol_type = protein
                        organism = synthetic construct
SEQUENCE: 219
DIVLTQSPAT LSLSPGERAT LSCRASQSVS YMNWYQQKPG KAPKRWIYDT SKVASGVPAR  60
FSGSGSGTDY SLTINSLEAE DAATYYCQQW SSNPLTFGGG TKVEIK                106

SEQ ID NO: 220          moltype = AA  length = 10
FEATURE                 Location/Qualifiers
source                  1..10
                        mol_type = protein
                        organism = synthetic construct
SEQUENCE: 220
RASQSVSYMN                                                        10

SEQ ID NO: 221          moltype = AA  length = 7
FEATURE                 Location/Qualifiers
source                  1..7
                        mol_type = protein
                        organism = synthetic construct
SEQUENCE: 221
DTSKVAS                                                           7

SEQ ID NO: 222          moltype = AA  length = 9
FEATURE                 Location/Qualifiers
source                  1..9
                        mol_type = protein
                        organism = synthetic construct
SEQUENCE: 222
QQWSSNPLT                                                         9

SEQ ID NO: 223          moltype = AA  length = 241
FEATURE                 Location/Qualifiers
source                  1..241
                        mol_type = protein
                        organism = synthetic construct
SEQUENCE: 223
DVQLVQSGAE VKKPGASVKV SCKASGYTFT RYTMHWVRQA PGQGLEWIGY INPSRGYTNY  60
ADSVKGRFTI TTDKSTSTAY MELSSLRSED TATYYCARYY DDQYCLDYWG QGTTVTVSSS  120
GGGGSGGGGS GGGGSDIVLT QSPATLSLSP GERATLSCRA SQSVSYMNWY QQKPGKAPKR  180
WIYDTSKVAS GVPARFSGSG SGTDYSLTIN SLEAEDAATY YCQQWSSNPL TFGGGTKVEI  240
K                                                                 241

SEQ ID NO: 224          moltype = AA  length = 241
FEATURE                 Location/Qualifiers
source                  1..241
                        mol_type = protein
                        organism = synthetic construct
SEQUENCE: 224
DIVLTQSPAT LSLSPGERAT LSCRASQSVS YMNWYQQKPG KAPKRWIYDT SKVASGVPAR  60
FSGSGSGTDY SLTINSLEAE DAATYYCQQW SSNPLTFGGG TKVEIKSGGG GSGGGGSGGG  120
GSDVQLVQSG AEVKKPGASV KVSCKASGYT FTRYTMHWVR QAPGQGLEWI GYINPSRGYT  180
NYADSVKGRF TITTDKSTST AYMELSSLRS EDTATYYCAR YYDDQYCLDY WGQGTTVTVS  240
S                                                                 241

SEQ ID NO: 225          moltype = AA  length = 45
FEATURE                 Location/Qualifiers
source                  1..45
                        mol_type = protein
                        organism = synthetic construct
SEQUENCE: 225
```

TTTPAPRPPT PAPTIASQPL SLRPEACRPA AGGAVHTRGL DFACD 45

SEQ ID NO: 226 moltype = AA length = 39
FEATURE Location/Qualifiers
source 1..39
mol_type = protein
organism = synthetic construct
SEQUENCE: 226
IEVMYPPPYL DNEKSNGTII HVKGKHLCPS PLFPGPSKP 39

SEQ ID NO: 227 moltype = AA length = 22
FEATURE Location/Qualifiers
source 1..22
mol_type = protein
organism = synthetic construct
SEQUENCE: 227
SGQVLLESNI KVLPTWSTPV QP 22

SEQ ID NO: 228 moltype = AA length = 12
FEATURE Location/Qualifiers
source 1..12
mol_type = protein
organism = synthetic construct
SEQUENCE: 228
ESKYGPPCPP CP 12

SEQ ID NO: 229 moltype = AA length = 228
FEATURE Location/Qualifiers
source 1..228
mol_type = protein
organism = synthetic construct
SEQUENCE: 229
ESKYGPPCPP CPAPPVAGPS VFLFPPKPKD TLMISRTPEV TCVVVDVSQE DPEVQFNWYV 60
DGVEVHNAKT KPREEQFQST YRVVSVLTVL HQDWLNGKEY KCKVSNKGLP SSIEKTISKA 120
KGQPREPQVY TLPPSQEEMT KNQVSLTCLV KGFYPSDIAV EWESNGQPEN NYKTTPPVLD 180
SDGSFFLYSR LTVDKSRWQE GNVFSCSVMH EALHNHYTQK SLSLSLGK 228

SEQ ID NO: 230 moltype = AA length = 16
FEATURE Location/Qualifiers
source 1..16
mol_type = protein
organism = synthetic construct
SEQUENCE: 230
LEPKSCDKTH TCPPCP 16

SEQ ID NO: 231 moltype = AA length = 24
FEATURE Location/Qualifiers
source 1..24
mol_type = protein
organism = synthetic construct
SEQUENCE: 231
IYIWAPLAGT CGVLLLSLVI TLYC 24

SEQ ID NO: 232 moltype = AA length = 27
FEATURE Location/Qualifiers
source 1..27
mol_type = protein
organism = synthetic construct
SEQUENCE: 232
IISFFLALTS TALLFLLFFL TLRFSVV 27

SEQ ID NO: 233 moltype = AA length = 27
FEATURE Location/Qualifiers
source 1..27
mol_type = protein
organism = synthetic construct
SEQUENCE: 233
FWVLVVVGGV LACYSLLVTV AFIIFWV 27

SEQ ID NO: 234 moltype = AA length = 21
FEATURE Location/Qualifiers
source 1..21
mol_type = protein
organism = synthetic construct
SEQUENCE: 234
VAAILGLGLV LGLLGPLAIL L 21

SEQ ID NO: 235 moltype = AA length = 23
FEATURE Location/Qualifiers

```
source                  1..23
                        mol_type = protein
                        organism = synthetic construct
SEQUENCE: 235
WLPIGCAAFV VVCILGCILI CWL                                          23

SEQ ID NO: 236          moltype = AA  length = 26
FEATURE                 Location/Qualifiers
source                  1..26
                        mol_type = protein
                        organism = synthetic construct
SEQUENCE: 236
VMSVATIVIV DICITGGLLL LVYYWS                                       26

SEQ ID NO: 237          moltype = AA  length = 22
FEATURE                 Location/Qualifiers
source                  1..22
                        mol_type = protein
                        organism = synthetic construct
SEQUENCE: 237
MALIVLGGVA GLLLFIGLGI FF                                           22

SEQ ID NO: 238          moltype = AA  length = 112
FEATURE                 Location/Qualifiers
source                  1..112
                        mol_type = protein
                        organism = synthetic construct
SEQUENCE: 238
RVKFSRSADA PAYQQGQNQL YNELNLGRRE EYDVLDKRRG RDPEMGGKPR RKNPQEGLYN  60
ELQKDKMAEA YSEIGMKGER RRGKGHDGLY QGLSTATKDT YDALHMQALP PR          112

SEQ ID NO: 239          moltype = AA  length = 42
FEATURE                 Location/Qualifiers
source                  1..42
                        mol_type = protein
                        organism = synthetic construct
SEQUENCE: 239
KRGRKKLLYI FKQPFMRPVQ TTQEEDGCSC RFPEEEEGGC EL                     42

SEQ ID NO: 240          moltype = AA  length = 41
FEATURE                 Location/Qualifiers
source                  1..41
                        mol_type = protein
                        organism = synthetic construct
SEQUENCE: 240
RSKRSRLLHS DYMNMTPRRP GPTRKHYQPY APPRDFAAYR S                      41

SEQ ID NO: 241          moltype = AA  length = 42
FEATURE                 Location/Qualifiers
source                  1..42
                        mol_type = protein
                        organism = synthetic construct
SEQUENCE: 241
ALYLLRRDQR LPPDAHKPPG GGSFRTPIQE EQADAHSTLA KI                     42

SEQ ID NO: 242          moltype = AA  length = 35
FEATURE                 Location/Qualifiers
source                  1..35
                        mol_type = protein
                        organism = synthetic construct
SEQUENCE: 242
TKKKYSSSVH DPNGEYMFMR AVNTAKKSRL TDVTL                             35

SEQ ID NO: 243          moltype = AA  length = 48
FEATURE                 Location/Qualifiers
source                  1..48
                        mol_type = protein
                        organism = synthetic construct
SEQUENCE: 243
QRRKYRSNKG ESPVEPAEPC HYSCPREEEG STIPIQEDYR KPEPACSP               48

SEQ ID NO: 244          moltype = AA  length = 174
FEATURE                 Location/Qualifiers
source                  1..174
                        mol_type = protein
                        organism = synthetic construct
SEQUENCE: 244
KKKPLCLQRE AKVPHLPADK ARGTQGPEQQ HLLITAPSSS SSSLESSASA LDRRAPTRNQ  60
PQAPGVEASG AGEARASTGS SDSSPGGHGT QVNVTCIVNV CSSSDHSSQC SSQASSTMGD  120
```

```
TDSSPSESPK DEQVPFSKEE CAFRSQLETP ETLLGSTEEK PLPLGVPDAG MKPS        174

SEQ ID NO: 245         moltype = AA  length = 21
FEATURE                Location/Qualifiers
source                 1..21
                       mol_type = protein
                       organism = synthetic construct
SEQUENCE: 245
MALPVTALLL PLALLLHAAR P                                            21

SEQ ID NO: 246         moltype = AA  length = 20
FEATURE                Location/Qualifiers
source                 1..20
                       mol_type = protein
                       organism = synthetic construct
SEQUENCE: 246
METDTLLLWV LLLWVPGSTG                                              20

SEQ ID NO: 247         moltype = AA  length = 22
FEATURE                Location/Qualifiers
source                 1..22
                       mol_type = protein
                       organism = synthetic construct
SEQUENCE: 247
MDMRVPAQLL GLLLLWLRGA RC                                           22

SEQ ID NO: 248         moltype = AA  length = 16
FEATURE                Location/Qualifiers
source                 1..16
                       mol_type = protein
                       organism = synthetic construct
SEQUENCE: 248
MPLLLLLPLL WAGALA                                                  16

SEQ ID NO: 249         moltype = AA  length = 23
FEATURE                Location/Qualifiers
source                 1..23
                       mol_type = protein
                       organism = synthetic construct
SEQUENCE: 249
MDAMKRGLCC VLLLCGAVFV SPS                                          23

SEQ ID NO: 250         moltype = AA  length = 17
FEATURE                Location/Qualifiers
source                 1..17
                       mol_type = protein
                       organism = synthetic construct
SEQUENCE: 250
MLLLLLLLGL RLQLSLG                                                 17

SEQ ID NO: 251         moltype = AA  length = 17
FEATURE                Location/Qualifiers
source                 1..17
                       mol_type = protein
                       organism = synthetic construct
SEQUENCE: 251
MWLQSLLLLG TVACSIS                                                 17

SEQ ID NO: 252         moltype = AA  length = 22
FEATURE                Location/Qualifiers
source                 1..22
                       mol_type = protein
                       organism = synthetic construct
SEQUENCE: 252
MLLLVTSLLL CELPHPAFLL IP                                           22

SEQ ID NO: 253         moltype = AA  length = 20
FEATURE                Location/Qualifiers
source                 1..20
                       mol_type = protein
                       organism = synthetic construct
SEQUENCE: 253
MSRSVALAVL ALLSLSGLEA                                              20

SEQ ID NO: 254         moltype = AA  length = 16
FEATURE                Location/Qualifiers
source                 1..16
                       mol_type = protein
                       organism = synthetic construct
```

```
SEQUENCE: 254
MLLLLLLLLL LALALA                                                  16

SEQ ID NO: 255         moltype = AA  length = 468
FEATURE                Location/Qualifiers
source                 1..468
                       mol_type = protein
                       organism = synthetic construct
SEQUENCE: 255
QITLKESGPT LVKPTQTLTL TCTFSGFSLS TSGVGVGWIR QPPGKALEWL ALIYWNDEKR  60
YSPSLKSRLT ITKDTSKNQV VLTMTNMDPV DTAVYYCARD EYGGFDIWGQ GTMVTVSSGG  120
GGSGGGGSGG GGSGGGGSEI VLTQSPATLS LSPGERATLS CRASQSVSSY LAWYQQKPGQ  180
APRLLIYDAS NRATGIPARF SGSGSGTDFT LTISSLEPED FAVYYCQQRV VYPITFGGGT  240
KVEIKTTTPA PRPPTPAPTI ASQPLSLRPE ACRPAAGGAV HTRGLDFACD IYIWAPLAGT  300
CGVLLLSLVI TLYCKRGRKK LLYIFKQPFM RPVQTTQEED GCSCRFPEEE EGGCELRVKF  360
SRSADAPAYQ QGQNQLYNEL NLGRREEYDV LDKRRGRDPE MGGKPRRKNP QEGLYNELQK  420
DKMAEAYSEI GMKGERRRGK GHDGLYQGLS TATKDTYDAL HMQALPPR            468

SEQ ID NO: 256         moltype = AA  length = 468
FEATURE                Location/Qualifiers
source                 1..468
                       mol_type = protein
                       organism = synthetic construct
SEQUENCE: 256
EIVLTQSPAT LSLSPGERAT LSCRASQSVS SYLAWYQQKP GQAPRLLIYD ASNRATGIPA  60
RFSGSGSGTD FTLTISSLEP EDFAVYYCQQ RVVYPITFGG GTKVEIKGGG GSGGGGSGGG  120
GSGGGGSQIT LKESGPTLVK PTQTLTLTCT FSGFSLSTSG VGVGWIRQPP GKALEWLALI  180
YWNDEKRYSP SLKSRLTITK DTSKNQVVLT MTNMDPVDTA VYYCARDEYG GFDIWGQGTM  240
VTVSSTTTPA PRPPTPAPTI ASQPLSLRPE ACRPAAGGAV HTRGLDFACD IYIWAPLAGT  300
CGVLLLSLVI TLYCKRGRKK LLYIFKQPFM RPVQTTQEED GCSCRFPEEE EGGCELRVKF  360
SRSADAPAYQ QGQNQLYNEL NLGRREEYDV LDKRRGRDPE MGGKPRRKNP QEGLYNELQK  420
DKMAEAYSEI GMKGERRRGK GHDGLYQGLS TATKDTYDAL HMQALPPR            468

SEQ ID NO: 257         moltype = AA  length = 468
FEATURE                Location/Qualifiers
source                 1..468
                       mol_type = protein
                       organism = synthetic construct
SEQUENCE: 257
QITLKESGPT LVKPTQTLTL TCTFSGFSLS TSGVGVGWIR QPPGKALEWL ALIYWNDDKR  60
YSPSLKSRLT ITKDTSKNQV VLTMTNMDPV DTAVYYCARD EYGGFDIWGQ GTMVTVSSGG  120
GGSGGGGSGG GGSGGGGSEI VLTQSPATLS LSPGERATLS CRASQSVSSY LAWYQQKPGQ  180
APRLLIYDAS NRATGIPARF SGSGSGTDFT LTISSLEPED FAVYYCQQRF DYPITFGGGT  240
KVEIKTTTPA PRPPTPAPTI ASQPLSLRPE ACRPAAGGAV HTRGLDFACD IYIWAPLAGT  300
CGVLLLSLVI TLYCKRGRKK LLYIFKQPFM RPVQTTQEED GCSCRFPEEE EGGCELRVKF  360
SRSADAPAYQ QGQNQLYNEL NLGRREEYDV LDKRRGRDPE MGGKPRRKNP QEGLYNELQK  420
DKMAEAYSEI GMKGERRRGK GHDGLYQGLS TATKDTYDAL HMQALPPR            468

SEQ ID NO: 258         moltype = AA  length = 468
FEATURE                Location/Qualifiers
source                 1..468
                       mol_type = protein
                       organism = synthetic construct
SEQUENCE: 258
EIVLTQSPAT LSLSPGERAT LSCRASQSVS SYLAWYQQKP GQAPRLLIYD ASNRATGIPA  60
RFSGSGSGTD FTLTISSLEP EDFAVYYCQQ RFDYPITFGG GTKVEIKGGG GSGGGGSGGG  120
GSGGGGSQIT LKESGPTLVK PTQTLTLTCT FSGFSLSTSG VGVGWIRQPP GKALEWLALI  180
YWNDDKRYSP SLKSRLTITK DTSKNQVVLT MTNMDPVDTA VYYCARDEYG GFDIWGQGTM  240
VTVSSTTTPA PRPPTPAPTI ASQPLSLRPE ACRPAAGGAV HTRGLDFACD IYIWAPLAGT  300
CGVLLLSLVI TLYCKRGRKK LLYIFKQPFM RPVQTTQEED GCSCRFPEEE EGGCELRVKF  360
SRSADAPAYQ QGQNQLYNEL NLGRREEYDV LDKRRGRDPE MGGKPRRKNP QEGLYNELQK  420
DKMAEAYSEI GMKGERRRGK GHDGLYQGLS TATKDTYDAL HMQALPPR            468

SEQ ID NO: 259         moltype = AA  length = 466
FEATURE                Location/Qualifiers
source                 1..466
                       mol_type = protein
                       organism = synthetic construct
SEQUENCE: 259
QVQLVESGGG VVQPGRSLRL SCAASGFTFS SYGMHWVRQA PGKGLEWVAV ISYEGSNKYY  60
ADSVKGRFTI SRDNSKNTLY LQMNSLRAED TAVYYCAREL GDGMDVWGQG TTVTVSSGGG  120
GSGGGGSGGG GSGGGGSEIV LTQSPATLSL SPGERATLSC RASQSVSSYL AWFQQKPGQA  180
PRLLIYDASN RATGIPARFS GSGSGTDFTL TISSLEPEDF AVYYCQQRVD LWTFGGGTKV  240
EIKTTTPAPR PPTPAPTIAS QPLSLRPEAC RPAAGGAVHT RGLDFACDIY IWAPLAGTCG  300
VLLLSLVITL YCKRGRKKLL YIFKQPFMRP VQTTQEEDGC SCRFPEEEEG GCELRVKFSR  360
SADAPAYQQG QNQLYNELNL GRREEYDVLD KRRGRDPEMG GKPRRKNPQE GLYNELQKDK  420
MAEAYSEIGM KGERRRGKGH DGLYQGLSTA TKDTYDALHM QALPPR               466

SEQ ID NO: 260         moltype = AA  length = 466
```

```
FEATURE                Location/Qualifiers
source                 1..466
                       mol_type = protein
                       organism = synthetic construct
SEQUENCE: 260
EIVLTQSPAT LSLSPGERAT LSCRASQSVS SYLAWFQQKP GQAPRLLIYD ASNRATGIPA  60
RFSGSGSGTD FTLTISSLEP EDFAVYYCQQ RVDLWTFGGG TKVEIKGGGG SGGGGSGGGG  120
SGGGGSQVQL VESGGGVVQP GRSLRLSCAA SGFTFSSYGM HWVRQAPGKG LEWVAVISYE  180
GSNKYYADSV KGRFTISRDN SKNTLYLQMN SLRAEDTAVY YCARELGDGM DVWGQGTTVT  240
VSSTTTPAPR PPTPAPTIAS QPLSLRPEAC RPAAGGAVHT RGLDFACDIY IWAPLAGTCG  300
VLLLSLVITL YCKRGRKKLL YIFKQPFMRP VQTTQEEDGC SCRFPEEEEG GCELRVKFSR  360
SADAPAYQQG QNQLYNELNL GRREEYDVLD KRRGRDPEMG GKPRRKNPQE GLYNELQKDK  420
MAEAYSEIGM KGERRRGKGH DGLYQGLSTA TKDTYDALHM QALPPR                466

SEQ ID NO: 261         moltype = AA  length = 468
FEATURE                Location/Qualifiers
source                 1..468
                       mol_type = protein
                       organism = synthetic construct
SEQUENCE: 261
EVQLVESGGG LVKPGGSLRL SCAASGFTFS DYYMSWIRQA PGKGLEWVSY ISSSGSTIYY  60
ADSVKGRFTI SRDNAKNSLY LQMNSLRAED TAVYYCARDQ GNYGVDVWGQ GTTVTVSSGG  120
GGSGGGGSGG GGSGGGGSDI QMTQSPSTLS ASVGDRVTIT CRASQSISSW LAWYQQKPGK  180
APKLLIYDAS SLESGVPSRF SGSGSGTEFT LTISSLQPDD FATYYCQQVS SLPPTFGGGT  240
KVEIKTTTPA PRPPTPAPTI ASQPLSLRPE ACRPAAGGAV HTRGLDFACD IYIWAPLAGT  300
CGVLLLSLVI TLYCKRGRKK LLYIFKQPFM RPVQTTQEED GCSCRFPEEE EGGCELRVKF  360
SRSADAPAYQ QGQNQLYNEL NLGRREEYDV LDKRRGRDPE MGGKPRRKNP QEGLYNELQK  420
DKMAEAYSEI GMKGERRRGK GHDGLYQGLS TATKDTYDAL HMQALPPR              468

SEQ ID NO: 262         moltype = AA  length = 468
FEATURE                Location/Qualifiers
source                 1..468
                       mol_type = protein
                       organism = synthetic construct
SEQUENCE: 262
DIQMTQSPST LSASVGDRVT ITCRASQSIS SWLAWYQQKP GKAPKLLIYD ASSLESGVPS  60
RFSGSGSGTE FTLTISSLQP DDFATYYCQQ VSSLPPTFGG GTKVEIKGGG GSGGGGSGGG  120
GSGGGGSEVQ LVESGGGLVK PGGSLRLSCA ASGFTFSDYY MSWIRQAPGK GLEWVSYISS  180
SGSTIYYADS VKGRFTISRD NAKNSLYLQM NSLRAEDTAV YYCARDQGNY GVDVWGQGTT  240
VTVSSTTTPA PRPPTPAPTI ASQPLSLRPE ACRPAAGGAV HTRGLDFACD IYIWAPLAGT  300
CGVLLLSLVI TLYCKRGRKK LLYIFKQPFM RPVQTTQEED GCSCRFPEEE EGGCELRVKF  360
SRSADAPAYQ QGQNQLYNEL NLGRREEYDV LDKRRGRDPE MGGKPRRKNP QEGLYNELQK  420
DKMAEAYSEI GMKGERRRGK GHDGLYQGLS TATKDTYDAL HMQALPPR              468

SEQ ID NO: 263         moltype = AA  length = 468
FEATURE                Location/Qualifiers
source                 1..468
                       mol_type = protein
                       organism = synthetic construct
SEQUENCE: 263
QVQLVESGGG LVKPGGSLRL SCAASGFTFS DYYMSWIRQA PGKGLEWVSY ISSSGSTIYY  60
ADSVKGRFTI SRDNAKNSLY LQMNSLRAED TAVYYCARDQ GNYGVDVWGQ GTTVTVSSGG  120
GGSGGGGSGG GGSGGGGSDI QMTQSPSTLS ASVGDRVTIT CRASQSISSW LAWYQQKPGK  180
APKLLIYEAS SLESGVPSRF SGSGSGTEFT LTISSLQPDD FATYYCQQSD SHPITFGGGT  240
KVEIKTTTPA PRPPTPAPTI ASQPLSLRPE ACRPAAGGAV HTRGLDFACD IYIWAPLAGT  300
CGVLLLSLVI TLYCKRGRKK LLYIFKQPFM RPVQTTQEED GCSCRFPEEE EGGCELRVKF  360
SRSADAPAYQ QGQNQLYNEL NLGRREEYDV LDKRRGRDPE MGGKPRRKNP QEGLYNELQK  420
DKMAEAYSEI GMKGERRRGK GHDGLYQGLS TATKDTYDAL HMQALPPR              468

SEQ ID NO: 264         moltype = AA  length = 468
FEATURE                Location/Qualifiers
source                 1..468
                       mol_type = protein
                       organism = synthetic construct
SEQUENCE: 264
DIQMTQSPST LSASVGDRVT ITCRASQSIS SWLAWYQQKP GKAPKLLIYE ASSLESGVPS  60
RFSGSGSGTE FTLTISSLQP DDFATYYCQQ SDSHPITFGG GTKVEIKGGG GSGGGGSGGG  120
GSGGGGSQVQ LVESGGGLVK PGGSLRLSCA ASGFTFSDYY MSWIRQAPGK GLEWVSYISS  180
SGSTIYYADS VKGRFTISRD NAKNSLYLQM NSLRAEDTAV YYCARDQGNY GVDVWGQGTT  240
VTVSSTTTPA PRPPTPAPTI ASQPLSLRPE ACRPAAGGAV HTRGLDFACD IYIWAPLAGT  300
CGVLLLSLVI TLYCKRGRKK LLYIFKQPFM RPVQTTQEED GCSCRFPEEE EGGCELRVKF  360
SRSADAPAYQ QGQNQLYNEL NLGRREEYDV LDKRRGRDPE MGGKPRRKNP QEGLYNELQK  420
DKMAEAYSEI GMKGERRRGK GHDGLYQGLS TATKDTYDAL HMQALPPR              468

SEQ ID NO: 265         moltype = AA  length = 468
FEATURE                Location/Qualifiers
source                 1..468
                       mol_type = protein
                       organism = synthetic construct
```

SEQUENCE: 265
EVQLVESGGG LVKPGGSLRL SCAASGFTFS DYYMSWIRQA PGKGLEWVSY ISSSGSTIYY 60
ADSVKGRFTI SRDNAKNSLY LQMNSLRAED TAVYYCARDQ GNYGVDVWGQ GTTVTVSSGG 120
GGSGGGGSGG GGSGGGGSDI QMTQSPSTLS ASVGDRVTIT CRASQSISSW LAWYQQKPGK 180
APKLLIYEAS SLESGVPSRF SGSGSGTEFT LTISSLQPDD FATYYCQQAN SHPITFGGGT 240
KVEIKTTTPA PRPPTPAPTI ASQPLSLRPE ACRPAAGGAV HTRGLDFACD IYIWAPLAGT 300
CGVLLLSLVI TLYCKRGRKK LLYIFKQPFM RPVQTTQEED GCSCRFPEEE EGGCELRVKF 360
SRSADAPAYQ QGQNQLYNEL NLGRREEYDV LDKRRGRDPE MGGKPRRKNP QEGLYNELQK 420
DKMAEAYSEI GMKGERRRGK GHDGLYQGLS TATKDTYDAL HMQALPPR 468

SEQ ID NO: 266 moltype = AA length = 468
FEATURE Location/Qualifiers
source 1..468
mol_type = protein
organism = synthetic construct
SEQUENCE: 266
DIQMTQSPST LSASVGDRVT ITCRASQSIS SWLAWYQQKP GKAPKLLIYE ASSLESGVPS 60
RFSGSGSGTE FTLTISSLQP DDFATYYCQQ ANSHPITFGG GTKVEIKGGG GSGGGGSGGG 120
GSGGGGSEVQ LVESGGGLVK PGGSLRLSCA ASGFTFSDYY MSWIRQAPGK GLEWVSYISS 180
SGSTIYYADS VKGRFTISRD NAKNSLYLQM NSLRAEDTAV YYCARDQGNY GVDVWGQGTT 240
VTVSSTTTPA PRPPTPAPTI ASQPLSLRPE ACRPAAGGAV HTRGLDFACD IYIWAPLAGT 300
CGVLLLSLVI TLYCKRGRKK LLYIFKQPFM RPVQTTQEED GCSCRFPEEE EGGCELRVKF 360
SRSADAPAYQ QGQNQLYNEL NLGRREEYDV LDKRRGRDPE MGGKPRRKNP QEGLYNELQK 420
DKMAEAYSEI GMKGERRRGK GHDGLYQGLS TATKDTYDAL HMQALPPR 468

SEQ ID NO: 267 moltype = AA length = 472
FEATURE Location/Qualifiers
source 1..472
mol_type = protein
organism = synthetic construct
SEQUENCE: 267
EVQLLESGGG LVQPGGSLRL SCAASGFTFS NYAMSWVRQA PGKGLEWVSA ISGSGGSTYY 60
ADSVKGRFTI SRDNSKNTLY LQMNSLRAED TAVYYCARPG DGYYEGVYFD YWGQGTLVTV 120
SSGGGGSGGG GSGGGGSGGG GSDIQMTQSP SSLSASVGDR VTITCRASQS ISSYLNWYQQ 180
KPGKAPKLLI YAASSLQSGV PSRFSGSGSG TDFTLTISSL QPEDFATYYC QQAHSSPITF 240
GGGTKVEIKT TTPAPRPPTP APTIASQPLS LRPEACRPAA GGAVHTRGLD FACDIYIWAP 300
LAGTCGVLLL SLVITLYCKR GRKKLLYIFK QPFMRPVQTT QEEDGCSCRF PEEEEGGCEL 360
RVKFSRSADA PAYQQGQNQL YNELNLGRRE EYDVLDKRRG RDPEMGGKPR RKNPQEGLYN 420
ELQKDKMAEA YSEIGMKGER RRGKGHDGLY QGLSTATKDT YDALHMQALP PR 472

SEQ ID NO: 268 moltype = AA length = 472
FEATURE Location/Qualifiers
source 1..472
mol_type = protein
organism = synthetic construct
SEQUENCE: 268
DIQMTQSPSS LSASVGDRVT ITCRASQSIS SYLNWYQQKP GKAPKLLIYA ASSLQSGVPS 60
RFSGSGSGTD FTLTISSLQP EDFATYYCQQ AHSSPITFGG GTKVEIKGGG GSGGGGSGGG 120
GSGGGGSEVQ LLESGGGLVQ PGGSLRLSCA ASGFTFSNYA MSWVRQAPGK GLEWVSAISG 180
SGGSTYYADS VKGRFTISRD NSKNTLYLQM NSLRAEDTAV YYCARPGDGY YEGVYFDYWG 240
QGTLVTVSST TTPAPRPPTP APTIASQPLS LRPEACRPAA GGAVHTRGLD FACDIYIWAP 300
LAGTCGVLLL SLVITLYCKR GRKKLLYIFK QPFMRPVQTT QEEDGCSCRF PEEEEGGCEL 360
RVKFSRSADA PAYQQGQNQL YNELNLGRRE EYDVLDKRRG RDPEMGGKPR RKNPQEGLYN 420
ELQKDKMAEA YSEIGMKGER RRGKGHDGLY QGLSTATKDT YDALHMQALP PR 472

SEQ ID NO: 269 moltype = AA length = 474
FEATURE Location/Qualifiers
source 1..474
mol_type = protein
organism = synthetic construct
SEQUENCE: 269
QITLKESGPT LVKPTQTLTL TCTFSGFSLS TSGVGVGWIR QPPGKALEWL ALIYWNDEKR 60
YSPSLKSRLT ITKDTSKNQV VLTMTNMDPV DTAVYYCARE GSHDYKSSNW FDPWGQGTLV 120
TVSSGGGGSG GGGSGGGGSG GGGSDIQMTQ SPSSLSASVG DRVTITCQAS QDIANYLNWY 180
QQKPGKAPKL LIYDASNLET GVPSRFSGSG SGTDFTFTIS SLQPEDIATY YCQQHFNLPL 240
TFGGGTKVEI KTTTPAPRPP TPAPTIASQP LSLRPEACRP AAGGAVHTRG LDFACDIYIW 300
APLAGTCGVL LLSLVITLYC KRGRKKLLYI FKQPFMRPVQ TTQEEDGCSC RFPEEEEGGC 360
ELRVKFSRSA DAPAYQQGQN QLYNELNLGR REEYDVLDKR RGRDPEMGGK PRRKNPQEGL 420
YNELQKDKMA EAYSEIGMKG ERRRGKGHDG LYQGLSTATK DTYDALHMQA LPPR 474

SEQ ID NO: 270 moltype = AA length = 474
FEATURE Location/Qualifiers
source 1..474
mol_type = protein
organism = synthetic construct
SEQUENCE: 270
DIQMTQSPSS LSASVGDRVT ITCQASQDIA NYLNWYQQKP GKAPKLLIYD ASNLETGVPS 60
RFSGSGSGTD FTFTISSLQP EDIATYYCQQ HFNLPLTFGG GTKVEIKGGG GSGGGGSGGG 120
GSGGGGSQIT LKESGPTLVK PTQTLTLTCT FSGFSLSTSG VGVGWIRQPP GKALEWLALI 180

```
YWNDEKRYSP SLKSRLTITK DTSKNQVVLT MTNMDPVDTA VYYCAREGSH DYKSSNWFDP  240
WGQGTLVTVS STTTPAPRPP TPAPTIASQP LSLRPEACRP AAGGAVHTRG LDFACDIYIW  300
APLAGTCGVL LLSLVITLYC KRGRKKLLYI FKQPFMRPVQ TTQEEDGCSC RFPEEEEGGC  360
ELRVKFSRSA DAPAYQQGQN QLYNELNLGR REEYDVLDKR RGRDPEMGGK PRRKNPQEGL  420
YNELQKDKMA EAYSEIGMKG ERRRGKGHDG LYQGLSTATK DTYDALHMQA LPPR        474

SEQ ID NO: 271          moltype = AA  length = 478
FEATURE                 Location/Qualifiers
source                  1..478
                        mol_type = protein
                        organism = synthetic construct
SEQUENCE: 271
EVQLVESGGG LVKPGGSLRL SCAASGFTFS SYSMNWVRQA PGKGLEWVSS ISSSSSYIYY  60
ADSVKGRFTI SRDNAKNSLY LQMNSLRAED TAVYYCARAG DTYSAADYYY MDVWGKGTTV  120
TVSSGGGGSG GGGSGGGGSG GGGSDIVMTQ SPLSLPVTPG EPASISCRSS QSLLHSNGYN  180
YLDWYLQKPG QSPQLLIYLG SNRASGVPDR FSGSGSGTDF TLKISRVEAE DVGVYYCMQA  240
LGLITFGGGT KVEIKTTTPA PRPPTPAPTI ASQPLSLRPE ACRPAAGGAV HTRGLDFACD  300
IYIWAPLAGT CGVLLLSLVI TLYCKRGRKK LLYIFKQPFM RPVQTTQEED GCSCRFPEEE  360
EGGCELRVKF SRSADAPAYQ QGQNQLYNEL NLGRREEYDV LDKRRGRDPE MGGKPRRKNP  420
QEGLYNELQK DKMAEAYSEI GMKGERRRGK GHDGLYQGLS TATKDTYDAL HMQALPPR    478

SEQ ID NO: 272          moltype = AA  length = 478
FEATURE                 Location/Qualifiers
source                  1..478
                        mol_type = protein
                        organism = synthetic construct
SEQUENCE: 272
DIVMTQSPLS LPVTPGEPAS ISCRSSQSLL HSNGYNYLDW YLQKPGQSPQ LLIYLGSNRA  60
SGVPDRFSGS GSGTDFTLKI SRVEAEDVGV YYCMQALGLI TFGGGTKVEI KGGGGSGGGG  120
SGGGGSGGGG SEVQLVESGG GLVKPGGSLR LSCAASGFTF SSYSMNWVRQ APGKGLEWVS  180
SISSSSSYIY YADSVKGRFT ISRDNAKNSL YLQMNSLRAE DTAVYYCARA GDTYSAADYY  240
YMDVWGKGTT VTVSSTTTPA PRPPTPAPTI ASQPLSLRPE ACRPAAGGAV HTRGLDFACD  300
IYIWAPLAGT CGVLLLSLVI TLYCKRGRKK LLYIFKQPFM RPVQTTQEED GCSCRFPEEE  360
EGGCELRVKF SRSADAPAYQ QGQNQLYNEL NLGRREEYDV LDKRRGRDPE MGGKPRRKNP  420
QEGLYNELQK DKMAEAYSEI GMKGERRRGK GHDGLYQGLS TATKDTYDAL HMQALPPR    478

SEQ ID NO: 273          moltype = AA  length = 339
FEATURE                 Location/Qualifiers
source                  1..339
                        mol_type = protein
                        organism = synthetic construct
SEQUENCE: 273
EVQLLESGGG LVQPGGSLRL SCAASGFTFG SEAMSWVRQA PGKERELVSA ISGSGEVTYY  60
ADSVKGRFTI SRDNSKNTLY LQMNSLRAED TAVYYCQRLV EAKRHWGQGT QVTVSSTTTP  120
APRPPTPAPT IASQPLSLRP EACRPAAGGA VHTRGLDFAC DIYIWAPLAG TCGVLLLSLV  180
ITLYCKRGRK KLLYIFKQPF MRPVQTTQEE DGCSCRFPEE EEGGCELRVK FSRSADAPAY  240
QQGQNQLYNE LNLGRREEYD VLDKRRGRDP EMGGKPRRKN PQEGLYNELQ KDKMAEAYSE  300
IGMKGERRRG KGHDGLYQGL STATKDTYDA LHMQALPPR                        339

SEQ ID NO: 274          moltype = AA  length = 339
FEATURE                 Location/Qualifiers
source                  1..339
                        mol_type = protein
                        organism = synthetic construct
SEQUENCE: 274
EVQLLESGGG LVQPGGSLRL SCAASGFTFE SEAMSWYRQA PGKERELVSV ITSEGSTYYA  60
DSVKGRFTIS RDNSKNTLYL QMNSLRAEDT AVYYCAHIEW ETRLNWGQGT QVTVSSTTTP  120
APRPPTPAPT IASQPLSLRP EACRPAAGGA VHTRGLDFAC DIYIWAPLAG TCGVLLLSLV  180
ITLYCKRGRK KLLYIFKQPF MRPVQTTQEE DGCSCRFPEE EEGGCELRVK FSRSADAPAY  240
QQGQNQLYNE LNLGRREEYD VLDKRRGRDP EMGGKPRRKN PQEGLYNELQ KDKMAEAYSE  300
IGMKGERRRG KGHDGLYQGL STATKDTYDA LHMQALPPR                        339

SEQ ID NO: 275          moltype = AA  length = 341
FEATURE                 Location/Qualifiers
source                  1..341
                        mol_type = protein
                        organism = synthetic construct
SEQUENCE: 275
EVQLLESGGG LVQPGGSLRL SCAASGFTFD EYTMHWFRQA PGKEREFVSA ISGGGSETYY  60
ADSVKGRFTI SRDNSKNTLY LQMNSLRAED TAVYYCAAGG EEAGVGYWGQ GTQVTVSSTT  120
TPAPRPPTPA PTIASQPLSL RPEACRPAAG GAVHTRGLDF ACDIYIWAPL AGTCGVLLLS  180
LVITLYCKRG RKKLLYIFKQ PFMRPVQTTQ EEDGCSCRFP EEEEGGCELR VKFSRSADAP  240
AYQQGQNQLY NELNLGRREE YDVLDKRRGR DPEMGGKPRR KNPQEGLYNE LQKDKMAEAY  300
SEIGMKGERR RGKGHDGLYQ GLSTATKDTY DALHMQALPP R                      341

SEQ ID NO: 276          moltype = AA  length = 343
FEATURE                 Location/Qualifiers
source                  1..343
                        mol_type = protein
```

```
                         organism = synthetic construct
SEQUENCE: 276
EVQLLESGGG LVQPGGSLRL SCAASGFTFE DYAMSWFRQA PGKEREGVSA ISGKGGSTYY  60
ADSVKGRFTI SRDNSKNTLY LQMNSLRAED TAVYYCAVLD EEAGAEGGYW GQGTQVTVSS  120
TTTPAPRPPT PAPTIASQPL SLRPEACRPA AGGAVHTRGL DFACDIYIWA PLAGTCGVLL  180
LSLVITLYCK RGRKKLLYIF KQPFMRPVQT TQEEDGCSCR FPEEEEGGCE LRVKFSRSAD  240
APAYQQGQNQ LYNELNLGRR EEYDVLDKRR GRDPEMGGKP RRKNPQEGLY NELQKDKMAE  300
AYSEIGMKGE RRRGKGHDGL YQGLSTATKD TYDALHMQAL PPR                    343

SEQ ID NO: 277           moltype = AA  length = 343
FEATURE                  Location/Qualifiers
source                   1..343
                         mol_type = protein
                         organism = synthetic construct
SEQUENCE: 277
EVQLLESGGG LVQPGGSLRL SCAASGFTFD RYAMSWFRQA PGKEREGVSA ISTSGDSTYY  60
ADSVKGRFTI SRDNSKNTLY LQMNSLRAED TAVYYCAVLD EEAGAEGGYW GQGTQVTVSS  120
TTTPAPRPPT PAPTIASQPL SLRPEACRPA AGGAVHTRGL DFACDIYIWA PLAGTCGVLL  180
LSLVITLYCK RGRKKLLYIF KQPFMRPVQT TQEEDGCSCR FPEEEEGGCE LRVKFSRSAD  240
APAYQQGQNQ LYNELNLGRR EEYDVLDKRR GRDPEMGGKP RRKNPQEGLY NELQKDKMAE  300
AYSEIGMKGE RRRGKGHDGL YQGLSTATKD TYDALHMQAL PPR                    343

SEQ ID NO: 278           moltype = AA  length = 344
FEATURE                  Location/Qualifiers
source                   1..344
                         mol_type = protein
                         organism = synthetic construct
SEQUENCE: 278
EVQLLESGGG LVQPGGSLRL SCAASGFTFA SDAMSWYRQA PGKERELVSA ISGSGGSTYY  60
ADSVKGRFTI SRDNSKNTLY LQMNSLRAED TAVYYCAAHD SGEAYLAFDY WGQGTQVTVS  120
STTTPAPRPP TPAPTIASQP LSLRPEACRP AAGGAVHTRG LDFACDIYIW APLAGTCGVL  180
LLSLVITLYC KRGRKKLLYI FKQPFMRPVQ TTQEEDGCSC RFPEEEEGGC ELRVKFSRSA  240
DAPAYQQGQN QLYNELNLGR REEYDVLDKR RGRDPEMGGK PRRKNPQEGL YNELQKDKMA  300
EAYSEIGMKG ERRRGKGHDG LYQGLSTATK DTYDALHMQA LPPR                   344

SEQ ID NO: 279           moltype = AA  length = 344
FEATURE                  Location/Qualifiers
source                   1..344
                         mol_type = protein
                         organism = synthetic construct
SEQUENCE: 279
EVQLLESGGG LVQPGGSLRL SCAASGFTFD SYTMSWYRQA PGKERELVSA ISGHGDSTYY  60
ADSVKGRFTI SRDNSKNTLY LQMNSLRAED TAVYYCTRIS ITTEWLAGDY WGQGTQVTVS  120
STTTPAPRPP TPAPTIASQP LSLRPEACRP AAGGAVHTRG LDFACDIYIW APLAGTCGVL  180
LLSLVITLYC KRGRKKLLYI FKQPFMRPVQ TTQEEDGCSC RFPEEEEGGC ELRVKFSRSA  240
DAPAYQQGQN QLYNELNLGR REEYDVLDKR RGRDPEMGGK PRRKNPQEGL YNELQKDKMA  300
EAYSEIGMKG ERRRGKGHDG LYQGLSTATK DTYDALHMQA LPPR                   344

SEQ ID NO: 280           moltype = AA  length = 346
FEATURE                  Location/Qualifiers
source                   1..346
                         mol_type = protein
                         organism = synthetic construct
SEQUENCE: 280
EVQLLESGGG LVQPGGSLRL SCAASGFTFS SYAMSWFRQA PGKEREFVSF ISGSGDSTYY  60
ADSVKGRFTI SRDNSKNTLY LQMNSLRAED TAVYYCTRWP YDFEEPSEPG VYWGQGTQVT  120
VSSTTTPAPR PPTPAPTIAS QPLSLRPEAC RPAAGGAVHT RGLDFACDIY IWAPLAGTCG  180
VLLLSLVITL YCKRGRKKLL YIFKQPFMRP VQTTQEEDGC SCRFPEEEEG GCELRVKFSR  240
SADAPAYQQG QNQLYNELNL GRREEYDVLD KRRGRDPEMG GKPRRKNPQE GLYNELQKDK  300
MAEAYSEIGM KGERRRGKGH DGLYQGLSTA TKDTYDALHM QALPPR                 346

SEQ ID NO: 281           moltype = AA  length = 346
FEATURE                  Location/Qualifiers
source                   1..346
                         mol_type = protein
                         organism = synthetic construct
SEQUENCE: 281
EVQLLESGGG LVQPGGSLRL SCAASGFTFT DYDMSWYRQA PGKERELVSV IHSGGSTYYA  60
DSVKGRFTIS RDNSKNTLYL QMNSLRAEDT AVYYCAPGYY SDLSFDYYNF DYWGQGTQVT  120
VSSTTTPAPR PPTPAPTIAS QPLSLRPEAC RPAAGGAVHT RGLDFACDIY IWAPLAGTCG  180
VLLLSLVITL YCKRGRKKLL YIFKQPFMRP VQTTQEEDGC SCRFPEEEEG GCELRVKFSR  240
SADAPAYQQG QNQLYNELNL GRREEYDVLD KRRGRDPEMG GKPRRKNPQE GLYNELQKDK  300
MAEAYSEIGM KGERRRGKGH DGLYQGLSTA TKDTYDALHM QALPPR                 346

SEQ ID NO: 282           moltype = AA  length = 346
FEATURE                  Location/Qualifiers
source                   1..346
                         mol_type = protein
                         organism = synthetic construct
```

```
SEQUENCE: 282
EVQLLESGGG LVQPGGSLRL SCAASGFTFS DYAMHWFRQA PGKERVLVSS IDSGGSTYYA  60
DSVKGRFTIS RDNSKNTLYL QMNSLRAEDT AVYYCNAGFK GDHPHPKDAF DIWGQGTQVT  120
VSSTTTPAPR PPTPAPTIAS QPLSLRPEAC RPAAGGAVHT RGLDFACDIY IWAPLAGTCG  180
VLLLSLVITL YCKRGRKKLL YIFKQPFMRP VQTTQEEDGC SCRFPEEEEG GCELRVKFSR  240
SADAPAYQQG QNQLYNELNL GRREEYDVLD KRRGRDPEMG GKPRRKNPQE GLYNELQKDK  300
MAEAYSEIGM KGERRRGKGH DGLYQGLSTA TKDTYDALHM QALPPR                346

SEQ ID NO: 283          moltype = AA  length = 348
FEATURE                 Location/Qualifiers
source                  1..348
                        mol_type = protein
                        organism = synthetic construct
SEQUENCE: 283
EVQLLESGGG LVQPGGSLRL SCAASGFTFS SEGMSWVRQA PGKERELVSA ISGSGDHTYY  60
ADSVRGRFTI SRDNSKNTLY LQMNSLRAED TAVYYCNALE GGPTTAIQPG GPDYWGQGTQ  120
VTVSSTTTPA PRPPTPAPTI ASQPLSLRPE ACRPAAGGAV HTRGLDFACD IYIWAPLAGT  180
CGVLLLSLVI TLYCKRGRKK LLYIFKQPFM RPVQTTQEED GCSCRFPEEE EGGCELRVKF  240
SRSADAPAYQ QGQNQLYNEL NLGRREEYDV LDKRRGRDPE MGGKPRRKNP QEGLYNELQK  300
DKMAEAYSEI GMKGERRRGK GHDGLYQGLS TATKDTYDAL HMQALPPR              348

SEQ ID NO: 284          moltype = DNA  length = 135
FEATURE                 Location/Qualifiers
source                  1..135
                        mol_type = other DNA
                        organism = synthetic construct
SEQUENCE: 284
accacaacac ctgctccaag gcccccaca cccgctccaa ctatagccag ccaaccattg  60
agcctcagac ctgaagcttg caggcccgca gcaggaggcg ccgtccatac gcgaggcctg  120
gacttcgcgt gtgat                                                  135

SEQ ID NO: 285          moltype = DNA  length = 117
FEATURE                 Location/Qualifiers
source                  1..117
                        mol_type = other DNA
                        organism = synthetic construct
SEQUENCE: 285
attgaagtta tgtatcctcc tccttaccta gacaatgaga agagcaatgg aaccattatc  60
catgtgaaag ggaaacacct ttgtccaagt cccctatttc ccggaccttc taagccc    117

SEQ ID NO: 286          moltype = DNA  length = 36
FEATURE                 Location/Qualifiers
source                  1..36
                        mol_type = other DNA
                        organism = synthetic construct
SEQUENCE: 286
gagtccaaat atggtccccc gtgcccacca tgccca                           36

SEQ ID NO: 287          moltype = DNA  length = 48
FEATURE                 Location/Qualifiers
source                  1..48
                        mol_type = other DNA
                        organism = synthetic construct
SEQUENCE: 287
cttgagccca aatcttgtga caaaactcac acatgcccac cgtgccca              48

SEQ ID NO: 288          moltype = DNA  length = 72
FEATURE                 Location/Qualifiers
source                  1..72
                        mol_type = other DNA
                        organism = synthetic construct
SEQUENCE: 288
atttatattt gggcaccttt ggccggaaca tgtggggtgt tgcttctctc ccttgtgatc  60
actctgtatt gt                                                     72

SEQ ID NO: 289          moltype = DNA  length = 81
FEATURE                 Location/Qualifiers
source                  1..81
                        mol_type = other DNA
                        organism = synthetic construct
SEQUENCE: 289
ttttgggtgc tggtggtggt tggtggagtc ctggcttgct atagcttgct agtaacagtg  60
gcctttatta ttttctgggt g                                           81

SEQ ID NO: 290          moltype = DNA  length = 126
FEATURE                 Location/Qualifiers
source                  1..126
                        mol_type = other DNA
                        organism = synthetic construct
```

```
SEQUENCE: 290
aagcgcggga gaaagaagct cctgtacatc ttcaagcagc cttttatgcg acctgtgcaa  60
accactcagg aagaagatgg gtgttcatgc cgcttccccg aggaggaaga aggagggtgt  120
gaactg                                                             126

SEQ ID NO: 291         moltype = DNA  length = 123
FEATURE                Location/Qualifiers
source                 1..123
                       mol_type = other DNA
                       organism = synthetic construct
SEQUENCE: 291
aggagtaaga ggagcaggct cctgcacagt gactacatga acatgactcc ccgccgcccc  60
gggcccaccc gcaagcatta ccagccctat gccccaccac gcgacttcgc agcctatcgc  120
tcc                                                                123

SEQ ID NO: 292         moltype = DNA  length = 105
FEATURE                Location/Qualifiers
source                 1..105
                       mol_type = other DNA
                       organism = synthetic construct
SEQUENCE: 292
acaaaaaaga agtattcatc cagtgtgcac gaccctaacg gtgaatacat gttcatgaga  60
gcagtgaaca cagccaaaaa atctagactc acagatgtga cccta                  105

SEQ ID NO: 293         moltype = DNA  length = 336
FEATURE                Location/Qualifiers
source                 1..336
                       mol_type = other DNA
                       organism = synthetic construct
SEQUENCE: 293
agggtgaaat tttctagaag cgccgatgct cccgcatatc agcagggtca gaatcagctc  60
tacaatgaat tgaatctcgg caggcgagaa gagtacgatg ttctggacaa aagacggggc  120
agggatcccg agatgggggg aaagccccgg agaaaaaatc ctcaggaggg gttgtacaat  180
gagctgcaga aggacaagat ggctgaagcc tatagcgaga tcggaatgaa aggcgaaaga  240
cgcagaggca aggggcatga cggtctgtac cagggtctct ctacagccac caaggacact  300
tatgatgcgt tgcatatgca agccttgcca ccccgc                            336

SEQ ID NO: 294         moltype = DNA  length = 63
FEATURE                Location/Qualifiers
source                 1..63
                       mol_type = other DNA
                       organism = synthetic construct
SEQUENCE: 294
atggctcttc ccgtaacagc ccttttgttg ccccttgcac tccttctgca tgcagcacga  60
ccg                                                                63

SEQ ID NO: 295         moltype = DNA  length = 1404
FEATURE                Location/Qualifiers
source                 1..1404
                       mol_type = other DNA
                       organism = synthetic construct
SEQUENCE: 295
gagatcgtgc tgacacagtc tcccgccaca ctgtcactgt ctccaggcga aagagccaca  60
ctgagctgta gagccagcca gagcgtgtcc tcttacctgg cctggtatca gcagaagcct  120
ggacaggctc cccggctgct gatctacgat gccagcaata gagccacagg catccccgcc  180
agatttctg gcagcggctc tggcaccgat ttcaccctga ccataagcag cctggaacct  240
gaggacttcg ccgtgtacta ctgccagcag agagtggtgt accccatcac ctttggcgga  300
ggcaccaagg tggaaatcaa aggcggcgga ggaagcggag gcggaggatc tggtggtggt  360
ggatctggcg gaggtggcag ccagatcaca ctgaaagagt ctggccccac actggtcaag  420
cccacacaga ccctgacact gacctgcacc ttcagcggct ttagcctgag cacatctggc  480
gtcggcgttg gctggattag acagcctcct ggaaaggccc tggaatggct ggccctgatc  540
tactggaacg acgagaagag atacagcccc agcctgaagt cccggctgac catcaccaag  600
gacaccagca agaaccaggt ggtgctgacc atgacaaaca tggaccccgt ggacaccgcc  660
gtgtattatt gcgccagaga tgagtacggc ggcttcgaca tttggggcca gggcacaatg  720
gtcaccgtgt ctagtaccac aacacctgct ccaaggcccc ccacacccgc tccaactata  780
gccagccaac cattgagcct cagacctgaa gcttgcaggc ccgcagcagg aggcgccgtc  840
catacgcgag gcctggactt cgcgtgtgat atttatattt gggcaccttt ggccggaaca  900
tgtggggtgt tgcttctctc ccttgtgatc actctgtatt gtaagcgcgg gagaaagaag  960
ctcctgtaca tcttcaagca gccttttatg cgacctgtgc aaaccactca ggaagaagat  1020
gggtgttcat gccgcttccc cgaggaggaa gaaggagggt gtgaactgag ggtgaaattt  1080
tctagaagcg ccgatgctcc cgcatatcag cagggtcaga atcagctcta caatgaattg  1140
aatctcggca ggcgagaaga gtacgatgtt ctggacaaaa gacggggcag ggatcccgag  1200
atggggggaa agccccggag aaaaaatcct caggaggggt tgtacaatga gctgcagaag  1260
gacaagatgg ctgaagccta tagcgagatc ggaatgaaag gcgaaagacg cagaggcaag  1320
gggcatgacg gtctgtacca gggtctctct acagccacca aggacactta tgatgcgttg  1380
catatgcaag ccttgccacc ccgc                                         1404

SEQ ID NO: 296         moltype = DNA  length = 1404
FEATURE                Location/Qualifiers
```

```
source                  1..1404
                        mol_type = other DNA
                        organism = synthetic construct
SEQUENCE: 296
gagatcgtgc tgacccagtc ccctgctacc ctgagcctgt ctccaggcga gcgggccaca  60
ctgagctgta gagcttctca gagcgtgtcc agctacctgg cctggtatca gcagaaacct  120
ggccaggccc ctagactgct gatctacgac gccagcaacc gggccaccgg catccccgcc  180
agattcagcg gatctggcag cggcacagat tttaccctca ccatcagcag cctggaacct  240
gaggacttcg ccgtctacta ctgccagcaa agattcgact accccatcac cttcggcggc  300
ggaacaaagg tggaaattaa gggtggtggg ggcagcggtg gaggtgggag cggaggcggg  360
ggtagcggag gcgggggtag ccaaatcaca ctgaaagaga gcggccctac actcgtgaaa  420
cctacccaga ccctgacact gacatgtacc ttcagcggct tctccctgag cacctctggc  480
gtcggcgttg gatggatcag acagcctcca ggcaaggccc tggaatggct ggctctgatc  540
tattggaacg acgacaagcg gtacagcccc agcctgaagt ctagactgac catcacaaag  600
gacaccagca agaaccaggt ggtgctgacc atgacaaata tggaccccgt ggacaccgcc  660
gtgtactact gcgccagaga tgagtacggc ggatttgata tctggggcca gggcaccatg  720
gtgaccgtgt ccagcaccac aacacctgct ccaaggcccc ccacacccgc tccaactata  780
gccagccaac cattgagcct cagacctgaa gcttgcaggc ccgcagcagg aggcgccgtc  840
catacgcgag gcctggactt cgcgtgtgat atttatattt gggcaccttt ggccggaaca  900
tgtggggtgt tgcttctctc ccttgtgatc actctgtatt gtaagcgcgg gagaaagaag  960
ctcctgtaca tcttcaagca gccttttatg cgacctgtgc aaaccactca ggaagaagat  1020
gggtgttcat gccgcttccc cgaggaggaa gaaggagggt gtgaactgag ggtgaaattt  1080
tctagaagcg ccgatgctcc cgcatatcag cagggtcaga atcagctcta caatgaattg  1140
aatctcggca ggcgagaaga gtacgatgtt ctggacaaaa gacggggcag ggatcccgag  1200
atgggggggaa agccccggag aaaaaatcct caggaggggt tgtacaatga gctgcagaag  1260
gacaagatgg ctgaagccta tagcgagatc ggaatgaaag gcgaaagacg cagaggcaag  1320
gggcatgacg gtctgtacca gggtctctct acagccacca aggacactta tgatgcgttg  1380
catatgcaag ccttgccacc ccgc                                        1404

SEQ ID NO: 297          moltype = DNA  length = 1398
FEATURE                 Location/Qualifiers
source                  1..1398
                        mol_type = other DNA
                        organism = synthetic construct
SEQUENCE: 297
caagtgcagc tcgtggaaag cggcggcgga gtggtgcagc ccggccggag cctgagactg  60
tcctgcgccg cttctggatt taccttcagc agctacggca tgcactgggt cagacaggcc  120
cctggcaaag gcctggagtg ggtggccgtt atcagctacg agggcagcaa caagtattac  180
gccgacagcg tgaagggccg cttcacaatc tctagagata atagcaagaa caccctgtac  240
ctgcagatga acagcctgcg ggccgaagat accgccgtgt actactgtgc tagagagctg  300
ggcgacggca tggacgtgtg gggacagggc acaaccgtga ccgtgtcctc tggtggtggg  360
ggcagcggtg gaggtgggag cggaggcggg ggtagcggag gcgggggtag cgagatcgtg  420
ctgacccagt cccctgctac actgagcctg tctccaggcg agcgggccac actgagctgt  480
agagcttctc agagcgtgtc cagctatctg gcctggttcc agcagaaacc tggccaggcc  540
cctagactgc tgatctacga cgccagcaac cgggccaccg gcatccccgc cagattcagc  600
ggctctggca gcggcaccga cttcaccctc accatcagca gcctggaacc cgaggatttt  660
gccgtctact actgccagca aagagtggac ctgtggacct tcggcggagg aacaaaggtg  720
gaaatcaaga ccacaacacc tgctccaagg ccccccacac ccgctccaac tatagccagc  780
caaccattga gcctcagacc tgaagcttgc aggcccgcag caggaggcgc cgtccatacg  840
cgaggcctgg acttcgcgtg tgatatttat atttgggcac ctttggccgg aacatgtggg  900
gtgttgcttc tctcccttgt gatcactctg tattgtaagc gcgggagaaa gaagctcctg  960
tacatcttca agcagccttt tatgcgacct gtgcaaacca ctcaggaaga agatgggtgt  1020
tcatgccgct tccccgagga ggaagaagga gggtgtgaac tgagggtgaa attttctaga  1080
agcgccgatg ctcccgcata tcagcagggt cagaatcagc tctacaatga attgaatctc  1140
ggcaggcgag aagagtacga tgttctggac aaaagacggg gcagggatcc cgagatgggg  1200
ggaaagcccc ggagaaaaaa tcctcaggag gggttgtaca atgagctgca gaaggacaag  1260
atggctgaag cctatagcga gatcggaatg aaaggcgaaa gacgcagagg caaggggcat  1320
gacggtctgt accagggtct ctctacagcc accaaggaca cttatgatgc gttgcatatg  1380
caagccttgc caccccgc                                               1398

SEQ ID NO: 298          moltype = DNA  length = 1404
FEATURE                 Location/Qualifiers
source                  1..1404
                        mol_type = other DNA
                        organism = synthetic construct
SEQUENCE: 298
gacatccaga tgacccagag cccttcgacc ctatccgctt ccgtgggtga ccgtgtgacc  60
atcacctgtc gcgcgtcgca gagcatctcc tcctggctcg cgtggtacca acagaagcct  120
ggcaaggccc ccaagctgct gatttacgac gccagttccc tggagtctgg cgtgccatcc  180
cgcttctccg gcagcggcag cggtaccgag ttcaccctga cgatcagctc cctgcagccg  240
gatgactttg ctacctacta ctgtcagcag gtctcctccc tcccccccac cttcggtggc  300
ggtaccaagg tggagatcaa gggcggcggc ggctctggtg gcggaggttc tggcgggggga  360
ggttcggggg ggggaggctc cgaggtgcaa ctggtagaga gcggcggggg actggtaaaa  420
cccggcggct ccctgcggct gtcatgcgct gctagcggct tcacgttcag cgattactac  480
atgagttgga tccgccaggc ccccgggaag ggtttggagt gggtctcgta tatctcttcc  540
agcggatcta ccatttacta tgcggacagc gtgaaggggc gcttcaccat atctcgggac  600
aacgccaaga actccctgta cctgcagatg aattccctgc gtgccgagga cacggccgtg  660
tattactgtg cccgcgacca gggcaactac ggcgtcgacg tgtggggcca gggtacaacc  720
gtcaccgtgt ccagtaccac aacacctgct ccaaggcccc ccacacccgc tccaactata  780
```

```
gccagccaac cattgagcct cagacctgaa gcttgcaggc ccgcagcagg aggcgccgtc  840
catacgcgag gcctggactt cgcgtgtgat atttatattt gggcaccttt ggccggaaca  900
tgtggggtgt tgcttctctc ccttgtgatc actctgtatt gtaagcgcgg gagaaagaag  960
ctcctgtaca tcttcaagca gccttttatg cgacctgtgc aaaccactca ggaagaagat  1020
gggtgttcat gccgcttccc cgaggaggaa gaaggagggt gtgaactgag ggtgaaattt  1080
tctagaagcg ccgatgctcc cgcatatcag cagggtcaga atcagctcta caatgaattg  1140
aatctcggca ggcgagaaga gtacgatgtt ctggacaaaa gacggggcag ggatcccgag  1200
atggggggaa agccccggag aaaaaatcct caggaggggt tgtacaatga gctgcagaag  1260
gacaagatgg ctgaagccta tagcgagatc ggaatgaaag gcgaaagacg cagaggcaag  1320
gggcatgacg gtctgtacca gggtctctct acagccacca aggacactta tgatgcgttg  1380
catatgcaag ccttgccacc ccgc                                        1404

SEQ ID NO: 299         moltype = DNA  length = 1404
FEATURE                Location/Qualifiers
source                 1..1404
                       mol_type = other DNA
                       organism = synthetic construct
SEQUENCE: 299
caagtgcagc tggtcgagag cggaggaggc ctggttaagc ccggcggatc tctcagactg  60
agctgcgccg ctagcggctt tacattcagc gactactaca tgagctggat ccggcaggcc  120
cctggcaagg gcctggaatg ggtgtcctac atcagctcct ccggcagcac catctactac  180
gccgacagcg tgaaaggcag attcacaatc tctagagata atgccaagaa cagcctgtac  240
ctgcagatga acagcctgcg ggccgaggac accgccgtgt actattgtgc tagagatcag  300
ggcaactacg gcgtggacgt gtggggccag ggcaccaccg tgaccgtgtc tagcggtggt  360
gggggcagcg gtggaggtgg gagcggaggc gggggtagcg gaggcggggg tagcgatatc  420
cagatgaccc agtccccatc tacactgagc gcctctgtgg gcgaccgggt gaccattaca  480
tgtagagcca gccagagcat cagcagctgg ctggcttggt atcagcagaa acctggcaag  540
gcccctaagc tgctgatcta cgaggccagc agcctggaaa gcggcgtccc cagcagattc  600
agcggcagcg gctctggaac agagttcacc ctgaccatct cctccctgca gcctgacgac  660
ttcgccacct actactgcca gcaatctgat agccacccca tcacctttgg cggaggcacc  720
aaggtggaaa tcaagaccac aacacctgct ccaaggcccc ccacacccgc tccaactata  780
gccagccaac cattgagcct cagacctgaa gcttgcaggc ccgcagcagg aggcgccgtc  840
catacgcgag gcctggactt cgcgtgtgat atttatattt gggcaccttt ggccggaaca  900
tgtggggtgt tgcttctctc ccttgtgatc actctgtatt gtaagcgcgg gagaaagaag  960
ctcctgtaca tcttcaagca gccttttatg cgacctgtgc aaaccactca ggaagaagat  1020
gggtgttcat gccgcttccc cgaggaggaa gaaggagggt gtgaactgag ggtgaaattt  1080
tctagaagcg ccgatgctcc cgcatatcag cagggtcaga atcagctcta caatgaattg  1140
aatctcggca ggcgagaaga gtacgatgtt ctggacaaaa gacggggcag ggatcccgag  1200
atggggggaa agccccggag aaaaaatcct caggaggggt tgtacaatga gctgcagaag  1260
gacaagatgg ctgaagccta tagcgagatc ggaatgaaag gcgaaagacg cagaggcaag  1320
gggcatgacg gtctgtacca gggtctctct acagccacca aggacactta tgatgcgttg  1380
catatgcaag ccttgccacc ccgc                                        1404

SEQ ID NO: 300         moltype = DNA  length = 1404
FEATURE                Location/Qualifiers
source                 1..1404
                       mol_type = other DNA
                       organism = synthetic construct
SEQUENCE: 300
gatatccaga tgacccagtc cccatctaca ctgagcgcct ctgtgggcga ccgggtgaca  60
attacctgta gagctagcca gagcatctcc tcctggctgg cttggtacca gcaaaaacct  120
ggcaaggccc ctaagctgct gatctacgag gccagcagcc tggaaagcgg cgtcccctct  180
agattcagcg gcagcggctc tggaaccgag ttcaccctga caatcagcag cctgcagcct  240
gacgacttcg ccacctatta ctgccagcag gccaacagcc accccatcac ctttggcgga  300
ggcaccaagg tggaaatcaa gggtggtggg ggcagcggtg gaggtgggag cggaggcggg  360
ggtagcggag gcgggggtag cgaggtgcag ctggtggaaa gcggcggagg actcgttaag  420
cccggcggca gcctgagact gagctgcgcc gctagcggat ttaccttcag cgactactac  480
atgagctgga tccggcaggc ccctggcaag ggcctggaat gggtcagcta catcagctcc  540
tctggctcta caatctacta cgccgacagc gtgaaaggca gattcaccat ctctagagat  600
aatgccaaga acagcctgta cctgcaaatg aacagcctgc gggccgagga caccgccgtg  660
tactattgtg ctagagatca gggcaactac ggcgtggacg tgtggggcca gggcaccacc  720
gtgacagtgt cctccaccac aacacctgct ccaaggcccc ccacacccgc tccaactata  780
gccagccaac cattgagcct cagacctgaa gcttgcaggc ccgcagcagg aggcgccgtc  840
catacgcgag gcctggactt cgcgtgtgat atttatattt gggcaccttt ggccggaaca  900
tgtggggtgt tgcttctctc ccttgtgatc actctgtatt gtaagcgcgg gagaaagaag  960
ctcctgtaca tcttcaagca gccttttatg cgacctgtgc aaaccactca ggaagaagat  1020
gggtgttcat gccgcttccc cgaggaggaa gaaggagggt gtgaactgag ggtgaaattt  1080
tctagaagcg ccgatgctcc cgcatatcag cagggtcaga atcagctcta caatgaattg  1140
aatctcggca ggcgagaaga gtacgatgtt ctggacaaaa gacggggcag ggatcccgag  1200
atggggggaa agccccggag aaaaaatcct caggaggggt tgtacaatga gctgcagaag  1260
gacaagatgg ctgaagccta tagcgagatc ggaatgaaag gcgaaagacg cagaggcaag  1320
gggcatgacg gtctgtacca gggtctctct acagccacca aggacactta tgatgcgttg  1380
catatgcaag ccttgccacc ccgc                                        1404

SEQ ID NO: 301         moltype = DNA  length = 1416
FEATURE                Location/Qualifiers
source                 1..1416
                       mol_type = other DNA
                       organism = synthetic construct
```

SEQUENCE: 301
gacatccaga tgacccagag ccctagctcc ctgagcgcca gcgtgggcga tagagtgacc 60
attacctgta gagcctctca gagcatctcc tcctacctga actggtatca gcagaaaccc 120
ggcaaggccc ctaagctgct gatctacgcc gctagcagcc tgcagtctgg cgtccccagc 180
cggttcagcg gcagcggatc tggcaccgac ttcaccctga caatcagcag cctgcaacct 240
gaggactttg ctacatacta ctgccagcag gcccacagct ctccaatcac cttcggcggc 300
ggaacaaagg tggaaatcaa gggtggtggg ggcagcggtg gaggtgggag cggaggcggg 360
ggtagcggag gcgggggtag cgaggtgcag ctgctggaaa gcggaggcgg actcgttcaa 420
cctggcggca gcctgagact gagctgcgcc gcttctggat ttaccttcag caactacgcc 480
atgagctggg tgcggcaggc ccctggcaaa ggcctggaat gggtctccgc catcagcggc 540
tctggcggct ccacctacta cgccgacagc gtgaagggca gattcaccat ctctagagat 600
aatagcaaga acaccctgta cctgcagatg aacagcctgc gggccgagga caccgccgtg 660
tactattgtg ctagacccgg agatggctac tacgagggcg tgtacttcga ctactggggc 720
cagggcacac tggtgacagt gtccagcacc acaacacctg ctccaaggcc ccccacaccc 780
gctccaacta tagccagcca accattgagc ctcagacctg aagcttgcag gcccgcagca 840
ggaggcgccg tccatacgcg aggcctggac ttcgcgtgtg atatttatat ttgggcacct 900
ttggccggaa catgtggggt gttgcttctc tcccttgtga tcactctgta ttgtaagcgc 960
gggagaaaga agctcctgta catcttcaag cagcctttta tgcgacctgt gcaaaccact 1020
caggaagaag atgggtgttc atgccgcttc cccgaggagg aagaaggagg gtgtgaactg 1080
agggtgaaat tttctagaag cgccgatgct cccgcatatc agcagggtca gaatcagctc 1140
tacaatgaat tgaatctcgg caggcgagaa gagtacgatg ttctggacaa aagacggggc 1200
agggatcccg agatgggggg aaagccccgg agaaaaaatc ctcaggaggg gttgtacaat 1260
gagctgcaga aggacaagat ggctgaagcc tatagcgaga tcggaatgaa aggcgaaaga 1320
cgcagaggca aggggcatga cggtctgtac cagggtctct ctacagccac caaggacact 1380
tatgatgcgt tgcatatgca agccttgcca ccccgc 1416

SEQ ID NO: 302 moltype = DNA length = 1422
FEATURE Location/Qualifiers
source 1..1422
mol_type = other DNA
organism = synthetic construct
SEQUENCE: 302
gatattcaga tgacccagag cccatctagc ctgagcgcca gcgtgggcga tagagtgacc 60
atcacctgtc aggcctctca ggacatcgct aattacctga actggtatca gcagaaaccc 120
ggcaaggccc ctaagctgct gatctacgac gcctccaacc tggaaaccgg cgtgcccagc 180
cggttcagcg gcagcggatc tggcacagac ttcaccttta ccatcagctc cctccagcct 240
gaggacatcg ccacatacta ctgccagcaa cacttcaacc tgcctctgac cttcggcggc 300
ggaacaaagg tcgagatcaa gggtggtggg ggcagcggtg gaggtgggag cggaggcggg 360
ggtagcggag gcgggggtag ccaaatcacc ctgaaagaga gcggacctac actggtcaag 420
cctacccaga cactgaccct cacatgtaca ttcagcggct ttagcctgag cacctccggc 480
gtgggagtgg gctggatcag acagcccccc ggcaaggccc tggaatggct ggctctgatc 540
tattggaatg acgagaagcg gtacagccct agcctgaaat ctagactgac aatcaccaag 600
gacaccagca agaaccaggt ggtgctgacc atgaccaaca tggatcctgt ggataccgcc 660
gtgtactact gcgccagaga aggctctcac gactacaaga gctccaactg gttcgaccca 720
tggggccagg gcaccctggt tacagtgtct agcaccacaa cacctgctcc aaggcccccc 780
acacccgctc caactatagc cagccaacca ttgagcctca gacctgaagc ttgcaggccc 840
gcagcaggag gcgccgtcca tacgcgaggc ctggacttcg cgtgtgatat ttatatttgg 900
gcacctttgg ccggaacatg tggggtgttg cttctctccc ttgtgatcac tctgtattgt 960
aagcgcggga gaaagaagct cctgtacatc ttcaagcagc cttttatgcg acctgtgcaa 1020
accactcagg aagaagatgg gtgttcatgc cgcttccccg aggaggaaga aggagggtgt 1080
gaactgaggg tgaaattttc tagaagcgcc gatgctcccg catatcagca gggtcagaat 1140
cagctctaca atgaattgaa tctcggcagg cgagaagagt acgatgttct ggacaaaaga 1200
cggggcaggg atcccgagat ggggggaaag ccccggagaa aaaatcctca ggaggggttg 1260
tacaatgagc tgcagaagga caagatggct gaagcctata gcgagatcgg aatgaaaggc 1320
gaaagacgca gaggcaaggg gcatgacggt ctgtaccagg gtctctctac agccaccaag 1380
gacacttatg atgcgttgca tatgcaagcc ttgccacccc gc 1422

SEQ ID NO: 303 moltype = DNA length = 1434
FEATURE Location/Qualifiers
source 1..1434
mol_type = other DNA
organism = synthetic construct
SEQUENCE: 303
gatatcgtga tgacccaatc tccactgagc ctgcctgtga cacctggcga gcctgcttct 60
atcagctgta gaagcagcca gtccctgctg cacagcaacg gctacaacta cctggactgg 120
tatctgcaga aacccggcca gagcccccag ctgctgatct acctcggctc taatcgggcc 180
agcggagtgc ctgatagatt cagcggaagc ggctccggca ccgacttcac cctgaagatc 240
agcagagtgg aagccgagga cgtgggcgtc tactactgca tgcaggccct gggcctgatt 300
acatttggcg gcggaaccaa ggtggaaatc aagggtggtg ggggcagcgg tggaggtggg 360
agcggaggcg gggggtagcgg aggcgggggt agcgaagtgc agctggttga gagcggcggc 420
ggactggtga agcccggagg cagcctcaga ctgagctgtg ctgcttctgg ctttaccttc 480
agctcttata gcatgaactg ggtgcggcag gcccctggca agggcctgga atgggtcagc 540
tccatcagct cttctagcag ctacatctac tacgccgaca gcgtgaaggg cagattcacc 600
atcagcagag ataacgccaa gaacagcctg tacctgcaga tgaatagcct gcgggccgag 660
gacaccgccg tgtactactg cgccagagcc ggcgacacct acagcgccgc cgattactac 720
tacatggacg tgtggggcaa aggaacaacc gtgacagtgt cctccaccac aacacctgct 780
ccaaggcccc ccacacccgc tccaactata gccagccaac cattgagcct cagacctgaa 840
gcttgcaggc ccgcagcagg aggcgccgtc catacgcgag gcctggactt cgcgtgtgat 900
atttatattt gggcaccttt ggccggaaca tgtggggtgt tgcttctctc ccttgtgatc 960

```
actctgtatt gtaagcgcgg gagaaagaag ctcctgtaca tcttcaagca gccttttatg  1020
cgacctgtgc aaaccactca ggaagaagat gggtgttcat gccgcttccc cgaggaggaa  1080
gaaggagggt gtgaactgag ggtgaaattt tctagaagcg ccgatgctcc cgcatatcag  1140
cagggtcaga atcagctcta caatgaattg aatctcggca ggcgagaaga gtacgatgtt  1200
ctggacaaaa gacggggcag ggatcccgag atgggggaa agccccggag aaaaaatcct  1260
caggaggggt tgtacaatga gctgcagaag gacaagatgg ctgaagccta tagcgagatc  1320
ggaatgaaag gcgaaagacg cagaggcaag gggcatgacg gtctgtacca gggtctctct  1380
acagccacca aggacactta tgatgcgttg catatgcaag ccttgccacc ccgc        1434

SEQ ID NO: 304         moltype = DNA  length = 1017
FEATURE                Location/Qualifiers
source                 1..1017
                       mol_type = other DNA
                       organism = synthetic construct
SEQUENCE: 304
gaagtgcaac tgctggaaag cggcggaggc ctggtccagc ccggcggctc tctgcggctc  60
agctgcgccg cttctggatt taccttcggc agcgaggcta tgagctgggt gcggcaggcc  120
cctggaaaag agagagagct ggtgtccgcc atcagcggca gcggcgaggt gacctactac  180
gccgacagcg tgaagggcag attcaccatc tctagagata atagcaagaa caccctgtac  240
ctgcagatga acagcctgag agccgaggac accgccgtgt actattgtca gagactggtg  300
gaagccaagc ggcactgggg ccagggcaca caggttacag tgtccagcac cacaacacct  360
gctccaaggc cccccacacc cgctccaact atagccagcc aaccattgag cctcagacct  420
gaagcttgca ggcccgcagc aggaggcgcc gtccatacgc gaggcctgga cttcgcgtgt  480
gatatttata tttgggcacc tttggccgga acatgtgggg tgttgcttct ctcccttgtg  540
atcactctgt attgtaagcg cgggagaaag aagctcctgt acatcttcaa gcagcctttt  600
atgcgacctg tgcaaaccac tcaggaagaa gatgggtgtt catgccgctt ccccgaggag  660
gaagaaggag ggtgtgaact gagggtgaaa ttttctagaa gcgccgatgc tcccgcatat  720
cagcagggtc agaatcagct ctacaatgaa ttgaatctcg gcaggcgaga agagtacgat  780
gttctggaca aaagacgggg cagggatccc gagatggggg gaaagccccg gagaaaaaat  840
cctcaggagg ggttgtacaa tgagctgcag aaggacaaga tggctgaagc ctatagcgag  900
atcggaatga aaggcgaaag acgcagaggc aaggggcatg acggtctgta ccagggtctc  960
tctacagcca ccaaggacac ttatgatgcg ttgcatatgc aagccttgcc accccgc     1017

SEQ ID NO: 305         moltype = DNA  length = 1017
FEATURE                Location/Qualifiers
source                 1..1017
                       mol_type = other DNA
                       organism = synthetic construct
SEQUENCE: 305
gaagtgcaac tgctggaatc tggcggagga ctggtgcagc ccggcggcag cctgcggctg  60
agctgtgctg cttctggctt taccttcgag tctgaggcca tgagctggta tagacaggcc  120
cctggcaagg aaagagagct ggtcagcgtg atcaccagcg agggctccac ctactacgcc  180
gacagcgtga aaggcagatt cacaatcagc cgggacaata gcaagaacac cctgtacctg  240
cagatgaaca gcctgcgcgc cgaagataca gccgtgtact actgcgccca catcgagtgg  300
gagacaagac tcaactgggg ccagggcacc caggtgaccg tgtccagcac cacaacacct  360
gctccaaggc cccccacacc cgctccaact atagccagcc aaccattgag cctcagacct  420
gaagcttgca ggcccgcagc aggaggcgcc gtccatacgc gaggcctgga cttcgcgtgt  480
gatatttata tttgggcacc tttggccgga acatgtgggg tgttgcttct ctcccttgtg  540
atcactctgt attgtaagcg cgggagaaag aagctcctgt acatcttcaa gcagcctttt  600
atgcgacctg tgcaaaccac tcaggaagaa gatgggtgtt catgccgctt ccccgaggag  660
gaagaaggag ggtgtgaact gagggtgaaa ttttctagaa gcgccgatgc tcccgcatat  720
cagcagggtc agaatcagct ctacaatgaa ttgaatctcg gcaggcgaga agagtacgat  780
gttctggaca aaagacgggg cagggatccc gagatggggg gaaagccccg gagaaaaaat  840
cctcaggagg ggttgtacaa tgagctgcag aaggacaaga tggctgaagc ctatagcgag  900
atcggaatga aaggcgaaag acgcagaggc aaggggcatg acggtctgta ccagggtctc  960
tctacagcca ccaaggacac ttatgatgcg ttgcatatgc aagccttgcc accccgc     1017

SEQ ID NO: 306         moltype = DNA  length = 1023
FEATURE                Location/Qualifiers
source                 1..1023
                       mol_type = other DNA
                       organism = synthetic construct
SEQUENCE: 306
gaggtgcagc tgctggaaag cggaggggc ctggtccaac ccggcgggtc tcttcgccta  60
agctgtgccg cttctggctt caccttcgac gagtacacca tgcactggtt cagacaggcc  120
cccggcaagg agcgcgagtt cgtcagtgca atcagcggag gcggtagcga gacttattac  180
gcggactccg tgaagggccg cttcaccatt agccgcgaca actccaagaa cacgctgtac  240
ctgcagatga attcgctgcg cgccgaagat acggccgtgt actactgtgc cgctggtggg  300
gaggaggctg gcgtgggcta ttggggccag ggcacccagg tcaccgtgtc gtccaccaca  360
acacctgctc caaggccccc cacacccgct ccaactatag ccagccaacc attgagcctc  420
agacctgaag cttgcaggcc cgcagcagga ggcgccgtcc atacgcgagg cctggacttc  480
gcgtgtgata tttatatttg ggcacctttg gccggaacat gtggggtgtt gcttctctcc  540
cttgtgatca ctctgtattg taagcgcggg agaaagaagc tcctgtacat cttcaagcag  600
ccttttatgc gacctgtgca aaccactcag gaagaagatg ggtgttcatg ccgcttcccc  660
gaggaggaag aaggagggtg tgaactgagg gtgaaatttt ctagaagcgc cgatgctccc  720
gcatatcagc agggtcagaa tcagctctac aatgaattga atctcggcag gcgagaagag  780
tacgatgttc tggacaaaag acggggcagg gatcccgaga tggggggaaa gccccggaga  840
aaaaatcctc aggaggggtt gtacaatgag ctgcagaagg acaagatggc tgaagcctat  900
agcgagatcg gaatgaaagg cgaaagacgc agaggcaagg ggcatgacgg tctgtaccag  960
```

```
ggtctctcta cagccaccaa ggacacttat gatgcgttgc atatgcaagc cttgccaccc  1020
cgc                                                                1023

SEQ ID NO: 307          moltype = DNA  length = 1029
FEATURE                 Location/Qualifiers
source                  1..1029
                        mol_type = other DNA
                        organism = synthetic construct
SEQUENCE: 307
gaggtgcagc tgctggagag cggaggcggc ctcgtgcagc caggaggttc cctacgactc  60
tcctgtgccg ccagcggctt caccttcgag gactacgcca tgagttggtt ccgccaggcc  120
ccggggaagg agcgcgaggg cgtgagcgcg atttctggaa agggcggctc cacctattac  180
gcggactccg tgaagggtcg ctttaccatc tctcgcgaca actccaagaa cacgctgtac  240
ctgcagatga atagcctgcg cgctgaggac actgccgtgt actactgtgc tgtcttggac  300
gaggaggccg gcgcagaggg cggctattgg ggccagggta cccaggtcac cgtgtcgtcc  360
accacaacac ctgctccaag gccccccaca cccgctccaa ctatagccag ccaaccattg  420
agcctcagac ctgaagcttg caggcccgca gcaggaggcg ccgtccatac gcgaggcctg  480
gacttcgcgt gtgatattta tatttgggca cctttggccg gaacatgtgg ggtgttgctt  540
ctctcccttg tgatcactct gtattgtaag cgcgggagaa agaagctcct gtacatcttc  600
aagcagcctt ttatgcgacc tgtgcaaacc actcaggaag aagatgggtg ttcatgccgc  660
ttccccgagg aggaagaagg agggtgtgaa ctgagggtga aattttctag aagcgccgat  720
gctcccgcat atcagcaggg tcagaatcag ctctacaatg aattgaatct cggcaggcga  780
gaagagtacg atgttctgga caaaagacgg ggcagggatc ccgagatggg gggaaagccc  840
cggagaaaaa atcctcagga ggggttgtac aatgagctgc agaaggacaa gatggctgaa  900
gcctatagcg agatcggaat gaaaggcgaa agacgcagag gcaaggggca tgacggtctg  960
taccagggtc tctctacagc caccaaggac acttatgatg cgttgcatat gcaagccttg  1020
ccaccccgc                                                          1029

SEQ ID NO: 308          moltype = DNA  length = 1029
FEATURE                 Location/Qualifiers
source                  1..1029
                        mol_type = other DNA
                        organism = synthetic construct
SEQUENCE: 308
gaggtgcaac tgctggaaag cggcggtgga ctggtgcagc ccggcggcag cctgagactg  60
tcttgtgctg cttctggatt tacattcgac agatacgcca tgagctggtt ccgccaggcc  120
cctggcaaag agcgggaagg cgtgtccgcc atctccacaa gcggagatag cacatactat  180
gccgacagcg tgaagggcag attcaccatc agcagagata atagcaagaa caccctgtac  240
ctgcagatga acagcctccg ggccgaggac accgccgtct actactgcgc cgtgctggac  300
gaggaagccg gcgccgaggg cggctactgg ggccagggca cccaggtgac cgtgtctagc  360
accacaacac ctgctccaag gccccccaca cccgctccaa ctatagccag ccaaccattg  420
agcctcagac ctgaagcttg caggcccgca gcaggaggcg ccgtccatac gcgaggcctg  480
gacttcgcgt gtgatattta tatttgggca cctttggccg gaacatgtgg ggtgttgctt  540
ctctcccttg tgatcactct gtattgtaag cgcgggagaa agaagctcct gtacatcttc  600
aagcagcctt ttatgcgacc tgtgcaaacc actcaggaag aagatgggtg ttcatgccgc  660
ttccccgagg aggaagaagg agggtgtgaa ctgagggtga aattttctag aagcgccgat  720
gctcccgcat atcagcaggg tcagaatcag ctctacaatg aattgaatct cggcaggcga  780
gaagagtacg atgttctgga caaaagacgg ggcagggatc ccgagatggg gggaaagccc  840
cggagaaaaa atcctcagga ggggttgtac aatgagctgc agaaggacaa gatggctgaa  900
gcctatagcg agatcggaat gaaaggcgaa agacgcagag gcaaggggca tgacggtctg  960
taccagggtc tctctacagc caccaaggac acttatgatg cgttgcatat gcaagccttg  1020
ccaccccgc                                                          1029

SEQ ID NO: 309          moltype = DNA  length = 1032
FEATURE                 Location/Qualifiers
source                  1..1032
                        mol_type = other DNA
                        organism = synthetic construct
SEQUENCE: 309
gaggtgcaac tgctggaaag cggcggagga ctcgtccagc ccggcggcag cctgcggctg  60
agctgtgctg cttctggatt taccttcgcc agcgacgcca tgagctggta tagacaggcc  120
cctggcaaag agcgggaact ggtgtccgcc atcagcggct ctggcggctc cacctactac  180
gccgatagcg tgaagggcag attcacaatc tctagagata atagcaagaa caccctgtac  240
ctgcagatga acagcctgag agccgaggac accgccgtgt actactgcgc cgctcacgac  300
agcggcgagg cctacctggc cttcgactac tggggccagg gcacacaggt gaccgtgtct  360
agcaccacaa cacctgctcc aaggccccccc acacccgctc caactatagc cagccaacca  420
ttgagcctca gacctgaagc ttgcaggccc gcagcaggag gcgccgtcca tacgcgaggc  480
ctggacttcg cgtgtgatat ttatatttgg gcacctttgg ccggaacatg tggggtgttg  540
cttctctccc ttgtgatcac tctgtattgt aagcgcggga gaaagaagct cctgtacatc  600
ttcaagcagc cttttatgcg acctgtgcaa accactcagg aagaagatgg gtgttcatgc  660
cgcttccccg aggaggaaga aggagggtgt gaactgaggg tgaaattttc tagaagcgcc  720
gatgctcccg catatcagca gggtcagaat cagctctaca atgaattgaa tctcggcagg  780
cgagaagagt acgatgttct ggacaaaaga cggggcaggg atcccgagat gggggggaaag  840
ccccggagaa aaaatcctca ggaggggttg tacaatgagc tgcagaagga caagatggct  900
gaagcctata gcgagatcgg aatgaaaggc gaaagacgca gaggcaaggg gcatgacggt  960
ctgtaccagg gtctctctac agccaccaag gacacttatg atgcgttgca tatgcaagcc  1020
ttgccacccc gc                                                      1032

SEQ ID NO: 310          moltype = DNA  length = 1032
```

```
FEATURE                Location/Qualifiers
source                 1..1032
                       mol_type = other DNA
                       organism = synthetic construct
SEQUENCE: 310
gaggtgcaac tgctggaaag cggcggagga ctcgtccagc ccggcggcag cctgaggctg  60
agctgtgctg cttctggctt taccttcgac tcctacacaa tgagctggta tagacaggcc  120
cctggcaagg agcgggaact ggtgtccgcc atcagcggcc acggcgactc tacatactac  180
gccgacagcg tgaaaggcag attcacaatc tctagagata atagcaagaa caccctgtac  240
ctgcagatga acagcctgcg ggccgaggac accgccgtgt actactgcac cagaatcagc  300
atcaccaccg agtggctggc cggagattac tggggccagg gcacccaggt gacagtgtcc  360
agcaccacaa cacctgctcc aaggcccccc acacccgctc caactatagc cagccaacca  420
ttgagcctca gacctgaagc ttgcaggccc gcagcaggag gcgccgtcca tacgcgaggc  480
ctggacttcg cgtgtgatat ttatatttgg gcacctttgg ccggaacatg tggggtgttg  540
cttctctccc ttgtgatcac tctgtattgt aagcgcggga gaaagaagct cctgtacatc  600
ttcaagcagc cttttatgcg acctgtgcaa accactcagg aagaagatgg gtgttcatgc  660
cgcttccccg aggaggaaga aggagggtgt gaactgaggg tgaaattttc tagaagcgcc  720
gatgctcccg catatcagca gggtcagaat cagctctaca atgaattgaa tctcggcagg  780
cgagaagagt acgatgttct ggacaaaaga cggggcaggg atcccgagat ggggggaaag  840
ccccggagaa aaaatcctca ggagggggttg tacaatgagc tgcagaagga caagatggct  900
gaagcctata gcgagatcgg aatgaaaggc gaaagacgca gaggcaaggg gcatgacggt  960
ctgtaccagg gtctctctac agccaccaag gacacttatg atgcgttgca tatgcaagcc  1020
ttgccacccc gc                                                      1032

SEQ ID NO: 311         moltype = DNA  length = 1038
FEATURE                Location/Qualifiers
source                 1..1038
                       mol_type = other DNA
                       organism = synthetic construct
SEQUENCE: 311
gaggtgcagc tgctggaaag cggaggaggc ctggtccaac ctggcggcag cctgcggctg  60
agctgcgccg cttctggctt caccttcagc agctacgcca tgagctggtt ccggcaggcc  120
cctggcaagg aaagagagtt cgtgtctttt atcagcggat ctggcgactc cacctactac  180
gctgatagcg tgaaaggcag atttaccatc tctagagata atagcaagaa caccctgtac  240
ctccagatga acagcctgcg cgccgaggac acagccgtgt actattgtac cagatggcct  300
tacgacttcg aggaaccaag cgagcccggc gtgtactggg gccagggcac acaggtgaca  360
gtgtcctcca ccacaacacc tgctccaagg ccccccacac ccgctccaac tatagccagc  420
caaccattga gcctcagacc tgaagcttgc aggcccgcag caggaggcgc cgtccatacg  480
cgaggcctgg acttcgcgtg tgatatttat atttgggcac ctttggccgg aacatgtggg  540
gtgttgcttc tctcccttgt gatcactctg tattgtaagc gcgggagaaa gaagctcctg  600
tacatcttca agcagccttt tatgcgacct gtgcaaacca ctcaggaaga agatgggtgt  660
tcatgccgct tccccgagga ggaagaagga gggtgtgaac tgagggtgaa attttctaga  720
agcgccgatg ctcccgcata tcagcagggt cagaatcagc tctacaatga attgaatctc  780
ggcaggcgag aagagtacga tgttctggac aaaagacggg gcagggatcc cgagatgggg  840
ggaaagcccc ggagaaaaaa tcctcaggag ggttgtaca atgagctgca gaaggacaag  900
atggctgaag cctatagcga gatcggaatg aaaggcgaaa gacgcagagg caaggggcat  960
gacggtctgt accagggtct ctctacagcc accaaggaca cttatgatgc gttgcatatg  1020
caagccttgc caccccgc                                                1038

SEQ ID NO: 312         moltype = DNA  length = 1038
FEATURE                Location/Qualifiers
source                 1..1038
                       mol_type = other DNA
                       organism = synthetic construct
SEQUENCE: 312
gaggtgcagc tgctggaaag cggcggaggc ctggtgcaac ctggcggatc tctcagactg  60
agctgtgctg cttctggctt cacattcacc gactacgaca tgagctggta tagacaggcc  120
cctggaaaag agcgggaact ggtctccgtg atccacagcg gcggctccac ctactacgcc  180
gatagcgtga agggcagatt caccatcagc agagataata gcaagaacac cctgtacctg  240
cagatgaaca gcctgcgggc cgaggacacc gccgtgtact actgcgcccc cggctactac  300
agcgacctgt cttttgatta ttacaacttc gactactggg gccagggcac acaggtgaca  360
gtgtccagca ccacaacacc tgctccaagg ccccccacac ccgctccaac tatagccagc  420
caaccattga gcctcagacc tgaagcttgc aggcccgcag caggaggcgc cgtccatacg  480
cgaggcctgg acttcgcgtg tgatatttat atttgggcac ctttggccgg aacatgtggg  540
gtgttgcttc tctcccttgt gatcactctg tattgtaagc gcgggagaaa gaagctcctg  600
tacatcttca agcagccttt tatgcgacct gtgcaaacca ctcaggaaga agatgggtgt  660
tcatgccgct tccccgagga ggaagaagga gggtgtgaac tgagggtgaa attttctaga  720
agcgccgatg ctcccgcata tcagcagggt cagaatcagc tctacaatga attgaatctc  780
ggcaggcgag aagagtacga tgttctggac aaaagacggg gcagggatcc cgagatgggg  840
ggaaagcccc ggagaaaaaa tcctcaggag ggttgtaca atgagctgca gaaggacaag  900
atggctgaag cctatagcga gatcggaatg aaaggcgaaa gacgcagagg caaggggcat  960
gacggtctgt accagggtct ctctacagcc accaaggaca cttatgatgc gttgcatatg  1020
caagccttgc caccccgc                                                1038

SEQ ID NO: 313         moltype = DNA  length = 1038
FEATURE                Location/Qualifiers
source                 1..1038
                       mol_type = other DNA
                       organism = synthetic construct
```

```
SEQUENCE: 313
gaggtgcagc tgctggagag cggtggaggg ttggtgcagc ccgggggtag cctgcgtctg  60
tcgtgcgccg cttccggctt cacgttctct gattacgcca tgcactggtt ccggcaggcc  120
cccggtaagg agcgcgtgct ggtgtcgtct attgactccg gcggctccac ttactacgca  180
gacagtgtca agggccgttt caccatcagc cgcgacaaca gcaagaacac gctgtacctg  240
cagatgaact cccttcgagc agaggacacc gcggtgtact actgtaatgc gggcttcaag  300
ggcgatcacc cccaccccaa ggatgccttc gacatttggg gccagggcac ccaggtcacc  360
gtgtcgtcca ccacaacacc tgctccaagg ccccccacac ccgctccaac tatagccagc  420
caaccattga gcctcagacc tgaagcttgc aggcccgcag caggaggcgc cgtccatacg  480
cgaggcctgg acttcgcgtg tgatatttat atttgggcac ctttggccgg aacatgtggg  540
gtgttgcttc tctcccttgt gatcactctg tattgtaagc gcgggagaaa gaagctcctg  600
tacatcttca agcagccttt tatgcgacct gtgcaaacca ctcaggaaga agatgggtgt  660
tcatgccgct tccccgagga ggaagaagga gggtgtgaac tgagggtgaa attttctaga  720
agcgccgatg ctcccgcata tcagcagggt cagaatcagc tctacaatga attgaatctc  780
ggcaggcgag aagagtacga tgttctggac aaaagacggg gcagggatcc cgagatgggg  840
ggaaagcccc ggagaaaaaa tcctcaggag gggttgtaca atgagctgca gaaggacaag  900
atggctgaag cctatagcga gatcggaatg aaaggcgaaa gacgcagagg caaggggcat  960
gacggtctgt accagggtct ctctacagcc accaaggaca cttatgatgc gttgcatatg  1020
caagccttgc caccccgc                                                1038

SEQ ID NO: 314          moltype = DNA  length = 1044
FEATURE                 Location/Qualifiers
source                  1..1044
                        mol_type = other DNA
                        organism = synthetic construct
SEQUENCE: 314
gaggtgcaac tgctggaatc cggcggaggc ctggtgcagc ccggcggcag cctcagactg  60
agctgtgccg cttctggctt taccttcagc agcgagggca tgagctgggt gcggcaggcc  120
cctggcaagg aaagagagct ggtctccgcc atcagcggat ctggcgacca cacctactat  180
gccgatagcg tgcgcggaag attcacaatc tctagagata atagcaagaa caccctgtac  240
ctgcagatga acagcctgcg ggccgaggac accgccgtgt actactgcaa cgccctggaa  300
ggcggcccta caacagctat ccagccagga ggccctgact actggggcca gggcacccag  360
gtgaccgtgt ccagcaccac aacacctgct ccaaggcccc ccacacccgc tccaactata  420
gccagccaac cattgagcct cagacctgaa gcttgcaggc ccgcagcagg aggcgccgtc  480
catacgcgag gcctggactt cgcgtgtgat atttatattt gggcaccttt ggccggaaca  540
tgtggggtgt tgcttctctc ccttgtgatc actctgtatt gtaagcgcgg gagaaagaag  600
ctcctgtaca tcttcaagca gccttttatg cgacctgtgc aaaccactca ggaagaagat  660
gggtgttcat gccgcttccc cgaggaggaa gaaggagggt gtgaactgag ggtgaaattt  720
tctagaagcg ccgatgctcc cgcatatcag cagggtcaga atcagctcta caatgaattg  780
aatctcggca ggcgagaaga gtacgatgtt ctggacaaaa gacggggcag ggatcccgag  840
atggggggaa agccccggag aaaaaatcct caggaggggt tgtacaatga gctgcagaag  900
gacaagatgg ctgaagccta tagcgagatc ggaatgaaag gcgaaagacg cagaggcaag  960
gggcatgacg gtctgtacca gggtctctct acagccacca aggacactta tgatgcgttg  1020
catatgcaag ccttgccacc ccgc                                         1044

SEQ ID NO: 315          moltype = DNA  length = 592
FEATURE                 Location/Qualifiers
source                  1..592
                        mol_type = other DNA
                        organism = synthetic construct
SEQUENCE: 315
aatcaacctc tggattacaa aatttgtgaa agattgactg gtattcttaa ctatgttgct  60
ccttttacgc tatgtggata cgctgcttta atgcctttgt atcatgctat tgcttcccgt  120
atggctttca ttttctcctc cttgtataaa tcctggttgc tgtctcttta tgaggagttg  180
tggcccgttg tcaggcaacg tggcgtggtg tgcactgtgt ttgctgacgc aacccccact  240
ggttggggca ttgccaccac ctgtcagctc ctttccggga ctttcgcttt ccccctccct  300
attgccacgg cggaactcat cgccgcctgc cttgcccgct gctggacagg ggctcggctg  360
ttgggcactg acaattccgt ggtgttgtcg gggaagctga cgtcctttcc atggctgctc  420
gcctgtgttg ccacctggat tctgcgcggg acgtccttct gctacgtccc ttcggccctc  480
aatccagcgg accttccttc ccgcggcctg ctgccggctc tgcggcctct tccgcgtctt  540
cgccttcgcc ctcagacgag tcggatctcc ctttgggccg cctccccgcc tg          592

SEQ ID NO: 316          moltype = DNA  length = 592
FEATURE                 Location/Qualifiers
source                  1..592
                        mol_type = other DNA
                        organism = synthetic construct
SEQUENCE: 316
aatcaacctc tggattacaa aatttgtgaa agattgactg gtattcttaa ctatgttgct  60
ccttttacgc tatgtggata cgctgcttta atgcctttgt atcatgctat tgcttcccgt  120
atggctttca ttttctcctc cttgtataaa tcctggttgc tgtctcttta tgaggagttg  180
tggcccgttg tcaggcaacg tggcgtggtg tgcactgtgt ttgctgacgc aacccccact  240
ggttggggca ttgccaccac ctgtcagctc ctttccggga ctttcgcttt ccccctccct  300
attgccacgg cggaactcat cgccgcctgc cttgcccgct gctggacagg ggctcggctg  360
ttgggcactg acaattccgt ggtgttgtcg gggaaggtct gctgagactc ggggctgctc  420
gcctgtgttg ccacctggat tctgcgcggg acgtccttct gctacgtccc ttcggccctc  480
aatccagcgg accttccttc ccgcggcctg ctgccggctc tgcggcctct tccgcgtctt  540
cgccttcgcc ctcagacgag tcggatctcc ctttgggccg cctccccgcc tg          592
```

```
SEQ ID NO: 317          moltype = DNA  length = 389
FEATURE                 Location/Qualifiers
source                  1..389
                        mol_type = other DNA
                        organism = synthetic construct
SEQUENCE: 317
aatcaacctc tggattacaa aatttgtgaa agattgactg atattcttaa ctatgttgct  60
ccttttacgc tgtgtggata tgctgcttta atgcctctgt atcatgctat tgcttcccgt  120
acggctttcg ttttctcctc cttgtataaa tcctggttgc tgtctcttta tgaggagttg  180
tggcccgttg tccgtcaacg tggcgtggtg tgctctgtgt ttgctgacgc aacccccact  240
ggctggggca ttgccaccac ctgtcaactc ctttctggga ctttcgcttt ccccctcccg  300
atcgccacgg cagaactcat cgccgcctgc cttgcccgct gctggacagg ggctaggttg  360
ctgggcactg ataattccgt ggtgttgtc                                    389

SEQ ID NO: 318          moltype = DNA  length = 584
FEATURE                 Location/Qualifiers
source                  1..584
                        mol_type = other DNA
                        organism = synthetic construct
SEQUENCE: 318
gcgttacata acttacggta aatggcccgc ctggctgacc gcccaacgac ccccgcccat  60
tgacgtcaat aatgacgtat gttcccatag taacgccaat agggactttc cattgacgtc  120
aatgggtgga gtatttacgg taaactgccc acttggcagt acatcaagtg tatcatatgc  180
caagtacgcc ccctattgac gtcaatgacg gtaaatggcc cgcctggcat tatgcccagt  240
acatgacctt atgggacttt cctacttggc agtacatcta cgtattagtc atcgctatta  300
ccatggtcga ggtgagcccc acgttctgct tcactctccc catctccccc ccctccccac  360
ccccaatttt gtatttattt atttttaat tattttgtgc agcgatgggg gcgggggggg  420
gggggggcg cgcgccaggc ggggcggggc ggggcgaggg gcggggcggg gcgaggcgga  480
gaggtgcggc ggcagccaat cagagcggcg cgctccgaaa gtttcctttt atggcgaggc  540
ggcggcggcg gcggccctat aaaaagcgaa gcgcgcggcg ggcg                   584

SEQ ID NO: 319          moltype = DNA  length = 1184
FEATURE                 Location/Qualifiers
source                  1..1184
                        mol_type = other DNA
                        organism = synthetic construct
SEQUENCE: 319
cgtgaggctc cggtgcccgt cagtgggcag agcgcacatc gcccacagtc cccgagaagt  60
tggggggagg ggtcggcaat tgaaccggtg cctagagaag gtggcgcggg gtaaactggg  120
aaagtgatgt cgtgtactgg ctccgccttt ttcccgaggg tgggggagaa ccgtatataa  180
gtgcagtagt cgccgtgaac gttctttttc gcaacgggtt tgccgccaga acacaggtaa  240
gtgccgtgtg tggttcccgc gggcctggcc tctttacggg ttatggccct tgcgtgcctt  300
gaattacttc cacctggctg cagtacgtga ttcttgatcc cgagcttcgg gttggaagtg  360
ggtgggagag ttcgaggcct tgcgcttaag gagccccttc gcctcgtgct tgagttgagg  420
cctggcctgg gcgctggggc cgccgcgtgc gaatctggtg gcaccttcgc gcctgtctcg  480
ctgctttcga taagtctcta gccatttaaa atttttgatg acctgctgcg acgctttttt  540
tctggcaaga tagtcttgta aatgcgggcc aagatctgca cactggtatt tcggtttttg  600
gggccgcggg cggcgacggg gcccgtgcgt cccagcgcac atgttcggcg aggcggggcc  660
tgcgagcgcg gccaccgaga atcggacggg ggtagtctca agctggccgg cctgctctgg  720
tgcctggcct cgcgccgccg tgtatcgccc cgccctgggc ggcaaggctg gcccggtcgg  780
caccagttgc gtgagcggaa agatggccgc ttcccggccc tgctgcaggg agctcaaaat  840
ggaggacgcg gcgctcggga gagcgggcgg gtgagtcacc cacacaaagg aaaagggcct  900
ttccgtcctc agccgtcgct tcatgtgact ccacggagta ccgggcgccg tccaggcacc  960
tcgattagtt ctcgagcttt tggagtacgt cgtctttagg ttggggggag gggttttatg  1020
cgatggagtt tccccacact gagtgggtgg agactgaagt taggccagct tggcacttga  1080
tgtaattctc cttggaattt gcccttttg agtttggatc ttggttcatt ctcaagcctc  1140
agacagtggt tcaaagtttt tttcttccat ttcaggtgtc gtga                   1184

SEQ ID NO: 320          moltype = DNA  length = 388
FEATURE                 Location/Qualifiers
source                  1..388
                        mol_type = other DNA
                        organism = synthetic construct
SEQUENCE: 320
aatgaaagac cccacctgta ggtttggcaa gctaggatca aggttaggaa cagagagaca  60
gcagaatatg ggccaaacag gatatctgtg gtaagcagtt cctgccccgg ctcagggcca  120
agaacagttg gaacagcaga atatgggcca aacaggatat ctgtggtaag cagttcctgc  180
cccggctcag ggccaagaac agatggtccc cagatgcggt cccgccctca gcagtttcta  240
gagaaccatc agatgtttcc agggtgcccc aaggacctga aatgaccctg tgccttattt  300
gaactaacca atcagttcgc ttctcgcttc tgttcgcgcg cttctgctcc ccgagctcaa  360
taaaagagcc cacaacccct cactcggc                                     388

SEQ ID NO: 321          moltype = DNA  length = 500
FEATURE                 Location/Qualifiers
source                  1..500
                        mol_type = other DNA
                        organism = synthetic construct
SEQUENCE: 321
gggtagggga ggcgcttttc ccaaggcagt ctggagcatg cgctttagca gccccgctgg  60
```

```
gcacttggcg ctacacaagt ggcctctggc ctcgcacaca ttccacatcc accggtaggc  120
gccaaccggc tccgttcttt ggtggcccct tcgcgccacc ttctactcct cccctagtca  180
ggaagttccc cccgccccg cagctcgcgt cgtgcaggac gtgacaaatg gaagtagcac  240
gtctcactag tctcgtgcag atggacagca ccgctgagca atggaagcgg gtaggccttt  300
ggggcagcgg ccaatagcag ctttgctcct tcgctttctg ggctcagagg ctgggaaggg  360
gtgggtccgg gggcgggctc aggggcgggc tcaggggcgg ggcgggcgcc cgaaggtcct  420
ccggaggccc ggcattctgc acgcttcaaa agcgcacgtc tgccgcgctg ttctcctctt  480
cctcatctcc gggcctttcg                                              500
```

```
SEQ ID NO: 322          moltype = DNA  length = 443
FEATURE                 Location/Qualifiers
source                  1..443
                        mol_type = other DNA
                        organism = synthetic construct
SEQUENCE: 322
tgaaagaccc cacctgtagg tttggcaaga tagctgcagt aacgccattt tgcaaggcat  60
ggaaaaaatac caaaccaaga atagagaagt tcagatcaag ggcgggtaca tgaaaatagc  120
taacgttggg ccaaacagga tatctgcggt gagcagtttc ggccccggcc cggggccaag  180
aacagatggt caccgcagtt tcggccccgg cccgaggcca agaacagatg gtccccagat  240
atggcccaac cctcagcagt ttcttaagac ccatcagatg tttccaggct cccccaagga  300
cctgaaatga ccctgcgcct tatttgaatt aaccaatcag cctgcttctc gcttctgttc  360
gcgcgcttct gcttcccgag ctctataaaa gagctcacaa cccctcactc ggcgcgccag  420
tcctccgatt gactgagtcg ccc                                          443
```

```
SEQ ID NO: 323          moltype = DNA  length = 1212
FEATURE                 Location/Qualifiers
source                  1..1212
                        mol_type = other DNA
                        organism = synthetic construct
SEQUENCE: 323
ggcctccgcg ccgggttttg gcgcctcccg cgggcgcccc cctcctcacg gcgagcgctg  60
ccacgtcaga cgaagggcgc agcgagcgtc ctgatccttc cgcccggacg ctcaggacag  120
cggcccgctg ctcataagac tcggccttag aaccccagta tcagcagaag gacattttag  180
gacgggactt gggtgactct agggcactgg ttttctttcc agagagcgga acaggcgagg  240
aaaagtagtc ccttctcggc gattctgcgg agggatctcc gtggggcggt gaacgccgat  300
gattatataa ggacgcgccg ggtgtggcac agctagttcc gtcgcagccg ggatttgggt  360
cgcggttctt gtttgtggat cgctgtgatc gtcacttggt gagtagcggg ctgctgggct  420
ggccggggct ttcgtggccg ccgggccgct cggtgggacg gaagcgtgtg gagagaccgc  480
caagggctgt agtctgggtc cgcgagcaag gttgccctga actgggggtt ggggggagcg  540
cagcaaaatg gcggctgttc ccgagtcttg aatggaagac gcttgtgagg cgggctgtga  600
ggtcgttgaa acaaggtggg gggcatggtg ggcggcaaga acccaaggtc ttgaggcctt  660
cgctaatgcg ggaaagctct tattcgggtg agatgggctg gggcaccatc tggggaccct  720
gacgtgaagt ttgtcactga ctggagaact cggtttgtcg tctgttgcgg gggcggcagt  780
tatggcggtg ccgttgggca gtgcacccgt acctttggga gcgcgcgccc tcgtcgtgtc  840
gtgacgtcac ccgttctgtt ggcttataat gcagggtggg gccacctgcc ggtaggtgtg  900
cggtaggctt ttctccgtcg caggacgcag ggttcgggcc tagggtaggc tctcctgaat  960
cgacaggcgc cggacctctg gtgaggggag ggataagtga ggcgtcagtt tctttggtcg  1020
gttttatgta cctatcttct taagtagctg aagctccggt tttgaactat gcgctcgggg  1080
ttggcgagtg tgttttgtga agttttttag gcaccttttg aaatgtaatc atttgggtca  1140
atatgtaatt ttcagtgtta gactagtaaa ttgtccgcta aattctggcc gtttttggct  1200
tttttgttag ac                                                      1212
```

```
SEQ ID NO: 324          moltype = AA  length = 310
FEATURE                 Location/Qualifiers
source                  1..310
                        mol_type = protein
                        organism = synthetic construct
SEQUENCE: 324
DVQLVQSGAE VKKPGASVKV SCKASGYTFT RYTMHWVRQA PGQGLEWIGY INPSRGYTNY  60
ADSVKGRFTI TTDKSTSTAY MELSSLRSED TATYYCARYY DDHYCLDYWG QGTTVTVSSS  120
GGGGSGGGGS GGGGSDIVLT QSPATLSLSP GERATLSCRA SQSVSYMNWY QQKPGKAPKR  180
WIYDTSKVAS GVPARFSGSG SGTDYSLTIN SLEAEDAATY YCQQWSSNPL TFGGGTKVEI  240
KTTTPAPRPP TPAPTIASQP LSLRPEACRP AAGGAVHTRG LDFACDIYIW APLAGTCGVL  300
LLSLVITLYC                                                         310
```

```
SEQ ID NO: 325          moltype = AA  length = 310
FEATURE                 Location/Qualifiers
source                  1..310
                        mol_type = protein
                        organism = synthetic construct
SEQUENCE: 325
DVQLVQSGAE VKKPGASVKV SCKASGYTFT RYTMHWVRQA PGQGLEWIGY INPSRGYTNY  60
ADSVKGRFTI TTDKSTSTAY MELSSLRSED TATYYCARYY DDPYCLDYWG QGTTVTVSSS  120
GGGGSGGGGS GGGGSDIVLT QSPATLSLSP GERATLSCRA SQSVSYMNWY QQKPGKAPKR  180
WIYDTSKVAS GVPARFSGSG SGTDYSLTIN SLEAEDAATY YCQQWSSNPL TFGGGTKVEI  240
KTTTPAPRPP TPAPTIASQP LSLRPEACRP AAGGAVHTRG LDFACDIYIW APLAGTCGVL  300
LLSLVITLYC                                                         310
```

```
SEQ ID NO: 326          moltype = AA  length = 311
```

```
FEATURE                Location/Qualifiers
source                 1..311
                       mol_type = protein
                       organism = synthetic construct
SEQUENCE: 326
DVQLVQSGAE VKKPGASVKV SCKASGYTFT RYTMHWVRQA PGQGLEWIGY INPSRGYTNY  60
ADSVKGRFTI TTDKSTSTAY MELSSLRSED TATYYCARYY NDQYCLDYWG QGTTVTVSSS  120
SGGGGSGGGG SGGGGSDIVL TQSPATLSLS PGERATLSCR ASQSVSYMNW YQQKPGKAPK  180
RWIYDTSKVA SGVPARFSGS GSGTDYSLTI NSLEAEDAAT YYCQQWSSNP LTFGGGTKVE  240
IKTTTPAPRP PTPAPTIASQ PLSLRPEACR PAAGGAVHTR GLDFACDIYI WAPLAGTCGV  300
LLLSLVITLY C                                                       311

SEQ ID NO: 327         moltype = AA  length = 310
FEATURE                Location/Qualifiers
source                 1..310
                       mol_type = protein
                       organism = synthetic construct
SEQUENCE: 327
DVQLVQSGAE VKKPGASVKV SCKASGYTFT RYTMHWVRQA PGQGLEWIGY INPSRGYTNY  60
ADSVKGRFTI TTDKSTSTAY MELSSLRSED TATYYCARYY DAHNCLDYWG QGTTVTVSSS  120
GGGGSGGGGS GGGGSDIVLT QSPATLSLSP GERATLSCRA SQSVSYMNWY QQKPGKAPKR  180
WIYDTSKVAS GVPARFSGSG SGTDYSLTIN SLEAEDAATY YCQQWSSNPL TFGGGTKVEI  240
KTTTPAPRPP TPAPTIASQP LSLRPEACRP AAGGAVHTRG LDFACDIYIW APLAGTCGVL  300
LLSLVITLYC                                                         310

SEQ ID NO: 328         moltype = AA  length = 310
FEATURE                Location/Qualifiers
source                 1..310
                       mol_type = protein
                       organism = synthetic construct
SEQUENCE: 328
DVQLVQSGAE VKKPGASVKV SCKASGYTFT RYTMHWVRQA PGQGLEWIGY INPSRGYTNY  60
ADSVKGRFTI TTDKSTSTAY MELSSLRSED TATYYCARYS DDHYCLDYWG QGTTVTVSSS  120
GGGGSGGGGS GGGGSDIVLT QSPATLSLSP GERATLSCRA SQSVSYMNWY QQKPGKAPKR  180
WIYDTSKVAS GVPARFSGSG SGTDYSLTIN SLEAEDAATY YCQQWSSNPL TFGGGTKVEI  240
KTTTPAPRPP TPAPTIASQP LSLRPEACRP AAGGAVHTRG LDFACDIYIW APLAGTCGVL  300
LLSLVITLYC                                                         310

SEQ ID NO: 329         moltype = AA  length = 310
FEATURE                Location/Qualifiers
source                 1..310
                       mol_type = protein
                       organism = synthetic construct
SEQUENCE: 329
DVQLVQSGAE VKKPGASVKV SCKASGYTFT RYTMHWVRQA PGQGLEWIGY INPSRGYTNY  60
ADSVKGRFTI TTDKSTSTAY MELSSLRSED TATYYCARYS DDRYCLDYWG QGTTVTVSSS  120
GGGGSGGGGS GGGGSDIVLT QSPATLSLSP GERATLSCRA SQSVSYMNWY QQKPGKAPKR  180
WIYDTSKVAS GVPARFSGSG SGTDYSLTIN SLEAEDAATY YCQQWSSNPL TFGGGTKVEI  240
KTTTPAPRPP TPAPTIASQP LSLRPEACRP AAGGAVHTRG LDFACDIYIW APLAGTCGVL  300
LLSLVITLYC                                                         310

SEQ ID NO: 330         moltype = AA  length = 311
FEATURE                Location/Qualifiers
source                 1..311
                       mol_type = protein
                       organism = synthetic construct
SEQUENCE: 330
DVQLVQSGAE VKKPGASVKV SCKASGYTFT RYTMHWVRQA PGQGLEWIGY INPSRGYTNY  60
ADSVKGRFTI TTDKSTSTAY MELSSLRSED TATYYCARYY DDNYCLDYWG QGTTVTVSSS  120
SGGGGSGGGG SGGGGSDIVL TQSPATLSLS PGERATLSCR ASQSVSYMNW YQQKPGKAPK  180
RWIYDTSKVA SGVPARFSGS GSGTDYSLTI NSLEAEDAAT YYCQQWSSNP LTFGGGTKVE  240
IKTTTPAPRP PTPAPTIASQ PLSLRPEACR PAAGGAVHTR GLDFACDIYI WAPLAGTCGV  300
LLLSLVITLY C                                                       311

SEQ ID NO: 331         moltype = AA  length = 310
FEATURE                Location/Qualifiers
source                 1..310
                       mol_type = protein
                       organism = synthetic construct
SEQUENCE: 331
DVQLVQSGAE VKKPGASVKV SCKASGYTFT RYTMHWVRQA PGQGLEWIGY INPSRGYTNY  60
ADSVKGRFTI TTDKSTSTAY MELSSLRSED TATYYCARYY DDQYCLDYWG QGTTVTVSSS  120
GGGGSGGGGS GGGGSDIVLT QSPATLSLSP GERATLSCRA SQSVSYMNWY QQKPGKAPKR  180
WIYDTSKVAS GVPARFSGSG SGTDYSLTIN SLEAEDAATY YCQQWSSNPL TFGGGTKVEI  240
KTTTPAPRPP TPAPTIASQP LSLRPEACRP AAGGAVHTRG LDFACDIYIW APLAGTCGVL  300
LLSLVITLYC                                                         310

SEQ ID NO: 332         moltype = AA  length = 495
FEATURE                Location/Qualifiers
```

```
source                1..495
                      mol_type = protein
                      organism = synthetic construct
SEQUENCE: 332
KFTIVFPHNQ KGNWKNVPSN YHYCPSSSDL NWHNDLIGTA IQVKMPQSHK AIQADGWMCH  60
ASKWVTTCDF RWYGPKYITQ SIRSFTPSVE QCKESIEQTK QGTWLNPGFP PQSCGYATVT  120
DAEAVIVQVT PHHVLVDEYT GEWVDSQFIN GKCSNYICPT VHNSTTWHSD YKVKGLCDSN  180
LISMDITFFS EDGELSSLGK EGTGFRSNYF AYETGGKACK MQYCKHWGVR LPSGVWFEMA  240
DKDLFAAARF PECPEGSSIS APSQTSVDVS LIQDVERILD YSLCQETWSK IRAGLPISPV  300
DLSYLAPKNP GTGPAFTIIN GTLKYFETRY IRVDIAAPIL SRMVGMISGT TTEAELWDDW  360
APYEDVEIGP NGVLRTSSGY KFPLYMIGHG MLDSDLHLSS KAQVFEHPHI QDAASQLPDD  420
ESLFFGDTGL SKNPIELVEG WFSSWKSSIA SFFFIIGLII GLFLVLRVGI HLCIKLKHTK  480
KRQIYTDIEM NRLGK                                                 495

SEQ ID NO: 333        moltype = AA  length = 495
FEATURE               Location/Qualifiers
source                1..495
                      mol_type = protein
                      organism = synthetic construct
SEQUENCE: 333
KFTIVFPHNQ KGNWKNVPSN YHYCPSSSDL NWHNDLIGTA LQVKMPQSHK AIQADGWMCH  60
ASKWVTTCDF RWYGPKYITQ SIRSFTPSVE QCKESIEQTK QGTWLNPGFP PQSCGYATVT  120
DAEAVIVQVT PHHVLVDEYT GEWVDSQFIN GKCSNYICPT VHNSTTWHSD YKVKGLCDSN  180
LISMDITFFS EDGELSSLGK EGTGFRSNYF AYETGGKACK MQYCKHWGVR LPSGVWFEMA  240
DKDLFAAARF PECPEGSSIS APSQTSVDVS LIQDVERILD YSLCQETWSK IRAGLPISPV  300
DLSYLAPKNP GTGPAFTIIN GTLKYFETRY IRVDIAAPIL SRMVGMISGT TTEAELWDDW  360
APYEDVEIGP NGVLRTSSGY KFPLYMIGHG MLDSDLHLSS KAQVFEHPHI QDAASQLPDD  420
ESLFFGDTGL SKNPIELVEG WFSSWKSSIA SFFFIIGLII GLFLVLRVGI HLCIKLKHTK  480
KRQIYTDIEM NRLGK                                                 495

SEQ ID NO: 334        moltype = AA  length = 495
FEATURE               Location/Qualifiers
source                1..495
                      mol_type = protein
                      organism = synthetic construct
SEQUENCE: 334
KFTIVFPHNQ KGNWKNVPSN YHYCPSSSDL NWHNDLIGTA IQVKMPQSHK AIQADGWMCH  60
ASKWVTTCDF RWYGPKYITH SIRSFTPSVE QCKESIEQTK QGTWLNPGFP PQSCGYATVT  120
DAEAVIVQVT PHHVLVDEYT GEWVDSQFIN GKCSNYICPT VHNSTTWHSD YKVKGLCDSN  180
LISMDITFFS EDGELSSLGK EGTGFRSNYF AYETGGKACK MQYCKHWGVR LPSGVWFEMA  240
DKDLFAAARF PECPEGSSIS APSQTSVDVS LIQDVERILD YSLCQETWSK IRAGLPISPV  300
DLSYLAPKNP GTGPAFTIIN GTLKYFETRY IRVDIAAPIL SRMVGMISGT TTEAELWDDW  360
APYEDVEIGP NGVLRTSSGY KFPLYMIGHG MLDSDLHLSS KAQVFEHPHI QDAASQLPDD  420
ESLFFGDTGL SKNPIELVEG WFSSWKSSIA SFFFIIGLII GLFLVLRVGI HLCIKLKHTK  480
KRQIYTDIEM NRLGK                                                 495

SEQ ID NO: 335        moltype = AA  length = 495
FEATURE               Location/Qualifiers
source                1..495
                      mol_type = protein
                      organism = synthetic construct
SEQUENCE: 335
KFTIVFPHNQ KGNWKNVPSN YHYCPSSSDL NWHNDLIGTA LQVKMPQSHK AIQADGWMCH  60
ASKWVTTCDF RWYGPKYITH SIRSFTPSVE QCKESIEQTK QGTWLNPGFP PQSCGYATVT  120
DAEAVIVQVT PHHVLVDEYT GEWVDSQFIN GKCSNYICPT VHNSTTWHSD YKVKGLCDSN  180
LISMDITFFS EDGELSSLGK EGTGFRSNYF AYETGGKACK MQYCKHWGVR LPSGVWFEMA  240
DKDLFAAARF PECPEGSSIS APSQTSVDVS LIQDVERILD YSLCQETWSK IRAGLPISPV  300
DLSYLAPKNP GTGPAFTIIN GTLKYFETRY IRVDIAAPIL SRMVGMISGT TTEAELWDDW  360
APYEDVEIGP NGVLRTSSGY KFPLYMIGHG MLDSDLHLSS KAQVFEHPHI QDAASQLPDD  420
ESLFFGDTGL SKNPIELVEG WFSSWKSSIA SFFFIIGLII GLFLVLRVGI HLCIKLKHTK  480
KRQIYTDIEM NRLGK                                                 495

SEQ ID NO: 336        moltype = AA  length = 495
FEATURE               Location/Qualifiers
source                1..495
                      mol_type = protein
                      organism = synthetic construct
SEQUENCE: 336
KFSIVFPQSQ KGNWKNVPSS YHYCPSSSDQ NWHNDLLGIT MKVKMPATHK AIQADGWMCH  60
AAKWITTCDF RWYGPKYITH SIHSIQPTSE QCKESIKQTK QGTWMSPGFP PQNCGYATVT  120
DSVAVVVQAT PHHVLVDEYT GEWIDSQFPN GKCETEECET VHNSTVWYSD YKVTGLCDAT  180
LVDTEITFFS EDGKKESIGK PNTGYRSNYF AYEKGDKVCK MNYCKHAGVR LPSGVWFEFV  240
DQDVYAAAKL PECPVGATIS APTQTSVDVS LILDVERILD YSLCQETWSK IRSKQPVSPV  300
DLSYLAPKNP GTGPAFTIIN GTLKYFETRY IRIDIDNPII SKMVGKISGS QTEAELWTEW  360
FPYEGVEIGP NGILKTPTGY KFPLFMIGHG MLDSDLHKTS QAEVFEHPHL AEAPKQLPEE  420
ETLFFGDTGI SKNPVELIEG WFSSWKSTVV TFFFAIGVFI LLYVVARIVI AVRYRYQGSN  480
NKRIYNDIEM SRFRK                                                 495

SEQ ID NO: 337        moltype = AA  length = 495
```

```
FEATURE                Location/Qualifiers
source                 1..495
                       mol_type = protein
                       organism = synthetic construct
SEQUENCE: 337
KFSIVFPQSQ KGNWKNVPSS YHYCPSSSDQ NWHNDLLGIT MKVKMPATHK AIQADGWMCH  60
AAKWITTCDF RWYGPKYITH SIHSIQPTSE QCKESIKQTK QGTWMSPGFP PQNCGYATVT  120
DSVAVVVQAT PHHVLVDEYT GEWIDSQFPN GKCETEECET VHNSTVWYSD YKVTGLCDAT  180
LVDTEITFFS EDGKKESIGK PNTGYRSNYF AYEKGDKVCK MNYCKHAGVR LPSGVWFEFV  240
DQDVYAAAKL PECPVGATIS APTQTSVDVS LILDVERILD YSLCQETWSK IRSKQPVSPV  300
DLSYLAPKNP GTGPAFTIIN GTLKYFETRY IRIDIDNPII SKMVGKISGS QTEQELWTEW  360
FPYEGVEIGP NGILKTPTGY KFPLFMIGHG MLDSDLHKTS QAEVFEHPHL AEAPKQLPEE  420
ETLFFGDTGI SKNPVELIEG WFSSWKSTVV TFFFAIGVFI LLYVVARIVI AVRYRYQGSN  480
NKRIYNDIEM SRFRK                                                  495

SEQ ID NO: 338         moltype = AA  length = 495
FEATURE                Location/Qualifiers
source                 1..495
                       mol_type = protein
                       organism = synthetic construct
SEQUENCE: 338
KFSIVFPQSQ KGNWKNVPSS YHYCPSSSDQ NWHNDLLGIT MKVKMPQTHK AIQADGWMCH  60
AAKWITTCDF RWYGPKYITH SIHSIQPTSE QCKESIKQTK QGTWMSPGFP PQNCGYATVT  120
DSVAVVVQAT PHHVLVDEYT GEWIDSQFPN GKCETEECET VHNSTVWYSD YKVTGLCDAT  180
LVDTEITFFS EDGKKESIGK PNTGYRSNYF AYEKGDKVCK MNYCKHAGVR LPSGVWFEFV  240
DQDVYAAAKL PECPVGATIS APTQTSVDVS LILDVERILD YSLCQETWSK IRSKQPVSPV  300
DLSYLAPKNP GTGPAFTIIN GTLKYFETRY IRIDIDNPII SKMVGKISGS QTEAELWTEW  360
FPYEGVEIGP NGILKTPTGY KFPLFMIGHG MLDSDLHKTS QAEVFEHPHL AEAPKQLPEE  420
ETLFFGDTGI SKNPVELIEG WFSSWKSTVV TFFFAIGVFI LLYVVARIVI AVRYRYQGSN  480
NKRIYNDIEM SRFRK                                                  495

SEQ ID NO: 339         moltype = AA  length = 495
FEATURE                Location/Qualifiers
source                 1..495
                       mol_type = protein
                       organism = synthetic construct
SEQUENCE: 339
KFSIVFPQSQ KGNWKNVPSS YHYCPSSSDQ NWHNDLLGIT MKVKMPQTHK AIQADGWMCH  60
AAKWITTCDF RWYGPKYITH SIHSIQPTSE QCKESIKQTK QGTWMSPGFP PQNCGYATVT  120
DSVAVVVQAT PHHVLVDEYT GEWIDSQFPN GKCETEECET VHNSTVWYSD YKVTGLCDAT  180
LVDTEITFFS EDGKKESIGK PNTGYRSNYF AYEKGDKVCK MNYCKHAGVR LPSGVWFEFV  240
DQDVYAAAKL PECPVGATIS APTQTSVDVS LILDVERILD YSLCQETWSK IRSKQPVSPV  300
DLSYLAPKNP GTGPAFTIIN GTLKYFETRY IRIDIDNPII SKMVGKISGS QTEQELWTEW  360
FPYEGVEIGP NGILKTPTGY KFPLFMIGHG MLDSDLHKTS QAEVFEHPHL AEAPKQLPEE  420
ETLFFGDTGI SKNPVELIEG WFSSWKSTVV TFFFAIGVFI LLYVVARIVI AVRYRYQGSN  480
NKRIYNDIEM SRFRK                                                  495

SEQ ID NO: 340         moltype = AA  length = 472
FEATURE                Location/Qualifiers
source                 1..472
                       mol_type = protein
                       organism = synthetic construct
SEQUENCE: 340
DIVLTQSPPS LAMSLGKRAT ISCRASESVT ILGSHLIHWY QQKPGQPPTL LIQLASNVQT  60
GVPARFSGSG SRTDFTLTID PVEEDDVAVY YCLQSRTIPR TFGGGTKLEI KGSTSGSGKP  120
GSGEGSTKGQ IQLVQSGPEL KKPGETVKIS CKASGYTFTD YSINWVKRAP GKGLKWMGWI  180
NTETREPAYA YDFRGRFAFS LETSASTAYL QINNLKYEDT ATYFCALDYS YAMDYWGQGT  240
SVTVSSAAAT TTPAPRPPTP APTIASQPLS LRPEACRPAA GGAVHTRGLD FACDIYIWAP  300
LAGTCGVLLL SLVITLYCKR GRKKLLYIFK QPFMRPVQTT QEEDGCSCRF PEEEEGGCEL  360
RVKFSRSADA PAYQQGQNQL YNELNLGRRE EYDVLDKRRG RDPEMGGKPR RKNPQEGLYN  420
ELQKDKMAEA YSEIGMKGER RRGKGHDGLY QGLSTATKDT YDALHMQALP PR          472

SEQ ID NO: 341         moltype = AA  length = 467
FEATURE                Location/Qualifiers
source                 1..467
                       mol_type = protein
                       organism = synthetic construct
SEQUENCE: 341
QVKLEESGGG LVQAGRSLRL SCAASEHTFS SHVMGWFRQA PGKERESVAV IGWRDISTSY  60
ADSVKGRFTI SRDNAKKTLY LQMNSLKPED TAVYYCAARR IDAADFDSWG QGTQVTVSSG  120
GGGSEVQLVE SGGGLVQAGG SLRLSCAASG RTFTMGWFRQ APGKEREFVA AISLSPTLAY  180
YAESVKGRFT ISRDNAKNTV VLQMNSLKPE DTALYYCAAD RKSVMSIRPD YWGQGTQVTV  240
SSTSTTTPAP RPPTPAPTIA SQPLSLRPEA CRPAAGGAVH TRGLDFACDI YIWAPLAGTC  300
GVLLLSLVIT LYCKRGRKKL LYIFKQPFMR PVQTTQEEDG CSCRFPEEEE GGCELRVKFS  360
RSADAPAYQQ GQNQLYNELN LGRREEYDVL DKRRGRDPEM GGKPRRKNPQ EGLYNELQKD  420
KMAEAYSEIG MKGERRRGKG HDGLYQGLST ATKDTYDALH MQALPPR               467

SEQ ID NO: 342         moltype = AA  length = 5
FEATURE                Location/Qualifiers
```

```
source                  1..5
                        mol_type = protein
                        organism = synthetic construct
SEQUENCE: 342
TGEKP                                                                5

SEQ ID NO: 343          moltype = AA  length = 5
FEATURE                 Location/Qualifiers
source                  1..5
                        mol_type = protein
                        organism = synthetic construct
SEQUENCE: 343
GGGGS                                                                5

SEQ ID NO: 344          moltype = AA  length = 10
FEATURE                 Location/Qualifiers
source                  1..10
                        mol_type = protein
                        organism = synthetic construct
SEQUENCE: 344
GGGGSGGGGS                                                           10

SEQ ID NO: 345          moltype = AA  length = 15
FEATURE                 Location/Qualifiers
source                  1..15
                        mol_type = protein
                        organism = synthetic construct
SEQUENCE: 345
GGGGSGGGGS GGGGS                                                     15

SEQ ID NO: 346          moltype = AA  length = 20
FEATURE                 Location/Qualifiers
source                  1..20
                        mol_type = protein
                        organism = synthetic construct
SEQUENCE: 346
GGGGSGGGGS GGGGSGGGGS                                                20

SEQ ID NO: 347          moltype = AA  length = 25
FEATURE                 Location/Qualifiers
source                  1..25
                        mol_type = protein
                        organism = synthetic construct
SEQUENCE: 347
GGGGSGGGGS GGGGSGGGGS GGGGS                                          25

SEQ ID NO: 348          moltype = AA  length = 14
FEATURE                 Location/Qualifiers
source                  1..14
                        mol_type = protein
                        organism = synthetic construct
SEQUENCE: 348
EGKSSGSGSE SKVD                                                      14

SEQ ID NO: 349          moltype = AA  length = 18
FEATURE                 Location/Qualifiers
source                  1..18
                        mol_type = protein
                        organism = synthetic construct
SEQUENCE: 349
KESGSVSSEQ LAQFRSLD                                                  18

SEQ ID NO: 350          moltype = AA  length = 9
FEATURE                 Location/Qualifiers
source                  1..9
                        mol_type = protein
                        organism = synthetic construct
SEQUENCE: 350
LRQRDGERP                                                            9

SEQ ID NO: 351          moltype = AA  length = 12
FEATURE                 Location/Qualifiers
source                  1..12
                        mol_type = protein
                        organism = synthetic construct
SEQUENCE: 351
LRQKDGGGSE RP                                                        12

SEQ ID NO: 352          moltype = AA  length = 16
```

```
FEATURE                Location/Qualifiers
source                 1..16
                       mol_type = protein
                       organism = synthetic construct
SEQUENCE: 352
LRQKDGGGSG GGSERP                                              16

SEQ ID NO: 353         moltype = AA  length = 18
FEATURE                Location/Qualifiers
source                 1..18
                       mol_type = protein
                       organism = synthetic construct
SEQUENCE: 353
GEGTSTGSGG SGGSGGAD                                            18

SEQ ID NO: 354         moltype = AA  length = 18
FEATURE                Location/Qualifiers
source                 1..18
                       mol_type = protein
                       organism = synthetic construct
SEQUENCE: 354
GSTSGSGKPG SGEGSTKG                                            18

SEQ ID NO: 355         moltype = AA  length = 22
FEATURE                Location/Qualifiers
source                 1..22
                       mol_type = protein
                       organism = synthetic construct
SEQUENCE: 355
GSGATNFSLL KQAGDVEENP GP                                       22

SEQ ID NO: 356         moltype = AA  length = 19
FEATURE                Location/Qualifiers
source                 1..19
                       mol_type = protein
                       organism = synthetic construct
SEQUENCE: 356
ATNFSLLKQA GDVEENPGP                                           19

SEQ ID NO: 357         moltype = AA  length = 14
FEATURE                Location/Qualifiers
source                 1..14
                       mol_type = protein
                       organism = synthetic construct
SEQUENCE: 357
LLKQAGDVEE NPGP                                                14

SEQ ID NO: 358         moltype = AA  length = 21
FEATURE                Location/Qualifiers
source                 1..21
                       mol_type = protein
                       organism = synthetic construct
SEQUENCE: 358
GSGEGRGSLL TCGDVEENPG P                                        21

SEQ ID NO: 359         moltype = AA  length = 18
FEATURE                Location/Qualifiers
source                 1..18
                       mol_type = protein
                       organism = synthetic construct
SEQUENCE: 359
EGRGSLLTCG DVEENPGP                                            18

SEQ ID NO: 360         moltype = AA  length = 13
FEATURE                Location/Qualifiers
source                 1..13
                       mol_type = protein
                       organism = synthetic construct
SEQUENCE: 360
LLTCGDVEEN PGP                                                 13

SEQ ID NO: 361         moltype = AA  length = 23
FEATURE                Location/Qualifiers
source                 1..23
                       mol_type = protein
                       organism = synthetic construct
SEQUENCE: 361
GSGQCTNYAL LKLAGDVESN PGP                                      23
```

```
SEQ ID NO: 362          moltype = AA  length = 20
FEATURE                 Location/Qualifiers
source                  1..20
                        mol_type = protein
                        organism = synthetic construct
SEQUENCE: 362
QCTNYALLKL AGDVESNPGP                                                20

SEQ ID NO: 363          moltype = AA  length = 14
FEATURE                 Location/Qualifiers
source                  1..14
                        mol_type = protein
                        organism = synthetic construct
SEQUENCE: 363
LLKLAGDVES NPGP                                                      14

SEQ ID NO: 364          moltype = AA  length = 25
FEATURE                 Location/Qualifiers
source                  1..25
                        mol_type = protein
                        organism = synthetic construct
SEQUENCE: 364
GSGVKQTLNF DLLKLAGDVE SNPGP                                          25

SEQ ID NO: 365          moltype = AA  length = 22
FEATURE                 Location/Qualifiers
source                  1..22
                        mol_type = protein
                        organism = synthetic construct
SEQUENCE: 365
VKQTLNFDLL KLAGDVESNP GP                                             22

SEQ ID NO: 366          moltype = AA  length = 19
FEATURE                 Location/Qualifiers
source                  1..19
                        mol_type = protein
                        organism = synthetic construct
SEQUENCE: 366
LLNFDLLKLA GDVESNPGP                                                 19

SEQ ID NO: 367          moltype = AA  length = 19
FEATURE                 Location/Qualifiers
source                  1..19
                        mol_type = protein
                        organism = synthetic construct
SEQUENCE: 367
TLNFDLLKLA GDVESNPGP                                                 19

SEQ ID NO: 368          moltype = AA  length = 17
FEATURE                 Location/Qualifiers
source                  1..17
                        mol_type = protein
                        organism = synthetic construct
SEQUENCE: 368
NFDLLKLAGD VESNPGP                                                   17

SEQ ID NO: 369          moltype = AA  length = 20
FEATURE                 Location/Qualifiers
source                  1..20
                        mol_type = protein
                        organism = synthetic construct
SEQUENCE: 369
QLLNFDLLKL AGDVESNPGP                                                20

SEQ ID NO: 370          moltype = AA  length = 24
FEATURE                 Location/Qualifiers
source                  1..24
                        mol_type = protein
                        organism = synthetic construct
SEQUENCE: 370
APVKQTLNFD LLKLAGDVES NPGP                                           24

SEQ ID NO: 371          moltype = AA  length = 40
FEATURE                 Location/Qualifiers
source                  1..40
                        mol_type = protein
                        organism = synthetic construct
SEQUENCE: 371
VTELLYRMKR AETYCPRPLL AIHPTEARHK QKIVAPVKQT                          40
```

-continued

```
SEQ ID NO: 372          moltype = AA  length = 18
FEATURE                 Location/Qualifiers
source                  1..18
                        mol_type = protein
                        organism = synthetic construct
SEQUENCE: 372
LNFDLLKLAG DVESNPGP                                                    18

SEQ ID NO: 373          moltype = AA  length = 40
FEATURE                 Location/Qualifiers
source                  1..40
                        mol_type = protein
                        organism = synthetic construct
SEQUENCE: 373
LLAIHPTEAR HKQKIVAPVK QTLNFDLLKL AGDVESNPGP                            40

SEQ ID NO: 374          moltype = AA  length = 33
FEATURE                 Location/Qualifiers
source                  1..33
                        mol_type = protein
                        organism = synthetic construct
SEQUENCE: 374
EARHKQKIVA PVKQTLNFDL LKLAGDVESN PGP                                   33
```

COMPOSITIONS FOR TREATING CANCER

CROSS REFERENCE TO RELATED APPLICATIONS

This application is a continuation application of International Application No. PCT/US2024/048301, filed Sep. 25, 2024, which claims the benefit of and priority to U.S. Provisional Application No. 63/540,336, filed Sep. 25, 2023, and U.S. Provisional Application No. 63/618,878, filed Jan. 8, 2024. The entire teachings of the applications are incorporated herein by reference.

STATEMENT REGARDING SEQUENCE LISTING

The Sequence Listing associated with this application is provided in XML format in lieu of a paper copy and is hereby incorporated by reference into the specification. The name of the XML file containing the Sequence Listing is KELO-012-101X_ST26.xml. The XML file is 385 KB, was created on Sep. 20, 2024, and is being submitted electronically via Patent Center, concurrent with the filing of the specification.

TECHNICAL FIELD

The present disclosure relates to recombinant particles engineered to deliver a chimeric antigen receptor to a cell. More particularly, the disclosure relates to recombinant particles engineered to deliver a chimeric antigen receptor to cells in vivo.

DESCRIPTION OF THE RELATED ART

B cell maturation antigen (BCMA) is a member of the tumor necrosis factor receptor superfamily and is also known as tumor necrosis factor receptor superfamily member 17 (TNFRSF17). BCMA is normally expressed in mature B lymphocytes and plasma cells. BCMA expression is also detected in various lymphomas and multiple myelomas. Multiple myeloma is an incurable plasma cell malignancy that originates in the bone marrow.

Multiple myeloma is the second most prevalent hematological malignancy after non-lymphoma. In 2020, an estimated 176,404 people world-wide were diagnosed with multiple myeloma and about 117,077 patients succumbed to the disease. In 2023, an estimated 35,730 people in the United States alone will be diagnosed with multiple myeloma and an estimated 12,590 multiple myeloma patients will pass from the disease or associated complications. The 5-year relative survival rate for multiple myeloma in the United States is only about 58%

Multiple myeloma may initially be treated with an autologous stem cell transplantation (ASCT) and/or various drug combinations (e.g., proteasome inhibitors including bortezomib, carfilzomib, ixazomib; immunomodulatory drugs (IMiDs) including pomalidomide, lenalidomide, thalidomide; and corticosteroids like dexamethasone) but patients eventually relapse with the disease becoming refractory to treatment. Subsequent lines of treatment include monoclonal antibodies, bispecific antibodies, e.g., BiTEs, antibody-drug conjugates, and finally chimeric antigen receptor T cell therapy.

Ex vivo gene therapies are potentially one-time therapeutic modalities that generally involve harvesting cells from a subject, modifying the cells by culturing them with a gene therapy vector, and delivering the modified cells back to the subject. Because ex vivo gene therapies are manufactured in a controlled environment, they do not generally require specialized targeting moieties and instead, targeting moieties with a broad tropism and that are highly efficient in delivering a gene therapy to most cell types are used.

In contrast, in vivo gene therapies are manufactured in the patient, in an uncontrolled environment. Accordingly, in vivo delivery of gene therapy vectors to specific cell types is orders of magnitude more complex than ex vivo delivery. In vivo gene therapy vectors encounter many non-target or off-target cells and may require a narrower or more specific tropism to deliver therapeutic payloads to a particular cell type. The potential of in vivo gene therapies has yet to be realized primarily due to inefficient delivery to desired cell types in combination with substantial off-target delivery. Use of specialized targeting moieties to deliver gene therapies in vivo has proven difficult in abrogating the off-target delivery to undesired cell types. In addition, on-target delivery of in vivo gene therapies using such specialized targeting moieties is often inefficient.

BRIEF SUMMARY

The present disclosure generally relates, in part, to a recombinant particle comprising a mutated vesiculovirus envelope glycoprotein, a tropism polypeptide that binds to an immune effector cell, and a lentiviral vector encoding or comprising a promoter operably linked to a polynucleotide encoding a chimeric antigen receptor that binds B cell maturation antigen (BCMA).

In various embodiments, the disclosure contemplates, in part, a recombinant lentiviral particle comprising: (a) a viral envelope comprising (i) a mutated cocal virus envelope glycoprotein (COCV-G) or a mutated vesicular stomatitis Indiana virus envelope glycoprotein (VSIV-G), wherein the mutated COCV-G or VSIV-G comprises amino acid substitutions at positions 47 and 354; and (ii) a non-viral membrane-bound tropism polypeptide comprising an anti-CD3ε scFv and a human CD8α hinge and transmembrane domain; and (b) a recombinant lentiviral vector comprising a polynucleotide encoding a myeloproliferative sarcoma virus enhancer, negative control region deleted, dl587rev primer-binding site substituted (MND) U3 promoter or an EF1α promoter operably linked to a polynucleotide encoding an anti-BCMA chimeric antigen receptor comprising an anti-BCMA scFv or anti-BCMA VHH, a CD8α hinge and transmembrane domain, a CD137 costimulatory domain, a CD3ζ primary signaling domain.

In particular embodiments, the mutated COCV-G or the mutated VSIV-G comprises amino acid substitutions selected from the group consisting of: K47A and R354A; K47A and R354Q; K47Q and R354A; and K47Q and R354Q.

In some embodiments, the mutated COCV-G or the mutated VSIV-G comprises the amino acid substitutions K47A and R354A.

In certain embodiments, the mutated COCV-G or the mutated VSIV-G comprises the amino acid substitutions K47A and R354Q.

In particular embodiments, the mutated COCV-G or the mutated VSIV-G comprises the amino acid substitutions K47Q and R354A.

In some embodiments, the mutated COCV-G or the mutated VSIV-G comprises the amino acid substitutions K47Q and R354Q.

In additional embodiments, the mutated COCV-G or the mutated VSIV-G comprises the amino acid sequence set forth in any one of SEQ ID NOs: 332, 333, 334, 335, 336, 337, 338, and 339.

In particular embodiments, the mutated VSIV-G comprises the amino acid sequence set forth in any one of SEQ ID NOs: 332, 333, 334, and 335.

In further embodiments, the mutated COCV-G comprises the amino acid sequence set forth in any one of SEQ ID NOs: 336, 337, 338, and 339.

In certain embodiments, the anti-CD3ε scFv is isolated from an antibody selected from the group consisting of: OKT3, UCHT1, YTH12.5, TR66, and variants thereof.

In particular embodiments, the anti-CD3ε scFv is isolated from OKT3.

In additional embodiments, the anti-CD3ε scFv is isolated from UCHT1.

In some embodiments, the anti-CD3ε scFv is isolated from YTH12.5.

In further embodiments, the anti-CD3ε scFv is isolated from TR66.

In certain embodiments, the anti-CD3ε scFv comprises an amino acid sequence set forth in any one of SEQ ID NOs: 153, 154, 163, 164, 173, 174, 183, 184, 193, 194, 203, 204, 213, 214, 223, and 224.

In particular embodiments, the non-viral membrane-bound tropism polypeptide comprises an amino acid sequence set forth in any one of SEQ ID NOs: 324, 325, 326, 327, 328, 329, 330, and 331.

In some embodiments, the MND U3 promoter comprises the polynucleotide sequence set forth in SEQ ID NO: 320.

In certain embodiments, the EF1α promoter comprises the polynucleotide sequence set forth in SEQ ID NO: 319.

In particular embodiments, the anti-BCMA CAR comprises an anti-BCMA scFv comprising an amino acid sequence selected from the group consisting of: 19, 20, 29, 30, 39, 40, 49, 50, 59, 60, 69, 70, 79, 80, 89, 90, 99, and 100.

In additional embodiments, the anti-BCMA CAR comprises an anti-BCMA scFv comprising an amino acid sequence selected from the group consisting of: 20, 30, 39, 50, 59, 70, 80, 90, and 100.

In particular embodiments, the anti-BCMA CAR comprises an anti-BCMA scFv comprising an amino acid sequence selected from the group consisting of: 39, 59, 70, and 90.

In particular embodiments, the anti-BCMA CAR comprises an anti-BCMA VHH comprising an amino acid sequence selected from the group consisting of: 101, 105, 109, 113, 117, 121, 125, 129, 133, 137, and 141.

In some embodiments, the anti-BCMA CAR comprises an anti-BCMA VHH comprising an amino acid sequence selected from the group consisting of: 101 and 117.

In further embodiments, the anti-BCMA CAR comprises the amino acid sequence set forth in any one of SEQ ID NOs: 259, 263, 266, 270, 273 and 277, preferably SEQ ID NO: 266.

In certain embodiments, the polynucleotide encoding the anti-BCMA CAR comprises the polynucleotide sequence set forth in any one of SEQ ID NOs: 297, 299, 300, 302, 304, and 308.

In particular embodiments, the polynucleotide encoding the anti-BCMA CAR further comprises a polynucleotide sequence encoding a signal peptide.

In additional embodiments, the polynucleotide encoding the anti-BCMA CAR further comprises a polynucleotide sequence encoding a signal peptide isolated from a polypeptide selected from the group consisting of: CD8a, mIgGκ, hIgGk, CD33, tPA, SEAP, hGM-CSF, CSF2R, and B2M.

In certain embodiments, the polynucleotide encoding the anti-BCMA CAR further comprises a polynucleotide sequence encoding a signal peptide comprising an amino acid sequence set forth in any one of SEQ ID NOs: 245, 246, 247, 248, 249, 250, 251, 252, 253, and 254.

In particular embodiments, the polynucleotide encoding the signal peptide comprises the polynucleotide sequence set forth in SEQ ID NO: 294.

In further embodiments, the lentiviral vector further comprises a WPRE operably linked to the 3' end of the polynucleotide encoding the anti-BCMA CAR.

In some embodiments, the lentiviral vector further comprises a WPRE that comprises, consists essentially of, or consists of a polynucleotide sequence set forth in any one of SEQ ID NOs: 315, 316, and 317.

In various embodiments, the disclosure contemplates, in part, a recombinant lentiviral particle comprising: (a) a viral envelope comprising (i) a mutated viral envelope glycoprotein comprising an amino acid sequence set forth in any one of SEQ ID NOs: 332, 333, 334, and 335 and (ii) a non-viral membrane-bound tropism polypeptide comprising an amino acid sequence set forth in any one of SEQ ID NOs: 324, 325, 326, 327, 328, 329, 330, and 331; and (b) a recombinant lentiviral vector comprising a 5' long terminal repeat (LTR) comprising R and U5 regions; a Psi (Ψ) packaging signal, a cPPT/FLAP, a rev response element (RRE); a polynucleotide encoding an MND promoter or an EF1α promoter operably linked to a polynucleotide encoding an anti-BCMA chimeric antigen receptor (CAR) comprising an amino acid sequence set forth in any one of SEQ ID NOs: 259, 263, 266, 270, 273, and 277 or an amino acid sequence at least 95%, at least 96%, at least 97%, at least 98%, at least 99% identical thereto; optionally a WPRE; a 3' LTR comprising U3 and R regions; a polyadenylation signal and a poly(A) tail.

In particular embodiments, the mutated viral envelope glycoprotein comprises an amino acid sequence set forth in SEQ ID NO: 332.

In some embodiments, the mutated viral envelope glycoprotein comprises an amino acid sequence set forth in SEQ ID NO: 333.

In certain embodiments, the mutated viral envelope glycoprotein comprises an amino acid sequence set forth in SEQ ID NO: 334.

In additional embodiments, the mutated viral envelope glycoprotein comprises an amino acid sequence set forth in SEQ ID NO: 335.

In various embodiments, the disclosure contemplates, in part, a recombinant lentiviral particle comprising: (a) a viral envelope comprising (i) a mutated viral envelope glycoprotein comprising an amino acid sequence set forth in any one of SEQ ID NOs: 336, 337, 338, and 339 and (ii) a non-viral membrane-bound tropism polypeptide comprising an amino acid sequence set forth in any one of SEQ ID NOs: 324, 325, 326, 327, 328, 329, 330, and 331; and (b) a recombinant lentiviral vector comprising a 5' long terminal repeat (LTR) comprising R and U5 regions; a Psi (Ψ) packaging signal, a cPPT/FLAP, a rev response element (RRE); a polynucleotide encoding an MND promoter or an EF1α promoter operably linked to a polynucleotide encoding an anti-BCMA chimeric antigen receptor (CAR) comprising an amino acid sequence set forth in any one of SEQ ID NOs: 259, 263, 266, 270, 273, and 277 or an amino acid sequence at least 95%, at least 96%, at least 97%, at least 98%, at least 99% identical thereto; optionally a WPRE; a 3' LTR comprising U3 and R regions; a polyadenylation signal and a poly(A) tail.

In some embodiments, the mutated viral envelope glycoprotein comprises an amino acid sequence set forth in SEQ ID NO: 336.

In further embodiments, the mutated viral envelope glycoprotein comprises an amino acid sequence set forth in SEQ ID NO: 337.

In certain embodiments, the mutated viral envelope glycoprotein comprises an amino acid sequence set forth in SEQ ID NO: 338.

In some embodiments, the mutated viral envelope glycoprotein comprises an amino acid sequence set forth in SEQ ID NO: 339.

In particular embodiments, the non-viral membrane-bound tropism polypeptide comprises an amino acid sequence set forth in SEQ ID NO: 324.

In additional embodiments, the non-viral membrane-bound tropism polypeptide comprises an amino acid sequence set forth in SEQ ID NO: 325.

In certain embodiments, the non-viral membrane-bound tropism polypeptide comprises an amino acid sequence set forth in SEQ ID NO: 326.

In particular embodiments, the non-viral membrane-bound tropism polypeptide comprises an amino acid sequence set forth in SEQ ID NO: 327.

In further embodiments, the non-viral membrane-bound tropism polypeptide comprises an amino acid sequence set forth in SEQ ID NO: 328.

In some embodiments, the non-viral membrane-bound tropism polypeptide comprises an amino acid sequence set forth in SEQ ID NO: 329.

In additional embodiments, the non-viral membrane-bound tropism polypeptide comprises an amino acid sequence set forth in SEQ ID NO: 330.

In particular embodiments, the non-viral membrane-bound tropism polypeptide comprises an amino acid sequence set forth in SEQ ID NO: 331.

In particular embodiments, the recombinant lentiviral vector is derived from HIV-1 or HIV-2.

In additional embodiments, the MND U3 promoter comprises the polynucleotide sequence set forth in SEQ ID NO: 320.

In some embodiments, the EF1α promoter comprises the polynucleotide sequence set forth in SEQ ID NO: 319.

In particular embodiments, the polynucleotide encoding the anti-BCMA CAR comprises the polynucleotide sequence set forth in any one of SEQ ID NOs: 297, 299, 300, 302, 304, and 308.

In some embodiments, the polynucleotide encoding the anti-BCMA CAR further comprises a polynucleotide sequence encoding a signal peptide.

In further embodiments, the polynucleotide encoding the anti-BCMA CAR further comprises a polynucleotide sequence encoding a signal peptide isolated from a polypeptide selected from the group consisting of: CD8a, mIgGκ, hIgGk, CD33, tPA, SEAP, hGM-CSF, CSF2R, and B2M.

In particular embodiments, the polynucleotide encoding the anti-BCMA CAR further comprises a polynucleotide sequence encoding a signal peptide comprising an amino acid sequence set forth in any one of SEQ ID NOs: 245, 246, 247, 248, 249, 250, 251, 252, 253, and 254.

In certain embodiments, the lentiviral vector further comprises a WPRE operably linked to the 3' end of the polynucleotide encoding the anti-BCMA CAR.

In some embodiments, the lentiviral vector further comprises a WPRE operably linked to the 3' end of the polynucleotide encoding the anti-BCMA CAR, wherein the WPRE comprises, consists essentially of, or consists of the polynucleotide sequence set forth in any one of SEQ ID NOs: 315, 316, and 317.

In various embodiments, the disclosure contemplates, in part, a cell transduced with a particle contemplated herein.

In further embodiments, the cell is an immune effector cell.

In additional embodiments, the cell is a T cell or a natural killer T (NKT) cell.

In various embodiments, the disclosure contemplates, in part, a composition comprising a particle or a cell contemplated herein.

In various embodiments, the disclosure contemplates, in part, a pharmaceutical composition comprising a pharmaceutically acceptable carrier and a particle, a cell, or a composition contemplated herein.

In various embodiments, the disclosure contemplates, in part, a method of treating, preventing, or ameliorating at least one symptom of a disease, disorder or condition associated therewith in a subject, comprising administering to the subject an effective amount of a particle, a cell, a composition, or a pharmaceutical composition contemplated herein.

In some embodiments, the disease, disorder, or condition is a cancer.

In certain embodiments, the cancer is a multiple myeloma (MM).

In particular embodiments, the cancer is MM selected from the group consisting of: active multiple myeloma, smoldering multiple myeloma, light chain myeloma, non-secretory myeloma, IgD myeloma, IgE myeloma, osteosclerotic myeloma, solitary plasmacytoma of bone, and extramedullary plasmacytoma.

In further embodiments, the cancer is relapsed and/or refractory.

In various embodiments, the disclosure contemplates, in part, a method of treating a subject that has, or has been diagnosed with, a multiple myeloma, comprising administering the subject an effective amount of a particle, a cell, a composition, or a pharmaceutical composition contemplated herein.

In some embodiments, the administration is parenteral administration.

In particular embodiments, the administration is intravenous.

In various embodiments, the disclosure contemplates, in part, a method of transducing an immune effector cell in vivo, comprising administering to a subject a pharmaceutical composition comprising a pharmaceutically acceptable carrier and an effective amount of a particle, a cell, a composition, or a pharmaceutical composition contemplated herein.

In various embodiments, the disclosure contemplates, in part, a method of making a recombinant lentivirus comprising (a) transfecting a host cell with four polynucleotides: a first polynucleotide that encodes lentiviral gag-pol, a second polynucleotide that encodes lentiviral rev, a third polynucleotide that encodes a mutated viral envelope glycoprotein and a non-viral membrane-bound tropism polypeptide contemplated herein, and a fourth polynucleotide that is a transfer plasmid encoding the recombinant lentiviral vector contemplated herein; and b) culturing the transduced cell for about 1 to 3 days to produce the recombinant lentivirus.

In various embodiments, the disclosure contemplates, in part, a kit comprising the particle contemplated herein, a pharmaceutically acceptable carrier, and instructions for use.

Figure 4A:
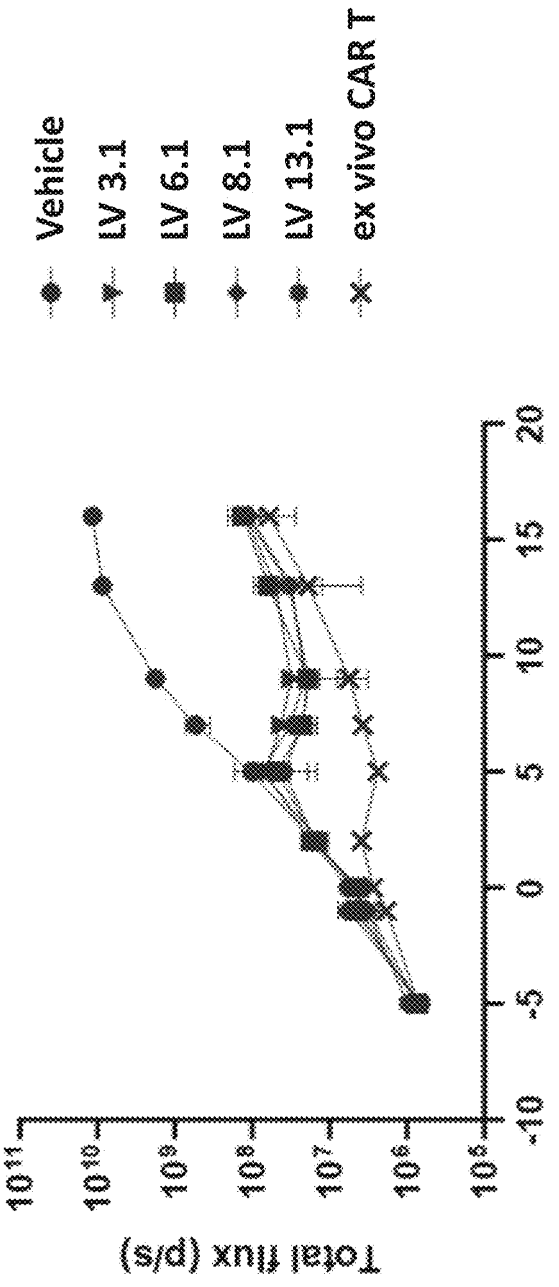
FIG. 4A shows the results from an in vivo Daudi mouse model. Mice were administered a recombinant lentivirus comprising a viral envelope expressing a mutated VSIV-G and a non-viral membrane-bound tropism polypeptide that binds CD3 and a lentiviral vector encoding either an MNDU3 promoter operably linked to a polynucleotide encoding a CD8α signal peptide and an anti-BCMA CAR (4 anti-BCMA CARs were evaluated) and a wild-type WPRE operably linked to the 3' prime end of the polynucleotide encoding the anti-BCMA CAR; ex vivo CAR T cells, or vehicle.
Figure 4B:
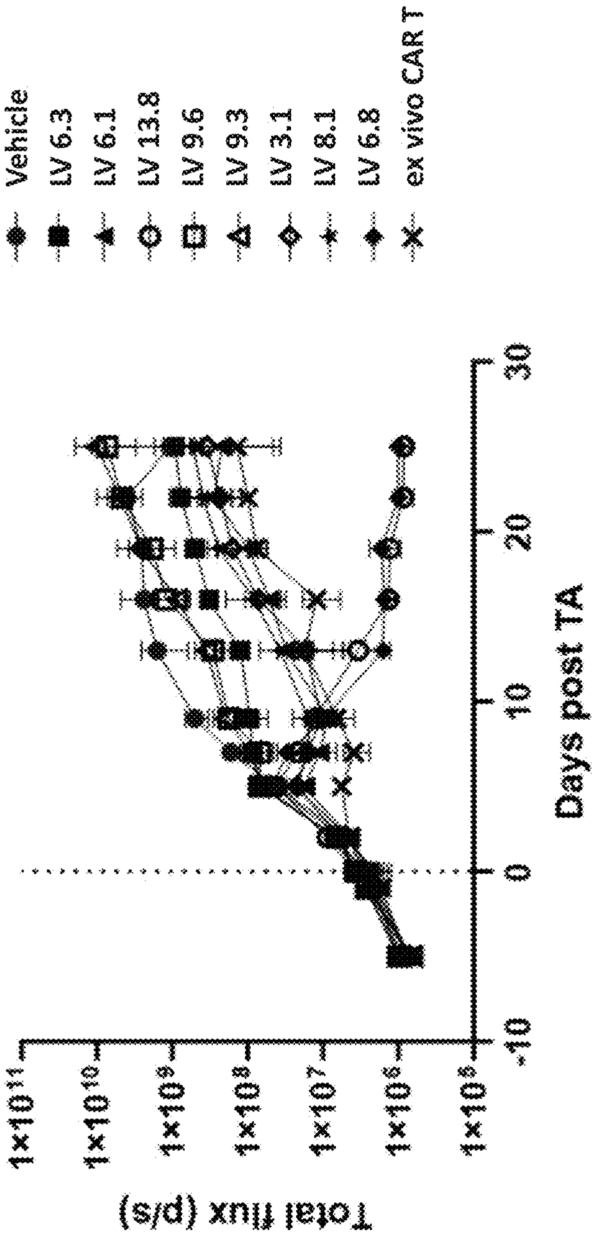
FIG. 4B shows the results from an in vivo Daudi mouse model. Mice were administered a recombinant lentivirus comprising a viral envelope expressing a mutated VSIV-G and a non-viral membrane-bound tropism polypeptide that binds CD3 and a lentiviral vector comprising one of the following lentiviral vector architectures, MNDU3 promoter and wild-type WPRE, MNDU3 promoter and a mutated WPRE, SFFV promoter and a mutated WPRE, and EF1α promoter and no WPRE and encoding an anti-BCMA CAR (5 anti-BCMA CARs were evaluated); ex vivo CAR T cells, or vehicle.
Figure 4C:
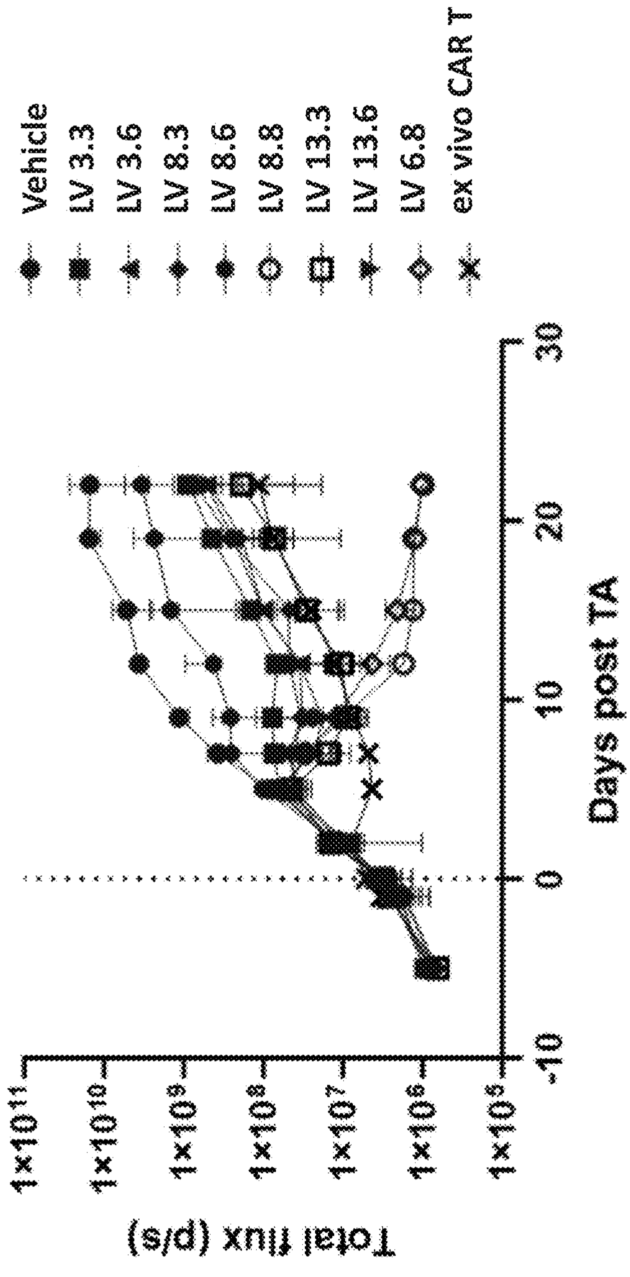

FIG. 4C shows the results from an in vivo Daudi mouse model. Mice were administered a recombinant lentivirus comprising a viral envelope expressing a mutated VSIV-G and a non-viral membrane-bound tropism polypeptide that binds CD3 and a lentiviral vector comprising one of the following lentiviral vector architectures, MNDU3 promoter and a mutated WPRE, SFFV promoter and a mutated WPRE, and EF1α promoter and no WPRE and encoding an anti-BCMA CAR (4 anti-BCMA CARs were evaluated); ex vivo CAR T cells, or vehicle.

Figure 4D:
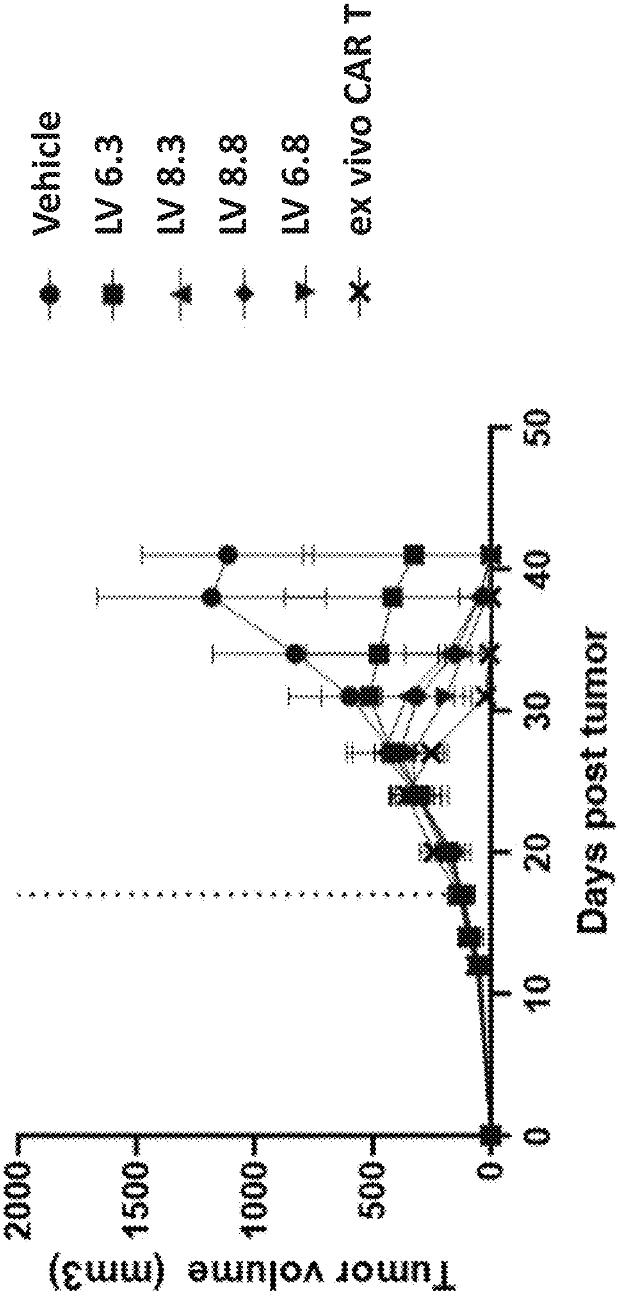

FIG. 4D shows the results from an in vivo RPMI-8226 mouse model. Mice were administered a recombinant lentivirus comprising a viral envelope expressing a mutated VSIV-G and a non-viral membrane-bound tropism polypeptide that binds CD3 and a lentiviral vector comprising one of the following lentiviral vector architectures, MNDU3 promoter and a mutated WPRE, or EF1α promoter and no WPRE and encoding an anti-BCMA CAR (2 anti-BCMA CARs were evaluated); ex vivo CAR T cells, or vehicle.

Figure 4E:
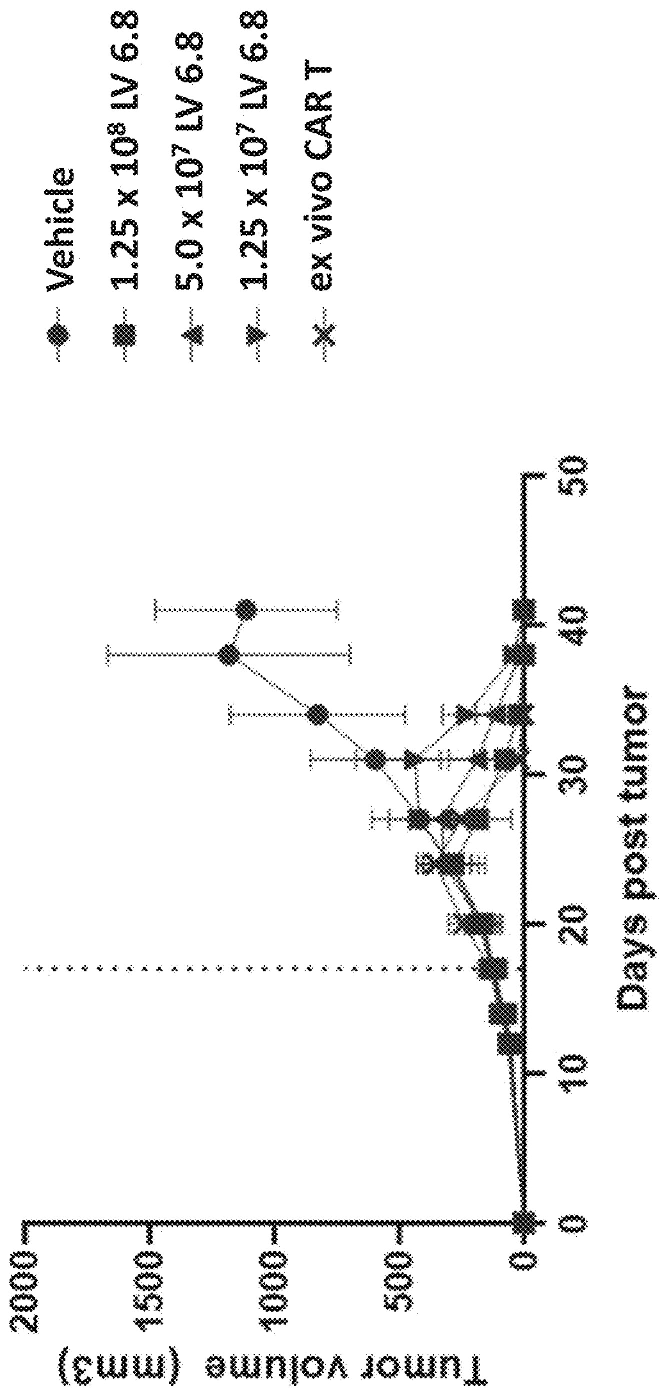

FIG. 4E shows the results from an in vivo RPMI-8226 mouse model. Mice were administered three doses ($1.25\times10^7$ IU, $5.0\times10^7$ IU, or $1.25\times10^8$ IU) of a recombinant lentivirus comprising a viral envelope expressing a mutated VSIV-G and a non-viral membrane-bound tropism polypeptide that binds CD3 and a lentiviral vector comprising an EF1α promoter operably linked to a polynucleotide encoding an anti-BCMA CAR without a PRE; ex vivo CAR T cells, or vehicle.

Figure 4F:
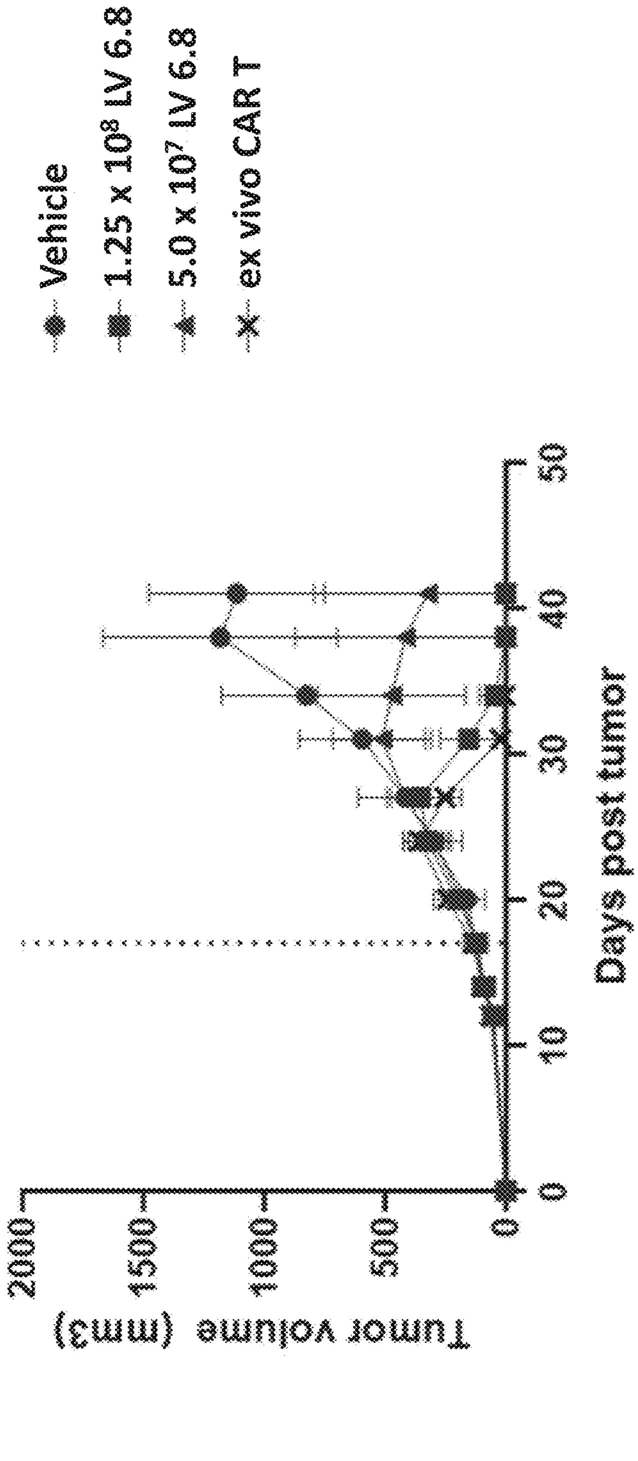

FIG. 4F shows the results from an in vivo RPMI-8226 mouse model. Mice were administered two doses ($5.0\times10^7$ IU or $1.25\times10^8$ IU) of a recombinant lentivirus comprising a viral envelope expressing a mutated VSIV-G and a non-viral membrane-bound tropism polypeptide that binds CD3 and a lentiviral vector comprising an EF1α promoter operably linked to a polynucleotide encoding an anti-BCMA CAR without a PRE; ex vivo CAR T cells, or vehicle.

Figure 4G:
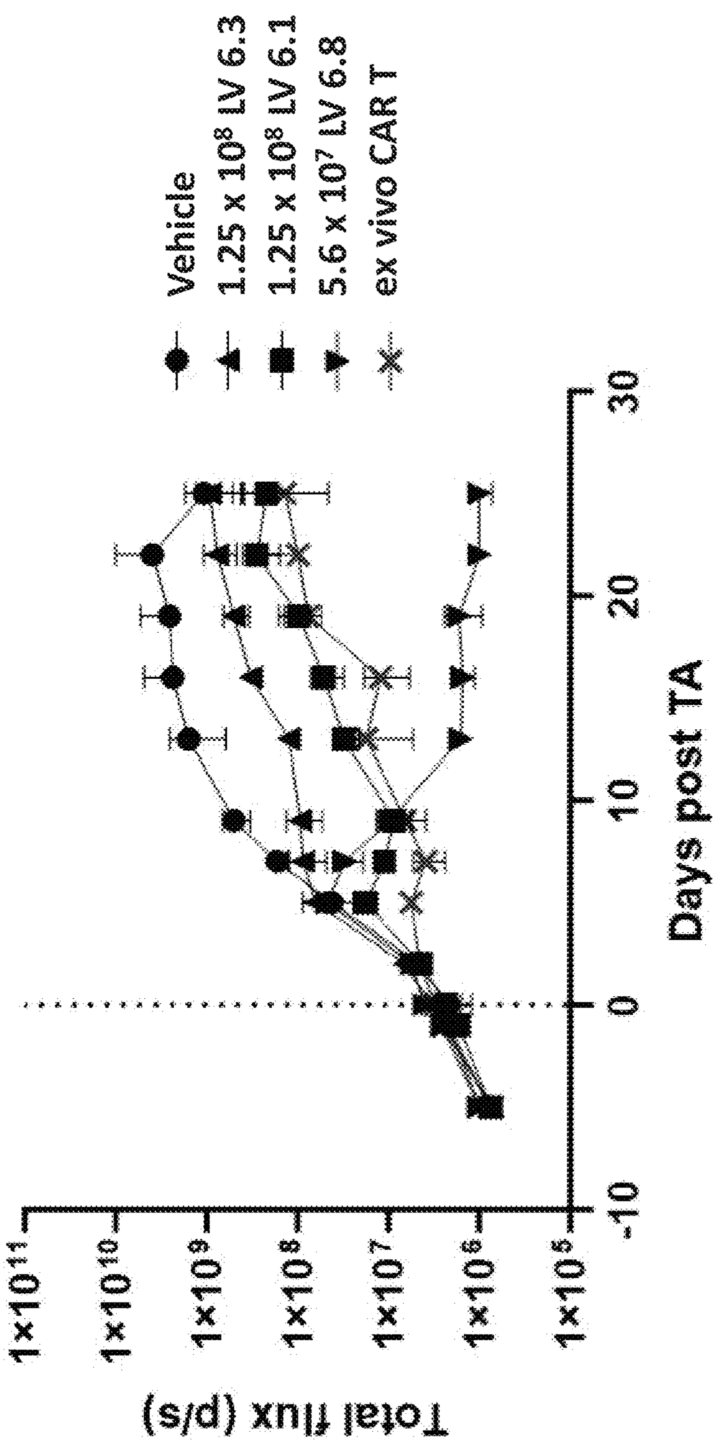

FIG. 4G shows the results from an in vivo Daudi mouse model. Mice were administered a recombinant lentivirus comprising a viral envelope expressing a mutated VSIV-G and a non-viral membrane-bound tropism polypeptide that binds CD3 and a lentiviral vector and encoding an anti-BCMA CAR and comprising one of the following lentiviral vector architectures, MNDU3 promoter and a mutated WPRE or MNDU3 promoter and a mutated WPRE (at $1.25\times10^8$ IU) or an EF1α promoter and no WPRE ($5.6\times10^7$ IU); ex vivo CAR T cells, or vehicle.

Figure 5A:
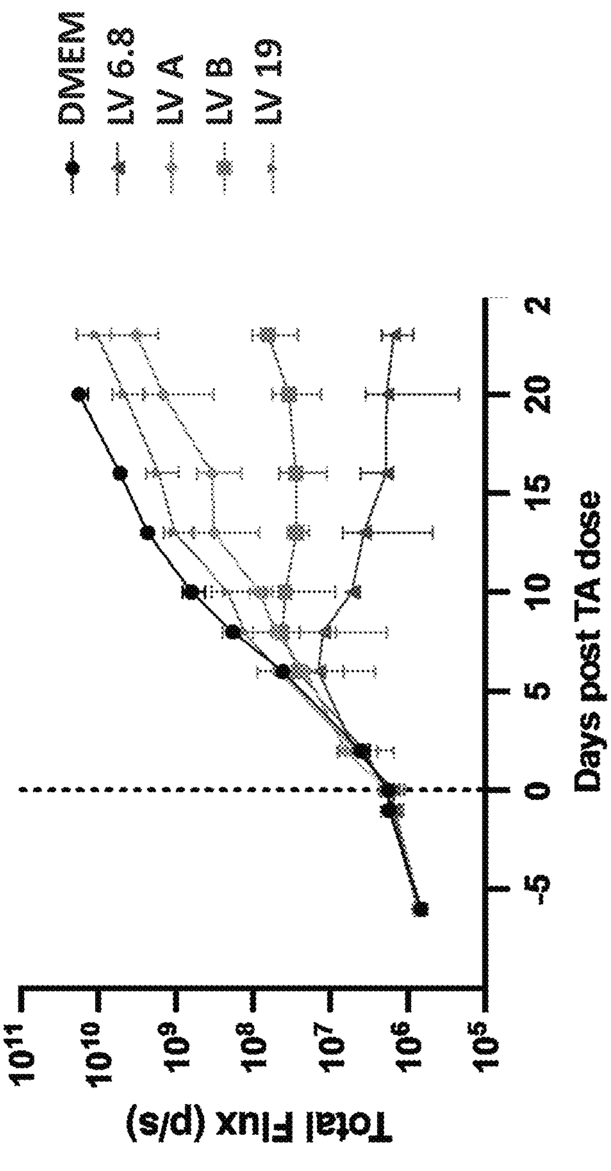

FIG. 5A shows the results from a Daudi mouse model interrogated with in vivo lentivirus. Mice were administered vehicle control or recombinant lentivirus comprising a viral envelope expressing a mutated VSIV-G and a non-viral membrane-bound tropism polypeptide that binds CD3 and a lentiviral vector encoding one of three anti-BCMA CARs or a GFP control.

Figure 5B:
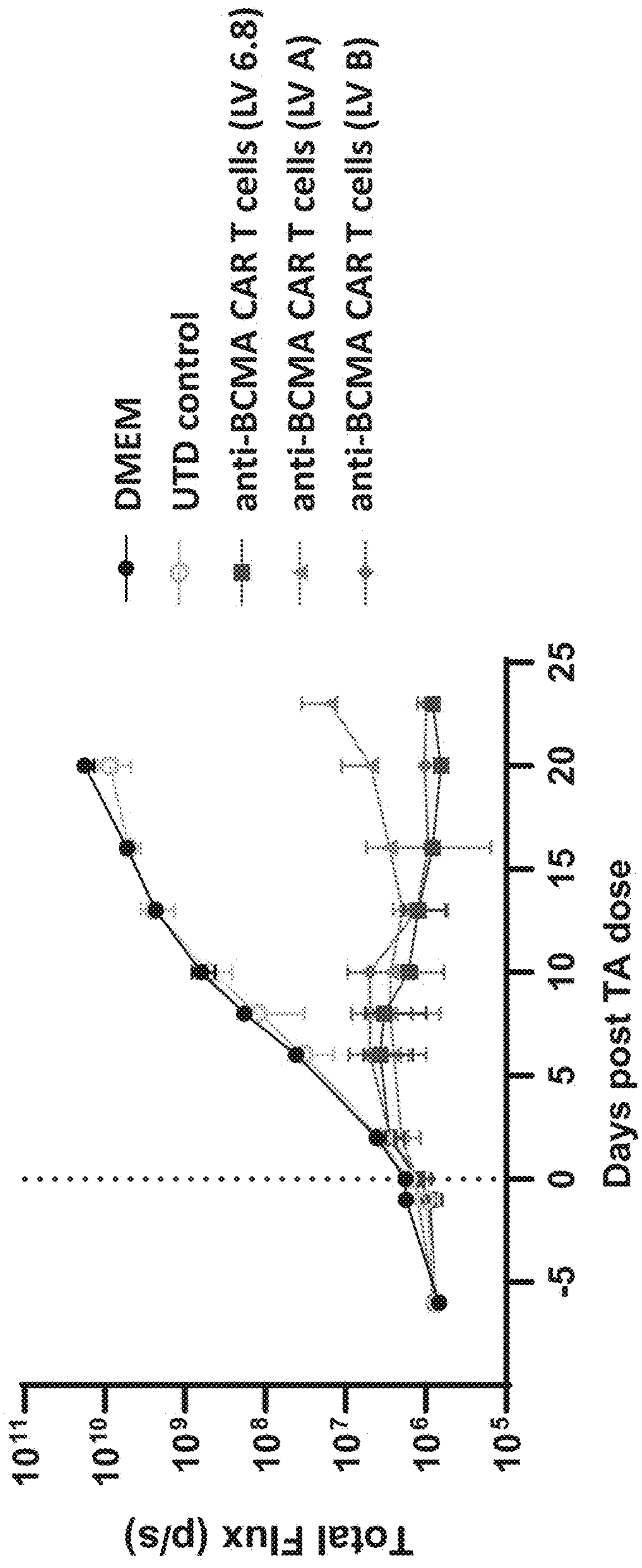

FIG. 5B shows the results from a Daudi mouse model interrogated with ex vivo manufactured CAR T cells. Mice were administered vehicle control, untransduced PBMCS, or PBMCs transduced with a recombinant lentivirus comprising a viral envelope expressing a mutated VSIV-G and a non-viral membrane-bound tropism polypeptide that binds CD3 and a lentiviral vector and encoding one of three anti-BCMA CARs.

BRIEF DESCRIPTION OF THE SEQUENCE IDENTIFIERS

SEQ ID NOs: 1-9 set forth amino acid sequences of fusogens.

SEQ ID NO: 10 sets forth an amino acid sequence of BCMA.

SEQ ID NOs: 11-224 set forth amino acid sequences of antibodies.

SEQ ID NOs: 225-230 set forth amino acid sequences of spacer/hinge domains.

SEQ ID NOs: 231-237 set forth amino acid sequences of transmembrane domains.

SEQ ID NOs: 238-244 set forth amino acid sequences of intracellular domains.

SEQ ID NOs: 245-254 set forth amino acid sequences of signal peptides.

SEQ ID NOs: 255-283 set forth amino acid sequences of chimeric antigen receptors.

SEQ ID NOs: 284-287 set forth nucleic acid sequences encoding spacer/hinge domains.

SEQ ID NOs: 288-289 set forth nucleic acid sequences encoding transmembrane domains.

SEQ ID NOs: 290-293 set forth nucleic acid sequences encoding intracellular signaling domains.

SEQ ID NO: 294 sets forth the nucleic acid sequence encoding a signal peptide.

SEQ ID NOs: 295-314 set forth nucleic acid sequences encoding chimeric antigen receptors without a signal peptide.

SEQ ID NOs: 315-317 set forth nucleic acid sequences of post-transcriptional response elements.

SEQ ID NOs: 318-323 set forth nucleic acid sequences of promoters.

SEQ ID NOs: 324-331 set forth amino acid sequences of non-viral membrane bound tropism polypeptides.

SEQ ID NOs: 332-339 set forth amino acid sequences of fusogens.

SEQ ID NOs: 340-341 set forth amino acid sequences of anti-BCMA CARs.

SEQ ID NOs: 342-354 set forth amino acid sequences of polypeptide linkers.

SEQ ID NOs: 355-374 set forth amino acid sequences of viral self-cleaving peptides.

In the foregoing sequences, X, if present, refers to any amino acid, a specified group of amino acids or the absence of an amino acid.

Throughout the disclosure, the amino acid positions of a fusogen are with reference to the fusogen lacking a signal sequence (i.e., the amino acid sequence after the signal peptide has been cleaved).

DETAILED DESCRIPTION

A. Overview

The field of ex vivo gene therapy is not new and has been evolving for decades. Despite huge potential, ex vivo gene therapy has been met with limited success. Moreover, substantial obstacles still plague the field of ex vivo gene therapy, obstacles including limited precision and lack of commercial viability are likely among the reasons that it has yet to see widespread adoption in a clinical setting.

Recently, ex vivo CAR T cell therapies that target B cell maturation antigen (BCMA) have been used to treat relapsed and refractory multiple myeloma. Although many multiple myeloma patients that have been treated with ex vivo anti-BCMA CAR T cell therapies experience partial or complete remissions, most relapse and succumb to the disease. There is a significant unmet need for a durable, one-time, and potentially curative treatment for multiple myeloma.

Recombinant lentiviral particles that enable delivery of vectors encoding chimeric antigen receptors to immune effector cells in vivo are new and offer the potential to deliver life-altering therapies on an unprecedented scale. In vivo CAR T cell therapy solves the commercial viability issues associated with the astronomical costs associated with ex vivo CAR T cell manufacturing. But in vivo CAR T cell therapy also comes with its own set of challenges related to the delivery mechanism, including potential off-target toxicity, low efficacy, and immunogenicity.

The present disclosure offers solutions to foregoing challenges and others that exist in the field of using recombinant lentiviral particles to efficiently and safely provide in vivo CAR T cell therapy.

The present disclosure generally relates to, in part, to an engineered cell-targeting particle (e.g., a fusosome; an extracellular vesicle, including a microvesicle, an apoptotic body, and an exosome; a lipid nanoparticle; a virus-like particle (VLPs); or a viral particle) that has a surface that expresses a non-viral tropism polypeptide engineered to bind an immune effector cell and a mutated viral glycoprotein that promotes fusion of the particle and the immune effector cell; and one or more copies of a vector that encodes or comprises a promoter operably linked to a polynucleotide encoding a chimeric antigen receptor that binds B cell maturation antigen (BCMA).

The disclosure contemplates, in part, recombinant lentiviral particles engineered to bind and transduce immune effector cells with a vector encoding an anti-BCMA CAR, in vivo. In various embodiments, a recombinant lentiviral particle comprises an envelope engineered to express a non-viral tropism polypeptide that bind an immune effector cell and a mutated vesiculovirus glycoprotein that does not bind its cognate receptor, e.g., low density lipoprotein receptor (LDLR), but that promotes fusion of the particle and the immune effector cell; and one or more copies of a lentiviral vector that encodes or comprises a promoter operably linked to a polynucleotide encoding an anti-BCMA CAR. The recombinant lentiviral particles may be used for ex vivo CAR T cell therapy but provide substantial advantages for use in in vivo CAR T cell therapy.

The disclosure further contemplates, in part, methods of making the recombinant lentiviral particles contemplated herein, along with methods of using the particles for treating a subject in need thereof.

In particular embodiments, the disclosure contemplates, methods of using a recombinant lentiviral particle contemplated herein to generate anti-BCMA immune effector cells, e.g., T cells, in vivo, to treat a disorder, disease, condition or symptoms associated therewith, preferably to treat cancer, and more preferably, to treat a multiple myeloma, e.g., relapsed refractory multiple myeloma.

Compositions, pharmaceutical compositions, and kits comprising one or more recombinant lentiviral particles contemplated herein and methods of making and using the same are also provided in particular embodiments.

Techniques for recombinant (i.e., engineered) DNA, peptide and oligonucleotide synthesis, immunoassays, tissue culture, transformation (e.g., electroporation, lipofection), enzymatic reactions, purification and related techniques and procedures may be generally performed as described in various general and more specific references in microbiology, molecular biology, biochemistry, molecular genetics, cell biology, virology and immunology as cited and discussed throughout the present specification. See, e.g., Sambrook et al., *Molecular Cloning: A Laboratory Manual,* 4th ed., Cold Spring Harbor Laboratory Press, Cold Spring Harbor, N.Y.; *Current Protocols in Molecular Biology* (John Wiley and Sons, updated July 2008); *Short Protocols in Molecular Biology: A Compendium of Methods from Current Protocols in Molecular Biology*, Greene Pub. Associates and Wiley-Interscience (2002); Glover, *DNA Cloning: A Practical Approach*, vol. I & II (IRL Press, Oxford Univ. Press USA, 1985); *Current Protocols in Immunology* (Edited by: John E. Coligan, Ada M. Kruisbeck, David H. Margulies, Ethan M. Shevach, Warren Strober 2001 John Wiley & Sons, NY, NY); *Real-Time PCR: Current Technology and Applications*, Edited by Julie Logan, Kirstin Edwards and Nick Saunders, 2009, Caister Academic Press, Norfolk, UK; Anand, *Techniques for the Analysis of Complex Genomes*, (Academic Press, New York, 1992); Guthrie and Fink, *Guide to Yeast Genetics and Molecular Biology* (Academic Press, New York, 1991); *Oligonucleotide Synthesis* (N. Gait, Ed., 1984); *Nucleic Acid the Hybridization* (B. Hames & S. Higgins, Eds., 1985); *Transcription and Translation* (B. Hames & S. Higgins, Eds., 1984); *Animal Cell Culture* (R. Freshney, Ed., 1986); Perbal, *A Practical Guide to Molecular Cloning* (1984); Next-Generation Genome Sequencing (Janitz, 2008 Wiley-VCH); *PCR Protocols* (Methods in Molecular Biology) (Park, Ed., 3rd Edition, 2010 Humana Press); *Immobilized Cells and Enzymes* (IRL Press, 1986); the treatise, *Methods in Enzymology* (Academic Press, Inc., N.Y.); *Gene Transfer Vectors for Mammalian Cells* (J. H. Miller and M. P. Calos eds., 1987, Cold Spring Harbor Laboratory); Harlow and Lane, *Antibodies*, (Cold Spring Harbor Laboratory Press, Cold Spring Harbor, N.Y., 1998); *Immunochemical Methods in Cell and Molecular Biology* (Mayer and Walker, eds., Academic Press, London, 1987); *Handbook of Experimental Immunology*, Volumes I-IV (D. M. Weir and CC Blackwell, eds., 1986); Roitt, *Essential Immunology,* 6th Edition, (Blackwell Scientific Publications, Oxford, 1988); *Current Protocols in Immunology* (Q. E. Coligan, A. M. Kruisbeek, D. H. Margulies, E. M. Shevach and W. Strober, eds., 1991); *Annual Review of Immunology*; as well as monographs in journals such as *Advances in Immunology.*

B. Definitions

Prior to setting forth this disclosure in more detail, it may be helpful to an understanding thereof to provide definitions of certain terms to be used herein.

Unless defined otherwise, all technical and scientific terms used herein have the same meaning as commonly understood by those of ordinary skill in the art to which the invention belongs. Although any methods and materials similar or equivalent to those described herein can be used in the practice or testing of particular embodiments, preferred embodiments of compositions, methods and materials are described herein. For the purposes of the present disclosure, the following terms are defined below.

The articles "a," "an," and "the" are used herein to refer to one or to more than one (i.e., to at least one, or to one or more) of the grammatical object of the article. By way of example, "an element" means one element or one or more elements.

The use of the alternative (e.g., "or") should be understood to mean either one, both, or any combination of the recited alternatives.

The term "and/or" should be understood to mean either one of, or both of, the alternatives.

As used herein, the term "about" or "approximately" refers to a quantity, level, value, number, frequency, percentage, dimension, size, amount, weight or length that varies by as much as 15%, 10%, 9%, 8%, 7%, 6%, 5%, 4%, 3%, 2% or 1% to a reference quantity, level, value, number, frequency, percentage, dimension, size, amount, weight or length. In one embodiment, the term "about" or "approximately" refers a range of quantity, level, value, number, frequency, percentage, dimension, size, amount, weight or length ±15%, ±10%, ±9%, ±8%, ±7%, ±6%, ±5%, ±4%, ±3%, ±2%, or ±1% of a reference quantity, level, value, number, frequency, percentage, dimension, size, amount, weight or length.

In one embodiment, a range, e.g., 1 to 5, about 1 to 5, or about 1 to about 5, refers to each numerical value encompassed by the range. For example, in one non-limiting and merely illustrative embodiment, the range "1 to 5" is equivalent to the expression 1, 2, 3, 4, 5; or 1.0, 1.5, 2.0, 2.5, 3.0, 3.5, 4.0, 4.5, or 5.0; or 1.0, 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, 3.0, 3.1, 3.2, 3.3, 3.4, 3.5, 3.6, 3.7, 3.8, 3.9, 4.0, 4.1, 4.2, 4.3, 4.4, 4.5, 4.6, 4.7, 4.8, 4.9, or 5.0.

As used herein, the term "substantially" refers to a quantity, level, value, number, frequency, percentage, dimension, size, amount, weight or length that is 80%, 85%, 90%, 91%, 92%, 93%, 94%, 95%, 96%, 97%, 98%, 99% or higher compared to a reference quantity, level, value, number, frequency, percentage, dimension, size, amount, weight or length. In one embodiment, "substantially the same" refers to a quantity, level, value, number, frequency, percentage, dimension, size, amount, weight or length that produces an effect, e.g., a physiological effect, that is approximately the same as a reference quantity, level, value, number, frequency, percentage, dimension, size, amount, weight or length. In particular embodiments, "substantially lacks cell binding or cell attachment activity and/or cognate receptor binding activity" or "substantially abates cell binding or cell attachment activity and/or cognate receptor binding activity" refers to the negligible or undetectable or absent cell binding activity or cell attachment activity of a modified membrane-bound viral glycoprotein contemplated herein to bind or attach to its cognate receptor on the surface of a cell compared to the cell binding activity or cell attachment activity of the unmodified membrane-bound viral glycoprotein to bind or attach to its cognate receptor on the surface of the cell.

Throughout this specification, unless the context requires otherwise, the words "comprise", "comprises" and "comprising" will be understood to imply the inclusion of a stated step or element or group of steps or elements but not the exclusion of any other step or element or group of steps or elements. By "consisting of" is meant including, and limited to, whatever follows the phrase "consisting of." Thus, the phrase "consisting of" indicates that the listed elements are required or mandatory and that no other elements may be present. The phrase "consisting essentially of" means including any elements listed after the phrase and other elements that do not interfere with or contribute to the activity or action specified in the disclosure for the listed elements. Thus, the phrase "consisting essentially of" indicates that the listed elements are required or mandatory but that no other elements are present that materially affect the activity or action of the listed elements.

Reference throughout this specification to "one embodiment," "an embodiment," "a particular embodiment," "a related embodiment," "a certain embodiment," "an additional embodiment," or "a further embodiment" or combinations thereof means that a particular feature, structure or characteristic described in connection with the embodiment is included in at least one embodiment. Thus, the appearances of the foregoing phrases in various places throughout this specification are not necessarily all referring to the same embodiment. Furthermore, the particular features, structures, or characteristics may be combined in any suitable manner in one or more embodiments. It is also understood that the positive recitation of a feature in one embodiment, serves as a basis for excluding the feature in a particular embodiment.

The terms "spacer," "spacer domain," or "spacer polypeptide" are used interchangeably and refer to a polypeptide domain or sequence of amino acids in a non-viral membrane-bound tropism polypeptide disposed between an extracellular antigen targeting domain and a transmembrane domain. A spacer positions the extracellular antigen targeting domain away from the particle surface to enable proper particle/target cell contact, attachment, or binding. A spacer may be derived either from a natural, synthetic, semi-synthetic, or recombinant source. Illustrative examples of spacer domains include but are not limited to hinge or stalk domains derived, obtained, or isolated from CD8α, CD28, and CD45 isoforms, and polypeptide linkers of similar amino acid composition, rigidity, flexibility and/or length.

A "hinge domain," is a type of spacer domain that plays a role in positioning the antigen binding domain away from the effector cell surface to enable proper cell/cell contact, antigen binding and activation. A hinge domain is placed between a binding domain and a transmembrane domain (TM) of a non-viral membrane-bound tropism polypeptide or between an anti-BCMA antibody or antigen binding fragment thereof and a TM domain of a chimeric antigen receptor. A hinge domain may be derived either from a natural, synthetic, semi-synthetic, or recombinant source. A hinge domain may be altered by substituting one or more cysteine and/or proline residues in a naturally occurring immunoglobulin hinge domain with one or more other amino acid residues (e.g., one or more serine residues).

A "transmembrane domain" or "TM domain" refers to a hydrophobic portion of polypeptide that anchors the polypeptide to the plasma membrane of the cell. The TM domain may be derived either from a natural, synthetic, semi-synthetic, or recombinant source.

An "intracellular signaling domain" refers to a polypeptide domain that participates in transducing the message of effective binding of a target antigen by a chimeric antigen receptor expressed on an immune effector cell to the immune effector cell's interior to elicit one or more effector functions (an "effector function" refers to a specialized function of an immune effector cell), e.g., activation, cytokine production, proliferation and cytotoxic activity, including the release of cytotoxic factors, or other cellular responses elicited with antigen binding to the receptor expressed on the immune effector cell. "Intracellular signaling domains" include a polypeptide domain or functional fragment thereof, which transduces an effector function signal and that directs a cell to perform a specialized function. The term intracellular signaling domain is meant to include any truncated portion of an intracellular signaling domain sufficient to transduce effector function signal.

T cell activation can be said to be mediated by two distinct classes of intracellular signaling domains: primary signaling domains that initiate antigen-dependent primary activation through the TCR (e.g., a TCR/CD3 complex) and costimulatory signaling domains that act in an antigen-independent manner to provide a secondary or costimulatory signal.

A "primary signaling domain" refers to a signaling domain that regulates the primary activation of a TCR complex either in a stimulatory way, or in an inhibitory way.

Primary signaling domains that act in a stimulatory manner may contain one or more signaling motifs which are known as immunoreceptor tyrosine-based activation motifs or ITAMs.

A "costimulatory signaling domain" or "costimulatory domain" refers to an intracellular signaling domain of a costimulatory molecule. Costimulatory molecules are cell surface molecules other than antigen receptors or Fc receptors that provide a second signal required for efficient activation and function of T lymphocytes upon binding to antigen.

"Linker," "peptide linker," and "polypeptide linker" are used interchangeably and refer to a plurality of amino acid residues between various polypeptide domains added for appropriate spacing, conformation, and function. A polypeptide linker sequence may be employed to separate any two or more polypeptide components by a distance sufficient to ensure that each polypeptide folds into its appropriate secondary and tertiary structures so as to allow the polypeptide domains to exert their desired functions. Linkers include a "variable domain linking sequence," an amino acid sequence that connects two or more domains of an antibody or antigen binding fragments thereof and provides a spacer function compatible with interaction of the two sub-binding domains so that the resulting polypeptide retains a specific binding affinity to the same target molecule as an antibody that comprises the same light and/or heavy chain variable domains. A linker may be 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50 or more amino acids long. Illustrative examples of linkers include, but are not limited to the following amino acid sequences:

(SEQ ID NO: 342)
TGEKP;

(SEQ ID NOs: 343-347)
(GGGGS)n wherein n = 1, 2, 3, 4 or 5;

(SEQ ID NO: 348)
EGKSSGSGSESKVD;

(SEQ ID NO: 349)
KESGSVSSEQLAQFRSLD;

(SEQ ID NO: 350)
LRQRDGERP;

(SEQ ID NO: 351)
LRQKDGGGSERP;

(SEQ ID NO: 352)
LRQKD(GGGS)$_2$ERP, (SEQ ID NO: 353)
GEGTSTGSGGSGGSGGAD,
and (SEQ ID NO: 354)
GSTSGSGKPGSGEGSTKG.

The terms "individual" and "subject" are often used interchangeably and refer to any animal that exhibits a symptom of a disease, disorder, or condition, e.g., cancer, that can be treated with the recombinant particles, e.g., recombinant lentiviral particles contemplated elsewhere herein. Suitable subjects (e.g., patients) include laboratory animals (e.g., mouse, rat, rabbit, or guinea pig), farm animals, and domestic animals or pets (e.g., cat or dog). Non-human primates and, preferably, human patients, are preferred subjects.

A "patient" refers to a subject that has been diagnosed with a particular disease, disorder, or condition that can be treated with the recombinant particles disclosed elsewhere herein.

"Treatment" or "treating," as used herein includes any beneficial or desirable effect on the symptoms or pathology of a disease or pathological condition and may include even minimal reductions in one or more measurable markers of the disease or condition being treated. Optionally, treatment can include reducing the disease burden or delaying disease progression. "Treatment" may, but does not necessarily, indicate complete eradication or cure of the disease or condition, or associated symptoms thereof.

"Prevent," "prevention," "preventing" and the like, as used herein, indicate an approach for preventing, inhibiting, or reducing the likelihood of occurrence or recurrence of a disease or condition. It also refers to delaying the onset or recurrence of a disease or condition or delaying the occurrence or recurrence of the symptoms of a disease or condition. Prevention includes reducing the intensity, effect, symptoms and/or burden of a disease or condition prior to onset or recurrence of the disease or condition.

"Ameliorating at least one symptom of" as used herein, refers to decreasing one or more symptoms of the disease or condition for which a subject is being treated. In particular embodiments, the disease or condition being treated is a cancer, and the one or more symptoms ameliorated include, but are not limited to, weakness, fatigue, shortness of breath, easy bruising and bleeding, frequent infections, enlarged lymph nodes, distended or painful abdomen (due to enlarged abdominal organs), bone or joint pain, fractures, unplanned weight loss, poor appetite, night sweats, persistent mild fever, and decreased urination (due to impaired kidney function).

Additional definitions are set forth throughout this disclosure.

C. Recombinant Particles

Various particles may be used as gene delivery vehicles, e.g., a fusosome; an extracellular vesicle, including a microvesicle, an apoptotic body, and an exosome; a lipid nanoparticle; a virus-like particle (VLPs); or a recombinant viral particle. The present disclosure contemplates, in part, a recombinant lentiviral particle engineered to bind to an immune effector cell and transduce the cell with a vector encoding an anti-BCMA CAR.

Recombinant retroviral particles have been used as a gene delivery platform for treatments of severe genetic diseases and cancer. A "lentivirus" refers to a complex retrovirus. Among retroviruses, lentiviruses are the most efficient at transducing resting or growth-arrested cells. In preferred embodiments, a recombinant particle is a recombinant lentiviral particle or recombinant lentivirus. The terms "recombinant lentiviral particle" and "recombinant lentivirus" are used interchangeably.

Lentiviruses suitable for deriving or engineering recombinant lentiviruses contemplated in particular embodiments herein include but are not limited to human immunodeficiency virus (HIV), including HIV type 1 (HIV-1) and HIV type 2 (HIV-2); visna-maedi virus (VMV); caprine arthritis-encephalitis virus (CAEV); equine infectious anemia virus (EIAV); feline immunodeficiency virus (FIV); bovine immune deficiency virus (BIV); and simian immunodeficiency virus (SIV).

In particular embodiments, a recombinant lentiviral particle is derived or engineered from an HIV-1 or HIV-2 lentivirus.

In particular embodiments, a recombinant lentiviral particle comprises (i) a particle surface comprising (a) a mutated viral envelope glycoprotein and (b) a non-viral membrane-bound tropism polypeptide that binds an immune effector cell; and (ii) two copies of a lentiviral vector comprising or encoding a promoter operably linked to a polynucleotide encoding an anti-BCMA CAR.

D. Particle Surface

Recombinant particles are engineered to bind to an immune effector cell, e.g., a CD3+ cell and deliver one or more copies of a vector encoding an anti-BCMA chimeric antigen receptor to the cell.

In particular embodiments, a recombinant lentiviral particle comprises a viral envelope comprising a mutated vesiculovirus envelope glycoprotein that does not bind its cognate receptor, e.g., LDLR, but that mediates virus-cell fusion and a non-viral membrane-bound tropism polypeptide that redirects the particle to immune effector cells that express CD3; and a lentiviral vector encoding or comprising a promoter operably linked to a polynucleotide encoding an anti-BCMA CAR. The foregoing engineering strategy enables highly efficient on-target delivery of vectors encoding CARs to immune effector cells while minimizing, reducing and/or eliminating delivery to undesired cell types.

1. Viral Envelope Glycoproteins

In particular embodiments, a recombinant lentiviral particle comprises a mutated vesiculovirus envelope glycoprotein in which the native or a heterologous signal peptide has been cleaved. Thus, amino acid positions identified in mutated vesiculovirus envelope glycoproteins are with reference to the mature polypeptide, in which the signal peptide has been cleaved.

In particular embodiments, a vesiculovirus is vesicular stomatitis Indiana virus (VSIV). In particular embodiments, a mutated viral envelope glycoprotein is derived from a VSIV envelope glycoprotein (VSIV-G) set forth in Table 1.

TABLE 1

VSIV-G polypeptides

| SEQ ID NO: | AMINO ACID SEQUENCE |
|---|---|
| 1 | KFTIVFPHNQKGNWKNVPSNYHYCPSSSDLNWHNDLIGTALQVKMPKSHKAIQADGWMCHASKWVTT<br>CDFRWYGPKYITHSIRSFTPSVEQCKESIEQTKQGTWLNPGFPPQSCGYATVIDAEAVIVQVTPHHV<br>LVDEYTGEWVDSQFINGKCSNYICPTVHNSTTWHSDYKVKGLCDSNLISMDITFFSEDGELSSLGKE<br>GTGFRSNYFAYETGGKACKMQYCKHWGVRLPSGVWFEMADKDLFAAARFPECPEGSSISAPSQTSVD<br>VSLIQDVERILDYSLCQETWSKIRAGLPISPVDLSYLAPKNPGTGPAFTIINGTLKYFETRYIRVDI<br>AAPILSRMVGMISGTTTERELWDDWAPYEDVEIGPNGVLRTSSGYKFPLYMIGHGMLDSDLHLSSKA<br>QVFEHPHIQDAASQLPDDESLFFGDTGLSKNPIELVEGWFSSWKSSIASFFFIIGLIIGLFLVLRVG<br>IHLCIKLKHTKKRQIYTDIEMNRLGK |
| 2 | KFTIVFPHNQKGNWKNVPSNYHYCPSSSDLNWHNDLIGTAIQVKMPKSHKAIQADGWMCHASKWVTT<br>CDFRWYGPKYITQSIRSFTPSVEQCKESIEQTKQGTWLNPGFPPQSCGYATVIDAEAVIVQVTPHHV<br>LVDEYTGEWVDSQFINGKCSNYICPTVHNSTTWHSDYKVKGLCDSNLISMDITFFSEDGELSSLGKE<br>GTGFRSNYFAYETGGKACKMQYCKHWGVRLPSGVWFEMADKDLFAAARFPECPEGSSISAPSQTSVD<br>VSLIQDVERILDYSLCQETWSKIRAGLPISPVDLSYLAPKNPGTGPAFTIINGTLKYFETRYIRVDI<br>AAPILSRMVGMISGTTTERELWDDWAPYEDVEIGPNGVLRTSSGYKFPLYMIGHGMLDSDLHLSSKA<br>QVFEHPHIQDAASQLPDDESLFFGDTGLSKNPIELVEGWFSSWKSSIASFFFIIGLIIGLFLVLRVG<br>IHLCIKLKHTKKRQIYTDIEMNRLGK |
| 3 | KFTIVFPHNQKGNWKNVPSNYHYCPSSSDLNWHNDLIGTAIQVKMPKSHKAIQADGWMCHASKWVTT<br>CDFRWYGPKYITHSIRSFTPSVEQCKESIEQTKQGTWLNPGFPPQSCGYATVIDAEAVIVQVTPHHV<br>LVDEYTGEWVDSQFINGKCSNYICPTVHNSTTWHSDYKVKGLCDSNLISMDITFFSEDGELSSLGKE<br>GTGFRSNYFAYETGGKACKMQYCKHWGVRLPSGVWFEMADKDLFAAARFPECPEGSSISAPSQTSVD<br>VSLIQDVERILDYSLCQETWSKIRAGLPISPVDLSYLAPKNPGTGPAFTIINGTLKYFETRYIRVDI<br>AAPILSRMVGMISGTTTERELWDDWAPYEDVEIGPNGVLRTSSGYKFPLYMIGHGMLDSDLHLSSKA<br>QVFEHPHIQDAASQLPDDESLFFGDTGLSKNPIELVEGWFSSWKSSIASFFFIIGLIIGLFLVLRVG<br>IHLCIKLKHTKKRQIYTDIEMNRLGK |
| 4 | KFTIVFPHNQKGNWKNVPSNYHYCPSSSDLNWHNDLIGTALQVKMPKSHKAIQADGWMCHASKWVTT<br>CDFRWYGPKYITQSIRSFTPSVEQCKESIEQTKQGTWLNPGFPPQSCGYATVTDAEAVIVQVTPHHV<br>LVDEYTGEWVDSQFINGKCSNYICPTVHNSTTWHSDYKVKGLCDSNLISMDITFFSEDGELSSLGKE<br>GTGFRSNYFAYETGGKACKMQYCKHWGVRLPSGVWFEMADKDLFAAARFPECPEGSSISAPSQTSVD<br>VSLIQDVERILDYSLCQETWSKIRAGLPISPVDLSYLAPKNPGTGPAFTIINGTLKYFETRYIRVDI<br>AAPILSRMVGMISGTTTERELWDDWAPYEDVEIGPNGVLRTSSGYKFPLYMIGHGMLDSDLHLSSKA<br>QVFEHPHIQDAASQLPDDESLFFGDTGLSKNPIELVEGWFSSWKSSIASFFFIIGLIIGLFLVLRVG<br>IHLCIKLKHTKKRQIYTDIEMNRLGK |
| 5 | KFTIVFPHNQKGNWKNVPSNYHYCPSSSDLNWHNDLIGTALQVKMPKSHKAIQADGWMCHASKWITT<br>CDFRWYGPKYITHSIQSFTPSVEQCKESIEQTKQGTWLNPGFPPQSCGYATVIDAEAVIVQVTPHHV<br>LVDEYTGEWVDSQFINGKCSNDICLTVHNSTTWHSDYKVKGLCDSNLISMDITFFSEDGELSSLGKA<br>GTGFRSNYFAYETGDKACKMQYCKHWGVRLPSGVWFEMADKDLFAAAKFPECPEGSSISAPSQTSVD<br>VSLIQDVERILDYSLCQETWSKIRAGLPISPVDLSYLAPKNPGTGPAFTIINGTLKYFETRYIRVDI<br>AAPILSRMVGMISGTNTERELWEDWAPYEDVEIGPNGVLRTSSGYKFPLYMIGHGMLDSDLHLSSKV<br>QVFEHPHIQDAASQLPDDETLFFGDTGLSKNPIELVEGWFSGWKSSIASFFFIIGLIIGLFLVLRVG<br>IYLCIKLKHTRKRKIYADIEMNRLGK |
| 6 | KFTTVFPHNKKGDWKNVPSNYHYCPSSSDLNWHNDLIGTALQVKMPKSHKAIQADGWMCHASKWVTT<br>CDFRWYGPKYITHSIRSFTPSVEQCKESIEQTKQGTWLNPGFPPQSCGYATVIDAEAVIVQVTPHHV |

TABLE 1-continued

VSIV-G polypeptides

| SEQ ID NO: | AMINO ACID SEQUENCE |
|---|---|
| | LVDEYTGEWVDSQFINGKCSDDICPTVHNSTTWHSDYKVKGLCDSNLISMDITFFSEDGELSSLGKE<br>GTGFRSNYFAYETGDKACKMQYCKHWGVRLPSGVWFEMADKNLFAAAKFPECPEGSSISAPSQTSVD<br>VSLIQDVERILDYSLCQETWSKIRAGLPISPVDLSYLAPKNPGTGPAFTIINGTLKYFETRYIRVDI<br>AAPILSRMVGMISGTTTERELWEDWAPYEDVEIGPNGVLRTSSGYKFPLYMIGHGMLDSDLHLSSKA<br>QVFEHPHIPDATSQLPDDETLFFGDTGLSKDPIELVEGWFSGWKSSIASFFFIIGLIIGLFFVLRIG<br>VYLCIKLKHTNKRQIYTDIEMNRLGK |
| 7 | KFTIVFPHNQKGTWKNVPSNYHYCPSSSDLNWHNDLIGTALQVKMPKSHKAIQADGWMCHASKWVTT<br>CDFRWYGPKYITHSIRSFTPSVEQCRESIEQTKQGTWLNPGFPPQSCGYATVIDAEAVIVQVTPHHV<br>LVDEYTGEWVDSQFINGKCSNDICPTVHNSTTWHSDYKVKGLCDSNLISMDITFFSEDGELSSLGKE<br>GTGFRSNHFAYETGDKACKMQYCKHWGVRLPSGVWFEMADQDLFAAARFPECPEGSSISAPSQTSVD<br>VSLIQDVERILDYSLCQETWSKIGAGLPISPVDLSYLAPKNPGTGPAFTIINGTLKYFETRYIRVDI<br>AAPILSRMVGMISGTTTERELWDDWAPYEDVEIGPNGVLRTSSGYKFPLYMIGHGMLDSDLHLSSKA<br>QVFEHPHIQDAASQLPDDETLFFGDTGLSKNPIELVEGWFSGWKSSIASFFFIIGLIIGLFLVLRVG<br>IYLCIKLKHTKKRQIYTDIEMNRLGK |
| 8 | KFTIVFPHNQKGNWKNVPSNYHYCPSSSDLNWHNDLIGTGLQVKMPKSHKAIQADGWMCHASKWVTT<br>CDFRWYGPKYITHSIRSFTPSVEQCKESIEQTKQGTWLNPGFPPQSCGYATVIDAEAVIVQVTPHHV<br>LVDEYTGEWVDSQFINGKCSNDICPTVHNSTTWHSDYKVKGLCDSNLISTDITFFSEDRELSSLGKE<br>GTGFRSNYFAYETGDKACKMQYCKHWGVRLPSGVWFEMADKDLFAAARFPECPEGSSISAPSQTSVD<br>VSLIQDVERILDYSLCQETWSKIRAGLPISPVDLSYLAPKNPGTGPAFTIINGTLKYFETRYIRVDI<br>AAPILSRMVGMISGTTTERELWDDWAPYEDVEIGPNGVLRTSSGYKFPLYMIGHGMLDSGLHLSSKA<br>QVFEHPHIQDAASQLPDDEILFFGDTGLSKNPIDFVEGWFSSWKSSIASFFFIIGLIIGLFLVLRVG<br>IYLYIKLKHTKKRQIYTDIEMNRLGR |

In particular embodiments, a mutated viral envelope glycoprotein is derived from a VSIV envelope glycoprotein (VSIV-G) comprising an amino acid sequence set forth in any one of SEQ ID NOs: 1-8 or an amino acid sequence at least 95%, 96%, 97%, 98%, or 99% identical thereto.

In particular embodiments, a mutated VSIV-G polypeptide comprises one or more amino acid substitutions at K47, 1182, and/or R354 (substitution with any amino acid; a conservation substitution; a disruptive substitution; substitution with D, E, A, G, F, or Q; or substitution with A, G, F, or Q). In particular embodiments, a mutated VSIV-G polypeptide comprises amino acid substitutions at K47, 1182, or R354; K47 and 1182; K47 and R354; 1182 and R354; or at K47, 1182, and R354 of any one of SEQ ID NOs: 1-8.

In particular embodiments, a mutated VSIV-G polypeptide comprises one or more of the following amino acid substitutions: K47A, K47Q, I182E, I182D, R354A, and/or R354Q. In particular embodiments, a mutated VSIV-G polypeptide comprises the following amino acid substitutions: K47A, K47Q, I182E, I182D, R354A, or R354Q; K47A and I182E; K47A and I182D; K47Q and I182E; K47Q and I182D; I182E and R354A; I182E and R354Q; I182D and R354A; I182D and R354Q; K47A and R354A; K47A and R354Q; K47Q and R354A; K47Q and R354Q; K47A, I182E, and R354A; K47A, I182D, and R354A; K47Q, I182E, and R354A; K47Q, I182D, and R354A; K47A, I182E, and R354Q; K47A, I182D, and R354Q; K47Q, I182E, and R354Q; or K47Q, I182D, and R354Q of any one of SEQ ID NOs: 1-8. In a preferred embodiment, a VSIV-G polypeptide comprises the amino acid substitutions K47Q and R354A of any one of SEQ ID NOs: 1, 2, 3, 4, 5, 6, 7, or 8.

In particular embodiments, a mutated VSIV-G polypeptide comprises an amino acid sequence set forth in Table 2 (SEQ ID NOs: 332, 333, 334, or 335) or an amino acid sequence at least 95%, 96%, 97%, 98%, or 99% identical thereto that mediates fusion of the lentiviral particle and an immune effector cell but that substantially ablates or ablates the polypeptide's ability to bind its cognate receptor expressed on a cell, e.g., LDL-R.

TABLE 2

| SEQ ID NO: | AMINO ACID SEQUENCE |
|---|---|
| 332 | KFTIVFPHNQKGNWKNVPSNYHYCPSSSDLNWHNDLIGTAIQVKMPQSHKAIQADGWMCHASKW<br>VTTCDFRWYGPKYITQSIRSFTPSVEQCKESIEQTKQGTWLNPGFPPQSCGYATVTDAEAVIVQ<br>VTPHHVLVDEYTGEWVDSQFINGKCSNYICPTVHNSTTWHSDYKVKGLCDSNLISMDITFFSED<br>GELSSLGKEGTGFRSNYFAYETGGKACKMQYCKHWGVRLPSGVWFEMADKDLFAAARFPECPEG<br>SSISAPSQTSVDVSLIQDVERILDYSLCQETWSKIRAGLPISPVDLSYLAPKNPGTGPAFTIIN<br>GTLKYFETRYIRVDIAAPILSRMVGMISGTTTEAELWDDWAPYEDVEIGPNGVLRTSSGYKFPL<br>YMIGHGMLDSDLHLSSKAQVFEHPHIQDAASQLPDDESLFFGDTGLSKNPIELVEGWFSSWKSS<br>IASFFFIIGLIIGLFLVLRVGIHLCIKLKHTKKRQIYTDIEMNRLGK |
| 333 | KFTIVFPHNQKGNWKNVPSNYHYCPSSSDLNWHNDLIGTALQVKMPQSHKAIQADGWMCHASKW<br>VTTCDFRWYGPKYITQSIRSFTPSVEQCKESIEQTKQGTWLNPGFPPQSCGYATVTDAEAVIVQ<br>VTPHHVLVDEYTGEWVDSQFINGKCSNYICPTVHNSTTWHSDYKVKGLCDSNLISMDITFFSED<br>GELSSLGKEGTGFRSNYFAYETGGKACKMQYCKHWGVRLPSGVWFEMADKDLFAAARFPECPEG<br>SSISAPSQTSVDVSLIQDVERILDYSLCQETWSKIRAGLPISPVDLSYLAPKNPGTGPAFTIIN<br>GTLKYFETRYIRVDIAAPILSRMVGMISGTTTEAELWDDWAPYEDVEIGPNGVLRTSSGYKFPL |

TABLE 2-continued

| SEQ ID NO: | AMINO ACID SEQUENCE |
|---|---|
| | YMIGHGMLDSDLHLSSKAQVFEHPHIQDAASQLPDDESLFFGDTGLSKNPIELVEGWFSSWKSS IASFFFIIGLIIGLFLVLRVGIHLCIKLKHTKKRQIYTDIEMNRLGK |
| 334 | KFTIVFPHNQKGNWKNVPSNYHYCPSSSDLNWHNDLIGTAIQVKMPQSHKAIQADGWMCHASKW VTTCDFRWYGPKYITHSIRSFTPSVEQCKESIEQTKQGTWLNPGFPPQSCGYATVIDAEAVIVQ VTPHHVLVDEYTGEWVDSQFINGKCSNYICPTVHNSTTWHSDYKVKGLCDSNLISMDITFFSED GELSSLGKEGTGFRSNYFAYETGGKACKMQYCKHWGVRLPSGVWFEMADKDLFAAARFPECPEG SSISAPSQTSVDVSLIQDVERILDYSLCQETWSKIRAGLPISPVDLSYLAPKNPGTGPAFTIIN GTLKYFETRYIRVDIAAPILSRMVGMISGTTTEAELWDDWAPYEDVEIGPNGVLRTSSGYKFPL YMIGHGMLDSDLHLSSKAQVFEHPHIQDAASQLPDDESLFFGDTGLSKNPIELVEGWFSSWKSS IASFFFIIGLIIGLFLVLRVGIHLCIKLKHTKKRQIYTDIEMNRLGK |
| 335 | KFTIVFPHNQKGNWKNVPSNYHYCPSSSDLNWHNDLIGTALQVKMPQSHKAIQADGWMCHASKW VTTCDFRWYGPKYITHSIRSFTPSVEQCKESIEQTKQGTWLNPGFPPQSCGYATVTDAEAVIVQ VTPHHVLVDEYTGEWVDSQFINGKCSNYICPTVHNSTTWHSDYKVKGLCDSNLISMDITFFSED GELSSLGKEGTGFRSNYFAYETGGKACKMQYCKHWGVRLPSGVWFEMADKDLFAAARFPECPEG SSISAPSQTSVDVSLIQDVERILDYSLCQETWSKIRAGLPISPVDLSYLAPKNPGTGPAFTIIN GTLKYFETRYIRVDIAAPILSRMVGMISGTTTEAELWDDWAPYEDVEIGPNGVLRTSSGYKFPL YMIGHGMLDSDLHLSSKAQVFEHPHIQDAASQLPDDESLFFGDTGLSKNPIELVEGWFSSWKSS IASFFFIIGLIIGLFLVLRVGIHLCIKLKHTKKRQIYTDIEMNRLGK |

In particular embodiments, a vesiculovirus is cocal virus (COCV). In particular embodiments, a mutated viral envelope glycoprotein is derived from a COCV envelope glycoprotein (COCV-G) set forth in Table 3.

TABLE 3

| COCV-G polypeptide | |
|---|---|
| SEQ ID NO | AMINO ACID SEQUENCE |
| 9 | KFSIVFPQSQKGNWKNVPSSYHYCPSSSDQNWHNDLLGITMKVKM PKTHKAIQADGWMCHAAKWITTCDFRWYGPKYITHSIHSIQPTSE QCKESIKQTKQGTWMSPGFPPQNCGYATVTDSVAVVVQATPHHVL VDEYTGEWIDSQFPNGKCETEECETVHNSTVWYSDYKVTGLCDAT LVDTEITFFSEDGKKESIGKPNTGYRSNYFAYEKGDKVCKMNYCK HAGVRLPSGVWFEFVDQDVYAAAKLPECPVGATISAPTQTSVDVS LILDVERILDYSLCQETWSKIRSKQPVSPVDLSYLAPKNPGTGPA FTIINGTLKYFETRYIRIDIDNPIISKMVGKISGSQTERELWTEW FPYEGVEIGPNGILKTPTGYKFPLFMIGHGMLDSDLHKTSQAEVF EHPHLAEAPKQLPEEETLFFGDTGISKNPVELIEGWESSWKSTVV TFFFAIGVFILLYVVARIVIAVRYRYQGSNNKRIYNDIEMSRFRK |

In particular embodiments, a mutated viral envelope glycoprotein is derived from a COCV envelope glycoprotein (COCV-G) comprising an amino acid sequence set forth in SEQ ID NO: 9 or an amino acid sequence at least 95%, 96%, 97%, 98%, or 99% identical thereto.

In particular embodiments, a mutated COCV-G polypeptide comprises one or more amino acid substitutions at K47, V182, and/or R354 (substitution with any amino acid; a conservation substitution; a disruptive substitution; substitution with D, E, A, G, F, or Q; or substitution with A, G, F, or Q). In particular embodiments, a mutated COCV-G polypeptide comprises amino acid substitutions at K47, V182, or R354; K47 and V182; K47 and R354; V182 and R354; or at K47, V182, and R354 of SEQ ID NO: 9.

In particular embodiments, a mutated COCV-G polypeptide comprises one or more of the following amino acid substitutions: K47A, K47Q, V182E, V182D, R354A, and/or R354Q. In particular embodiments, a mutated VSIV-G polypeptide comprises the following amino acid substitutions: K47A, K47Q, V182E, V182D, R354A, or R354Q; K47A and V182E; K47A and V182D; K47Q and V182E; K47Q and V182D; V182E and R354A; V182E and R354Q; V182D and R354A; V182D and R354Q; K47A and R354A; K47A and R354Q; K47Q and R354A; K47Q and R354Q; K47A, V182E, and R354A; K47A, V182D, and R354A; K47Q, V182E, and R354A; K47Q, V182D, and R354A; K47A, V182E, and R354Q; K47A, V182D, and R354Q; K47Q, V182E, and R354Q; or K47Q, V182D, and R354Q of SEQ ID NO: 9. In a preferred embodiment, a COCV-G polypeptide comprises the amino acid substitutions K47Q and R354A of SEQ ID NO: 9.

In particular embodiments, a mutated COCV-G polypeptide comprises an amino acid sequence set forth in Table 4 (SEQ ID NOs: 336, 337, 338, and 339) or an amino acid sequence at least 95%, 96%, 97%, 98%, or 99% identical thereto that mediates fusion of the lentiviral particle and an immune effector cell but that substantially ablates or ablates the polypeptide's ability to bind its cognate receptor expressed on a cell, e.g., LDLR.

TABLE 4

| SEQ ID NO: | AMINO ACID SEQUENCE |
|---|---|
| 336 | KFSIVFPQSQKGNWKNVPSSYHYCPSSSDQNWHNDLLGITMKVKMPATHKAIQADGWMCHAAKW ITTCDFRWYGPKYITHSIHSIQPTSEQCKESIKQTKQGTWMSPGFPPQNCGYATVTDSVAVVVQ ATPHHVLVDEYTGEWIDSQFPNGKCETEECETVHNSTVWYSDYKVTGLCDATLVDTEITFFSED GKKESIGKPNTGYRSNYFAYEKGDKVCKMNYCKHAGVRLPSGVWFEFVDQDVYAAAKLPECPVG ATISAPTQTSVDVSLILDVERILDYSLCQETWSKIRSKQPVSPVDLSYLAPKNPGTGPAFTIIN GTLKYFETRYIRIDIDNPIISKMVGKISGSQTEAELWTEWFPYEGVEIGPNGILKTPTGYKFPL FMIGHGMLDSDLHKTSQAEVFEHPHLAEAPKQLPEEETLFFGDTGISKNPVELIEGWFSSWKST VVTFFFAIGVFILLYVVARIVIAVRYRYQGSNNKRIYNDIEMSRFRK |

TABLE 4-continued

| SEQ ID NO: | AMINO ACID SEQUENCE |
|---|---|
| 337 | KFSIVFPQSQKGNWKNVPSSYHYCPSSSDQNWHNDLLGITMKVKMPATHKAIQADGWMCHAAKW ITTCDFRWYGPKYITHSIHSIQPTSEQCKESIKQTKQGTWMSPGFPPQNCGYATVTDSVAVVVQ ATPHHVLVDEYTGEWIDSQFPNGKCETEECETVHNSTVWYSDYKVTGLCDATLVDTEITFFSED GKKESIGKPNTGYRSNYFAYEKGDKVCKMNYCKHAGVRLPSGVWFEFVDQDVYAAAKLPECPVG ATISAPTQTSVDVSLILDVERILDYSLCQETWSKIRSKQPVSPVDLSYLAPKNPGTGPAFTIIN GTLKYFETRYIRIDIDNPIISKMVGKISGSQTEQELWTEWFPYEGVEIGPNGILKTPTGYKFPL FMIGHGMLDSDLHKTSQAEVFEHPHLAEAPKQLPEEETLFFGDTGISKNPVELIEGWFSSWKST VVTFFFAIGVFILLYVVARIVIAVRYRYQGSNNKRIYNDIEMSRFRK |
| 338 | KFSIVFPQSQKGNWKNVPSSYHYCPSSSDQNWHNDLLGITMKVKMPQTHKAIQADGWMCHAAKW ITTCDFRWYGPKYITHSIHSIQPTSEQCKESIKQTKQGTWMSPGFPPQNCGYATVTDSVAVVVQ ATPHHVLVDEYTGEWIDSQFPNGKCETEECETVHNSTVWYSDYKVTGLCDATLVDTEITFFSED GKKESIGKPNTGYRSNYFAYEKGDKVCKMNYCKHAGVRLPSGVWFEFVDQDVYAAAKLPECPVG ATISAPTQTSVDVSLILDVERILDYSLCQETWSKIRSKQPVSPVDLSYLAPKNPGTGPAFTIIN GTLKYFETRYIRIDIDNPIISKMVGKISGSQTEAELWTEWFPYEGVEIGPNGILKTPTGYKFPL FMIGHGMLDSDLHKTSQAEVFEHPHLAEAPKQLPEEETLFFGDTGISKNPVELIEGWESSWKST VVTFFFAIGVFILLYVVARIVIAVRYRYQGSNNKRIYNDIEMSRFRK |
| 339 | KFSIVFPQSQKGNWKNVPSSYHYCPSSSDQNWHNDLLGITMKVKMPQTHKAIQADGWMCHAAKW ITTCDFRWYGPKYITHSIHSIQPTSEQCKESIKQTKQGTWMSPGFPPQNCGYATVTDSVAVVVQ ATPHHVLVDEYTGEWIDSQFPNGKCETEECETVHNSTVWYSDYKVTGLCDATLVDTEITFFSED GKKESIGKPNTGYRSNYFAYEKGDKVCKMNYCKHAGVRLPSGVWFEFVDQDVYAAAKLPECPVG ATISAPTQTSVDVSLILDVERILDYSLCQETWSKIRSKQPVSPVDLSYLAPKNPGTGPAFTIIN GTLKYFETRYIRIDIDNPIISKMVGKISGSQTEQELWTEWFPYEGVEIGPNGILKTPTGYKFPL FMIGHGMLDSDLHKTSQAEVFEHPHLAEAPKQLPEEETLFFGDTGISKNPVELIEGWFSSWKST VVTFFFAIGVFILLYVVARIVIAVRYRYQGSNNKRIYNDIEMSRFRK |

2. Tropism Polypeptides

Recombinant particles contemplated herein comprise a tropism polypeptide that governs targeting the particle to an immune effector cell. A "tropism polypeptide" is a polypeptide that binds one or more antigens on a desired cell type. A "non-viral membrane bound tropism polypeptide" is a polypeptide that binds one or more antigens on a desired cell type; that is not native to, or derived from, either in whole or in part, a virus.

In particular embodiments, a recombinant lentiviral particle comprises an envelope comprising or expressing a mutated VSIV-G polypeptide comprising one or more amino acid substitutions at positions K47, I182, and/or R354 or a mutated COCV-G polypeptide comprising one or more amino acid substitutions at positions K47, V182, and/or R354; a non-viral membrane-bound tropism polypeptide that binds an antigen expressed on an immune effector cell, e.g., CD3; and one or more copies of a lentiviral vector encoding or comprising a promoter operably linked to a polynucleotide encoding an anti-BCMA CAR. In particular embodiments, a recombinant lentiviral particle comprises an envelope that further comprises a secondary non-viral membrane-bound tropism polypeptide that an antigen specifically expressed on an immune effector cell, e.g., CD80, CD86, OX40L, 4-1BBL, and ICOSL.

Non-viral membrane-bound tropism polypeptides contemplated herein comprise, consist essentially of, or consist of an extracellular antigen targeting domain, a spacer and a transmembrane domain. As used herein, an "extracellular antigen targeting domain" (also referred to as an "extracellular targeting domain," "antigen targeting domain," or "targeting domain") refers to any naturally occurring, synthetic, semi-synthetic, or recombinantly produced binding partner that binds a biological molecule or target antigen expressed or displayed on the surface of a cell. In preferred embodiments, an extracellular antigen targeting domain binds an antigen, e.g., CD3ε, expressed on an immune effector cell.

In particular embodiments, a non-viral membrane-bound tropism polypeptide comprises an extracellular antigen targeting domain comprising an antibody or antigen binding fragment thereof that binds CD3ε. In particular embodiments, an extracellular antigen targeting domain comprises an anti-CD3ε scFv isolated from an antibody selected from the group consisting of: OKT3, UCHT1, YTH12.5, TR66, and variants thereof.

In certain embodiments, a non-viral membrane-bound tropism polypeptide comprises an extracellular antigen targeting domain comprising an anti-CD3ε scFv comprising an amino acid sequence set forth in Table 5.

TABLE 5

| anti-CD3 antibodies | | | |
|---|---|---|---|
| Ab ID | SEQ ID NO | ID | AMINO ACID SEQUENCE |
| CD3.9 | 145 | VH | DVQLVQSGAEVKKPGASVKVSCKASGYTFTRYTMHWVRQAPGQGL EWIGYINPSRGYTNYADSVKGRFTITTDKSTSTAYMELSSLRSED TATYYCARYYDDHYCLDYWGQGTTVTVSS |
| | 146 | CDRH1 | RYTMH |
| | 147 | CDRH2 | YINPSRGYTNYADSVKG |
| | 148 | CDRH3 | YYDDHYCLDY |

TABLE 5-continued

| anti-CD3 antibodies | | | |
|---|---|---|---|
| Ab ID | SEQ ID NO | ID | AMINO ACID SEQUENCE |
| | 149 | VL | DIVLTQSPATLSLSPGERATLSCRASQSVSYMNWYQQKPGKAPKRWIYDTSKVASGVPARFSGSGSGTDYSLTINSLEAEDAATYYCQQWSSNPLTFGGGTKVEIK |
| | 150 | CDRL1 | RASQSVSYMN |
| | 151 | CDRL2 | DTSKVAS |
| | 152 | CDRL3 | QQWSSNPLT |
| | 153 | scFv | DVQLVQSGAEVKKPGASVKVSCKASGYTFTRYTMHWVRQAPGQGLEWIGYINPSRGYTNYADSVKGRFTITTDKSTSTAYMELSSLRSEDTATYYCARYYDDHYCLDYWGQGTTVTVSSSGGGGSGGGGSGGGGSDIVLTQSPATLSLSPGERATLSCRASQSVSYMNWYQQKPGKAPKRWIYDTSKVASGVPARFSGSGSGTDYSLTINSLEAEDAATYYCQQWSSNPLTFGGGTKVEIK |
| | 154 | scFv | DIVLTQSPATLSLSPGERATLSCRASQSVSYMNWYQQKPGKAPKRWIYDTSKVASGVPARFSGSGSGTDYSLTINSLEAEDAATYYCQQWSSNPLTFGGGTKVEIKSGGGGSGGGGSGGGGSDVQLVQSGAEVKKPGASVKVSCKASGYTFTRYTMHWVRQAPGQGLEWIGYINPSRGYTNYADSVKGRFTITTDKSTSTAYMELSSLRSEDTATYYCARYYDDHYCLDYWGQGTTVTVSS |
| CD3.10 | 155 | VH | DVQLVQSGAEVKKPGASVKVSCKASGYTFTRYTMHWVRQAPGQGLEWIGYINPSRGYTNYADSVKGRFTITTDKSTSTAYMELSSLRSEDTATYYCARYYDDPYCLDYWGQGTTVTVSS |
| | 156 | CDRH1 | RYTMH |
| | 157 | CDRH2 | YINPSRGYTNYADSVKG |
| | 158 | CDRH3 | YYDDPYCLDY |
| | 159 | VL | DIVLTQSPATLSLSPGERATLSCRASQSVSYMNWYQQKPGKAPKRWIYDTSKVASGVPARFSGSGSGTDYSLTINSLEAEDAATYYCQQWSSNPLTFGGGTKVEIK |
| | 160 | CDRL1 | RASQSVSYMN |
| | 161 | CDRL2 | DTSKVAS |
| | 162 | CDRL3 | QQWSSNPLT |
| | 163 | scFv | DVQLVQSGAEVKKPGASVKVSCKASGYTFTRYTMHWVRQAPGQGLEWIGYINPSRGYTNYADSVKGRFTITTDKSTSTAYMELSSLRSEDTATYYCARYYDDPYCLDYWGQGTTVTVSSSGGGGSGGGGSGGGGSDIVLTQSPATLSLSPGERATLSCRASQSVSYMNWYQQKPGKAPKRWIYDTSKVASGVPARFSGSGSGTDYSLTINSLEAEDAATYYCQQWSSNPLTFGGGTKVEIK |
| | 164 | scFv | DIVLTQSPATLSLSPGERATLSCRASQSVSYMNWYQQKPGKAPKRWIYDTSKVASGVPARFSGSGSGTDYSLTINSLEAEDAATYYCQQWSSNPLTFGGGTKVEIKSGGGGSGGGGSGGGGSDVQLVQSGAEVKKPGASVKVSCKASGYTFTRYTMHWVRQAPGQGLEWIGYINPSRGYTNYADSVKGRFTITTDKSTSTAYMELSSLRSEDTATYYCARYYDDPYCLDYWGQGTTVTVSS |
| CD3.11 | 165 | VH | DVQLVQSGAEVKKPGASVKVSCKASGYTFTRYTMHWVRQAPGQGLEWIGYINPSRGYTNYADSVKGRFTITTDKSTSTAYMELSSLRSEDTATYYCARYYNDQYCLDYWGQGTTVTVSSS |
| | 166 | CDRH1 | RYTMH |
| | 167 | CDRH2 | YINPSRGYTNYADSVKG |
| | 168 | CDRH3 | YYNDQYCLDY |
| | 169 | VL | DIVLTQSPATLSLSPGERATLSCRASQSVSYMNWYQQKPGKAPKRWIYDTSKVASGVPARFSGSGSGTDYSLTINSLEAEDAATYYCQQWSSNPLTFGGGTKVEIK |
| | 170 | CDRL1 | RASQSVSYMN |
| | 171 | CDRL2 | DTSKVAS |
| | 172 | CDRL3 | QQWSSNPLT |
| | 173 | scFv | DVQLVQSGAEVKKPGASVKVSCKASGYTFTRYTMHWVRQAPGQGLEWIGYINPSRGYTNYADSVKGRFTITTDKSTSTAYMELSSLRSEDTATYYCARYYNDQYCLDYWGQGTTVTVSSSSGGGGSGGGGSGGGGSDIVLTQSPATLSLSPGERATLSCRASQSVSYMNWYQQKPGKAPKRWIYDTSKVASGVPARFSGSGSGTDYSLTINSLEAEDAATYYCQQWSSNPLTFGGGTKVEIK |
| | 174 | scFv | DIVLTQSPATLSLSPGERATLSCRASQSVSYMNWYQQKPGKAPKRWIYDTSKVASGVPARFSGSGSGTDYSLTINSLEAEDAATYYCQQWSSNPLTFGGGTKVEIKSGGGGSGGGGSGGGGSDVQLVQSGAEVKKPGASVKVSCKASGYTFTRYTMHWVRQAPGQGLEWIGYINPSRGYTNYADSVKGRFTITTDKSTSTAYMELSSLRSEDTATYYCARYYNDQYCLDYWGQGTTVTVSSS |
| CD3.12 | 175 | VH | DVQLVQSGAEVKKPGASVKVSCKASGYTFTRYTMHWVRQAPGQGLEWIGYINPSRGYTNYADSVKGRFTITTDKSTSTAYMELSSLRSEDTATYYCARYYDAHNCLDYWGQGTTVTVSS |
| | 176 | CDRH1 | RYTMH |
| | 177 | CDRH2 | YINPSRGYTNYADSVKG |
| | 178 | CDRH3 | YYDAHNCLDY |

TABLE 5-continued anti-CD3 antibodies

| Ab ID | SEQ ID NO | ID | AMINO ACID SEQUENCE |
|---|---|---|---|
| | 179 | VL | DIVLTQSPATLSLSPGERATLSCRASQSVSYMNWYQQKPGKAPKR WIYDTSKVASGVPARFSGSGSGTDYSLTINSLEAEDAATYYCQQW SSNPLTFGGGTKVEIK |
| | 180 | CDRL1 | RASQSVSYMN |
| | 181 | CDRL2 | DTSKVAS |
| | 182 | CDRL3 | QQWSSNPLT |
| | 183 | scFv | DVQLVQSGAEVKKPGASVKVSCKASGYTFTRYTMHWVRQAPGQGL EWIGYINPSRGYTNYADSVKGRFTITTDKSTSTAYMELSSLRSED TATYYCARYYDAHNCLDYWGQGTTVTVSSSGGGGSGGGGSGGGGS DIVLTQSPATLSLSPGERATLSCRASQSVSYMNWYQQKPGKAPKR WIYDTSKVASGVPARFSGSGSGTDYSLTINSLEAEDAATYYCQQW SSNPLTFGGGTKVEIK |
| | 184 | scFv | DIVLTQSPATLSLSPGERATLSCRASQSVSYMNWYQQKPGKAPKR WIYDTSKVASGVPARFSGSGSGTDYSLTINSLEAEDAATYYCQQW SSNPLTFGGGTKVEIKSGGGGSGGGGSGGGGSDVQLVQSGAEVKK PGASVKVSCKASGYTFTRYTMHWVRQAPGQGLEWIGYINPSRGYT NYADSVKGRFTITTDKSTSTAYMELSSLRSEDTATYYCARYYDAH NCLDYWGQGTTVTVSS |
| CD3.13 | 185 | VH | DVQLVQSGAEVKKPGASVKVSCKASGYTFTRYTMHWVRQAPGQGL EWIGYINPSRGYTNYADSVKGRFTITTDKSTSTAYMELSSLRSED TATYYCARYSDDHYCLDYWGQGTTVTVSS |
| | 186 | CDRH1 | RYTMH |
| | 187 | CDRH2 | YINPSRGYTNYADSVKG |
| | 188 | CDRH3 | YSDDHYCLDY |
| | 189 | VL | DIVLTQSPATLSLSPGERATLSCRASQSVSYMNWYQQKPGKAPKR WIYDTSKVASGVPARFSGSGSGTDYSLTINSLEAEDAATYYCQQW SSNPLTFGGGTKVEIK |
| | 190 | CDRL1 | RASQSVSYMN |
| | 191 | CDRL2 | DTSKVAS |
| | 192 | CDRL3 | QQWSSNPLT |
| | 193 | scFv | DVQLVQSGAEVKKPGASVKVSCKASGYTFTRYTMHWVRQAPGQGL EWIGYINPSRGYTNYADSVKGRFTITTDKSTSTAYMELSSLRSED TATYYCARYSDDHYCLDYWGQGTTVTVSSSGGGGSGGGGSGGGGS DIVLTQSPATLSLSPGERATLSCRASQSVSYMNWYQQKPGKAPKR WIYDTSKVASGVPARFSGSGSGTDYSLTINSLEAEDAATYYCQQW SSNPLTFGGGTKVEIK |
| | 194 | scFv | DIVLTQSPATLSLSPGERATLSCRASQSVSYMNWYQQKPGKAPKR WIYDTSKVASGVPARFSGSGSGTDYSLTINSLEAEDAATYYCQQW SSNPLTFGGGTKVEIKSGGGGSGGGGSGGGGSDVQLVQSGAEVKK PGASVKVSCKASGYTFTRYTMHWVRQAPGQGLEWIGYINPSRGYT NYADSVKGRFTITTDKSTSTAYMELSSLRSEDTATYYCARYSDDH YCLDYWGQGTTVTVSS |
| CD3.14 | 195 | VH | DVQLVQSGAEVKKPGASVKVSCKASGYTFTRYTMHWVRQAPGQGL EWIGYINPSRGYTNYADSVKGRFTITTDKSTSTAYMELSSLRSED TATYYCARYSDDRYCLDYWGQGTTVTVSS |
| | 196 | CDRH1 | RYTMH |
| | 197 | CDRH2 | YINPSRGYTNYADSVKG |
| | 198 | CDRH3 | YSDDRYCLDY |
| | 199 | VL | DIVLTQSPATLSLSPGERATLSCRASQSVSYMNWYQQKPGKAPKR WIYDTSKVASGVPARFSGSGSGTDYSLTINSLEAEDAATYYCQQW SSNPLTFGGGTKVEIK |
| | 200 | CDRL1 | RASQSVSYMN |
| | 201 | CDRL2 | DTSKVAS |
| | 202 | CDRL3 | QQWSSNPLT |
| | 203 | scFv | DVQLVQSGAEVKKPGASVKVSCKASGYTFTRYTMHWVRQAPGQGL EWIGYINPSRGYTNYADSVKGRFTITTDKSTSTAYMELSSLRSED TATYYCARYSDDRYCLDYWGQGTTVTVSSSGGGGSGGGGSGGGGS DIVLTQSPATLSLSPGERATLSCRASQSVSYMNWYQQKPGKAPKR WIYDTSKVASGVPARFSGSGSGTDYSLTINSLEAEDAATYYCQQW SSNPLTFGGGTKVEIK |
| | 204 | scFv | DIVLTQSPATLSLSPGERATLSCRASQSVSYMNWYQQKPGKAPKR WIYDTSKVASGVPARFSGSGSGTDYSLTINSLEAEDAATYYCQQW SSNPLTFGGGTKVEIKSGGGGSGGGGSGGGGSDVQLVQSGAEVKK PGASVKVSCKASGYTFTRYTMHWVRQAPGQGLEWIGYINPSRGYT NYADSVKGRFTITTDKSTSTAYMELSSLRSEDTATYYCARYSDDR YCLDYWGQGTTVTVSS |
| CD3.15 | 205 | VH | DVQLVQSGAEVKKPGASVKVSCKASGYTFTRYTMHWVRQAPGQGL EWIGYINPSRGYTNYADSVKGRFTITTDKSTSTAYMELSSLRSED TATYYCARYYDDNYCLDYWGQGTTVTVSSS |
| | 206 | CDRH1 | RYTMH |
| | 207 | CDRH2 | YINPSRGYTNYADSVKG |
| | 208 | CDRH3 | YYDDNYCLDY |

TABLE 5-continued

| anti-CD3 antibodies | | | |
|---|---|---|---|
| Ab ID | SEQ ID NO | ID | AMINO ACID SEQUENCE |
| | 209 | VL | DIVLTQSPATLSLSPGERATLSCRASQSVSYMNWYQQKPGKAPKR WIYDTSKVASGVPARFSGSGSGTDYSLTINSLEAEDAATYYCQQW SSNPLTFGGGTKVEIK |
| | 210 | CDRL1 | RASQSVSYMN |
| | 211 | CDRL2 | DTSKVAS |
| | 212 | CDRL3 | QQWSSNPLT |
| | 213 | scFv | DVQLVQSGAEVKKPGASVKVSCKASGYTFTRYTMHWVRQAPGQGL EWIGYINPSRGYTNYADSVKGRFTITTDKSTSTAYMELSSLRSED TATYYCARYYDDNYCLDYWGQGTTVTVSSSSGGGGSGGGGSGGGG SDIVLTQSPATLSLSPGERATLSCRASQSVSYMNWYQQKPGKAPK RWIYDTSKVASGVPARFSGSGSGTDYSLTINSLEAEDAATYYCQQ WSSNPLTFGGGTKVEIK |
| | 214 | scFv | DIVLTQSPATLSLSPGERATLSCRASQSVSYMNWYQQKPGKAPKR WIYDTSKVASGVPARFSGSGSGTDYSLTINSLEAEDAATYYCQQW SSNPLTFGGGTKVEIKSGGGGSGGGGSGGGGSDVQLVQSGAEVKK PGASVKVSCKASGYTFTRYTMHWVRQAPGQGLEWIGYINPSRGYT NYADSVKGRFTITTDKSTSTAYMELSSLRSEDTATYYCARYYDDN YCLDYWGQGTTVTVSSS |
| CD3.16 | 215 | VH | DVQLVQSGAEVKKPGASVKVSCKASGYTFTRYTMHWVRQAPGQGL EWIGYINPSRGYTNYADSVKGRFTITTDKSTSTAYMELSSLRSED TATYYCARYYDDQYCLDYWGQGTTVTVSS |
| | 216 | CDRH1 | RYTMH |
| | 217 | CDRH2 | YINPSRGYTNYADSVKG |
| | 218 | CDRH3 | YYDDQYCLDY |
| | 219 | VL | DIVLTQSPATLSLSPGERATLSCRASQSVSYMNWYQQKPGKAPKR WIYDTSKVASGVPARFSGSGSGTDYSLTINSLEAEDAATYYCQQW SSNPLTFGGGTKVEIK |
| | 220 | CDRL1 | RASQSVSYMN |
| | 221 | CDRL2 | DTSKVAS |
| | 222 | CDRL3 | QQWSSNPLT |
| | 223 | scFv | DVQLVQSGAEVKKPGASVKVSCKASGYTFTRYTMHWVRQAPGQGL EWIGYINPSRGYTNYADSVKGRFTITTDKSTSTAYMELSSLRSED TATYYCARYYDDQYCLDYWGQGTTVTVSSSGGGGSGGGGSGGGGS DIVLTQSPATLSLSPGERATLSCRASQSVSYMNWYQQKPGKAPKR WIYDTSKVASGVPARFSGSGSGTDYSLTINSLEAEDAATYYCQQW SSNPLTFGGGTKVEIK |
| | 224 | scFv | DIVLTQSPATLSLSPGERATLSCRASQSVSYMNWYQQKPGKAPKR WIYDTSKVASGVPARFSGSGSGTDYSLTINSLEAEDAATYYCQQW SSNPLTFGGGTKVEIKSGGGGSGGGGSGGGGSDVQLVQSGAEVKK PGASVKVSCKASGYTFTRYTMHWVRQAPGQGLEWIGYINPSRGYT NYADSVKGRFTITTDKSTSTAYMELSSLRSEDTATYYCARYYDDQ YCLDYWGQGTTVTVSS |

In particular embodiments, a non-viral membrane-bound tropism polypeptide comprises an extracellular antigen targeting domain comprising an anti-CD3ε scFv that comprises an amino acid sequence set forth in any one of SEQ ID NOs: 153, 154, 163, 164, 173, 174, 183, 184, 193, 194, 203, 204, 213, 214, 223, and 224. In particular preferred embodiments, the anti-CD3ε scFv comprises an amino acid sequence set forth in SEQ ID NO: 153 or 154. In particular embodiments, the anti-CD3ε scFv comprises an amino acid sequence set forth in SEQ ID NO: 163 or 164. In particular embodiments, the anti-CD3ε scFv comprises an amino acid sequence set forth in SEQ ID NO: 173 or 174. In particular embodiments, the anti-CD3ε scFv comprises an amino acid sequence set forth in SEQ ID NO: 183 or 184. In particular embodiments, the anti-CD3ε scFv comprises an amino acid sequence set forth in SEQ ID NO: 193 or 194. In particular embodiments, the anti-CD3ε scFv comprises an amino acid sequence set forth in SEQ ID NO: 203 or 204. In particular embodiments, the anti-CD3ε scFv comprises an amino acid sequence set forth in SEQ ID NO: 213 or 214. In particular embodiments, the anti-CD3ε scFv comprises an amino acid sequence set forth in SEQ ID NO: 223 or 224.

Non-viral membrane-bound tropism polypeptides contemplated herein comprise, consist essentially of, or consist of an anti-CD3ε scFv comprising an amino acid sequence set forth in any one of SEQ ID NOs: 153, 154, 163, 164, 173, 174, 183, 184, 193, 194, 203, 204, 213, 214, 223, and 224, a spacer domain comprising a hinge domain isolated from a polypeptide selected from the group consisting of CD4, CD8α, CD28, IgG4, or IgG1 and a transmembrane domain.

Non-viral membrane-bound tropism polypeptides contemplated herein comprise, consist essentially of, or consist of an anti-CD3ε scFv comprising an amino acid sequence set forth in any one of SEQ ID NOs: 153, 154, 163, 164, 173, 174, 183, 184, 193, 194, 203, 204, 213, 214, 223, and 224, a spacer domain comprising an amino acid sequence set forth in Table 6 and a transmembrane domain.

TABLE 6

| Spacer Domains | |
|---|---|
| SEQ ID NO: | AMINO ACID SEQUENCE |
| 225 | TTTPAPRPPTPAPTIASQPLSLRPEACRPAAGGAVHTRGLDFACD |
| 226 | IEVMYPPPYLDNEKSNGTIIHVKGKHLCPSPLFPGPSKP |

TABLE 6-continued

Spacer Domains

| SEQ ID NO: | AMINO ACID SEQUENCE |
|---|---|
| 227 | SGQVLLESNIKVLPTWSTPVQP |
| 228 | ESKYGPPCPPCP |
| 229 | ESKYGPPCPPCPAPPVAGPSVFLFPPKPKDTLMISRTPEVTCVVV<br>DVSQEDPEVQFNWYVDGVEVHNAKTKPREEQFQSTYRVVSVLTVL<br>HQDWLNGKEYKCKVSNKGLPSSIEKTISKAKGQPREPQVYTLPPS<br>QEEMTKNQVSLTCLVKGFYPSDIAVEWESNGQPENNYKTTPPVLD<br>SDGSFFLYSRLTVDKSRWQEGNVFSCSVMHEALHNHYTQKSLSLS<br>LGK |
| 230 | LEPKSCDKTHTCPPCP |

Non-viral membrane-bound tropism polypeptides contemplated herein comprise, consist essentially of, or consist of an anti-CD3ε scFv comprising an amino acid sequence set forth in any one of SEQ ID NOs: 153, 154, 163, 164, 173, 174, 183, 184, 193, 194, 203, 204, 213, 214, 223, and 224, a spacer domain comprising an amino acid sequence set forth in any one of SEQ ID NOs: 225, 226, 227, 228, 229, and 230 and a transmembrane domain.

Non-viral membrane-bound tropism polypeptides contemplated herein comprise, consist essentially of, or consist of an anti-CD3ε scFv comprising an amino acid sequence set forth in any one of SEQ ID NOs: 153, 154, 163, 164, 173, 174, 183, 184, 193, 194, 203, 204, 213, 214, 223, and 224, a spacer domain comprising an amino acid sequence set forth in any one of SEQ ID NOs: 225, 226, 227, 228, 229, and 230 and a transmembrane domain isolated from a polypeptide selected from the group consisting of CD3ε, CD4, CD8α, CD28, CD134, CD137, and CD278.

Non-viral membrane-bound tropism polypeptides contemplated herein comprise, consist essentially of, or consist of an anti-CD3ε scFv comprising an amino acid sequence set forth in any one of SEQ ID NOs: 153, 154, 163, 164, 173, 174, 183, 184, 193, 194, 203, 204, 213, 214, 223, and 224, a spacer domain comprising an amino acid sequence set forth in any one of SEQ ID NOs: 225, 226, 227, 228, 229, and 230 and a transmembrane domain comprising an amino acid sequence set forth in Table 7.

TABLE 7

Transmembrane Domains

| SEQ ID NO: | AMINO ACID SEQUENCE |
|---|---|
| 231 | IYIWAPLAGTCGVLLLSLVITLYC |
| 232 | IISFFLALTSTALLFLLFFLTLRFSVV |
| 233 | FWVLVVVGGVLACYSLLVTVAFIIFWV |
| 234 | VAAILGLGLVLGLLGPLAILL |
| 235 | WLPIGCAAFVVVCILGCILICWL |
| 236 | VMSVATIVIVDICITGGLLLLVYYWS |
| 237 | MALIVLGGVAGLLLFIGLGIFF |

Non-viral membrane-bound tropism polypeptides contemplated herein comprise, consist essentially of, or consist of an anti-CD3ε scFv comprising an amino acid sequence set forth in any one of SEQ ID NOs: 153, 154, 163, 164, 173, 174, 183, 184, 193, 194, 203, 204, 213, 214, 223, and 224, a spacer domain comprising an amino acid sequence set forth in any one of SEQ ID NOs: 225, 226, 227, 228, 229, and 230 and a transmembrane domain comprising an amino acid sequence set forth in any one of SEQ ID NOs: 231, 232, 2333, 234, 235, 236, and 237.

In particular embodiments, a non-viral membrane bound tropism polypeptide comprises, consists essentially of, or consists of an amino acid sequence set forth in Table 8.

TABLE 8

Non-viral membrane bound tropism polypeptides

| SEQ ID NO: | AMINO ACID SEQUENCE |
|---|---|
| 324 | DVQLVQSGAEVKKPGASVKVSCKASGYTFTRYTMHWVRQAPGQGLEWIGYINPSRGYTNYADS<br>VKGRFTITTDKSTSTAYMELSSLRSEDTATYYCARYYDDHYCLDYWGQGTTVTVSSSGGGGSG<br>GGGSGGGGSDIVLTQSPATLSLSPGERATLSCRASQSVSYMNWYQQKPGKAPKRWIYDTSKVA<br>SGVPARFSGSGSGTDYSLTINSLEAEDAATYYCQQWSSNPLTFGGGTKVEIKTTTPAPRPPTP<br>APTIASQPLSLRPEACRPAAGGAVHTRGLDFACDIYIWAPLAGTCGVLLLSLVITLYC |
| 325 | DVQLVQSGAEVKKPGASVKVSCKASGYTFTRYTMHWVRQAPGQGLEWIGYINPSRGYTNYADS<br>VKGRFTITTDKSTSTAYMELSSLRSEDTATYYCARYYDDPYCLDYWGQGTTVTVSSSGGGGSG<br>GGGSGGGGSDIVLTQSPATLSLSPGERATLSCRASQSVSYMNWYQQKPGKAPKRWIYDTSKVA<br>SGVPARFSGSGSGTDYSLTINSLEAEDAATYYCQQWSSNPLTFGGGTKVEIKTTTPAPRPPTP<br>APTIASQPLSLRPEACRPAAGGAVHTRGLDFACDIYIWAPLAGTCGVLLLSLVITLYC |
| 326 | DVQLVQSGAEVKKPGASVKVSCKASGYTFTRYTMHWVRQAPGQGLEWIGYINPSRGYTNYADS<br>VKGRFTITTDKSTSTAYMELSSLRSEDTATYYCARYYNDQYCLDYWGQGTTVTVSSSSGGGGS<br>GGGGSGGGGSDIVLTQSPATLSLSPGERATLSCRASQSVSYMNWYQQKPGKAPKRWIYDTSKV<br>ASGVPARFSGSGSGTDYSLTINSLEAEDAATYYCQQWSSNPLTFGGGTKVEIKTTTPAPRPPT<br>PAPTIASQPLSLRPEACRPAAGGAVHTRGLDFACDIYIWAPLAGTCGVLLLSLVITLYC |
| 327 | DVQLVQSGAEVKKPGASVKVSCKASGYTFTRYTMHWVRQAPGQGLEWIGYINPSRGYTNYADS<br>VKGRFTITTDKSTSTAYMELSSLRSEDTATYYCARYYDAHNCLDYWGQGTTVTVSSSGGGGSG<br>GGGSGGGGSDIVLTQSPATLSLSPGERATLSCRASQSVSYMNWYQQKPGKAPKRWIYDTSKVA<br>SGVPARFSGSGSGTDYSLTINSLEAEDAATYYCQQWSSNPLTFGGGTKVEIKTTTPAPRPPTP<br>APTIASQPLSLRPEACRPAAGGAVHTRGLDFACDIYIWAPLAGTCGVLLLSLVITLYC |

TABLE 8-continued

Non-viral membrane bound tropism polypeptides

| SEQ ID NO: | AMINO ACID SEQUENCE |
|---|---|
| 328 | DVQLVQSGAEVKKPGASVKVSCKASGYTFTRYTMHWVRQAPGQGLEWIGYINPSRGYTNYADS VKGRFTITTDKSTSTAYMELSSLRSEDTATYYCARYSDDHYCLDYWGQGTTVTVSSSGGGGSG GGGSGGGGSDIVLTQSPATLSLSPGERATLSCRASQSVSYMNWYQQKPGKAPKRWIYDTSKVA SGVPARFSGSGSGTDYSLTINSLEAEDAATYYCQQWSSNPLTFGGGTKVEIKTTTPAPRPPTP APTIASQPLSLRPEACRPAAGGAVHTRGLDFACDIYIWAPLAGTCGVLLLSLVITLYC |
| 329 | DVQLVQSGAEVKKPGASVKVSCKASGYTFTRYTMHWVRQAPGQGLEWIGYINPSRGYTNYADS VKGRFTITTDKSTSTAYMELSSLRSEDTATYYCARYSDDRYCLDYWGQGTTVTVSSSGGGGSG GGGSGGGGSDIVLTQSPATLSLSPGERATLSCRASQSVSYMNWYQQKPGKAPKRWIYDTSKVA SGVPARFSGSGSGTDYSLTINSLEAEDAATYYCQQWSSNPLTFGGGTKVEIKTTTPAPRPPTP APTIASQPLSLRPEACRPAAGGAVHTRGLDFACDIYIWAPLAGTCGVLLLSLVITLYC |
| 330 | DVQLVQSGAEVKKPGASVKVSCKASGYTFTRYTMHWVRQAPGQGLEWIGYINPSRGYTNYADS VKGRFTITTDKSTSTAYMELSSLRSEDTATYYCARYYDDNYCLDYWGQGTTVTVSSSSGGGGS GGGGSGGGGSDIVLTQSPATLSLSPGERATLSCRASQSVSYMNWYQQKPGKAPKRWIYDTSKV ASGVPARFSGSGSGTDYSLTINSLEAEDAATYYCQQWSSNPLTFGGGTKVEIKTTTPAPRPPT PAPTIASQPLSLRPEACRPAAGGAVHTRGLDFACDIYIWAPLAGTCGVLLLSLVITLYC |
| 331 | DVQLVQSGAEVKKPGASVKVSCKASGYTFTRYTMHWVRQAPGQGLEWIGYINPSRGYTNYADS VKGRFTITTDKSTSTAYMELSSLRSEDTATYYCARYYDDQYCLDYWGQGTTVTVSSSGGGGSG GGGSGGGGSDIVLTQSPATLSLSPGERATLSCRASQSVSYMNWYQQKPGKAPKRWIYDTSKVA SGVPARFSGSGSGTDYSLTINSLEAEDAATYYCQQWSSNPLTFGGGTKVEIKTTTPAPRPPTP APTIASQPLSLRPEACRPAAGGAVHTRGLDFACDIYIWAPLAGTCGVLLLSLVITLYC |

In particular embodiments, a non-viral membrane bound tropism polypeptide comprises an amino acid sequence set forth in any one of SEQ ID NOs: 324, 325, 326, 327, 328, 329, 330, and 331, preferably SEQ ID NO: 324.

In particular embodiments, a non-viral membrane bound tropism polypeptide consists essentially of an amino acid sequence set forth in any one of SEQ ID NOs: 324, 325, 326, 327, 328, 329, 330, and 331.

In particular embodiments, a non-viral membrane bound tropism polypeptide consists of an amino acid sequence set forth in any one of SEQ ID NOs: 324, 325, 326, 327, 328, 329, 330, and 331.

E. Chimeric Antigen Receptors

Recombinant particles contemplated herein are engineered to efficiently deliver one or more copies of a vector encoding or comprising a promotor operably linked to a polynucleotide encoding an anti-BCMA chimeric antigen receptor. Chimeric antigen receptors (CARs) contemplated herein are fusion polypeptides that exploit antibody-based specificity for BCMA to redirect immune effector cell specificity thereby triggering proliferation, cytokine production, phagocytosis or production of molecules that can mediate cell death of BCMA-expressing cells in a major histocompatibility (MHC) independent manner. As used herein, the term "chimeric" refers to a molecule that is composed of two or more polypeptides, or polynucleotides, of different origins.

The present disclosure contemplates improved anti-BCMA CARs that are suitable for in vivo modification, or ex vivo manufacture, of immune effector cells to redirect cytotoxicity toward BCMA-expressing cells (e.g., B cells, plasma cells).

In various embodiments, a CAR comprises an anti-BCMA scFv or VHH; a hinge domain; a transmembrane domain; one or more costimulatory signaling domains; and a primary signaling domain.

In particular embodiments, a CAR comprises an extracellular antigen binding domain that comprises an antibody or antigen binding fragment thereof that specifically binds to a human BCMA polypeptide. The term "binding domain" or "extracellular antigen binding domain" are used interchangeably and refer to one or more antibodies or antigen binding fragments thereof that bind BCMA. The binding domain may be derived either from a natural, synthetic, semi-synthetic, or recombinant source.

B cell maturation antigen (BCMA) is a member of the tumor necrosis factor receptor superfamily 17 (TNFRSF17) and is highly expressed on the plasma cells of multiple myeloma (MM) patients. The restricted expression of BCMA makes it a suitable therapeutic target for treating multiple myeloma. The present disclosure contemplates antibodies and antigen binding fragments thereof that bind BCMA. An "antibody" refers to a polypeptide or antigen binding fragment thereof that comprises at least a light chain immunoglobulin variable region and/or a heavy chain immunoglobulin variable region, which specifically recognizes and binds one or more epitopes of a BCMA polypeptide, e.g., SEQ ID NO: 10 (MLQMAGQCSQNEYFDSLLHACIPCQLRCSSNTPPLTCQRYCNASVTNSVKGTNA ILWTCLGLSLIISLAVFVLMFLLRKINSEPLKDEFKNTGSGLLGMANIDLEKSRTGD EIILPRGLEYTVEECTCEDCIKSKPKVDSDHCFPLPAMEEGATILVTTKTNDYCKSL PAALSATEIEKSISAR).

In various embodiments, a CAR comprises an anti-BCMA antibody or antigen binding fragment thereof comprising an amino acid sequence set forth in Table 9; a hinge domain; a transmembrane domain; one or more costimulatory signaling domains; and a primary signaling domain.

TABLE 9 anti-BCMA antibodies

| AB ID | SEQ ID NO | ID | AMINO ACID SEQUENCE |
|---|---|---|---|
| BCMA.1 | 11 | VH | QITLKESGPTLVKPTQTLTLTCTFSGFSLSTSGVGVGWIRQPPG<br>KALEWLALIYWNDEKRYSPSLKSRLTITKDTSKNQVVLTMTNMD<br>PVDTAVYYCARDEYGGFDIWGQGTMVTVSS |
| | 12 | CDRH1 | TSGVGVG |
| | 13 | CDRH2 | LIYWNDEKRYSPSLKS |
| | 14 | CDRH3 | DEYGGFDI |
| | 15 | VL | EIVLTQSPATLSLSPGERATLSCRASQSVSSYLAWYQQKPGQAP<br>RLLIYDASNRATGIPARFSGSGSGTDFTLTISSLEPEDFAVYYC<br>QQRVVYPITFGGGTKVEIK |
| | 16 | CDRL1 | RASQSVSSYLA |
| | 17 | CDRL2 | DASNRAT |
| | 18 | CDRL3 | QQRVVYPIT |
| | 19 | scFv | QITLKESGPTLVKPTQTLTLTCTFSGFSLSTSGVGVGWIRQPPG<br>KALEWLALIYWNDEKRYSPSLKSRLTITKDTSKNQVVLTMTNMD<br>PVDTAVYYCARDEYGGFDIWGQGTMVTVSSGGGGSGGGGSGGGG<br>SGGGGSEIVLTQSPATLSLSPGERATLSCRASQSVSSYLAWYQQ<br>KPGQAPRLLIYDASNRATGIPARFSGSGSGTDFTLTISSLEPED<br>FAVYYCQQRVVYPITFGGGTKVEIK |
| | 20 | scFv | EIVLTQSPATLSLSPGERATLSCRASQSVSSYLAWYQQKPGQAP<br>RLLIYDASNRATGIPARFSGSGSGTDFTLTISSLEPEDFAVYYC<br>QQRVVYPITFGGGTKVEIKGGGGSGGGGSGGGGSGGGGSQITLK<br>ESGPTLVKPTQTLTLTCTFSGFSLSTSGVGVGWIRQPPGKALEW<br>LALIYWNDEKRYSPSLKSRLTITKDTSKNQVVLTMTNMDPVDTA<br>VYYCARDEYGGFDIWGQGTMVTVSS |
| BCMA.2 | 21 | VH | QITLKESGPTLVKPTQTLTLTCTFSGFSLSTSGVGVGWIRQPPG<br>KALEWLALIYWNDDKRYSPSLKSRLTITKDTSKNQVVLTMTNMD<br>PVDTAVYYCARDEYGGFDIWGQGTMVTVSS |
| | 22 | CDRH1 | TSGVGVG |
| | 23 | CDRH2 | LIYWNDDKRYSPSLKS |
| | 24 | CDRH3 | DEYGGFDI |
| | 25 | VL | EIVLTQSPATLSLSPGERATLSCRASQSVSSYLAWYQQKPGQAP<br>RLLIYDASNRATGIPARFSGSGSGTDFTLTISSLEPEDFAVYYC<br>QQRFDYPITFGGGTKVEIK |
| | 26 | CDRL1 | RASQSVSSYLA |
| | 27 | CDRL2 | DASNRAT |
| | 28 | CDRL3 | QQRFDYPIT |
| | 29 | scFv | QITLKESGPTLVKPTQTLTLTCTFSGFSLSTSGVGVGWIRQPPG<br>KALEWLALIYWNDDKRYSPSLKSRLTITKDTSKNQVVLTMTNMD<br>PVDTAVYYCARDEYGGFDIWGQGTMVTVSSGGGGSGGGGSGGGG<br>SGGGGSEIVLTQSPATLSLSPGERATLSCRASQSVSSYLAWYQQ<br>KPGQAPRLLIYDASNRATGIPARFSGSGSGTDFTLTISSLEPED<br>FAVYYCQQRFDYPITFGGGTKVEIK |
| | 30 | scFv | EIVLTQSPATLSLSPGERATLSCRASQSVSSYLAWYQQKPGQAP<br>RLLIYDASNRATGIPARFSGSGSGTDFTLTISSLEPEDFAVYYC<br>QQRFDYPITFGGGTKVEIKGGGGSGGGGSGGGGSGGGGSQITLK<br>ESGPTLVKPTQTLTLTCTFSGFSLSTSGVGVGWIRQPPGKALEW<br>LALIYWNDDKRYSPSLKSRLTITKDTSKNQVVLTMTNMDPVDTA<br>VYYCARDEYGGFDIWGQGTMVTVSS |
| BCMA.3 | 31 | VH | QVQLVESGGGVVQPGRSLRLSCAASGFTFSSYGMHWVRQAPGKG<br>LEWVAVISYEGSNKYYADSVKGRFTISRDNSKNTLYLQMNSLRA<br>EDTAVYYCARELGDGMDVWGQGTTVTVSS |
| | 32 | CDRH1 | SYGMH |
| | 33 | CDRH2 | VISYEGSNKYYADSVKG |
| | 34 | CDRH3 | ELGDGMDV |
| | 35 | VL | EIVLTQSPATLSLSPGERATLSCRASQSVSSYLAWFQQKPGQAP<br>RLLIYDASNRATGIPARFSGSGSGTDFTLTISSLEPEDFAVYYC<br>QQRVDLWTFGGGTKVEIK |
| | 36 | CDRL1 | RASQSVSSYLA |
| | 37 | CDRL2 | DASNRAT |
| | 38 | CDRL3 | QQRVDLWT |
| | 39 | scFv | QVQLVESGGGVVQPGRSLRLSCAASGFTFSSYGMHWVRQAPGKG<br>LEWVAVISYEGSNKYYADSVKGRFTISRDNSKNTLYLQMNSLRA<br>EDTAVYYCARELGDGMDVWGQGTTVTVSSGGGGSGGGGSGGGGS<br>GGGGSEIVLTQSPATLSLSPGERATLSCRASQSVSSYLAWFQQK<br>PGQAPRLLIYDASNRATGIPARFSGSGSGTDFTLTISSLEPEDF<br>AVYYCQQRVDLWTFGGGTKVEIK |
| | 40 | scFv | EIVLTQSPATLSLSPGERATLSCRASQSVSSYLAWFQQKPGQAP<br>RLLIYDASNRATGIPARFSGSGSGTDFTLTISSLEPEDFAVYYC<br>QQRVDLWTFGGGTKVEIKGGGGSGGGGSGGGGSGGGGSQVQLVE<br>SGGGVVQPGRSLRLSCAASGFTFSSYGMHWVRQAPGKGLEWVAV<br>ISYEGSNKYYADSVKGRFTISRDNSKNTLYLQMNSLRAEDTAVY<br>YCARELGDGMDVWGQGTTVTVSS |

TABLE 9-continued

| anti-BCMA antibodies | | | |
|---|---|---|---|
| AB ID | SEQ ID NO | ID | AMINO ACID SEQUENCE |
| BCMA.4 | 41 | VH | EVQLVESGGGLVKPGGSLRLSCAASGFTFSDYYMSWIRQAPGKG LEWVSYISSSGSTIYYADSVKGRFTISRDNAKNSLYLQMNSLRA EDTAVYYCARDQGNYGVDVWGQGTTVTVSS |
| | 42 | CDRH1 | DYYMS |
| | 43 | CDRH2 | YISSSGSTIYYADSVKG |
| | 44 | CDRH3 | DQGNYGVDV |
| | 45 | VL | DIQMTQSPSTLSASVGDRVTITCRASQSISSWLAWYQQKPGKAP KLLIYDASSLESGVPSRFSGSGSGTEFTLTISSLQPDDFATYYC QQVSSLPPTFGGGTKVEIK |
| | 46 | CDRL1 | RASQSISSWLA |
| | 47 | CDRL2 | DASSLES |
| | 48 | CDRL3 | QQVSSLPPT |
| | 49 | scFv | EVQLVESGGGLVKPGGSLRLSCAASGFTFSDYYMSWIRQAPGKG LEWVSYISSSGSTIYYADSVKGRFTISRDNAKNSLYLQMNSLRA EDTAVYYCARDQGNYGVDVWGQGTTVTVSSGGGGSGGGGSGGGG SGGGGSDIQMTQSPSTLSASVGDRVTITCRASQSISSWLAWYQQ KPGKAPKLLIYDASSLESGVPSRFSGSGSGTEFTLTISSLQPDD FATYYCQQVSSLPPTFGGGTKVEIK |
| | 50 | scFv | DIQMTQSPSTLSASVGDRVTITCRASQSISSWLAWYQQKPGKAP KLLIYDASSLESGVPSRFSGSGSGTEFTLTISSLQPDDFATYYC QQVSSLPPTFGGGTKVEIKGGGGSGGGGSGGGGSGGGGSEVQLV ESGGGLVKPGGSLRLSCAASGFTFSDYYMSWIRQAPGKGLEWVS YISSSGSTIYYADSVKGRFTISRDNAKNSLYLQMNSLRAEDTAV YYCARDQGNYGVDVWGQGTTVTVSS |
| BCMA.5 | 51 | VH | QVQLVESGGGLVKPGGSLRLSCAASGFTFSDYYMSWIRQAPGKG LEWVSYISSSGSTIYYADSVKGRFTISRDNAKNSLYLQMNSLRA EDTAVYYCARDQGNYGVDVWGQGTTVTVSS |
| | 52 | CDRH1 | DYYMS |
| | 53 | CDRH2 | YISSSGSTIYYADSVKG |
| | 54 | CDRH3 | DQGNYGVDV |
| | 55 | VL | DIQMTQSPSTLSASVGDRVTITCRASQSISSWLAWYQQKPGKAP KLLIYEASSLESGVPSRFSGSGSGTEFTLTISSLQPDDFATYYC QQSDSHPITFGGGTKVEIK |
| | 56 | CDRL1 | RASQSISSWLA |
| | 57 | CDRL2 | EASSLES |
| | 58 | CDRL3 | QQSDSHPIT |
| | 59 | scFv | QVQLVESGGGLVKPGGSLRLSCAASGFTFSDYYMSWIRQAPGKG LEWVSYISSSGSTIYYADSVKGRFTISRDNAKNSLYLQMNSLRA EDTAVYYCARDQGNYGVDVWGQGTTVTVSSGGGGSGGGGSGGGG SGGGGSDIQMTQSPSTLSASVGDRVTITCRASQSISSWLAWYQQ KPGKAPKLLIYEASSLESGVPSRFSGSGSGTEFTLTISSLQPDD FATYYCQQSDSHPITFGGGTKVEIK |
| | 60 | scFv | DIQMTQSPSTLSASVGDRVTITCRASQSISSWLAWYQQKPGKAP KLLIYEASSLESGVPSRFSGSGSGTEFTLTISSLQPDDFATYYC QQSDSHPITFGGGTKVEIKGGGGSGGGGSGGGGSGGGGSQVQLV ESGGGLVKPGGSLRLSCAASGFTFSDYYMSWIRQAPGKGLEWVS YISSSGSTIYYADSVKGRFTISRDNAKNSLYLQMNSLRAEDTAV YYCARDQGNYGVDVWGQGTTVTVSS |
| BCMA.6 | 61 | VH | EVQLVESGGGLVKPGGSLRLSCAASGFTFSDYYMSWIRQAPGKG LEWVSYISSSGSTIYYADSVKGRFTISRDNAKNSLYLQMNSLRA EDTAVYYCARDQGNYGVDVWGQGTTVTVSS |
| | 62 | CDRH1 | DYYMS |
| | 63 | CDRH2 | YISSSGSTIYYADSVKG |
| | 64 | CDRH3 | DQGNYGVDV |
| | 65 | VL | DIQMTQSPSTLSASVGDRVTITCRASQSISSWLAWYQQKPGKAP KLLIYEASSLESGVPSRFSGSGSGTEFTLTISSLQPDDFATYYC QQANSHPITFGGGTKVEIK |
| | 66 | CDRL1 | RASQSISSWLA |
| | 67 | CDRL2 | EASSLES |
| | 68 | CDRL3 | QQANSHPIT |
| | 69 | scFv | EVQLVESGGGLVKPGGSLRLSCAASGFTFSDYYMSWIRQAPGKG LEWVSYISSSGSTIYYADSVKGRFTISRDNAKNSLYLQMNSLRA EDTAVYYCARDQGNYGVDVWGQGTTVTVSSGGGGSGGGGSGGGG SGGGGSDIQMTQSPSTLSASVGDRVTITCRASQSISSWLAWYQQ KPGKAPKLLIYEASSLESGVPSRFSGSGSGTEFTLTISSLQPDD FATYYCQQANSHPITFGGGTKVEIK |
| | 70 | scFv | DIQMTQSPSTLSASVGDRVTITCRASQSISSWLAWYQQKPGKAP KLLIYEASSLESGVPSRFSGSGSGTEFTLTISSLQPDDFATYYC QQANSHPITFGGGTKVEIKGGGGSGGGGSGGGGSGGGGSEVQLV ESGGGLVKPGGSLRLSCAASGFTFSDYYMSWIRQAPGKGLEWVS |

TABLE 9-continued anti-BCMA antibodies

| AB ID | SEQ ID NO | ID | AMINO ACID SEQUENCE |
|---|---|---|---|
| | | | YISSSGSTIYYADSVKGRFTISRDNAKNSLYLQMNSLRAEDTAV<br>YYCARDQGNYGVDVWGQGTTVTVSS |
| BCMA.7 | 71 | VH | EVQLLESGGGLVQPGGSLRLSCAASGFTFSNYAMSWVRQAPGKG<br>LEWVSAISGSGGSTYYADSVKGRFTISRDNSKNTLYLQMNSLRA<br>EDTAVYYCARPGDGYYEGVYFDYWGQGTLVTVSS |
| | 72 | CDRH1 | NYAMS |
| | 73 | CDRH2 | AISGSGGSTYYADSVKG |
| | 74 | CDRH3 | PGDGYYEGVYFDY |
| | 75 | VL | DIQMTQSPSSLSASVGDRVTITCRASQSISSYLNWYQQKPGKAP<br>KLLIYAASSLQSGVPSRFSGSGSGTDFTLTISSLQPEDFATYYC<br>QQAHSSPITFGGGTKVEIK |
| | 76 | CDRL1 | RASQSISSYLN |
| | 77 | CDRL2 | AASSLQS |
| | 78 | CDRL3 | QQAHSSPIT |
| | 79 | scFv | EVQLLESGGGLVQPGGSLRLSCAASGFTFSNYAMSWVRQAPGKG<br>LEWVSAISGSGGSTYYADSVKGRFTISRDNSKNTLYLQMNSLRA<br>EDTAVYYCARPGDGYYEGVYFDYWGQGTLVTVSSGGGGSGGGGS<br>GGGGSGGGGSDIQMTQSPSSLSASVGDRVTITCRASQSISSYLN<br>WYQQKPGKAPKLLIYAASSLQSGVPSRFSGSGSGTDFTLTISSL<br>QPEDFATYYCQQAHSSPITFGGGTKVEIK |
| | 80 | scFv | DIQMTQSPSSLSASVGDRVTITCRASQSISSYLNWYQQKPGKAP<br>KLLIYAASSLQSGVPSRFSGSGSGTDFTLTISSLQPEDFATYYC<br>QQAHSSPITFGGGTKVEIKGGGGSGGGGSGGGGSGGGGSEVQLL<br>ESGGGLVQPGGSLRLSCAASGFTFSNYAMSWVRQAPGKGLEWVS<br>AISGSGGSTYYADSVKGRFTISRDNSKNTLYLQMNSLRAEDTAV<br>YYCARPGDGYYEGVYFDYWGQGTLVTVSS |
| BCMA.8 | 81 | VH | QITLKESGPTLVKPTQTLTLTCTFSGFSLSTSGVGVGWIRQPPG<br>KALEWLALIYWNDEKRYSPSLKSRLTITKDTSKNQVVLTMTNMD<br>PVDTAVYYCAREGSHDYKSSNWFDPWGQGTLVTVSS |
| | 82 | CDRH1 | TSGVGVG |
| | 83 | CDRH2 | LIYWNDEKRYSPSLKS |
| | 84 | CDRH3 | EGSHDYKSSNWFDP |
| | 85 | VL | DIQMTQSPSSLSASVGDRVTITCQASQDIANYLNWYQQKPGKAP<br>KLLIYDASNLETGVPSRFSGSGSGTDFTFTISSLQPEDIATYYC<br>QQHFNLPLTFGGGTKVEIK |
| | 86 | CDRL1 | QASQDIANYLN |
| | 87 | CDRL2 | DASNLET |
| | 88 | CDRL3 | QQHFNLPLTF |
| | 89 | scFv | QITLKESGPTLVKPTQTLTLTCTFSGFSLSTSGVGVGWIRQPPG<br>KALEWLALIYWNDEKRYSPSLKSRLTITKDTSKNQVVLTMTNMD<br>PVDTAVYYCAREGSHDYKSSNWFDPWGQGTLVTVSSGGGGSGGG<br>GSGGGGSGGGGSDIQMTQSPSSLSASVGDRVTITCQASQDIANY<br>LNWYQQKPGKAPKLLIYDASNLETGVPSRFSGSGSGTDFTFTIS<br>SLQPEDIATYYCQQHFNLPLTFGGGTKVEIK |
| | 90 | SCFv | DIQMTQSPSSLSASVGDRVTITCQASQDIANYLNWYQQKPGKAP<br>KLLIYDASNLETGVPSRFSGSGSGTDFTFTISSLQPEDIATYYC<br>QQHFNLPLTFGGGTKVEIKGGGGSGGGGSGGGGSGGGGSQITLK<br>ESGPTLVKPTQTLTLTCTFSGFSLSTSGVGVGWIRQPPGKALEW<br>LALIYWNDEKRYSPSLKSRLTITKDTSKNQVVLTMTNMDPVDTA<br>VYYCAREGSHDYKSSNWFDPWGQGTLVTVSS |
| BCMA.9 | 91 | VH | EVQLVESGGGLVKPGGSLRLSCAASGFTFSSYSMNWVRQAPGKG<br>LEWVSSISSSSSYIYYADSVKGRFTISRDNAKNSLYLQMNSLRA<br>EDTAVYYCARAGDTYSAADYYYMDVWGKGTTVTVSS |
| | 92 | CDRH1 | SYSMN |
| | 93 | CDRH2 | SISSSSSYIYYADSVKG |
| | 94 | CDRH3 | AGDTYSAADYYYMDV |
| | 95 | VL | DIVMTQSPLSLPVTPGEPASISCRSSQSLLHSNGYNYLDWYLQK<br>PGQSPQLLIYLGSNRASGVPDRFSGSGSGTDFTLKISRVEAEDV<br>GVYYCMQALGLITFGGGTKVEIK |
| | 96 | CDRL1 | RSSQSLLHSNGYNYLD |
| | 97 | CDRL2 | LGSNRAS |
| | 98 | CDRL3 | MQALGLIT |
| | 99 | scFv | EVQLVESGGGLVKPGGSLRLSCAASGFTFSSYSMNWVRQAPGKG<br>LEWVSSISSSSSYIYYADSVKGRFTISRDNAKNSLYLQMNSLRA<br>EDTAVYYCARAGDTYSAADYYYMDVWGKGTTVTVSSGGGGSGGG<br>GSGGGGSGGGGSDIVMTQSPLSLPVTPGEPASISCRSSQSLLHS<br>NGYNYLDWYLQKPGQSPQLLIYLGSNRASGVPDRESGSGSGTDF<br>TLKISRVEAEDVGVYYCMQALGLITFGGGTKVEIK |
| | 100 | scFv | DIVMTQSPLSLPVTPGEPASISCRSSQSLLHSNGYNYLDWYLQK<br>PGQSPQLLIYLGSNRASGVPDRFSGSGSGTDFTLKISRVEAEDV<br>GVYYCMQALGLITFGGGTKVEIKGGGGSGGGGSGGGGSGGGGSE |

TABLE 9-continued

| anti-BCMA antibodies | | | |
|---|---|---|---|
| AB ID | SEQ ID NO | ID | AMINO ACID SEQUENCE |
| | | | VQLVESGGGLVKPGGSLRLSCAASGFTFSSYSMNWVRQAPGKGLEWVSSISSSSSYIYYADSVKGRFTISRDNAKNSLYLQMNSLRAEDTAVYYCARAGDTYSAADYYYMDVWGKGTTVTVSS |
| BCMA.10 | 101 | VHH | EVQLLESGGGLVQPGGSLRLSCAASGFTFGSEAMSWVRQAPGKERELVSAISGSGEVTYYADSVKGRFTISRDNSKNTLYLQMNSLRAEDTAVYYCQRLVEAKRHWGQGTQVTVSS |
| | 102 | CDRH1 | SEAMS |
| | 103 | CDRH2 | AISGSGEVTYYADSVKG |
| | 104 | CDRH3 | LVEAKRH |
| BCMA.11 | 105 | VHH | EVQLLESGGGLVQPGGSLRLSCAASGFTFESEAMSWYRQAPGKERELVSVITSEGSTYYADSVKGRFTISRDNSKNTLYLQMNSLRAEDTAVYYCAHIEWETRLNWGQGTQVTVSS |
| | 106 | CDRH1 | SEAMS |
| | 107 | CDRH2 | VITSEGSTYYADSVKG |
| | 108 | CDRH3 | IEWETRLN |
| BCMA.12 | 109 | VHH | EVQLLESGGGLVQPGGSLRLSCAASGFTFDEYTMHWFRQAPGKEREFVSAISGGGSETYYADSVKGRFTISRDNSKNTLYLQMNSLRAEDTAVYYCAAGGEEAGVGYWGQGTQVTVSS |
| | 110 | CDRH1 | EYTMH |
| | 111 | CDRH2 | AISGGGSETYYADSVKG |
| | 112 | CDRH3 | GGEEAGVGY |
| BCMA.13 | 113 | VHH | EVQLLESGGGLVQPGGSLRLSCAASGFTFEDYAMSWFRQAPGKEREGVSAISGKGGSTYYADSVKGRFTISRDNSKNTLYLQMNSLRAEDTAVYYCAVLDEEAGAEGGYWGQGTQVTVSS |
| | 114 | CDRH1 | DYAMS |
| | 115 | CDRH2 | AISGKGGSTYYADSVKG |
| | 116 | CDRH3 | LDEEAGAEGGY |
| BCMA.14 | 117 | VHH | EVQLLESGGGLVQPGGSLRLSCAASGFTFDRYAMSWFRQAPGKEREGVSAISTSGDSTYYADSVKGRFTISRDNSKNTLYLQMNSLRAEDTAVYYCAVLDEEAGAEGGYWGQGTQVTVSS |
| | 118 | CDRH1 | RYAMS |
| | 119 | CDRH2 | AISTSGDSTYYADSVKG |
| | 120 | CDRH3 | LDEEAGAEGGY |
| BCMA.15 | 121 | VHH | EVQLLESGGGLVQPGGSLRLSCAASGFTFASDAMSWYRQAPGKERELVSAISGSGGSTYYADSVKGRFTISRDNSKNTLYLQMNSLRAEDTAVYYCAAHDSGEAYLAFDYWGQGTQVTVSS |
| | 122 | CDRH1 | SDAMS |
| | 123 | CDRH2 | AISGSGGSTYYADSVKG |
| | 124 | CDRH3 | HDSGEAYLAFDY |
| BCMA.16 | 125 | VHH | EVQLLESGGGLVQPGGSLRLSCAASGFTFDSYTMSWYRQAPGKERELVSAISGHGDSTYYADSVKGRFTISRDNSKNTLYLQMNSLRAEDTAVYYCTRISITTEWLAGDYWGQGTQVTVSS |
| | 126 | CDRH1 | SYTMS |
| | 127 | CDRH2 | AISGHGDSTYYADSVKG |
| | 128 | CDRH3 | ISITTEWLAGDY |
| BCMA.17 | 129 | VHH | EVQLLESGGGLVQPGGSLRLSCAASGFTFSSYAMSWFRQAPGKEREFVSFISGSGDSTYYADSVKGRFTISRDNSKNTLYLQMNSLRAEDTAVYYCTRWPYDFEEPSEPGVYWGQGTQVTVSS |
| | 130 | CDRH1 | SYAMS |
| | 131 | CDRH2 | FISGSGDSTYYADSVKG |
| | 132 | CDRH3 | WPYDFEEPSEPGVY |
| BCMA.18 | 133 | VHH | EVQLLESGGGLVQPGGSLRLSCAASGFTFTDYDMSWYRQAPGKERELVSVIHSGGSTYYADSVKGRFTISRDNSKNTLYLQMNSLRAEDTAVYYCAPGYYSDLSFDYYNFDYWGQGTQVTVSS |
| | 134 | CDRH1 | DYDMS |
| | 135 | CDRH2 | VIHSGGSTYYADSVKG |
| | 136 | CDRH3 | GYYSDLSFDYYNFDY |
| BCMA.19 | 137 | VHH | EVQLLESGGGLVQPGGSLRLSCAASGFTFSDYAMHWFRQAPGKERVLVSSIDSGGSTYYADSVKGRFTISRDNSKNTLYLQMNSLRAEDTAVYYCNAGFKGDHPHPKDAFDIWGQGTQVTVSS |
| | 138 | CDRH1 | DYAMH |
| | 139 | CDRH2 | SIDSGGSTYYADSVKG |
| | 140 | CDRH3 | GFKGDHPHPKDAFDI |

TABLE 9-continued

| anti-BCMA antibodies | | | |
|---|---|---|---|
| AB ID | SEQ ID NO | ID | AMINO ACID SEQUENCE |
| BCMA.20 | 141 | VHH | EVQLLESGGGLVQPGGSLRLSCAASGFTFSSEGMSWVRQAPGKERELVSAISGSGDHTYYADSVRGRFTISRDNSKNTLYLQMNSLRAEDTAVYYCNALEGGPTTAIQPGGPDYWGQGTQVTVSS |
| | 142 | CDRH1 | SEGMS |
| | 143 | CDRH2 | AISGSGDHTYYADSVRG |
| | 144 | CDRH3 | LEGGPTTAIQPGGPDY |

In particular embodiments, a CAR comprises a binding domain that comprises an anti-BCMA scFv comprising an amino acid sequence set forth in any one of SEQ ID NOS: 19, 20, 29, 30, 39, 40, 49, 50, 59, 60, 69, 70, 79, 80, 89, 90, 99, and 100; a hinge domain; a transmembrane domain; one or more costimulatory signaling domains; and a primary signaling domain. In particular embodiments, a CAR comprises a binding domain that comprises an anti-BCMA scFv comprising an amino acid sequence set forth in any one of SEQ ID NOs: 20, 30, 39, 50, 59, 70, 80, 90, and 100; a hinge domain; a transmembrane domain; one or more costimulatory signaling domains; and a primary signaling domain. In particular embodiments, a CAR comprises a binding domain that comprises an anti-BCMA scFv comprising an amino acid sequence set forth in any one of SEQ ID NOs: 39, 59, 70, and 90; a hinge domain; a transmembrane domain; one or more costimulatory signaling domains; and a primary signaling domain.

In particular embodiments, a CAR comprises a binding domain that comprises an anti-BCMA VHH comprising an amino acid sequence set forth in any one of SEQ ID NOS: 101, 105, 109, 113, 117, 121, 125, 129, 133, 137, and 141; a hinge domain; a transmembrane domain; one or more costimulatory signaling domains; and a primary signaling domain. In particular embodiments, a CAR comprises a binding domain that comprises an anti-BCMA VHH comprising an amino acid sequence set forth in SEQ ID NO: 101 or 117; a hinge domain; a transmembrane domain; one or more costimulatory signaling domains; and a primary signaling domain.

Chimeric antigen receptors contemplated herein comprise a hinge domain disposed between the extracellular antigen binding domain and the transmembrane domain of a CAR. A hinge domain plays a role in positioning the extracellular antigen binding domain away from the effector cell surface to enable proper cell/cell contact, antigen binding and activation. A hinge domain may be derived from a naturally occurring polypeptide or from a synthetic, semi-synthetic, or recombinant source.

In particular embodiments, a CAR comprises a binding domain that comprises an anti-BCMA scFv comprising an amino acid sequence set forth in any one of SEQ ID NOS: 19, 20, 29, 30, 39, 40, 49, 50, 59, 60, 69, 70, 79, 80, 89, 90, 99, and 100; a hinge domain isolated from CD4, CD8α, CD28, IgG1, and IgG4; a transmembrane domain; one or more costimulatory signaling domains; and a primary signaling domain. In particular embodiments, a CAR comprises a binding domain that comprises an anti-BCMA scFv comprising an amino acid sequence set forth in any one of SEQ ID NOs: 39, 59, 70, and 90; a hinge domain comprising an amino acid sequence set forth in any one of SEQ ID NOS: 225, 226, 227, 228, 229 and 230; a transmembrane domain; one or more costimulatory signaling domains; and a primary signaling domain.

In particular embodiments, a CAR comprises a binding domain that comprises an anti-BCMA VHH comprising an amino acid sequence set forth in any one of SEQ ID NOS: 101, 105, 109, 113, 117, 121, 125, 129, 133, 137, and 141; a hinge domain isolated from CD4, CD8α, CD28, IgG1, and IgG4; a transmembrane domain; one or more costimulatory signaling domains; and a primary signaling domain. In particular embodiments, a CAR comprises a binding domain that comprises an anti-BCMA VHH comprising an amino acid sequence set forth in SEQ ID NO: 101 or 117; a hinge domain comprising an amino acid sequence set forth in any one of SEQ ID NOs: 225, 226, 227, 228, 229 and 230; a transmembrane domain; one or more costimulatory signaling domains; and a primary signaling domain.

Chimeric antigen receptors contemplated herein comprise a transmembrane domain. The transmembrane domain is a hydrophobic domain that fuses the extracellular and intracellular portions of the CAR and anchors the CAR to the plasma membrane of the immune effector cell. The transmembrane domain may be derived either from a natural, synthetic, semi-synthetic, or recombinant source. In particular embodiments, the CAR further comprises a short oligo- or polypeptide linker, preferably between 1, 2, 3, 4, 5, 6, 7, 8, 9, or 10 amino acids in length disposed between the transmembrane domain and the intracellular domains of the CAR.

In particular embodiments, a CAR comprises a binding domain that comprises an anti-BCMA scFv comprising an amino acid sequence set forth in any one of SEQ ID NOS: 19, 20, 29, 30, 39, 40, 49, 50, 59, 60, 69, 70, 79, 80, 89, 90, 99, and 100; a hinge domain isolated from CD4, CD8α, CD28, IgG1, and IgG4; a transmembrane domain isolated or derived from a polypeptide selected from the group consisting of CD3ε, CD4, CD8α, CD28, CD33, CD134, CD137, and CD278; one or more costimulatory signaling domains; and a primary signaling domain. In particular embodiments, a CAR comprises a binding domain that comprises an anti-BCMA scFv comprising an amino acid sequence set forth in any one of SEQ ID NOs: 39, 59, 70, and 90; a hinge domain comprising an amino acid sequence set forth in any one of SEQ ID NOs: 225, 227, 228, 229, and 230; a transmembrane domain comprising an amino acid sequence set forth in any one of SEQ ID NOs: 231, 323, 233, 234, 235, 236, and 237; one or more costimulatory signaling domains; and a primary signaling domain.

In particular embodiments, a CAR comprises a binding domain that comprises an anti-BCMA VHH comprising an amino acid sequence set forth in any one of SEQ ID NOS: 101, 105, 109, 113, 117, 121, 125, 129, 133, 137, and 141; a hinge domain isolated from CD4, CD8α, CD28, IgG1, and IgG4; a transmembrane domain isolated or derived from a polypeptide selected from the group consisting of CD3ε, CD4, CD8α, CD28, CD33, CD134, CD137, and CD278; one or more costimulatory signaling domains; and a primary signaling domain. In particular embodiments, a CAR comprises a binding domain that comprises an anti-BCMA VHH comprising an amino acid sequence set forth in SEQ ID NO: 101 or 117; a hinge domain comprising an amino acid sequence set forth in any one of SEQ ID NOS: 225, 227, 228, 229, and 230; a transmembrane domain comprising an amino acid sequence set forth in any one of SEQ ID NOs: 231, 323, 233, 234, 235, 236, and 237; one or more costimulatory signaling domains; and a primary signaling domain.

Chimeric antigen receptors contemplated herein comprise on or more intracellular signaling domains that function to transduce a signal of extracellular antigen recognition to the interior of the immune effector cell and elicit one or more effector cell functions including but not limited to activation, cytokine production, proliferation and cytotoxic activity. T cell activation is mediated by two distinct classes of intracellular signaling domains: primary signaling domains that initiate antigen-dependent primary activation through the TCR (e.g., a TCR/CD3 complex) and costimulatory signaling domains that act in an antigen-independent manner to provide a secondary or costimulatory signal. The intracellular primary signaling and costimulatory signaling domains may be linked in any order in tandem to the carboxyl terminus of the transmembrane domain.

In particular embodiments, a CAR comprises a binding domain that comprises an anti-BCMA scFv comprising an one of SEQ ID NOs: 225, 227, 228, 229, and 230; a transmembrane domain comprising an amino acid sequence set forth in any one of SEQ ID NOs: 231, 323, 233, 234, 235, 236, and 237; a costimulatory signaling domain comprising an amino acid sequence set forth in any one of SEQ ID NOs: 239, 240, 241, 242, 243, and 244; and a primary signaling domain comprising an amino acid sequence set forth in SEQ ID NO: 238.

In particular embodiments, a CAR comprises a binding domain that comprises an anti-BCMA VHH comprising an amino acid sequence set forth in any one of SEQ ID NOS: 101, 105, 109, 113, 117, 121, 125, 129, 133, 137, and 141; a hinge domain isolated from CD4, CD8α, CD28, IgG1, and IgG4; a transmembrane domain isolated or derived from a polypeptide selected from the group consisting of CD3ε, CD4, CD8α, CD28, CD33, CD134, CD137, and CD278; a costimulatory signaling domain isolated or derived from a polypeptide selected from the group consisting of CD27, CD28, CD134, CD137, CD278, and TNRF2; and a CD3ζ primary signaling domain. In particular embodiments, a CAR comprises a binding domain that comprises an anti-BCMA VHH comprising an amino acid sequence set forth in SEQ ID NO: 101 or 117; a hinge domain comprising an amino acid sequence set forth in any one of SEQ ID NOs: 225, 227, 228, 229, and 230; a transmembrane domain comprising an amino acid sequence set forth in any one of SEQ ID NOs: 231, 323, 233, 234, 235, 236, and 237; a costimulatory signaling domain comprising an amino acid sequence set forth in any one of SEQ ID NOs: 239, 240, 241, 242, 243, and 244; and a primary signaling domain comprising an amino acid sequence set forth in SEQ ID NO: 238.

TABLE 10

| SEQ ID NO: | DOMAIN | AMINO ACID SEQUENCE |
|---|---|---|
| 238 | PRIMARY | RVKFSRSADAPAYQQGQNQLYNELNLGRREEYDVLDKRRGRDPEMGGKP RRKNPQEGLYNELQKDKMAEAYSEIGMKGERRRGKGHDGLYQGLSTATK DTYDALHMQALPPR |
| 239 | COSTIM | KRGRKKLLYIFKQPFMRPVQTTQEEDGCSCRFPEEEEGGCEL |
| 240 | COSTIM | RSKRSRLLHSDYMNMTPRRPGPTRKHYQPYAPPRDFAAYRS |
| 241 | COSTIM | ALYLLRRDQRLPPDAHKPPGGGSFRTPIQEEQADAHSTLAKI |
| 242 | COSTIM | TKKKYSSSVHDPNGEYMFMRAVNTAKKSRLTDVTL |
| 243 | COSTIM | QRRKYRSNKGESPVEPAEPCHYSCPREEEGSTIPIQEDYRKPEPACSP |
| 244 | COSTIM | KKKPLCLQREAKVPHLPADKARGTQGPEQQHLLITAPSSSSSSLESSAS ALDRRAPTRNQPQAPGVEASGAGEARASTGSSDSSPGGHGTQVNVTCIV NVCSSSDHSSQCSSQASSTMGDTDSSPSESPKDEQVPFSKEECAFRSQL ETPETLLGSTEEKPLPLGVPDAGMKPS |

amino acid sequence set forth in any one of SEQ ID NOS: 19, 20, 29, 30, 39, 40, 49, 50, 59, 60, 69, 70, 79, 80, 89, 90, 99, and 100; a hinge domain isolated from CD4, CD8α, CD28, IgG1, and IgG4; a transmembrane domain isolated or derived from a polypeptide selected from the group consisting of CD3ε, CD4, CD8α, CD28, CD33, CD134, CD137, and CD278; a costimulatory signaling domain isolated or derived from a polypeptide selected from the group consisting of CD27, CD28, CD134, CD137, CD278, and TNRF2; and a CD3ζ primary signaling domain. In particular embodiments, a CAR comprises a binding domain that comprises an anti-BCMA scFv comprising an amino acid sequence set forth in any one of SEQ ID NOs: 39, 59, 70, and 90; a hinge domain comprising an amino acid sequence set forth in any In particular embodiments, a CAR comprises an scFv or VHH comprising an amino acid sequence set forth in Table 9; a CD8α hinge, a CD8α transmembrane domain; a CD137 costimulatory signaling domain; and a CD3ζ primary signaling domain.

In particular embodiments, a CAR comprises a binding domain that comprises an anti-BCMA scFv comprising an amino acid sequence set forth in any one of SEQ ID NOs: 19, 20, 29, 30, 39, 40, 49, 50, 59, 60, 69, 70, 79, 80, 89, 90, 99, and 100; a CD8α hinge, a CD8α transmembrane domain; a CD137 costimulatory signaling domain; and a CD3ζ primary signaling domain. In particular embodiments, a CAR comprises a binding domain that comprises an anti-BCMA scFv comprising an amino acid sequence set forth in any one of SEQ ID NOs: 39, 59, 70, and 90; a CD8α hinge, a CD8α transmembrane domain; a CD137 costimulatory signaling domain; and a CD3ζ primary signaling domain.

In particular embodiments, a CAR comprises a binding domain that comprises an anti-BCMA VHH comprising an amino acid sequence set forth in any one of SEQ ID NOS: 101, 105, 109, 113, 117, 121, 125, 129, 133, 137, and 141; a CD8α hinge, a CD8α transmembrane domain; a CD137 costimulatory signaling domain; and a CD3ζ primary signaling domain. In particular embodiments, a CAR comprises a binding domain that comprises an anti-BCMA VHH comprising an amino acid sequence set forth in SEQ ID NO: 101 or 117; a CD8α hinge, a CD8α transmembrane domain; a CD137 costimulatory signaling domain; and a CD3ζ primary signaling domain.

In some embodiments, a CAR comprises an amino acid sequence set forth in Table 11.

TABLE 11

| Chimeric antigen receptors | |
|---|---|
| SEQ ID NO. | AMINO ACID SEQUENCE |
| 255 | QITLKESGPTLVKPTQTLTLTCTFSGFSLSTSGVGVGWIRQPPGKALEWLALIYWNDEKRYSPS<br>LKSRLTITKDTSKNQVVLTMTNMDPVDTAVYYCARDEYGGFDIWGQGTMVTVSSGGGGSGGGGS<br>GGGGSGGGGSEIVLTQSPATLSLSPGERATLSCRASQSVSSYLAWYQQKPGQAPRLLIYDASNR<br>ATGIPARFSGSGSGTDFTLTISSLEPEDFAVYYCQQRVVYPITFGGGTKVEIKTTTPAPRPPTP<br>APTIASQPLSLRPEACRPAAGGAVHTRGLDFACDIYIWAPLAGTCGVLLLSLVITLYCKRGRKK<br>LLYIFKQPFMRPVQTTQEEDGCSCRFPEEEEGGCELRVKFSRSADAPAYQQGQNQLYNELNLGR<br>REEYDVLDKRRGRDPEMGGKPRRKNPQEGLYNELQKDKMAEAYSEIGMKGERRRGKGHDGLYQG<br>LSTATKDTYDALHMQALPPR |
| 256 | EIVLTQSPATLSLSPGERATLSCRASQSVSSYLAWYQQKPGQAPRLLIYDASNRATGIPARFSG<br>SGSGTDFTLTISSLEPEDFAVYYCQQRVVYPITFGGGTKVEIKGGGGSGGGGSGGGGSGGGGSQ<br>ITLKESGPTLVKPTQTLTLTCTFSGFSLSTSGVGVGWIRQPPGKALEWLALIYWNDEKRYSPSL<br>KSRLTITKDTSKNQVVLTMTNMDPVDTAVYYCARDEYGGFDIWGQGTMVTVSSTTTPAPRPPTP<br>APTIASQPLSLRPEACRPAAGGAVHTRGLDFACDIYIWAPLAGTCGVLLLSLVITLYCKRGRKK<br>LLYIFKQPFMRPVQTTQEEDGCSCRFPEEEEGGCELRVKFSRSADAPAYQQGQNQLYNELNLGR<br>REEYDVLDKRRGRDPEMGGKPRRKNPQEGLYNELQKDKMAEAYSEIGMKGERRRGKGHDGLYQG<br>LSTATKDTYDALHMQALPPR |
| 257 | QITLKESGPTLVKPTQTLTLTCTFSGFSLSTSGVGVGWIRQPPGKALEWLALIYWNDDKRYSPS<br>LKSRLTITKDTSKNQVVLTMTNMDPVDTAVYYCARDEYGGFDIWGQGTMVTVSSGGGGSGGGGS<br>GGGGSGGGGSEIVLTQSPATLSLSPGERATLSCRASQSVSSYLAWYQQKPGQAPRLLIYDASNR<br>ATGIPARFSGSGSGTDFTLTISSLEPEDFAVYYCQQRFDYPITFGGGTKVEIKTTTPAPRPPTP<br>APTIASQPLSLRPEACRPAAGGAVHTRGLDFACDIYIWAPLAGTCGVLLLSLVITLYCKRGRKK<br>LLYIFKQPFMRPVQTTQEEDGCSCRFPEEEEGGCELRVKFSRSADAPAYQQGQNQLYNELNLGR<br>REEYDVLDKRRGRDPEMGGKPRRKNPQEGLYNELQKDKMAEAYSEIGMKGERRRGKGHDGLYQG<br>LSTATKDTYDALHMQALPPR |
| 258 | EIVLTQSPATLSLSPGERATLSCRASQSVSSYLAWYQQKPGQAPRLLIYDASNRATGIPARFSG<br>SGSGTDFTLTISSLEPEDFAVYYCQQRFDYPITFGGGTKVEIKGGGGSGGGGSGGGGSGGGGSQ<br>ITLKESGPTLVKPTQTLTLTCTFSGFSLSTSGVGVGWIRQPPGKALEWLALIYWNDDKRYSPSL<br>KSRLTITKDTSKNQVVLTMTNMDPVDTAVYYCARDEYGGFDIWGQGTMVTVSSTTTPAPRPPTP<br>APTIASQPLSLRPEACRPAAGGAVHTRGLDFACDIYIWAPLAGTCGVLLLSLVITLYCKRGRKK<br>LLYIFKQPFMRPVQTTQEEDGCSCRFPEEEEGGCELRVKFSRSADAPAYQQGQNQLYNELNLGR<br>REEYDVLDKRRGRDPEMGGKPRRKNPQEGLYNELQKDKMAEAYSEIGMKGERRRGKGHDGLYQG<br>LSTATKDTYDALHMQALPPR |
| 259 | QVQLVESGGGVVQPGRSLRLSCAASGFTFSSYGMHWVRQAPGKGLEWVAVISYEGSNKYYADSV<br>KGRFTISRDNSKNTLYLQMNSLRAEDTAVYYCARELGDGMDVWGQGTTVTVSSGGGGSGGGGSG<br>GGGSGGGGSEIVLTQSPATLSLSPGERATLSCRASQSVSSYLAWFQQKPGQAPRLLIYDASNRA<br>TGIPARFSGSGSGTDFTLTISSLEPEDFAVYYCQQRVDLWTFGGGTKVEIKTTTPAPRPPTPAP<br>TIASQPLSLRPEACRPAAGGAVHTRGLDFACDIYIWAPLAGTCGVLLLSLVITLYCKRGRKKLL<br>YIFKQPFMRPVQTTQEEDGCSCRFPEEEEGGCELRVKFSRSADAPAYQQGQNQLYNELNLGRRE<br>EYDVLDKRRGRDPEMGGKPRRKNPQEGLYNELQKDKMAEAYSEIGMKGERRRGKGHDGLYQGLS<br>TATKDTYDALHMQALPPR |
| 260 | EIVLTQSPATLSLSPGERATLSCRASQSVSSYLAWFQQKPGQAPRLLIYDASNRATGIPARFSG<br>SGSGTDFTLTISSLEPEDFAVYYCQQRVDLWTFGGGTKVEIKGGGGSGGGGSGGGGSGGGGSQV<br>QLVESGGGVVQPGRSLRLSCAASGFTFSSYGMHWVRQAPGKGLEWVAVISYEGSNKYYADSVKG<br>RFTISRDNSKNTLYLQMNSLRAEDTAVYYCARELGDGMDVWGQGTTVTVSSTTTPAPRPPTPAP<br>TIASQPLSLRPEACRPAAGGAVHTRGLDFACDIYIWAPLAGTCGVLLLSLVITLYCKRGRKKLL<br>YIFKQPFMRPVQTTQEEDGCSCRFPEEEEGGCELRVKFSRSADAPAYQQGQNQLYNELNLGRRE<br>EYDVLDKRRGRDPEMGGKPRRKNPQEGLYNELQKDKMAEAYSEIGMKGERRRGKGHDGLYQGLS<br>TATKDTYDALHMQALPPR |
| 261 | EVQLVESGGGLVKPGGSLRLSCAASGFTFSDYYMSWIRQAPGKGLEWVSYISSSGSTIYYADSV<br>KGRFTISRDNAKNSLYLQMNSLRAEDTAVYYCARDQGNYGVDVWGQGTTVTVSSGGGGSGGGGS<br>GGGGSGGGGSDIQMTQSPSTLSASVGDRVTITCRASQSISSWLAWYQQKPGKAPKLLIYDASSL<br>ESGVPSRFSGSGSGTEFTLTISSLQPDDFATYYCQQVSSLPPTFGGGTKVEIKTTTPAPRPPTP<br>APTIASQPLSLRPEACRPAAGGAVHTRGLDFACDIYIWAPLAGTCGVLLLSLVITLYCKRGRKK<br>LLYIFKQPFMRPVQTTQEEDGCSCRFPEEEEGGCELRVKFSRSADAPAYQQGQNQLYNELNLGR<br>REEYDVLDKRRGRDPEMGGKPRRKNPQEGLYNELQKDKMAEAYSEIGMKGERRRGKGHDGLYQG<br>LSTATKDTYDALHMQALPPR |

TABLE 11-continued

Chimeric antigen receptors

| SEQ ID NO. | AMINO ACID SEQUENCE |
| --- | --- |
| 262 | DIQMTQSPSTLSASVGDRVTITCRASQSISSWLAWYQQKPGKAPKLLIYDASSLESGVPSRFSG<br>SGSGTEFTLTISSLQPDDFATYYCQQVSSLPPTFGGGTKVEIKGGGGSGGGGSGGGGSGGGGSE<br>VQLVESGGGLVKPGGSLRLSCAASGFTFSDYYMSWIRQAPGKGLEWVSYISSSGSTIYYADSVK<br>GRFTISRDNAKNSLYLQMNSLRAEDTAVYYCARDQGNYGVDVWGQGTTVTVSSTTTPAPRPPTP<br>APTIASQPLSLRPEACRPAAGGAVHTRGLDFACDIYIWAPLAGTCGVLLLSLVITLYCKRGRKK<br>LLYIFKQPFMRPVQTTQEEDGCSCRFPEEEEGGCELRVKFSRSADAPAYQQGQNQLYNELNLGR<br>REEYDVLDKRRGRDPEMGGKPRRKNPQEGLYNELQKDKMAEAYSEIGMKGERRRGKGHDGLYQG<br>LSTATKDTYDALHMQALPPR |
| 263 | QVQLVESGGGLVKPGGSLRLSCAASGFTFSDYYMSWIRQAPGKGLEWVSYISSSGSTIYYADSV<br>KGRFTISRDNAKNSLYLQMNSLRAEDTAVYYCARDQGNYGVDVWGQGTTVTVSSGGGGSGGGGS<br>GGGGSGGGGSDIQMTQSPSTLSASVGDRVTITCRASQSISSWLAWYQQKPGKAPKLLIYEASSL<br>ESGVPSRFSGSGSGTEFTLTISSLQPDDFATYYCQQSDSHPITFGGGTKVEIKTTTPAPRPPTP<br>APTIASQPLSLRPEACRPAAGGAVHTRGLDFACDIYIWAPLAGTCGVLLLSLVITLYCKRGRKK<br>LLYIFKQPFMRPVQTTQEEDGCSCRFPEEEEGGCELRVKFSRSADAPAYQQGQNQLYNELNLGR<br>REEYDVLDKRRGRDPEMGGKPRRKNPQEGLYNELQKDKMAEAYSEIGMKGERRRGKGHDGLYQG<br>LSTATKDTYDALHMQALPPR |
| 264 | DIQMTQSPSTLSASVGDRVTITCRASQSISSWLAWYQQKPGKAPKLLIYEASSLESGVPSRFSG<br>SGSGTEFTLTISSLQPDDFATYYCQQSDSHPITFGGGTKVEIKGGGGSGGGGSGGGGSGGGGSQ<br>VQLVESGGGLVKPGGSLRLSCAASGFTFSDYYMSWIRQAPGKGLEWVSYISSSGSTIYYADSVK<br>GRFTISRDNAKNSLYLQMNSLRAEDTAVYYCARDQGNYGVDVWGQGTTVTVSSTTTPAPRPPTP<br>APTIASQPLSLRPEACRPAAGGAVHTRGLDFACDIYIWAPLAGTCGVLLLSLVITLYCKRGRKK<br>LLYIFKQPFMRPVQTTQEEDGCSCRFPEEEEGGCELRVKFSRSADAPAYQQGQNQLYNELNLGR<br>REEYDVLDKRRGRDPEMGGKPRRKNPQEGLYNELQKDKMAEAYSEIGMKGERRRGKGHDGLYQG<br>LSTATKDTYDALHMQALPPR |
| 265 | EVQLVESGGGLVKPGGSLRLSCAASGFTFSDYYMSWIRQAPGKGLEWVSYISSSGSTIYYADSV<br>KGRFTISRDNAKNSLYLQMNSLRAEDTAVYYCARDQGNYGVDVWGQGTTVTVSSGGGGSGGGGS<br>GGGGSGGGGSDIQMTQSPSTLSASVGDRVTITCRASQSISSWLAWYQQKPGKAPKLLIYEASSL<br>ESGVPSRFSGSGSGTEFTLTISSLQPDDFATYYCQQANSHPITFGGGTKVEIKTTTPAPRPPTP<br>APTIASQPLSLRPEACRPAAGGAVHTRGLDFACDIYIWAPLAGTCGVLLLSLVITLYCKRGRKK<br>LLYIFKQPFMRPVQTTQEEDGCSCRFPEEEEGGCELRVKFSRSADAPAYQQGQNQLYNELNLGR<br>REEYDVLDKRRGRDPEMGGKPRRKNPQEGLYNELQKDKMAEAYSEIGMKGERRRGKGHDGLYQG<br>LSTATKDTYDALHMQALPPR |
| 266 | DIQMTQSPSTLSASVGDRVTITCRASQSISSWLAWYQQKPGKAPKLLIYEASSLESGVPSRFSG<br>SGSGTEFTLTISSLQPDDFATYYCQQANSHPITFGGGTKVEIKGGGGSGGGGSGGGGSGGGGSE<br>VQLVESGGGLVKPGGSLRLSCAASGFTFSDYYMSWIRQAPGKGLEWVSYISSSGSTIYYADSVK<br>GRFTISRDNAKNSLYLQMNSLRAEDTAVYYCARDQGNYGVDVWGQGTTVTVSSTTTPAPRPPTP<br>APTIASQPLSLRPEACRPAAGGAVHTRGLDFACDIYIWAPLAGTCGVLLLSLVITLYCKRGRKK<br>LLYIFKQPFMRPVQTTQEEDGCSCRFPEEEEGGCELRVKFSRSADAPAYQQGQNQLYNELNLGR<br>REEYDVLDKRRGRDPEMGGKPRRKNPQEGLYNELQKDKMAEAYSEIGMKGERRRGKGHDGLYQG<br>LSTATKDTYDALHMQALPPR |
| 267 | EVQLLESGGGLVQPGGSLRLSCAASGFTFSNYAMSWVRQAPGKGLEWVSAISGSGGSTYYADSV<br>KGRFTISRDNSKNTLYLQMNSLRAEDTAVYYCARPGDGYYEGVYFDYWGQGTLVTVSSGGGGSG<br>GGGSGGGGSGGGGSDIQMTQSPSSLSASVGDRVTITCRASQSISSYLNWYQQKPGKAPKLLIYA<br>ASSLQSGVPSRFSGSGSGTDFTLTISSLQPEDFATYYCQQAHSSPITFGGGTKVEIKTTTPAPR<br>PPTPAPTIASQPLSLRPEACRPAAGGAVHTRGLDFACDIYIWAPLAGTCGVLLLSLVITLYCKR<br>GRKKLLYIFKQPFMRPVQTTQEEDGCSCRFPEEEEGGCELRVKFSRSADAPAYQQGQNQLYNEL<br>NLGRREEYDVLDKRRGRDPEMGGKPRRKNPQEGLYNELQKDKMAEAYSEIGMKGERRRGKGHDG<br>LYQGLSTATKDTYDALHMQALPPR |
| 268 | DIQMTQSPSSLSASVGDRVTITCRASQSISSYLNWYQQKPGKAPKLLIYAASSLQSGVPSRFSG<br>SGSGTDFTLTISSLQPEDFATYYCQQAHSSPITFGGGTKVEIKGGGGSGGGGSGGGGSGGGGSE<br>VQLLESGGGLVQPGGSLRLSCAASGFTFSNYAMSWVRQAPGKGLEWVSAISGSGGSTYYADSVK<br>GRFTISRDNSKNTLYLQMNSLRAEDTAVYYCARPGDGYYEGVYFDYWGQGTLVTVSSTTTPAPR<br>PPTPAPTIASQPLSLRPEACRPAAGGAVHTRGLDFACDIYIWAPLAGTCGVLLLSLVITLYCKR<br>GRKKLLYIFKQPFMRPVQTTQEEDGCSCRFPEEEEGGCELRVKFSRSADAPAYQQGQNQLYNEL<br>NLGRREEYDVLDKRRGRDPEMGGKPRRKNPQEGLYNELQKDKMAEAYSEIGMKGERRRGKGHDG<br>LYQGLSTATKDTYDALHMQALPPR |
| 269 | QITLKESGPTLVKPTQTLTLTCTFSGFSLSTSGVGVGWIRQPPGKALEWLALIYWNDEKRYSPS<br>LKSRLTITKDTSKNQVVLTMTNMDPVDTAVYYCAREGSHDYKSSNWFDPWGQGTLVTVSSGGGG<br>SGGGGSGGGGSGGGGSDIQMTQSPSSLSASVGDRVTITCQASQDIANYLNWYQQKPGKAPKLLI<br>YDASNLETGVPSRFSGSGSGTDFTFTISSLQPEDIATYYCQQHFNLPLTFGGGTKVEIKTTTPA<br>PRPPTPAPTIASQPLSLRPEACRPAAGGAVHTRGLDFACDIYIWAPLAGTCGVLLLSLVITLYC<br>KRGRKKLLYIFKQPFMRPVQTTQEEDGCSCRFPEEEEGGCELRVKFSRSADAPAYQQGQNQLYN<br>ELNLGRREEYDVLDKRRGRDPEMGGKPRRKNPQEGLYNELQKDKMAEAYSEIGMKGERRRGKGH<br>DGLYQGLSTATKDTYDALHMQALPPR |

TABLE 11-continued

| Chimeric antigen receptors | |
|---|---|
| SEQ ID NO. | AMINO ACID SEQUENCE |
| 270 | DIQMTQSPSSLSASVGDRVTITCQASQDIANYLNWYQQKPGKAPKLLIYDASNLETGVPSRFSG SGSGTDFTFTISSLQPEDIATYYCQQHFNLPLTFGGGTKVEIKGGGGSGGGGSGGGGSGGGGSQ ITLKESGPTLVKPTQTLTLTCTFSGFSLSTSGVGVGWIRQPPGKALEWLALIYWNDEKRYSPSL KSRLTITKDTSKNQVVLTMTNMDPVDTAVYYCAREGSHDYKSSNWFDPWGQGTLVTVSSTTTPA PRPPTPAPTIASQPLSLRPEACRPAAGGAVHTRGLDFACDIYIWAPLAGTCGVLLLSLVITLYC KRGRKKLLYIFKQPFMRPVQTTQEEDGCSCRFPEEEEGGCELRVKFSRSADAPAYQQGQNQLYN ELNLGRREEYDVLDKRRGRDPEMGGKPRRKNPQEGLYNELQKDKMAEAYSEIGMKGERRRGKGH DGLYQGLSTATKDTYDALHMQALPPR |
| 271 | EVQLVESGGGLVKPGGSLRLSCAASGFTFSSYSMNWVRQAPGKGLEWVSSISSSSSYIYYADSV KGRFTISRDNAKNSLYLQMNSLRAEDTAVYYCARAGDTYSAADYYYMDVWGKGTTVTVSSGGGG SGGGGSGGGGSGGGGSDIVMTQSPLSLPVTPGEPASISCRSSQSLLHSNGYNYLDWYLQKPGQS PQLLIYLGSNRASGVPDRFSGSGSGTDFTLKISRVEAEDVGVYYCMQALGLITFGGGTKVEIKT TTPAPRPPTPAPTIASQPLSLRPEACRPAAGGAVHTRGLDFACDIYIWAPLAGTCGVLLLSLVI TLYCKRGRKKLLYIFKQPFMRPVQTTQEEDGCSCRFPEEEEGGCELRVKFSRSADAPAYQQGQN QLYNELNLGRREEYDVLDKRRGRDPEMGGKPRRKNPQEGLYNELQKDKMAEAYSEIGMKGERRR GKGHDGLYQGLSTATKDTYDALHMQALPPR |
| 272 | DIVMTQSPLSLPVTPGEPASISCRSSQSLLHSNGYNYLDWYLQKPGQSPQLLIYLGSNRASGVP DRFSGSGSGTDFTLKISRVEAEDVGVYYCMQALGLITFGGGTKVEIKGGGGSGGGGSGGGGSGG GGSEVQLVESGGGLVKPGGSLRLSCAASGFTFSSYSMNWVRQAPGKGLEWVSSISSSSSYIYYA DSVKGRFTISRDNAKNSLYLQMNSLRAEDTAVYYCARAGDTYSAADYYYMDVWGKGTTVTVSST TTPAPRPPTPAPTIASQPLSLRPEACRPAAGGAVHTRGLDFACDIYIWAPLAGTCGVLLLSLVI TLYCKRGRKKLLYIFKQPFMRPVQTTQEEDGCSCRFPEEEEGGCELRVKFSRSADAPAYQQGQN QLYNELNLGRREEYDVLDKRRGRDPEMGGKPRRKNPQEGLYNELQKDKMAEAYSEIGMKGERRR GKGHDGLYQGLSTATKDTYDALHMQALPPR |
| 273 | EVQLLESGGGLVQPGGSLRLSCAASGFTFGSEAMSWVRQAPGKERELVSAISGSGEVTYYADSV KGRFTISRDNSKNTLYLQMNSLRAEDTAVYYCQRLVEAKRHWGQGTQVTVSSTTTPAPRPPTPA PTIASQPLSLRPEACRPAAGGAVHTRGLDFACDIYIWAPLAGTCGVLLLSLVITLYCKRGRKKL LYIFKQPFMRPVQTTQEEDGCSCRFPEEEEGGCELRVKFSRSADAPAYQQGQNQLYNELNLGRR EEYDVLDKRRGRDPEMGGKPRRKNPQEGLYNELQKDKMAEAYSEIGMKGERRRGKGHDGLYQGL STATKDTYDALHMQALPPR |
| 274 | EVQLLESGGGLVQPGGSLRLSCAASGFTFESEAMSWYRQAPGKERELVSVITSEGSTYYADSVK GRFTISRDNSKNTLYLQMNSLRAEDTAVYYCAHIEWETRLNWGQGTQVTVSSTTTPAPRPPTPA PTIASQPLSLRPEACRPAAGGAVHTRGLDFACDIYIWAPLAGTCGVLLLSLVITLYCKRGRKKL LYIFKQPFMRPVQTTQEEDGCSCRFPEEEEGGCELRVKFSRSADAPAYQQGQNQLYNELNLGRR EEYDVLDKRRGRDPEMGGKPRRKNPQEGLYNELQKDKMAEAYSEIGMKGERRRGKGHDGLYQGL STATKDTYDALHMQALPPR |
| 275 | EVQLLESGGGLVQPGGSLRLSCAASGFTFDEYTMHWFRQAPGKEREFVSAISGGGSETYYADSV KGRFTISRDNSKNTLYLQMNSLRAEDTAVYYCAAGGEEAGVGYWGQGTQVTVSSTTTPAPRPPT PAPTIASQPLSLRPEACRPAAGGAVHTRGLDFACDIYIWAPLAGTCGVLLLSLVITLYCKRGRK KLLYIFKQPFMRPVQTTQEEDGCSCRFPEEEEGGCELRVKFSRSADAPAYQQGQNQLYNELNLG RREEYDVLDKRRGRDPEMGGKPRRKNPQEGLYNELQKDKMAEAYSEIGMKGERRRGKGHDGLYQ GLSTATKDTYDALHMQALPPR |
| 276 | EVQLLESGGGLVQPGGSLRLSCAASGFTFEDYAMSWFRQAPGKEREGVSAISGKGGSTYYADSV KGRFTISRDNSKNTLYLQMNSLRAEDTAVYYCAVLDEEAGAEGGYWGQGTQVTVSSTTTPAPRP PTPAPTIASQPLSLRPEACRPAAGGAVHTRGLDFACDIYIWAPLAGTCGVLLLSLVITLYCKRG RKKLLYIFKQPFMRPVQTTQEEDGCSCRFPEEEEGGCELRVKFSRSADAPAYQQGQNQLYNELN LGRREEYDVLDKRRGRDPEMGGKPRRKNPQEGLYNELQKDKMAEAYSEIGMKGERRRGKGHDGL YQGLSTATKDTYDALHMQALPPR |
| 277 | EVQLLESGGGLVQPGGSLRLSCAASGFTFDRYAMSWFRQAPGKEREGVSAISTSGDSTYYADSV KGRFTISRDNSKNTLYLQMNSLRAEDTAVYYCAVLDEEAGAEGGYWGQGTQVTVSSTTTPAPRP PTPAPTIASQPLSLRPEACRPAAGGAVHTRGLDFACDIYIWAPLAGTCGVLLLSLVITLYCKRG RKKLLYIFKQPFMRPVQTTQEEDGCSCRFPEEEEGGCELRVKFSRSADAPAYQQGQNQLYNELN LGRREEYDVLDKRRGRDPEMGGKPRRKNPQEGLYNELQKDKMAEAYSEIGMKGERRRGKGHDGL YQGLSTATKDTYDALHMQALPPR |
| 278 | EVQLLESGGGLVQPGGSLRLSCAASGFTFASDAMSWYRQAPGKERELVSAISGSGGSTYYADSV KGRFTISRDNSKNTLYLQMNSLRAEDTAVYYCAAHDSGEAYLAFDYWGQGTQVTVSSTTTPAPR PPTPAPTIASQPLSLRPEACRPAAGGAVHTRGLDFACDIYIWAPLAGTCGVLLLSLVITLYCKR GRKKLLYIFKQPFMRPVQTTQEEDGCSCRFPEEEEGGCELRVKFSRSADAPAYQQGQNQLYNEL NLGRREEYDVLDKRRGRDPEMGGKPRRKNPQEGLYNELQKDKMAEAYSEIGMKGERRRGKGHDG LYQGLSTATKDTYDALHMQALPPR |
| 279 | EVQLLESGGGLVQPGGSLRLSCAASGFTFDSYTMSWYRQAPGKERELVSAISGHGDSTYYADSV KGRFTISRDNSKNTLYLQMNSLRAEDTAVYYCTRISITTEWLAGDYWGQGTQVTVSSTTTPAPR PPTPAPTIASQPLSLRPEACRPAAGGAVHTRGLDFACDIYIWAPLAGTCGVLLLSLVITLYCKR GRKKLLYIFKQPFMRPVQTTQEEDGCSCRFPEEEEGGCELRVKFSRSADAPAYQQGQNQLYNEL |

TABLE 11-continued

Chimeric antigen receptors

| SEQ ID NO. | AMINO ACID SEQUENCE |
|---|---|
| | NLGRREEYDVLDKRRGRDPEMGGKPRRKNPQEGLYNELQKDKMAEAYSEIGMKGERRRGKGHDG LYQGLSTATKDTYDALHMQALPPR |
| 280 | EVQLLESGGGLVQPGGSLRLSCAASGFTFSSYAMSWFRQAPGKEREFVSFISGSGDSTYYADSV KGRFTISRDNSKNTLYLQMNSLRAEDTAVYYCTRWPYDFEEPSEPGVYWGQGTQVTVSSTTTPA PRPPTPAPTIASQPLSLRPEACRPAAGGAVHTRGLDFACDIYIWAPLAGTCGVLLLSLVITLYC KRGRKKLLYIFKQPFMRPVQTTQEEDGCSCRFPEEEEGGCELRVKFSRSADAPAYQQGQNQLYN ELNLGRREEYDVLDKRRGRDPEMGGKPRRKNPQEGLYNELQKDKMAEAYSEIGMKGERRRGKGH DGLYQGLSTATKDTYDALHMQALPPR |
| 281 | EVQLLESGGGLVQPGGSLRLSCAASGFTFTDYDMSWYRQAPGKERELVSVIHSGGSTYYADSVK GRFTISRDNSKNTLYLQMNSLRAEDTAVYYCAPGYYSDLSFDYYNFDYWGQGTQVTVSSTTTPA PRPPTPAPTIASQPLSLRPEACRPAAGGAVHTRGLDFACDIYIWAPLAGTCGVLLLSLVITLYC KRGRKKLLYIFKQPFMRPVQTTQEEDGCSCRFPEEEEGGCELRVKFSRSADAPAYQQGQNQLYN ELNLGRREEYDVLDKRRGRDPEMGGKPRRKNPQEGLYNELQKDKMAEAYSEIGMKGERRRGKGH DGLYQGLSTATKDTYDALHMQALPPR |
| 282 | EVQLLESGGGLVQPGGSLRLSCAASGFTFSDYAMHWFRQAPGKERVLVSSIDSGGSTYYADSVK GRFTISRDNSKNTLYLQMNSLRAEDTAVYYCNAGFKGDHPHPKDAFDIWGQGTQVTVSSTTTPA PRPPTPAPTIASQPLSLRPEACRPAAGGAVHTRGLDFACDIYIWAPLAGTCGVLLLSLVITLYC KRGRKKLLYIFKQPFMRPVQTTQEEDGCSCRFPEEEEGGCELRVKFSRSADAPAYQQGQNQLYN ELNLGRREEYDVLDKRRGRDPEMGGKPRRKNPQEGLYNELQKDKMAEAYSEIGMKGERRRGKGH DGLYQGLSTATKDTYDALHMQALPPR |
| 283 | EVQLLESGGGLVQPGGSLRLSCAASGFTFSSEGMSWVRQAPGKERELVSAISGSGDHTYYADSV RGRFTISRDNSKNTLYLQMNSLRAEDTAVYYCNALEGGPTTAIQPGGPDYWGQGTQVTVSSTTT PAPRPPTPAPTIASQPLSLRPEACRPAAGGAVHTRGLDFACDIYIWAPLAGTCGVLLLSLVITL YCKRGRKKLLYIFKQPFMRPVQTTQEEDGCSCRFPEEEEGGCELRVKFSRSADAPAYQQGQNQL YNELNLGRREEYDVLDKRRGRDPEMGGKPRRKNPQEGLYNELQKDKMAEAYSEIGMKGERRRGK GHDGLYQGLSTATKDTYDALHMQALPPR |

In particular embodiments, a CAR comprises an amino acid sequence set forth in any one of SEQ ID NOs: 255, 256, 257, 258, 259, 260, 261, 262, 263, 264, 265, 266, 267, 268, 269, 270, 271, 272, 273, 274, 275, 276, 277, 278, 279, 280, 281, 282, and 283.

In particular embodiments, a CAR comprises an amino acid sequence set forth in any one of SEQ ID NOs: 256, 258, 259, 262, 263, 266, 268, 270, and 272.

In particular embodiments, a CAR comprises an amino acid sequence set forth in any one of SEQ ID NOs: 259, 263, 266, and 270.

In particular embodiments, a CAR comprises an amino acid sequence set forth in SEQ ID NO: 273 or 277.

F. Polypeptides

Polypeptides, fusion polypeptides, and polypeptide variants are contemplated in particular embodiments. Exemplary polypeptides contemplated herein include but not limited to fusion polypeptides, fusogens, tropism polypeptides, chimeric antigen receptors (CARs) and components thereof, and variants and/or fragments thereof, e.g., SEQ ID NOs: 1-283 and 324-374. Polypeptides contemplated herein also include those encoded by polynucleotide sequences set forth in any one of SEQ ID NOs: 284-323.

Polypeptide," "polypeptide," "peptide," and "protein" are used interchangeably, unless specified to the contrary, and according to conventional meaning, i.e., as a sequence of amino acids. In particular embodiments, a "polypeptide" is a fusion polypeptide or polypeptide variant. Polypeptides can be prepared using any of a variety of well-known recombinant and/or synthetic techniques. Polypeptides are not limited to a specific length, e.g., they may comprise a full-length protein sequence, a fragment of a full-length protein, or a fusion protein, and may include post-translational modifications, e.g., glycosylations, acetylations, phosphorylations and the like, as well as other modifications known in the art, both naturally occurring and non-naturally occurring.

An "isolated peptide," "isolated protein" or an "isolated polypeptide" as used herein, refers to isolation, separation, and/or purification of a polypeptide molecule from a cellular environment, and from association with other components of the cell, i.e., it is not significantly associated with in vivo substances.

Polypeptides include "polypeptide variants." In particular embodiments, a polypeptide variant is referred to as a "modified polypeptide." Polypeptide variants may differ from a naturally occurring polypeptide in one or more amino acid substitutions, deletions, additions and/or insertions. For example, in particular embodiments, it may be desirable to modulate one or more biological activities of a chimeric antigen receptor by introducing one or more amino acid substitutions, deletions, additions and/or insertions into the polypeptide. Such variants may be naturally occurring or may be synthetically generated. In particular embodiments, polypeptides include polypeptide variants having at least about 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 86%, 97%, 98%, or 99% amino acid identity to any reference sequence contemplated herein, typically where the variant maintains at least one biological activity of the reference sequence.

Polypeptides variants include "polypeptide fragments." Illustrative examples of polypeptide fragments include but are not limited to anti-BCMA antibodies or antigen binding fragments thereof, anti-CD3 antibodies or antigen binding fragments thereof, spacer domains, hinges, transmembrane domains, intracellular signaling domains, and the like. In particular embodiments, a polypeptide fragment is a biologically active polypeptide fragment. As used herein, the term "biologically active polypeptide fragment" refers to a polypeptide fragment that retains at least 100%, at least 95%, at least 90%, at least 85%, at least 80%, at least 75%, at least 70%, at least 65%, at least 60%, at least 55%, or at least 50% of the naturally occurring polypeptide activity. In certain embodiments, a polypeptide fragment comprises an amino acid sequence at least 5 to about 500 amino acids long. It will be appreciated that in certain embodiments, fragments are at least 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 55, 60, 65, 70, 75, 80, 85, 90, 95, 100, 110, 150, 200, 250, 300, 350, 400, 450, or 500 or more amino acids long.

In particular embodiments, polypeptides contemplated herein may comprise one or more amino acids denoted as "X" or "$X_n$" wherein n is an integer that denotes the particular X amino acid. "X" if present in an amino acid SEQ ID NO, refers to any one or more amino acids or particular amino acids if disclosed.

In particular embodiments, a polypeptide comprises one or more amino acid substitutions, deletions, truncations, or insertions using methods that are well known in the art. See, for example, Kunkel (Proc. Natl. Acad. Sci. USA. 82:488-492. (1985)), Kunkel et al., (*Methods in Enzymol,* 154:367-382. (1987)), U.S. Pat. No. 4,873,192, Watson, J. D. et al., (*Molecular Biology of the Gene*, Fourth Edition, Benjamin/Cummings, Menlo Park, Calif. (1987)) and the references cited therein. Guidance as to appropriate amino acid substitutions that do not affect biological activity of the protein of interest may be found in the model of Dayhoff et al., *Atlas of Protein Sequence and Structure* (Natl. Biomed. Res. Found., Washington, D.C. (1978)).

In certain embodiments, a polypeptide variant comprises one or more conservative substitutions or disruptive substitutions. A "conservative substitution" is one in which an amino acid is substituted for another amino acid that has similar properties. In particular embodiments, polypeptide variants contemplated herein comprise one or more conservative amino acid changes compared to a reference polypeptide. In particular embodiments, a conservative amino acid substitution involves substituting an amino acid with an amino acid having a related side chain. A "disruptive substitution" is one in which an amino acid is substituted for another amino acid that has different properties, e.g., polar vs. non-polar, bulky vs. non-bulky, charged vs. uncharged, acidic vs. basic. In particular embodiments, polypeptide variants contemplated herein comprise one or more disruptive amino acid changes compared to a reference polypeptide. In particular embodiments, a disruptive amino acid substitution involves substituting an amino acid with an amino acid having an unrelated side chain or side change with a different chemical property. Guidance in determining which amino acid residues can be substituted, inserted, or deleted can be found using computer programs well known in the art, such as DNASTAR, DNA Strider, Gencious, Mac Vector, or Vector NTI software.

Naturally occurring amino acids are generally divided into four families: acidic (aspartate, glutamate), basic (lysine, arginine, histidine), non-polar (alanine, valine, leucine, isoleucine, proline, phenylalanine, methionine, tryptophan), and uncharged polar (glycine, asparagine, glutamine, cysteine, serine, threonine, tyrosine) amino acids. Phenylalanine, tryptophan, and tyrosine are sometimes classified jointly as aromatic amino acids. In particular embodiments, a conservative amino acid substitution refers to substituting amino acids within the same group or family.

Those of skill in this art recognize that, in general, conservative single amino acid substitutions in non-essential regions of a polypeptide do not substantially alter biological activity (see, e.g., Watson et al. *Molecular Biology of the Gene,* 4th Edition, 1987, The Benjamin/Cummings Pub. Co., p. 224), whereas disruptive single amino acid substitutions may.

In particular embodiments, a conservative amino acid substitution refers to substituting amino acids having a similar hydropathic index or score. The importance of the hydropathic amino acid index in conferring interactive biologic function on a protein is generally understood in the art (Kyte and Doolittle, 1982, incorporated herein by reference). Each amino acid has been assigned a hydropathic index on the basis of its hydrophobicity and charge characteristics (Kyte and Doolittle, 1982). These values are: isoleucine (+4.5); valine (+4.2); leucine (+3.8); phenylalanine (+2.8); cysteine/cysteine (+2.5); methionine (+1.9); alanine (+1.8); glycine (−0.4); threonine (−0.7); serine (−0.8); tryptophan (−0.9); tyrosine (−1.3); proline (−1.6); histidine (−3.2); glutamate (−3.5); glutamine (−3.5); aspartate (−3.5); asparagine (−3.5); lysine (−3.9); and arginine (−4.5). In particular embodiments, a conservative amino acid substitution refers to substituting amino acids having a similar hydropathic index or score. In particular embodiments, substitution of amino acids whose hydropathic indices are within +2 is preferred, those within +1 are particularly preferred, and those within +0.5 are even more particularly preferred. It is also understood in the art that the substitution of like amino acids can be made effectively on the basis of hydrophilicity.

In particular embodiments, a conservative amino acid substitution refers to substituting amino acids having a similar hydrophilic index or score. As detailed in U.S. Pat. No. 4,554,101, the following hydrophilicity values have been assigned to amino acid residues: arginine (+3.0); lysine (+3.0); aspartate (+3.0±1); glutamate (+3.0±1); serine (+0.3); asparagine (+0.2); glutamine (+0.2); glycine (0); threonine (−0.4); proline (−0.5±1); alanine (−0.5); histidine (−0.5); cysteine (−1.0); methionine (−1.3); valine (−1.5); leucine (−1.8); isoleucine (−1.8); tyrosine (−2.3); phenylalanine (−2.5); tryptophan (−3.4). In particular embodiments, a conservative amino acid substitution refers to substituting amino acids having a similar hydrophilic index or score. In particular embodiments, substitution of amino acids whose hydrophilic indices are substitution of amino acids whose hydrophilicity values are within +2 is preferred, those within +1 are particularly preferred, and those within +0.5 are even more particularly preferred.

In particular embodiments, a conservative amino acid substitution may be based on the relative similarity of the amino acid side-chain substituents, for example, their hydrophobicity, hydrophilicity, charge, size, and the like. In particular embodiments, a disruptive amino acid substitution may be based on the relative dissimilarity of the amino acid side-chain substituents, for example, their hydrophobicity, hydrophilicity, charge, size, and the like.

In particular embodiments, a polypeptide comprises a vesiculovirus envelope glycoprotein G comprising one or more amino acid substitutions at positions 47 and/or 354 of the mature polypeptide lacking a signal peptide. In particular embodiments, a polypeptide comprises a mutated cocal virus envelope glycoprotein (COCV-G) or a mutated vesicular stomatitis Indiana virus envelope glycoprotein (VSIV- G), wherein the COCV-G or VSIV-G comprises amino acid substitutions at positions 47 and 354.

Polypeptides contemplated in particular embodiments include fusion polypeptides. In particular embodiments, fusion polypeptides and polynucleotides encoding fusion polypeptides are provided. Fusion polypeptides can include one or more polypeptide domains or segments including but not limited to signal peptides, antibodies or antigen binding fragments thereof, polypeptide linkers, spacer domains, transmembrane domains, intracellular signaling domains, and polypeptide cleavage signals. Fusion proteins and polypeptides are typically linked C-terminus to N-terminus, although they can also be linked C-terminus to C-terminus, N-terminus to N-terminus, or N-terminus to C-terminus. Fusion polypeptides and fusion proteins refer to a polypeptide having at least two, three, four, five, six, seven, eight, nine, or ten polypeptide segments.

Fusion polypeptides may optionally comprise a polypeptide linker contemplated elsewhere herein that can be used to link one or more polypeptides or domains within a polypeptide.

In particular embodiments, a polypeptide or fusion polypeptide comprises a non-viral membrane bound tropism polypeptide that binds an antigen expressed on an immune effector cell. In particular embodiments, a polypeptide comprises a non-viral membrane-bound tropism polypeptide comprising an anti-CD3ε scFv and a human CD8α hinge and transmembrane domain.

In particular embodiments, a polypeptide or fusion polypeptide comprises an anti-BCMA chimeric antigen receptor comprising an anti-BCMA antibody or antigen binding fragment thereof comprising an amino acid sequence set forth in any one of SEQ ID NOs: 39, 59, 70, 90, 101 and 117; a CD8α hinge, a CD8α transmembrane domain; a CD137 costimulatory signaling domain; and a CD3ζ primary signaling domain.

In particular embodiments, a polypeptide comprises signal peptide set forth in any one of SEQ ID NOs: 245, 246, 247, 248, 249, 250, 251, 252, 253, and 254 that is subsequently cleaved from the polypeptide. Signal peptides are short 16 to 30 amino acid N-terminal sequences of nascently synthesized polypeptide chains that mediate protein targeting to the membrane of the endoplasmic reticulum (ER). Typically, signal peptides are cleaved cotranslationally by signal peptidase, a heterooligomeric polypeptide complex. In particular embodiments, a polypeptide comprises a signal peptide. In preferred embodiments, a polynucleotide encoding a polypeptide comprises a polynucleotide encoding a signal polypeptide; and the translated polypeptide does not comprise a signal peptide. Exemplary signal peptides are set forth in Table 12.

TABLE 12

Exemplary Signal Peptides

| SEQ ID NO | AMINO ACID SEQUENCE |
|---|---|
| 245 | MALPVTALLLPLALLLHAARP |
| 246 | METDTLLLWVLLLWVPGSTG |
| 247 | MDMRVPAQLLGLLLLWLRGARC |
| 248 | MPLLLLLPLLWAGALA |
| 249 | MDAMKRGLCCVLLLCGAVFVSPS |
| 250 | MLLLLLLLGLRLQLSLG |

TABLE 12-continued

Exemplary Signal Peptides

| SEQ ID NO | AMINO ACID SEQUENCE |
|---|---|
| 251 | MWLQSLLLLGTVACSIS |
| 252 | MLLLVTSLLLCELPHPAFLLIP |
| 253 | MSRSVALAVLALLSLSGLEA |
| 254 | MLLLLLLLLLALALA |

In particular embodiments, a polypeptide comprises a signal peptide set forth in any one of SEQ ID NOs: 245, 246, 247, 248, 249, 250, 251, 252, 253, and 254 and a chimeric antigen receptor comprising an amino acid sequence set forth in any one of SEQ ID NOS: 255, 256, 257, 258, 259, 260, 261, 262, 263, 264, 265, 266, 267, 268, 269, 270, 271, 272, 273, 274, 275, 276, 277, 278, 279, 280, 281, 282, and 283.

In particular embodiments, a polypeptide comprises a signal peptide set forth in any one of SEQ ID NOs: 245, 246, 247, 248, 249, 250, 251, 252, 253, and 254 and a chimeric antigen receptor encoded by a polynucleotide sequence set forth in any one of SEQ ID NOS: 295, 296, 297, 298, 299, 300, 301, 302, 303, 304, 305, 306, 307, 308, 309, 310, 311, 312, 313 and 314.

In particular embodiments, two or more polypeptides can be expressed as a fusion polypeptide that comprises one or more polypeptide cleavage signals disposed between the two or more polypeptides.

Exemplary polypeptide cleavage signals include, but are not limited to, protease cleavage sites, nuclease cleavage sites and ribosomal skipping polypeptide or self-cleaving viral polypeptides (see, e.g., in Ryan et al., 1997. *J. Gener. Virol.* 78, 699-722; deFelipe and Ryan, 2004. *Traffic,* 5(8); 616-26; and Scymczak et al. (2004) *Nature Biotech.* 5, 589-594).

Exemplary protease cleavage sites include, but are not limited to the cleavage sites of potyvirus NIa proteases (e.g, tobacco etch virus protease), poty virus HC proteases, potyvirus PI (P35) proteases, byovirus NIa proteases, byovirus RNA-2-encoded proteases, aphthovirus L proteases, enterovirus 2A proteases, rhinovirus 2 A proteases, picoma 3C proteases, comovirus 24K proteases, nepovirus 24K proteases, RTSV (rice tungro spherical virus) 3C-like protease, PYVF (parsnip yellow fleck virus) 3C-like protease, heparin, thrombin, factor Xa and enterokinase.

Illustrative examples of ribosomal skipping polypeptides include but are not limited to: a viral 2A peptide or sequence (Donnelly et al, 2001. J. Gen. Virol. 82:1027-1041). In a particular embodiment, the viral 2A peptide is an aphthovirus 2A peptide, a potyvirus 2A peptide, or a cardiovirus 2A peptide.

In one embodiment, the viral 2A peptide is selected from the group consisting of: a foot-and-mouth disease virus (FMDV) 2A peptide, an equine rhinitis A virus (ERAV) 2A peptide, a Thosea asigna virus (TaV) 2A peptide, a porcine teschovirus-1 (PTV-1) 2A peptide, a Theilovirus 2A peptide, and an encephalomyocarditis virus 2A peptide.

Illustrative examples of viral 2A sequences include, but are not limited to:

(SEQ ID NO: 355)
GSGATNFSLLKQAGDVEENPGP;

(SEQ ID NO: 356)
ATNFSLLKQAGDVEENPGP;

(SEQ ID NO: 357)
LLKQAGDVEENPGP;

(SEQ ID NO: 358)
GSGEGRGSLLTCGDVEENPGP;

(SEQ ID NO: 359)
EGRGSLLTCGDVEENPGP;

(SEQ ID NO: 360)
LLTCGDVEENPGP;

(SEQ ID NO: 361)
GSGQCTNYALLKLAGDVESNPGP;

(SEQ ID NO: 362)
QCTNYALLKLAGDVESNPGP;

(SEQ ID NO: 363)
LLKLAGDVESNPGP;

(SEQ ID NO: 364)
GSGVKQTLNFDLLKLAGDVESNPGP;

(SEQ ID NO: 365)
VKQTLNFDLLKLAGDVESNPGP;

(SEQ ID NO: 366)
LLNFDLLKLAGDVESNPGP;

(SEQ ID NO: 367)
TLNFDLLKLAGDVESNPGP;

(SEQ ID NO: 368)
NFDLLKLAGDVESNPGP;

(SEQ ID NO: 369)
QLLNFDLLKLAGDVESNPGP;

(SEQ ID NO: 370)
APVKQTLNFDLLKLAGDVESNPGP;

(SEQ ID NO: 371)
VTELLYRMKRAETYCPRPLLAIHPTEARHKQKIVAPVKQT;

(SEQ ID NO: 372)
LNFDLLKLAGDVESNPGP;

(SEQ ID NO: 373)
LLAIHPTEARHKQKIVAPVKQTLNFDLLKLAGDVESNPGP;
and (SEQ ID NO: 374)
EARHKQKIVAPVKQTLNFDLLKLAGDVESNPGP.

G. Polynucleotides

Polynucleotides comprising or encoding fusogens, tropism polypeptides, chimeric antigen receptors (CARs) and components thereof, and variants and/or fragments thereof, vectors, promoters, enhancers, Kozak sequences, polyadenylation signals, untranslated regions, and posttranscriptional response elements as well as other polynucleotides are contemplated in various embodiments.

As used herein, the terms "polynucleotide" or "nucleic acid" refer to deoxyribonucleic acid (DNA), ribonucleic acid (RNA) and DNA/RNA hybrids. Polynucleotides may be single-stranded or double-stranded and either recombinant, synthetic, or isolated. Polynucleotides include but are not limited to: pre-messenger RNA (pre-mRNA), messenger RNA (mRNA), RNA, circular RNA (circRNA), synthetic RNA, short interfering RNA (siRNA), short hairpin RNA (shRNA), microRNA (miRNA), ribozymes, genomic RNA (gRNA), viral genomic RNA, plus strand RNA (RNA(+)), minus strand RNA (RNA(−)), tracrRNA, crRNA, single guide RNA (sgRNA), Doggybone DNA (dbDNA), linear DNA, circular DNA, PCR amplified DNA, complementary DNA (cDNA), synthetic DNA, or recombinant DNA. Polynucleotides refer to a polymeric form of nucleotides of at least 5, at least 10, at least 15, at least 20, at least 25, at least 30, at least 40, at least 50, at least 100, at least 200, at least 300, at least 400, at least 500, at least 1000, at least 5000, at least 10000, or at least 15000 or more nucleotides in length, either ribonucleotides or deoxyribonucleotides or a modified form of either type of nucleotide, as well as all intermediate lengths. It will be readily understood that "intermediate lengths," in this context, means any length between the quoted values, such as 6, 7, 8, 9, etc., 101, 102, 103, etc., 151, 152, 153, etc., 201, 202, 203, etc.

As used herein, "isolated polynucleotide" refers to a polynucleotide that has been isolated from or purified from the sequences which flank it in a naturally-occurring state. In particular embodiments, an isolated polynucleotide is a synthetic polynucleotide, a semi-synthetic polynucleotide, or a polynucleotide obtained or derived from a recombinant source, or other polynucleotide that does not exist in nature and that has been made by the hand of man.

In particular embodiments, polynucleotides contemplated herein are polynucleotide variants. As used herein, the terms "polynucleotide variant" and "variant" and the like refer to polynucleotides displaying substantial sequence identity with a reference polynucleotide sequence or polynucleotides that hybridize with a reference sequence under stringent conditions that are defined hereinafter. These terms also encompass polynucleotides that are distinguished from a reference polynucleotide by the addition, deletion, substitution, or modification of one or more nucleotides. Accordingly, the terms "polynucleotide variant" and "variant" include polynucleotides in which one or more nucleotides have been added or deleted, or modified, or replaced with different nucleotides. In this regard, it is well understood in the art that certain alterations inclusive of mutations, additions, deletions and substitutions can be made to a reference polynucleotide whereby the altered polynucleotide retains the biological function or activity of the reference polynucleotide or wherein the function or activity of the altered polynucleotide is modulated. In particular embodiments, polynucleotides or polynucleotide variants have at least or about 50%, 55%, 60%, 65%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or 100% sequence identity to a reference sequence.

In particular embodiments, a polynucleotide variant includes a polynucleotide fragment that encodes biologically active polypeptide fragments or variants. As used herein, the term "polynucleotide fragment" refers to a polynucleotide fragment at least 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 55, 60, 65, 70, 75, 80, 85, 90, 95, 100, 110, 150, 200, 250, 300, 350, 400, 450, 500, 550, 600, 650, 700, 750, 800, 850, 900, 950, 1000, 1100, 1200, 1300, 1400, 1500, 1600, 1700 or more nucleotides in length that encodes a polypeptide variant that retains at least 100%, at least 90%, at least 80%, at least 70%, at least 60%, at least 50%, at least 40%, at least 30%, at least 20%, at least 10%, or at least 5% of the naturally occurring polypeptide activity. Polynucleotide fragments refer to a polynucleotide that encodes a polypeptide that has an amino-terminal deletion, a carboxyl-terminal deletion, and/or an internal deletion or substitution of one or more amino acids of a naturally occurring or recombinantly-produced polypeptide.

Terms that describe the orientation of polynucleotides include: 5' (normally the end of the polynucleotide having a free phosphate group) and 3' (normally the end of the polynucleotide having a free hydroxyl (OH) group). Polynucleotide sequences can be annotated in the 5' to 3' orientation or the 3' to 5' orientation. For DNA and mRNA, the 5" to 5' strand is designated the "sense," "plus," or "coding" strand because its sequence is identical to the sequence of the RNA [except for uracil (U) in RNA, instead of thymine (T) in DNA]. For DNA and mRNA, the complementary 3' to 5' strand which is the strand transcribed by the RNA polymerase is designated as "template," "antisense," "minus," or "non-coding" strand. As used herein, the term "reverse orientation" refers to a 5' to 3" sequence written in the 3' to 5' orientation or a 3' to 5' sequence written in the 5' to 3' orientation.

As used herein, the phrases "sequence identity" or, for example, comprising a "sequence 50% identical to," refer to the extent that sequences are identical on a nucleotide-by-nucleotide basis or an amino acid-by-amino acid basis over a window of comparison. A "percentage of sequence identity" may be calculated by comparing two optimally aligned sequences over the window of comparison, determining the number of positions at which the identical nucleic acid base (e.g., A, T, C, G, I) or the identical amino acid residue (e.g., Ala, Pro, Ser, Thr, Gly, Val, Leu, Ile, Phe, Tyr, Trp, Lys, Arg, His, Asp, Glu, Asn, Gln, Cys and Met) occurs in both sequences to yield the number of matched positions, dividing the number of matched positions by the total number of positions in the window of comparison (i.e., the window size), and multiplying the result by 100 to yield the percentage of sequence identity. In particular embodiments, polynucleotides and polypeptides comprise at least about 50%, 55%, 60%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 86%, 97%, 98%, or 99% sequence identity to any of the reference sequences described herein, e.g., SEQ ID NOs: 1-339.

Illustrative examples of polynucleotides include, but are not limited to, polynucleotide sequences set forth in any one of SEQ ID NOs: 284-323 and polynucleotides encoding polypeptides set forth in SEQ ID NOs: 1-283 and 324-374.

In various embodiments, a polynucleotide encodes a polypeptide comprising an amino acid sequence set forth in any one of SEQ ID NOs: 1-283 and 324-374.

In particular embodiments, a polynucleotide encodes a chimeric antigen receptor comprising an amino acid sequence set forth in any one of SEQ ID NOs: 255, 256, 257, 258, 259, 260, 261, 262, 263, 264, 265, 266, 267, 268, 269, 270, 271, 272, 273, 274, 275, 276, 277, 278, 279, 280, 281, 282, and 283. In particular embodiments, a polynucleotide encodes a chimeric antigen receptor comprising an amino acid sequence set forth in any one of SEQ ID NOs: 256, 258, 259, 262, 263, 266, 268, 270, and 272. In particular embodiments, a polynucleotide encodes a chimeric antigen receptor comprising an amino acid sequence set forth in any one of SEQ ID NOs: 259, 263, 266, and 270. In particular embodiments, a polynucleotide encodes a chimeric antigen receptor comprising an amino acid sequence set forth in any one of SEQ ID NO: 273 or 277. In particular embodiments, a polynucleotide encoding a chimeric antigen receptor comprises a polynucleotide sequence set forth in any one of SEQ ID NOs: 295, 296, 297, 298, 299, 300, 301, 302, 303, 304, 305, 306, 307, 308, 309, 310, 311, 312, 313, and 314.

Table 13 sets forth the SEQ ID NOs. and associated nucleic acid sequences encoding chimeric antigen receptor components and chimeric antigen receptors and the corresponding amino acid SEQ ID NO (AA SEQ ID NO.) encoded by the nucleic acid sequence.

TABLE 13

| SEQ ID NO. | AA SEQ ID NO. | NUCLEIC ACID SEQUENCE |
|---|---|---|
| 284 | 225 | ACCACAACACCTGCTCCAAGGCCCCCACACCCGCTCCAACTATAGCCAGCCAA CCATTGAGCCTCAGACCTGAAGCTTGCAGGCCCGCAGCAGGAGGCGCCGTCCAT ACGCGAGGCCTGGACTTCGCGTGTGAT |
| 285 | 226 | ATTGAAGTTATGTATCCTCCTCCTTACCTAGACAATGAGAAGAGCAATGGAACC ATTATCCATGTGAAAGGGAAACACCTTTGTCCAAGTCCCCTATTTCCCGGACCT TCTAAGCCC |
| 286 | 228 | GAGTCCAAATATGGTCCCCCGTGCCCACCATGCCCA |
| 287 | 230 | CTTGAGCCCAAATCTTGTGACAAAACTCACACATGCCCACCGTGCCCA |
| 288 | 231 | ATTTATATTTGGGCACCTTTGGCCGGAACATGTGGGGTGTTGCTTCTCTCCCTT GTGATCACTCTGTATTGT |
| 289 | 233 | TTTTGGGTGCTGGTGGTGGTTGGTGGAGTCCTGGCTTGCTATAGCTTGCTAGTA ACAGTGGCCTTTATTATTTTCTGGGTG |
| 290 | 239 | AAGCGCGGGAGAAAGAAGCTCCTGTACATCTTCAAGCAGCCTTTTATGCGACCT GTGCAAACCACTCAGGAAGAAGATGGGTGTTCATGCCGCTTCCCCGAGGAGGAA GAAGGAGGGTGTGAACTG |
| 291 | 240 | AGGAGTAAGAGGAGCAGGCTCCTGCACAGTGACTACATGAACATGACTCCCCGC CGCCCCGGGCCCACCCGCAAGCATTACCAGCCCTATGCCCCACCACGCGACTTC GCAGCCTATCGCTCC |
| 292 | 242 | ACAAAAAAGAAGTATTCATCCAGTGTGCACGACCCTAACGGTGAATACATGTTC ATGAGAGCAGTGAACACAGCCAAAAAATCTAGACTCACAGATGTGACCCTA |

TABLE 13-continued

| SEQ ID NO. | AA SEQ ID NO. | NUCLEIC ACID SEQUENCE |
|---|---|---|
| 293 | 238 | AGGGTGAAATTTTCTAGAAGCGCCGATGCTCCCGCATATCAGCAGGGTCAGAAT CAGCTCTACAATGAATTGAATCTCGGCAGGCGAGAAGAGTACGATGTTCTGGAC AAAAGACGGGGCAGGGATCCCGAGATGGGGGGAAAGCCCCGGAGAAAAAATCCT CAGGAGGGGTTGTACAATGAGCTGCAGAAGGACAAGATGGCTGAAGCCTATAGC GAGATCGGAATGAAAGGCGAAAGACGCAGAGGCAAGGGGCATGACGGTCTGTAC CAGGGTCTCTCTACAGCCACCAAGGACACTTATGATGCGTTGCATATGCAAGCC TTGCCACCCCGC |
| 294 | 245 | ATGGCTCTTCCCGTAACAGCCCTTTTGTTGCCCCTTGCACTCCTTCTGCATGCA GCACGACCG |
| 295 | 256 | GAGATCGTGCTGACACAGTCTCCCGCCACACTGTCACTGTCTCCAGGCGAAAGA GCCACACTGAGCTGTAGAGCCAGCCAGAGCGTGTCCTCTTACCTGGCCTGGTAT CAGCAGAAGCCTGGACAGGCTCCCCGGCTGCTGATCTACGATGCCAGCAATAGA GCCACAGGCATCCCCGCCAGATTTTCTGGCAGCGGCTCTGGCACCGATTTCACC CTGACCATAAGCAGCCTGGAACCTGAGGACTTCGCCGTGTACTACTGCCAGCAG AGAGTGGTGTACCCCATCACCTTTGGCGGAGGCACCAAGGTGGAAATCAAAGGC GGCGGAGGAAGCGGAGGCGGAGGATCTGGTGGTGGTGGATCTGGCGGAGGTGGC AGCCAGATCACACTGAAAGAGTCTGGCCCCACACTGGTCAAGCCCACACAGACC CTGACACTGACCTGCACCTTCAGCGGCTTTAGCCTGAGCACATCTGGCGTCGGC GTTGGCTGGATTAGACAGCCTCCTGGAAAGGCCCTGGAATGGCTGGCCCTGATC TACTGGAACGACGAGAAGAGATACAGCCCCAGCCTGAAGTCCCGGCTGACCATC ACCAAGGACACCAGCAAGAACCAGGTGGTGCTGACCATGACAAACATGGACCCC GTGGACACCGCCGTGTATTATTGCGCCAGAGATGAGTACGGCGGCTTCGACATT TGGGGCCAGGGCACAATGGTCACCGTGTCTAGTACCACAACACCTGCTCCAAGG CCCCCCACACCCGCTCCAACTATAGCCAGCCAACCATTGAGCCTCAGACCTGAA GCTTGCAGGCCCGCAGCAGGAGGCGCCGTCCATACGCGAGGCCTGGACTTCGCG TGTGATATTTATATTTGGGCACCTTTGGCCGGAACATGTGGGGTGTTGCTTCTC TCCCTTGTGATCACTCTGTATTGTAAGCGCGGGAGAAAGAAGCTCCTGTACATC TTCAAGCAGCCTTTTATGCGACCTGTGCAAACCACTCAGGAAGAAGATGGGTGT TCATGCCGCTTCCCCGAGGAGGAAGAAGGAGGGTGTGAACTGAGGGTGAAATTT TCTAGAAGCGCCGATGCTCCCGCATATCAGCAGGGTCAGAATCAGCTCTACAAT GAATTGAATCTCGGCAGGCGAGAAGAGTACGATGTTCTGGACAAAAGACGGGGC AGGGATCCCGAGATGGGGGGAAAGCCCCGGAGAAAAAATCCTCAGGAGGGGTTG TACAATGAGCTGCAGAAGGACAAGATGGCTGAAGCCTATAGCGAGATCGGAATG AAAGGCGAAAGACGCAGAGGCAAGGGGCATGACGGTCTGTACCAGGGTCTCTCT ACAGCCACCAAGGACACTTATGATGCGTTGCATATGCAAGCCTTGCCACCCCGC |
| 296 | 258 | GAGATCGTGCTGACCCAGTCCCCTGCTACCCTGAGCCTGTCTCCAGGCGAGCGG GCCACACTGAGCTGTAGAGCTTCTCAGAGCGTGTCCAGCTACCTGGCCTGGTAT CAGCAGAAACCTGGCCAGGCCCCTAGACTGCTGATCTACGACGCCAGCAACCGG GCCACCGGCATCCCCGCCAGATTCAGCGGATCTGGCAGCGGCACAGATTTTACC CTCACCATCAGCAGCCTGGAACCTGAGGACTTCGCCGTCTACTACTGCCAGCAA AGATTCGACTACCCCATCACCTTCGGCGGCGGAACAAAGGTGGAAATTAAGGGT GGTGGGGGCAGCGGTGGAGGTGGGAGCGGAGGCGGGGGTAGCGGAGGCGGGGGT AGCCAAATCACACTGAAAGAGAGCGGCCCTACACTCGTGAAACCTACCCAGACC CTGACACTGACATGTACCTTCAGCGGCTTCTCCCTGAGCACCTCTGGCGTCGGC GTTGGATGGATCAGACAGCCTCCAGGCAAGGCCCTGGAATGGCTGGCTCTGATC TATTGGAACGACGACAAGCGGTACAGCCCCAGCCTGAAGTCTAGACTGACCATC ACAAAGGACACCAGCAAGAACCAGGTGGTGCTGACCATGACAAATATGGACCCC GTGGACACCGCCGTGTACTACTGCGCCAGAGATGAGTACGGCGGATTTGATATC TGGGGCCAGGGCACCATGGTGACCGTGTCCAGCACCACAACACCTGCTCCAAGG CCCCCCACACCCGCTCCAACTATAGCCAGCCAACCATTGAGCCTCAGACCTGAA GCTTGCAGGCCCGCAGCAGGAGGCGCCGTCCATACGCGAGGCCTGGACTTCGCG TGTGATATTTATATTTGGGCACCTTTGGCCGGAACATGTGGGGTGTTGCTTCTC TCCCTTGTGATCACTCTGTATTGTAAGCGCGGGAGAAAGAAGCTCCTGTACATC TTCAAGCAGCCTTTTATGCGACCTGTGCAAACCACTCAGGAAGAAGATGGGTGT TCATGCCGCTTCCCCGAGGAGGAAGAAGGAGGGTGTGAACTGAGGGTGAAATTT TCTAGAAGCGCCGATGCTCCCGCATATCAGCAGGGTCAGAATCAGCTCTACAAT GAATTGAATCTCGGCAGGCGAGAAGAGTACGATGTTCTGGACAAAAGACGGGGC AGGGATCCCGAGATGGGGGGAAAGCCCCGGAGAAAAAATCCTCAGGAGGGGTTG TACAATGAGCTGCAGAAGGACAAGATGGCTGAAGCCTATAGCGAGATCGGAATG AAAGGCGAAAGACGCAGAGGCAAGGGGCATGACGGTCTGTACCAGGGTCTCTCT ACAGCCACCAAGGACACTTATGATGCGTTGCATATGCAAGCCTTGCCACCCCGC |
| 297 | 259 | CAAGTGCAGCTCGTGGAAAGCGGCGGCGGAGTGGTGCAGCCCGGCCGGAGCCTG AGACTGTCCTGCGCCGCTTCTGGATTTACCTTCAGCAGCTACGGCATGCACTGG GTCAGACAGGCCCCTGGCAAAGGCCTGGAGTGGGTGGCCGTTATCAGCTACGAG GGCAGCAACAAGTATTACGCCGACAGCGTGAAGGGCCGCTTCACAATCTCTAGA GATAATAGCAAGAACACCCTGTACCTGCAGATGAACAGCCTGCGGGCCGAAGAT ACCGCCGTGTACTACTGTGCTAGAGAGCTGGGCGACGGCATGGACGTGTGGGGA CAGGGCACAACCGTGACCGTGTCCTCTGGTGGTGGGGGCAGCGGTGGAGGTGGG AGCGGAGGCGGGGGTAGCGGAGGCGGGGGTAGCGAGATCGTGCTGACCCAGTCC CCTGCTACACTGAGCCTGTCTCCAGGCGAGCGGGCCACACTGAGCTGTAGAGCT TCTCAGAGCGTGTCCAGCTATCTGGCCTGGTTCCAGCAGAAACCTGGCCAGGCC |

TABLE 13-continued

| SEQ ID NO. | AA SEQ ID NO. | NUCLEIC ACID SEQUENCE |
|---|---|---|
| | | CCTAGACTGCTGATCTACGACGCCAGCAACCGGGCCACCGGCATCCCCGCCAGA<br>TTCAGCGGCTCTGGCAGCGGCACCGACTTCACCCTCACCATCAGCAGCCTGGAA<br>CCCGAGGATTTTGCCGTCTACTACTGCCAGCAAAGAGTGGACCTGTGGACCTTC<br>GGCGGAGGAACAAAGGTGGAAATCAAGACCACAACACCTGCTCCAAGGCCCCCC<br>ACACCCGCTCCAACTATAGCCAGCCAACCATTGAGCCTCAGACCTGAAGCTTGC<br>AGGCCCGCAGCAGGAGGCGCCGTCCATACGCGAGGCCTGGACTTCGCGTGTGAT<br>ATTTATATTTGGGCACCTTTGGCCGGAACATGTGGGGTGTTGCTTCTCTCCCTT<br>GTGATCACTCTGTATTGTAAGCGCGGGAGAAAGAAGCTCCTGTACATCTTCAAG<br>CAGCCTTTTATGCGACCTGTGCAAACCACTCAGGAAGAAGATGGGTGTTCATGC<br>CGCTTCCCCGAGGAGGAAGAAGGAGGGTGTGAACTGAGGGTGAAATTTTCTAGA<br>AGCGCCGATGCTCCCGCATATCAGCAGGGTCAGAATCAGCTCTACAATGAATTG<br>AATCTCGGCAGGCGAGAAGAGTACGATGTTCTGGACAAAAGACGGGGCAGGGAT<br>CCCGAGATGGGGGGAAAGCCCCGGAGAAAAAATCCTCAGGAGGGGTTGTACAAT<br>GAGCTGCAGAAGGACAAGATGGCTGAAGCCTATAGCGAGATCGGAATGAAAGGC<br>GAAAGACGCAGAGGCAAGGGGCATGACGGTCTGTACCAGGGTCTCTCTACAGCC<br>ACCAAGGACACTTATGATGCGTTGCATATGCAAGCCTTGCCACCCCGC |
| 298 | 262 | GACATCCAGATGACCCAGAGCCCTTCGACCCTATCCGCTTCCGTGGGTGACCGT<br>GTGACCATCACCTGTCGCGCGTCGCAGAGCATCTCCTCCTGGCTCGCGTGGTAC<br>CAACAGAAGCCTGGCAAGGCCCCCAAGCTGCTGATTTACGACGCCAGTTCCCTG<br>GAGTCTGGCGTGCCATCCCGCTTCTCCGGCAGCGGCAGCGGTACCGAGTTCACC<br>CTGACGATCAGCTCCCTGCAGCCGGATGACTTTGCTACCTACTACTGTCAGCAG<br>GTCTCCTCCCTCCCCCCCACCTTCGGTGGCGGTACCAAGGTGGAGATCAAGGGC<br>GGCGGCGGCTCTGGTGGCGGAGGTTCTGGCGGGGGAGGTTCGGGGGGGGGAGGC<br>TCCGAGGTGCAACTGGTAGAGAGCGGCGGGGGACTGGTAAAACCCGGCGGCTCC<br>CTGCGGCTGTCATGCGCTGCTAGCGGCTTCACGTTCAGCGATTACTACATGAGT<br>TGGATCCGCCAGGCCCCCGGGAAGGGTTTGGAGTGGGTCTCGTATATCTCTTCC<br>AGCGGATCTACCATTTACTATGCGGACAGCGTGAAGGGGCGCTTCACCATATCT<br>CGGGACAACGCCAAGAACTCCCTGTACCTGCAGATGAATTCCCTGCGTGCCGAG<br>GACACGGCCGTGTATTACTGTGCCCGCGACCAGGGCAACTACGGCGTCGACGTG<br>TGGGGCCAGGGTACAACCGTCACCGTGTCCAGTACCACAACACCTGCTCCAAGG<br>CCCCCCACACCCGCTCCAACTATAGCCAGCCAACCATTGAGCCTCAGACCTGAA<br>GCTTGCAGGCCCGCAGCAGGAGGCGCCGTCCATACGCGAGGCCTGGACTTCGCG<br>TGTGATATTTATATTTGGGCACCTTTGGCCGGAACATGTGGGGTGTTGCTTCTC<br>TCCCTTGTGATCACTCTGTATTGTAAGCGCGGGAGAAAGAAGCTCCTGTACATC<br>TTCAAGCAGCCTTTTATGCGACCTGTGCAAACCACTCAGGAAGAAGATGGGTGT<br>TCATGCCGCTTCCCCGAGGAGGAAGAAGGAGGGTGTGAACTGAGGGTGAAATTT<br>TCTAGAAGCGCCGATGCTCCCGCATATCAGCAGGGTCAGAATCAGCTCTACAAT<br>GAATTGAATCTCGGCAGGCGAGAAGAGTACGATGTTCTGGACAAAAGACGGGGC<br>AGGGATCCCGAGATGGGGGGAAAGCCCCGGAGAAAAAATCCTCAGGAGGGGTTG<br>TACAATGAGCTGCAGAAGGACAAGATGGCTGAAGCCTATAGCGAGATCGGAATG<br>AAAGGCGAAAGACGCAGAGGCAAGGGGCATGACGGTCTGTACCAGGGTCTCTCT<br>ACAGCCACCAAGGACACTTATGATGCGTTGCATATGCAAGCCTTGCCACCCCGC |
| 299 | 263 | CAAGTGCAGCTGGTCGAGAGCGGAGGAGGCCTGGTTAAGCCCGGCGGATCTCTC<br>AGACTGAGCTGCGCCGCTAGCGGCTTTACATTCAGCGACTACTACATGAGCTGG<br>ATCCGGCAGGCCCCTGGCAAGGGCCTGGAATGGGTGTCCTACATCAGCTCCTCC<br>GGCAGCACCATCTACTACGCCGACAGCGTGAAAGGCAGATTCACAATCTCTAGA<br>GATAATGCCAAGAACAGCCTGTACCTGCAGATGAACAGCCTGCGGGCCGAGGAC<br>ACCGCCGTGTACTATTGTGCTAGAGATCAGGGCAACTACGGCGTGGACGTGTGG<br>GGCCAGGGCACCACCGTGACCGTGTCTAGCGGTGGTGGGGGCAGCGGTGGAGGT<br>GGGAGCGGAGGCGGGGGTAGCGGAGGCGGGGGTAGCGATATCCAGATGACCCAG<br>TCCCCATCTACACTGAGCGCCTCTGTGGGCGACCGGGTGACCATTACATGTAGA<br>GCCAGCCAGAGCATCAGCAGCTGGCTGGCTTGGTATCAGCAGAAACCTGGCAAG<br>GCCCCTAAGCTGCTGATCTACGAGGCCAGCAGCCTGGAAAGCGGCGTCCCCAGC<br>AGATTCAGCGGCAGCGGCTCTGGAACAGAGTTCACCCTGACCATCTCCTCCCTG<br>CAGCCTGACGACTTCGCCACCTACTACTGCCAGCAATCTGATAGCCACCCCATC<br>ACCTTTGGCGGAGGCACCAAGGTGGAAATCAAGACCACAACACCTGCTCCAAGG<br>CCCCCCACACCCGCTCCAACTATAGCCAGCCAACCATTGAGCCTCAGACCTGAA<br>GCTTGCAGGCCCGCAGCAGGAGGCGCCGTCCATACGCGAGGCCTGGACTTCGCG<br>TGTGATATTTATATTTGGGCACCTTTGGCCGGAACATGTGGGGTGTTGCTTCTC<br>TCCCTTGTGATCACTCTGTATTGTAAGCGCGGGAGAAAGAAGCTCCTGTACATC<br>TTCAAGCAGCCTTTTATGCGACCTGTGCAAACCACTCAGGAAGAAGATGGGTGT<br>TCATGCCGCTTCCCCGAGGAGGAAGAAGGAGGGTGTGAACTGAGGGTGAAATTT<br>TCTAGAAGCGCCGATGCTCCCGCATATCAGCAGGGTCAGAATCAGCTCTACAAT<br>GAATTGAATCTCGGCAGGCGAGAAGAGTACGATGTTCTGGACAAAAGACGGGGC<br>AGGGATCCCGAGATGGGGGGAAAGCCCCGGAGAAAAAATCCTCAGGAGGGGTTG<br>TACAATGAGCTGCAGAAGGACAAGATGGCTGAAGCCTATAGCGAGATCGGAATG<br>AAAGGCGAAAGACGCAGAGGCAAGGGGCATGACGGTCTGTACCAGGGTCTCTCT<br>ACAGCCACCAAGGACACTTATGATGCGTTGCATATGCAAGCCTTGCCACCCCGC |
| 300 | 266 | GATATCCAGATGACCCAGTCCCCATCTACACTGAGCGCCTCTGTGGGCGACCGG<br>GTGACAATTACCTGTAGAGCTAGCCAGAGCATCTCCTCCTGGCTGGCTTGGTAC<br>CAGCAAAAACCTGGCAAGGCCCCTAAGCTGCTGATCTACGAGGCCAGCAGCCTG<br>GAAAGCGGCGTCCCCTCTAGATTCAGCGGCAGCGGCTCTGGAACCGAGTTCACC<br>CTGACAATCAGCAGCCTGCAGCCTGACGACTTCGCCACCTATTACTGCCAGCAG |

TABLE 13-continued

| SEQ ID NO. | AA SEQ ID NO. | NUCLEIC ACID SEQUENCE |
|---|---|---|
| | | GCCAACAGCCACCCCATCACCTTTGGCGGAGGCACCAAGGTGGAAATCAAGGGT<br>GGTGGGGGCAGCGGTGGAGGTGGGAGCGGAGGCGGGGGTAGCGGAGGCGGGGGT<br>AGCGAGGTGCAGCTGGTGGAAAGCGGCGGAGGACTCGTTAAGCCCGGCGGCAGC<br>CTGAGACTGAGCTGCGCCGCTAGCGGATTTACCTTCAGCGACTACTACATGAGC<br>TGGATCCGGCAGGCCCCTGGCAAGGGCCTGGAATGGGTCAGCTACATCAGCTCC<br>TCTGGCTCTACAATCTACTACGCCGACAGCGTGAAAGGCAGATTCACCATCTCT<br>AGAGATAATGCCAAGAACAGCCTGTACCTGCAAATGAACAGCCTGCGGGCCGAG<br>GACACCGCCGTGTACTATTGTGCTAGAGATCAGGGCAACTACGGCGTGGACGTG<br>TGGGGCCAGGGCACCACCGTGACAGTGTCCTCCACCACAACACCTGCTCCAAGG<br>CCCCCCACACCCGCTCCAACTATAGCCAGCCAACCATTGAGCCTCAGACCTGAA<br>GCTTGCAGGCCCGCAGCAGGAGGCGCCGTCCATACGCGAGGCCTGGACTTCGCG<br>TGTGATATTTATATTTGGGCACCTTTGGCCGGAACATGTGGGGTGTTGCTTCTC<br>TCCCTTGTGATCACTCTGTATTGTAAGCGCGGGAGAAAGAAGCTCCTGTACATC<br>TTCAAGCAGCCTTTTATGCGACCTGTGCAAACCACTCAGGAAGAAGATGGGTGT<br>TCATGCCGCTTCCCCGAGGAGGAAGAAGGAGGGTGTGAACTGAGGGTGAAATTT<br>TCTAGAAGCGCCGATGCTCCCGCATATCAGCAGGGTCAGAATCAGCTCTACAAT<br>GAATTGAATCTCGGCAGGCGAGAAGAGTACGATGTTCTGGACAAAAGACGGGGC<br>AGGGATCCCGAGATGGGGGGAAAGCCCCGGAGAAAAAATCCTCAGGAGGGGTTG<br>TACAATGAGCTGCAGAAGGACAAGATGGCTGAAGCCTATAGCGAGATCGGAATG<br>AAAGGCGAAAGACGCAGAGGCAAGGGGCATGACGGTCTGTACCAGGGTCTCTCT<br>ACAGCCACCAAGGACACTTATGATGCGTTGCATATGCAAGCCTTGCCACCCCGC |
| 301 | 268 | GACATCCAGATGACCCAGAGCCCTAGCTCCCTGAGCGCCAGCGTGGGCGATAGA<br>GTGACCATTACCTGTAGAGCCTCTCAGAGCATCTCCTCCTACCTGAACTGGTAT<br>CAGCAGAAACCCGGCAAGGCCCCTAAGCTGCTGATCTACGCCGCTAGCAGCCTG<br>CAGTCTGGCGTCCCCAGCCGGTTCAGCGGCAGCGGATCTGGCACCGACTTCACC<br>CTGACAATCAGCAGCCTGCAACCTGAGGACTTTGCTACATACTACTGCCAGCAG<br>GCCCACAGCTCTCCAATCACCTTCGGCGGCGGAACAAAGGTGGAAATCAAGGGT<br>GGTGGGGGCAGCGGTGGAGGTGGGAGCGGAGGCGGGGGTAGCGGAGGCGGGGGT<br>AGCGAGGTGCAGCTGCTGGAAAGCGGAGGCGGACTCGTTCAACCTGGCGGCAGC<br>CTGAGACTGAGCTGCGCCGCTTCTGGATTTACCTTCAGCAACTACGCCATGAGC<br>TGGGTGCGGCAGGCCCCTGGCAAAGGCCTGGAATGGGTCTCCGCCATCAGCGGC<br>TCTGGCGGCTCCACCTACTACGCCGACAGCGTGAAGGGCAGATTCACCATCTCT<br>AGAGATAATAGCAAGAACACCCTGTACCTGCAGATGAACAGCCTGCGGGCCGAG<br>GACACCGCCGTGTACTATTGTGCTAGACCCGGAGATGGCTACTACGAGGGCGTG<br>TACTTCGACTACTGGGGCCAGGGCACACTGGTGACAGTGTCCAGCACCACAACA<br>CCTGCTCCAAGGCCCCCCACACCCGCTCCAACTATAGCCAGCCAACCATTGAGC<br>CTCAGACCTGAAGCTTGCAGGCCCGCAGCAGGAGGCGCCGTCCATACGCGAGGC<br>CTGGACTTCGCGTGTGATATTTATATTTGGGCACCTTTGGCCGGAACATGTGGG<br>GTGTTGCTTCTCTCCCTTGTGATCACTCTGTATTGTAAGCGCGGGAGAAAGAAG<br>CTCCTGTACATCTTCAAGCAGCCTTTTATGCGACCTGTGCAAACCACTCAGGAA<br>GAAGATGGGTGTTCATGCCGCTTCCCCGAGGAGGAAGAAGGAGGGTGTGAACTG<br>AGGGTGAAATTTTCTAGAAGCGCCGATGCTCCCGCATATCAGCAGGGTCAGAAT<br>CAGCTCTACAATGAATTGAATCTCGGCAGGCGAGAAGAGTACGATGTTCTGGAC<br>AAAAGACGGGGCAGGGATCCCGAGATGGGGGGAAAGCCCCGGAGAAAAAATCCT<br>CAGGAGGGGTTGTACAATGAGCTGCAGAAGGACAAGATGGCTGAAGCCTATAGC<br>GAGATCGGAATGAAAGGCGAAAGACGCAGAGGCAAGGGGCATGACGGTCTGTAC<br>CAGGGTCTCTCTACAGCCACCAAGGACACTTATGATGCGTTGCATATGCAAGCC<br>TTGCCACCCCGC |
| 302 | 270 | GATATTCAGATGACCCAGAGCCCATCTAGCCTGAGCGCCAGCGTGGGCGATAGA<br>GTGACCATCACCTGTCAGGCCTCTCAGGACATCGCTAATTACCTGAACTGGTAT<br>CAGCAGAAACCCGGCAAGGCCCCTAAGCTGCTGATCTACGACGCCTCCAACCTG<br>GAAACCGGCGTGCCCAGCCGGTTCAGCGGCAGCGGATCTGGCACAGACTTCACC<br>TTTACCATCAGCTCCCTCCAGCCTGAGGACATCGCCACATACTACTGCCAGCAA<br>CACTTCAACCTGCCTCTGACCTTCGGCGGCGGAACAAAGGTCGAGATCAAGGGT<br>GGTGGGGGCAGCGGTGGAGGTGGGAGCGGAGGCGGGGGTAGCGGAGGCGGGGGT<br>AGCCAAATCACCCTGAAAGAGAGCGGACCTACACTGGTCAAGCCTACCCAGACA<br>CTGACCCTCACATGTACATTCAGCGGCTTTAGCCTGAGCACCTCCGGCGTGGGA<br>GTGGGCTGGATCAGACAGCCCCCCGGCAAGGCCCTGGAATGGCTGGCTCTGATC<br>TATTGGAATGACGAGAAGCGGTACAGCCCTAGCCTGAAATCTAGACTGACAATC<br>ACCAAGGACACCAGCAAGAACCAGGTGGTGCTGACCATGACCAACATGGATCCT<br>GTGGATACCGCCGTGTACTACTGCGCCAGAGAAGGCTCTCACGACTACAAGAGC<br>TCCAACTGGTTCGACCCATGGGGCCAGGGCACCCTGGTTACAGTGTCTAGCACC<br>ACAACACCTGCTCCAAGGCCCCCCACACCCGCTCCAACTATAGCCAGCCAACCA<br>TTGAGCCTCAGACCTGAAGCTTGCAGGCCCGCAGCAGGAGGCGCCGTCCATACG<br>CGAGGCCTGGACTTCGCGTGTGATATTTATATTTGGGCACCTTTGGCCGGAACA<br>TGTGGGGTGTTGCTTCTCTCCCTTGTGATCACTCTGTATTGTAAGCGCGGGAGA<br>AAGAAGCTCCTGTACATCTTCAAGCAGCCTTTTATGCGACCTGTGCAAACCACT<br>CAGGAAGAAGATGGGTGTTCATGCCGCTTCCCCGAGGAGGAAGAAGGAGGGTGT<br>GAACTGAGGGTGAAATTTTCTAGAAGCGCCGATGCTCCCGCATATCAGCAGGGT<br>CAGAATCAGCTCTACAATGAATTGAATCTCGGCAGGCGAGAAGAGTACGATGTT<br>CTGGACAAAAGACGGGGCAGGGATCCCGAGATGGGGGGAAAGCCCCGGAGAAAA<br>AATCCTCAGGAGGGGTTGTACAATGAGCTGCAGAAGGACAAGATGGCTGAAGCC<br>TATAGCGAGATCGGAATGAAAGGCGAAAGACGCAGAGGCAAGGGGCATGACGGT |

TABLE 13-continued

| SEQ ID NO. | AA SEQ ID NO. | NUCLEIC ACID SEQUENCE |
|---|---|---|
| | | CTGTACCAGGGTCTCTCTACAGCCACCAAGGACACTTATGATGCGTTGCATATG<br>CAAGCCTTGCCACCCCGC |
| 303 | 272 | GATATCGTGATGACCCAATCTCCACTGAGCCTGCCTGTGACACCTGGCGAGCCT<br>GCTTCTATCAGCTGTAGAAGCAGCCAGTCCCTGCTGCACAGCAACGGCTACAAC<br>TACCTGGACTGGTATCTGCAGAAACCCGGCCAGAGCCCCCAGCTGCTGATCTAC<br>CTCGGCTCTAATCGGGCCAGCGGAGTGCCTGATAGATTCAGCGGAAGCGGCTCC<br>GGCACCGACTTCACCCTGAAGATCAGCAGAGTGGAAGCCGAGGACGTGGGCGTC<br>TACTACTGCATGCAGGCCCTGGGCCTGATTACATTTGGCGGCGGAACCAAGGTG<br>GAAATCAAGGGTGGTGGGGGCAGCGGTGGAGGTGGGAGCGGAGGCGGGGGTAGC<br>GGAGGCGGGGGTAGCGAAGTGCAGCTGGTTGAGAGCGGCGGCGGACTGGTGAAG<br>CCCGGAGGCAGCCTCAGACTGAGCTGTGCTGCTTCTGGCTTTACCTTCAGCTCT<br>TATAGCATGAACTGGGTGCGGCAGGCCCCTGGCAAGGGCCTGGAATGGGTCAGC<br>TCCATCAGCTCTTCTAGCAGCTACATCTACTACGCCGACAGCGTGAAGGGCAGA<br>TTCACCATCAGCAGAGATAACGCCAAGAACAGCCTGTACCTGCAGATGAATAGC<br>CTGCGGGCCGAGGACACCGCCGTGTACTACTGCGCCAGAGCCGGCGACACCTAC<br>AGCGCCGCCGATTACTACTACATGGACGTGTGGGGCAAAGGAACAACCGTGACA<br>GTGTCCTCCACCACAACACCTGCTCCAAGGCCCCCCACACCCGCTCCAACTATA<br>GCCAGCCAACCATTGAGCCTCAGACCTGAAGCTTGCAGGCCCGCAGCAGGAGGC<br>GCCGTCCATACGCGAGGCCTGGACTTCGCGTGTGATATTTATATTTGGGCACCT<br>TTGGCCGGAACATGTGGGGTGTTGCTTCTCTCCCTTGTGATCACTCTGTATTGT<br>AAGCGCGGGAGAAAGAAGCTCCTGTACATCTTCAAGCAGCCTTTTATGCGACCT<br>GTGCAAACCACTCAGGAAGAAGATGGGTGTTCATGCCGCTTCCCCGAGGAGGAA<br>GAAGGAGGGTGTGAACTGAGGGTGAAATTTTCTAGAAGCGCCGATGCTCCCGCA<br>TATCAGCAGGGTCAGAATCAGCTCTACAATGAATTGAATCTCGGCAGGCGAGAA<br>GAGTACGATGTTCTGGACAAAAGACGGGGCAGGGATCCCGAGATGGGGGGAAAG<br>CCCCGGAGAAAAAATCCTCAGGAGGGGTTGTACAATGAGCTGCAGAAGGACAAG<br>ATGGCTGAAGCCTATAGCGAGATCGGAATGAAAGGCGAAAGACGCAGAGGCAAG<br>GGGCATGACGGTCTGTACCAGGGTCTCTCTACAGCCACCAAGGACACTTATGAT<br>GCGTTGCATATGCAAGCCTTGCCACCCCGC |
| 304 | 273 | GAAGTGCAACTGCTGGAAAGCGGCGGAGGCCTGGTCCAGCCCGGCGGCTCTCTG<br>CGGCTCAGCTGCGCCGCTTCTGGATTTACCTTCGGCAGCGAGGCTATGAGCTGG<br>GTGCGGCAGGCCCCTGGAAAAGAGAGAGAGCTGGTGTCCGCCATCAGCGGCAGC<br>GGCGAGGTGACCTACTACGCCGACAGCGTGAAGGGCAGATTCACCATCTCTAGA<br>GATAATAGCAAGAACACCCTGTACCTGCAGATGAACAGCCTGAGAGCCGAGGAC<br>ACCGCCGTGTACTATTGTCAGAGACTGGTGGAAGCCAAGCGGCACTGGGGCCAG<br>GGCACACAGGTTACAGTGTCCAGCACCACAACACCTGCTCCAAGGCCCCCCACA<br>CCCGCTCCAACTATAGCCAGCCAACCATTGAGCCTCAGACCTGAAGCTTGCAGG<br>CCCGCAGCAGGAGGCGCCGTCCATACGCGAGGCCTGGACTTCGCGTGTGATATT<br>TATATTTGGGCACCTTTGGCCGGAACATGTGGGGTGTTGCTTCTCTCCCTTGTG<br>ATCACTCTGTATTGTAAGCGCGGGAGAAAGAAGCTCCTGTACATCTTCAAGCAG<br>CCTTTTATGCGACCTGTGCAAACCACTCAGGAAGAAGATGGGTGTTCATGCCGC<br>TTCCCCGAGGAGGAAGAAGGAGGGTGTGAACTGAGGGTGAAATTTTCTAGAAGC<br>GCCGATGCTCCCGCATATCAGCAGGGTCAGAATCAGCTCTACAATGAATTGAAT<br>CTCGGCAGGCGAGAAGAGTACGATGTTCTGGACAAAAGACGGGGCAGGGATCCC<br>GAGATGGGGGGAAAGCCCCGGAGAAAAAATCCTCAGGAGGGGTTGTACAATGAG<br>CTGCAGAAGGACAAGATGGCTGAAGCCTATAGCGAGATCGGAATGAAAGGCGAA<br>AGACGCAGAGGCAAGGGGCATGACGGTCTGTACCAGGGTCTCTCTACAGCCACC<br>AAGGACACTTATGATGCGTTGCATATGCAAGCCTTGCCACCCCGC |
| 305 | 274 | GAAGTGCAACTGCTGGAATCTGGCGGAGGACTGGTGCAGCCCGGCGGCAGCCTG<br>CGGCTGAGCTGTGCTGCTTCTGGCTTTACCTTCGAGTCTGAGGCCATGAGCTGG<br>TATAGACAGGCCCCTGGCAAGGAAAGAGAGCTGGTCAGCGTGATCACCAGCGAG<br>GGCTCCACCTACTACGCCGACAGCGTGAAAGGCAGATTCACAATCAGCCGGGAC<br>AATAGCAAGAACACCCTGTACCTGCAGATGAACAGCCTGCGCGCCGAAGATACA<br>GCCGTGTACTACTGCGCCCACATCGAGTGGGAGACAAGACTCAACTGGGGCCAG<br>GGCACCCAGGTGACCGTGTCCAGCACCACAACACCTGCTCCAAGGCCCCCCACA<br>CCCGCTCCAACTATAGCCAGCCAACCATTGAGCCTCAGACCTGAAGCTTGCAGG<br>CCCGCAGCAGGAGGCGCCGTCCATACGCGAGGCCTGGACTTCGCGTGTGATATT<br>TATATTTGGGCACCTTTGGCCGGAACATGTGGGGTGTTGCTTCTCTCCCTTGTG<br>ATCACTCTGTATTGTAAGCGCGGGAGAAAGAAGCTCCTGTACATCTTCAAGCAG<br>CCTTTTATGCGACCTGTGCAAACCACTCAGGAAGAAGATGGGTGTTCATGCCGC<br>TTCCCCGAGGAGGAAGAAGGAGGGTGTGAACTGAGGGTGAAATTTTCTAGAAGC<br>GCCGATGCTCCCGCATATCAGCAGGGTCAGAATCAGCTCTACAATGAATTGAAT<br>CTCGGCAGGCGAGAAGAGTACGATGTTCTGGACAAAAGACGGGGCAGGGATCCC<br>GAGATGGGGGGAAAGCCCCGGAGAAAAAATCCTCAGGAGGGGTTGTACAATGAG<br>CTGCAGAAGGACAAGATGGCTGAAGCCTATAGCGAGATCGGAATGAAAGGCGAA<br>AGACGCAGAGGCAAGGGGCATGACGGTCTGTACCAGGGTCTCTCTACAGCCACC<br>AAGGACACTTATGATGCGTTGCATATGCAAGCCTTGCCACCCCGC |
| 306 | 275 | GAGGTGCAGCTGCTGGAAAGCGGAGGGGGCCTGGTCCAACCCGGCGGGTCTCTT<br>CGCCTAAGCTGTGCCGCTTCTGGCTTCACCTTCGACGAGTACACCATGCACTGG<br>TTCAGACAGGCCCCCGGCAAGGAGCGCGAGTTCGTCAGTGCAATCAGCGGAGGC<br>GGTAGCGAGACTTATTACGCGGACTCCGTGAAGGGCCGCTTCACCATTAGCCGC<br>GACAACTCCAAGAACACGCTGTACCTGCAGATGAATTCGCTGCGCGCCGAAGAT |

TABLE 13-continued

| SEQ ID NO. | AA SEQ ID NO. | NUCLEIC ACID SEQUENCE |
|---|---|---|
| | | ACGGCCGTGTACTACTGTGCCGCTGGTGGGGAGGAGGCTGGCGTGGGCTATTGG<br>GGCCAGGGCACCCAGGTCACCGTGTCGTCCACCACAACACCTGCTCCAAGGCCC<br>CCCACACCCGCTCCAACTATAGCCAGCCAACCATTGAGCCTCAGACCTGAAGCT<br>TGCAGGCCCGCAGCAGGAGGCGCCGTCCATACGCGAGGCCTGGACTTCGCGTGT<br>GATATTTATATTTGGGCACCTTTGGCCGGAACATGTGGGGTGTTGCTTCTCTCC<br>CTTGTGATCACTCTGTATTGTAAGCGCGGGAGAAAGAAGCTCCTGTACATCTTC<br>AAGCAGCCTTTTATGCGACCTGTGCAAACCACTCAGGAAGAAGATGGGTGTTCA<br>TGCCGCTTCCCCGAGGAGGAAGAAGGAGGGTGTGAACTGAGGGTGAAATTTTCT<br>AGAAGCGCCGATGCTCCCGCATATCAGCAGGGTCAGAATCAGCTCTACAATGAA<br>TTGAATCTCGGCAGGCGAGAAGAGTACGATGTTCTGGACAAAAGACGGGGCAGG<br>GATCCCGAGATGGGGGGAAAGCCCCGGAGAAAAAATCCTCAGGAGGGGTTGTAC<br>AATGAGCTGCAGAAGGACAAGATGGCTGAAGCCTATAGCGAGATCGGAATGAAA<br>GGCGAAAGACGCAGAGGCAAGGGGCATGACGGTCTGTACCAGGGTCTCTCTACA<br>GCCACCAAGGACACTTATGATGCGTTGCATATGCAAGCCTTGCCACCCCGC |
| 307 | 276 | GAGGTGCAGCTGCTGGAGAGCGGAGGCGGCCTCGTGCAGCCAGGAGGTTCCCTA<br>CGACTCTCCTGTGCCGCCAGCGGCTTCACCTTCGAGGACTACGCCATGAGTTGG<br>TTCCGCCAGGCCCCGGGGAAGGAGCGCGAGGGCGTGAGCGCGATTTCTGGAAAG<br>GGCGGCTCCACCTATTACGCGGACTCCGTGAAGGGTCGCTTTACCATCTCTCGC<br>GACAACTCCAAGAACACGCTGTACCTGCAGATGAATAGCCTGCGCGCTGAGGAC<br>ACTGCCGTGTACTACTGTGCTGTCTTGGACGAGGAGGCCGGCGCAGAGGGCGGC<br>TATTGGGGCCAGGGTACCCAGGTCACCGTGTCGTCCACCACAACACCTGCTCCA<br>AGGCCCCCCACACCCGCTCCAACTATAGCCAGCCAACCATTGAGCCTCAGACCT<br>GAAGCTTGCAGGCCCGCAGCAGGAGGCGCCGTCCATACGCGAGGCCTGGACTTC<br>GCGTGTGATATTTATATTTGGGCACCTTTGGCCGGAACATGTGGGGTGTTGCTT<br>CTCTCCCTTGTGATCACTCTGTATTGTAAGCGCGGGAGAAAGAAGCTCCTGTAC<br>ATCTTCAAGCAGCCTTTTATGCGACCTGTGCAAACCACTCAGGAAGAAGATGGG<br>TGTTCATGCCGCTTCCCCGAGGAGGAAGAAGGAGGGTGTGAACTGAGGGTGAAA<br>TTTTCTAGAAGCGCCGATGCTCCCGCATATCAGCAGGGTCAGAATCAGCTCTAC<br>AATGAATTGAATCTCGGCAGGCGAGAAGAGTACGATGTTCTGGACAAAAGACGG<br>GGCAGGGATCCCGAGATGGGGGGAAAGCCCCGGAGAAAAAATCCTCAGGAGGGG<br>TTGTACAATGAGCTGCAGAAGGACAAGATGGCTGAAGCCTATAGCGAGATCGGA<br>ATGAAAGGCGAAAGACGCAGAGGCAAGGGGCATGACGGTCTGTACCAGGGTCTC<br>TCTACAGCCACCAAGGACACTTATGATGCGTTGCATATGCAAGCCTTGCCACCC<br>CGC |
| 308 | 277 | GAGGTGCAACTGCTGGAAAGCGGCGGTGGACTGGTGCAGCCCGGCGGCAGCCTG<br>AGACTGTCTTGTGCTGCTTCTGGATTTACATTCGACAGATACGCCATGAGCTGG<br>TTCCGCCAGGCCCCTGGCAAAGAGCGGGAAGGCGTGTCCGCCATCTCCACAAGC<br>GGAGATAGCACATACTATGCCGACAGCGTGAAGGGCAGATTCACCATCAGCAGA<br>GATAATAGCAAGAACACCCTGTACCTGCAGATGAACAGCCTCCGGGCCGAGGAC<br>ACCGCCGTCTACTACTGCGCCGTGCTGGACGAGGAAGCCGGCGCCGAGGGCGGC<br>TACTGGGGCCAGGGCACCCAGGTGACCGTGTCTAGCACCACAACACCTGCTCCA<br>AGGCCCCCCACACCCGCTCCAACTATAGCCAGCCAACCATTGAGCCTCAGACCT<br>GAAGCTTGCAGGCCCGCAGCAGGAGGCGCCGTCCATACGCGAGGCCTGGACTTC<br>GCGTGTGATATTTATATTTGGGCACCTTTGGCCGGAACATGTGGGGTGTTGCTT<br>CTCTCCCTTGTGATCACTCTGTATTGTAAGCGCGGGAGAAAGAAGCTCCTGTAC<br>ATCTTCAAGCAGCCTTTTATGCGACCTGTGCAAACCACTCAGGAAGAAGATGGG<br>TGTTCATGCCGCTTCCCCGAGGAGGAAGAAGGAGGGTGTGAACTGAGGGTGAAA<br>TTTTCTAGAAGCGCCGATGCTCCCGCATATCAGCAGGGTCAGAATCAGCTCTAC<br>AATGAATTGAATCTCGGCAGGCGAGAAGAGTACGATGTTCTGGACAAAAGACGG<br>GGCAGGGATCCCGAGATGGGGGGAAAGCCCCGGAGAAAAAATCCTCAGGAGGGG<br>TTGTACAATGAGCTGCAGAAGGACAAGATGGCTGAAGCCTATAGCGAGATCGGA<br>ATGAAAGGCGAAAGACGCAGAGGCAAGGGGCATGACGGTCTGTACCAGGGTCTC<br>TCTACAGCCACCAAGGACACTTATGATGCGTTGCATATGCAAGCCTTGCCACCC<br>CGC |
| 309 | 278 | GAGGTGCAACTGCTGGAAAGCGGCGGAGGACTCGTCCAGCCCGGCGGCAGCCTG<br>CGGCTGAGCTGTGCTGCTTCTGGATTTACCTTCGCCAGCGACGCCATGAGCTGG<br>TATAGACAGGCCCCTGGCAAAGAGCGGGAACTGGTGTCCGCCATCAGCGGCTCT<br>GGCGGCTCCACCTACTACGCCGATAGCGTGAAGGGCAGATTCACAATCTCTAGA<br>GATAATAGCAAGAACACCCTGTACCTGCAGATGAACAGCCTGAGAGCCGAGGAC<br>ACCGCCGTGTACTACTGCGCCGCTCACGACAGCGGCGAGGCCTACCTGGCCTTC<br>GACTACTGGGGCCAGGGCACACAGGTGACCGTGTCTAGCACCACAACACCTGCT<br>CCAAGGCCCCCCACACCCGCTCCAACTATAGCCAGCCAACCATTGAGCCTCAGA<br>CCTGAAGCTTGCAGGCCCGCAGCAGGAGGCGCCGTCCATACGCGAGGCCTGGAC<br>TTCGCGTGTGATATTTATATTTGGGCACCTTTGGCCGGAACATGTGGGGTGTTG<br>CTTCTCTCCCTTGTGATCACTCTGTATTGTAAGCGCGGGAGAAAGAAGCTCCTG<br>TACATCTTCAAGCAGCCTTTTATGCGACCTGTGCAAACCACTCAGGAAGAAGAT<br>GGGTGTTCATGCCGCTTCCCCGAGGAGGAAGAAGGAGGGTGTGAACTGAGGGTG<br>AAATTTTCTAGAAGCGCCGATGCTCCCGCATATCAGCAGGGTCAGAATCAGCTC<br>TACAATGAATTGAATCTCGGCAGGCGAGAAGAGTACGATGTTCTGGACAAAAGA<br>CGGGGCAGGGATCCCGAGATGGGGGGAAAGCCCCGGAGAAAAAATCCTCAGGAG<br>GGGTTGTACAATGAGCTGCAGAAGGACAAGATGGCTGAAGCCTATAGCGAGATC<br>GGAATGAAAGGCGAAAGACGCAGAGGCAAGGGGCATGACGGTCTGTACCAGGGT |

TABLE 13-continued

| SEQ ID NO. | AA SEQ ID NO. | NUCLEIC ACID SEQUENCE |
|---|---|---|
| | | CTCTCTACAGCCACCAAGGACACTTATGATGCGTTGCATATGCAAGCCTTGCCA CCCCGC |
| 310 | 279 | GAGGTGCAACTGCTGGAAAGCGGCGGAGGACTCGTCCAGCCCGGCGGCAGCCTG AGGCTGAGCTGTGCTGCTTCTGGCTTTACCTTCGACTCCTACACAATGAGCTGG TATAGACAGGCCCCTGGCAAGGAGCGGGAACTGGTGTCCGCCATCAGCGGCCAC GGCGACTCTACATACTACGCCGACAGCGTGAAAGGCAGATTCACAATCTCTAGA GATAATAGCAAGAACACCCTGTACCTGCAGATGAACAGCCTGCGGGCCGAGGAC ACCGCCGTGTACTACTGCACCAGAATCAGCATCACCACCGAGTGGCTGGCCGGA GATTACTGGGGCCAGGGCACCCAGGTGACAGTGTCCAGCACCACAACACCTGCT CCAAGGCCCCCCACACCCGCTCCAACTATAGCCAGCCAACCATTGAGCCTCAGA CCTGAAGCTTGCAGGCCCGCAGCAGGAGGCGCCGTCCATACGCGAGGCCTGGAC TTCGCGTGTGATATTTATATTTGGGCACCTTTGGCCGGAACATGTGGGGTGTTG CTTCTCTCCCTTGTGATCACTCTGTATTGTAAGCGCGGGAGAAAGAAGCTCCTG TACATCTTCAAGCAGCCTTTTATGCGACCTGTGCAAACCACTCAGGAAGAAGAT GGGTGTTCATGCCGCTTCCCCGAGGAGGAAGAAGGAGGGTGTGAACTGAGGGTG AAATTTTCTAGAAGCGCCGATGCTCCCGCATATCAGCAGGGTCAGAATCAGCTC TACAATGAATTGAATCTCGGCAGGCGAGAAGAGTACGATGTTCTGGACAAAAGA CGGGGCAGGGATCCCGAGATGGGGGGAAAGCCCCGGAGAAAAAATCCTCAGGAG GGGTTGTACAATGAGCTGCAGAAGGACAAGATGGCTGAAGCCTATAGCGAGATC GGAATGAAAGGCGAAAGACGCAGAGGCAAGGGGCATGACGGTCTGTACCAGGGT CTCTCTACAGCCACCAAGGACACTTATGATGCGTTGCATATGCAAGCCTTGCCA CCCCGC |
| 311 | 280 | GAGGTGCAGCTGCTGGAAAGCGGAGGAGGCCTGGTCCAACCTGGCGGCAGCCTG CGGCTGAGCTGCGCCGCTTCTGGCTTCACCTTCAGCAGCTACGCCATGAGCTGG TTCCGGCAGGCCCCTGGCAAGGAAAGAGAGTTCGTGTCTTTTATCAGCGGATCT GGCGACTCCACCTACTACGCTGATAGCGTGAAAGGCAGATTTACCATCTCTAGA GATAATAGCAAGAACACCCTGTACCTCCAGATGAACAGCCTGCGCGCCGAGGAC ACAGCCGTGTACTATTGTACCAGATGGCCTTACGACTTCGAGGAACCAAGCGAG CCCGGCGTGTACTGGGGCCAGGGCACACAGGTGACAGTGTCCTCCACCACAACA CCTGCTCCAAGGCCCCCCACACCCGCTCCAACTATAGCCAGCCAACCATTGAGC CTCAGACCTGAAGCTTGCAGGCCCGCAGCAGGAGGCGCCGTCCATACGCGAGGC CTGGACTTCGCGTGTGATATTTATATTTGGGCACCTTTGGCCGGAACATGTGGG GTGTTGCTTCTCTCCCTTGTGATCACTCTGTATTGTAAGCGCGGGAGAAAGAAG CTCCTGTACATCTTCAAGCAGCCTTTTATGCGACCTGTGCAAACCACTCAGGAA GAAGATGGGTGTTCATGCCGCTTCCCCGAGGAGGAAGAAGGAGGGTGTGAACTG AGGGTGAAATTTTCTAGAAGCGCCGATGCTCCCGCATATCAGCAGGGTCAGAAT CAGCTCTACAATGAATTGAATCTCGGCAGGCGAGAAGAGTACGATGTTCTGGAC AAAAGACGGGGCAGGGATCCCGAGATGGGGGGAAAGCCCCGGAGAAAAAATCCT CAGGAGGGGTTGTACAATGAGCTGCAGAAGGACAAGATGGCTGAAGCCTATAGC GAGATCGGAATGAAAGGCGAAAGACGCAGAGGCAAGGGGCATGACGGTCTGTAC CAGGGTCTCTCTACAGCCACCAAGGACACTTATGATGCGTTGCATATGCAAGCC TTGCCACCCCGC |
| 312 | 281 | GAGGTGCAGCTGCTGGAAAGCGGCGGAGGCCTGGTGCAACCTGGCGGATCTCTC AGACTGAGCTGTGCTGCTTCTGGCTTCACATTCACCGACTACGACATGAGCTGG TATAGACAGGCCCCTGGAAAAGAGCGGGAACTGGTCTCCGTGATCCACAGCGGC GGCTCCACCTACTACGCCGATAGCGTGAAGGGCAGATTCACCATCAGCAGAGAT AATAGCAAGAACACCCTGTACCTGCAGATGAACAGCCTGCGGGCCGAGGACACC GCCGTGTACTACTGCGCCCCCGGCTACTACAGCGACCTGTCTTTTGATTATTAC AACTTCGACTACTGGGGCCAGGGCACACAGGTGACAGTGTCCAGCACCACAACA CCTGCTCCAAGGCCCCCCACACCCGCTCCAACTATAGCCAGCCAACCATTGAGC CTCAGACCTGAAGCTTGCAGGCCCGCAGCAGGAGGCGCCGTCCATACGCGAGGC CTGGACTTCGCGTGTGATATTTATATTTGGGCACCTTTGGCCGGAACATGTGGG GTGTTGCTTCTCTCCCTTGTGATCACTCTGTATTGTAAGCGCGGGAGAAAGAAG CTCCTGTACATCTTCAAGCAGCCTTTTATGCGACCTGTGCAAACCACTCAGGAA GAAGATGGGTGTTCATGCCGCTTCCCCGAGGAGGAAGAAGGAGGGTGTGAACTG AGGGTGAAATTTTCTAGAAGCGCCGATGCTCCCGCATATCAGCAGGGTCAGAAT CAGCTCTACAATGAATTGAATCTCGGCAGGCGAGAAGAGTACGATGTTCTGGAC AAAAGACGGGGCAGGGATCCCGAGATGGGGGGAAAGCCCCGGAGAAAAAATCCT CAGGAGGGGTTGTACAATGAGCTGCAGAAGGACAAGATGGCTGAAGCCTATAGC GAGATCGGAATGAAAGGCGAAAGACGCAGAGGCAAGGGGCATGACGGTCTGTAC CAGGGTCTCTCTACAGCCACCAAGGACACTTATGATGCGTTGCATATGCAAGCC TTGCCACCCCGC |
| 313 | 282 | GAGGTGCAGCTGCTGGAGAGCGGTGGAGGGTTGGTGCAGCCCGGGGGTAGCCTG CGTCTGTCGTGCGCCGCTTCCGGCTTCACGTTCTCTGATTACGCCATGCACTGG TTCCGGCAGGCCCCCGGTAAGGAGCGCGTGCTGGTGTCGTCTATTGACTCCGGC GGCTCCACTTACTACGCAGACAGTGTCAAGGGCCGTTTCACCATCAGCCGCGAC AACAGCAAGAACACGCTGTACCTGCAGATGAACTCCCTTCGAGCAGAGGACACC GCGGTGTACTACTGTAATGCGGGCTTCAAGGGCGATCACCCCCACCCCAAGGAT GCCTTCGACATTTGGGGCCAGGGCACCCAGGTCACCGTGTCGTCCACCACAACA CCTGCTCCAAGGCCCCCCACACCCGCTCCAACTATAGCCAGCCAACCATTGAGC CTCAGACCTGAAGCTTGCAGGCCCGCAGCAGGAGGCGCCGTCCATACGCGAGGC CTGGACTTCGCGTGTGATATTTATATTTGGGCACCTTTGGCCGGAACATGTGGG |

TABLE 13-continued

| SEQ ID NO. | AA SEQ ID NO. | NUCLEIC ACID SEQUENCE |
|---|---|---|
| | | GTGTTGCTTCTCTCCCTTGTGATCACTCTGTATTGTAAGCGCGGGAGAAAGAAG<br>CTCCTGTACATCTTCAAGCAGCCTTTTATGCGACCTGTGCAAACCACTCAGGAA<br>GAAGATGGGTGTTCATGCCGCTTCCCCGAGGAGGAAGAAGGAGGGTGTGAACTG<br>AGGGTGAAATTTTCTAGAAGCGCCGATGCTCCCGCATATCAGCAGGGTCAGAAT<br>CAGCTCTACAATGAATTGAATCTCGGCAGGCGAGAAGAGTACGATGTTCTGGAC<br>AAAAGACGGGGCAGGGATCCCGAGATGGGGGGAAAGCCCCGGAGAAAAAATCCT<br>CAGGAGGGGTTGTACAATGAGCTGCAGAAGGACAAGATGGCTGAAGCCTATAGC<br>GAGATCGGAATGAAAGGCGAAAGACGCAGAGGCAAGGGGCATGACGGTCTGTAC<br>CAGGGTCTCTCTACAGCCACCAAGGACACTTATGATGCGTTGCATATGCAAGCC<br>TTGCCACCCCGC |
| 314 | 283 | GAGGTGCAACTGCTGGAATCCGGCGGAGGCCTGGTGCAGCCCGGCGGCAGCCTC<br>AGACTGAGCTGTGCCGCTTCTGGCTTTACCTTCAGCAGCGAGGGCATGAGCTGG<br>GTGCGGCAGGCCCCTGGCAAGGAAAGAGAGCTGGTCTCCGCCATCAGCGGATCT<br>GGCGACCACACCTACTATGCCGATAGCGTGCGCGGAAGATTCACAATCTCTAGA<br>GATAATAGCAAGAACACCCTGTACCTGCAGATGAACAGCCTGCGGGCCGAGGAC<br>ACCGCCGTGTACTACTGCAACGCCCTGGAAGGCGGCCCTACAACAGCTATCCAG<br>CCAGGAGGCCCTGACTACTGGGGCCAGGGCACCCAGGTGACCGTGTCCAGCACC<br>ACAACACCTGCTCCAAGGCCCCCCACACCCGCTCCAACTATAGCCAGCCAACCA<br>TTGAGCCTCAGACCTGAAGCTTGCAGGCCCGCAGCAGGAGGCGCCGTCCATACG<br>CGAGGCCTGGACTTCGCGTGTGATATTTATATTTGGGCACCTTTGGCCGGAACA<br>TGTGGGGTGTTGCTTCTCTCCCTTGTGATCACTCTGTATTGTAAGCGCGGGAGA<br>AAGAAGCTCCTGTACATCTTCAAGCAGCCTTTTATGCGACCTGTGCAAACCACT<br>CAGGAAGAAGATGGGTGTTCATGCCGCTTCCCCGAGGAGGAAGAAGGAGGGTGT<br>GAACTGAGGGTGAAATTTTCTAGAAGCGCCGATGCTCCCGCATATCAGCAGGGT<br>CAGAATCAGCTCTACAATGAATTGAATCTCGGCAGGCGAGAAGAGTACGATGTT<br>CTGGACAAAAGACGGGGCAGGGATCCCGAGATGGGGGGAAAGCCCCGGAGAAAA<br>AATCCTCAGGAGGGGTTGTACAATGAGCTGCAGAAGGACAAGATGGCTGAAGCC<br>TATAGCGAGATCGGAATGAAAGGCGAAAGACGCAGAGGCAAGGGGCATGACGGT<br>CTGTACCAGGGTCTCTCTACAGCCACCAAGGACACTTATGATGCGTTGCATATG<br>CAAGCCTTGCCACCCCGC |

In particular embodiments, polynucleotides encoding a chimeric antigen receptor may be codon-optimized. As used herein, the term "codon-optimized" refers to substituting codons in a polynucleotide encoding a polypeptide in order to modulate polypeptide expression, stability and/or activity. Factors that influence codon optimization include, but are not limited to one or more of: (i) variation of codon biases between two or more organisms or genes or synthetically constructed bias tables, (ii) variation in the degree of codon bias within an organism, gene, or set of genes, (iii) systematic variation of codons including context, (iv) variation of codons according to their decoding tRNAs, (v) variation of codons according to GC %, either overall or in one position of the triplet, (vi) variation in degree of similarity to a reference sequence for example a naturally occurring sequence, (vii) variation in the codon frequency cutoff, (viii) structural properties of mRNAs transcribed from the DNA sequence, (ix) prior knowledge about the function of the DNA sequences upon which design of the codon substitution set is to be based, (x) systematic variation of codon sets for each amino acid, and/or (xi) isolated removal of spurious translation initiation sites.

A "nucleic acid cassette," "expression cassette" or "nucleic acid expression cassette" refers to polynucleotide sequences sufficient to transcribe an RNA, which is ultimately translated to a polypeptide. In particular embodiments, a nucleic acid cassette comprises a polynucleotide-of-interest, a polynucleotide that encodes a polypeptide, e.g., a CAR. Nucleic acid expression cassettes contemplated in particular embodiments comprise one or more expression control sequences, e.g., a promoter, enhancer, poly(A) sequence, and one or more polynucleotide(s)-of-interest. In particular embodiments, a vector contemplated herein comprises one or more nucleic acid cassettes. In particular embodiments, a nucleic acid cassette is oriented in a vector to enable transcription of a polynucleotide-of-interest.

In particular embodiments, a polynucleotide encoding a polypeptide may be combined with other polynucleotide sequences, such as expression control sequences, promoters and/or enhancers, untranslated regions (UTRs), polynucleotides encoding signal peptides, Kozak sequences, polyadenylation signals, restriction enzyme sites, multiple cloning sites, internal ribosomal entry sites (IRES), recombinase recognition sites, termination codons, transcriptional termination signals, and polynucleotides encoding self-cleaving polypeptides or epitope tags, as disclosed elsewhere herein or as known in the art.

Polynucleotides can be prepared, manipulated, expressed and/or delivered using any of a variety of well-established techniques known and available in the art. In order to express a desired polypeptide, a nucleotide sequence encoding the polypeptide, can be inserted into an appropriate vector, e.g., a lentiviral vector.

In particular embodiments, a vector comprises a polynucleotide comprising or encoding one or more exogenous, endogenous, or heterologous expression control sequences operably linked to a polynucleotide encoding one or more polynucleotides and/or polypeptides contemplated herein.

"Expression control sequences," "control elements," or "regulatory sequences" contemplated in particular embodiments include but not limited to promoters, enhancers, translation initiation signals (Shine Dalgarno sequence or Kozak sequence), introns, polyadenylation signals, 5' and 3' untranslated regions, all of which may interact with host cell proteins to carry out transcription and translation.

The term "promoter" as used herein refers to a recognition site of a polynucleotide (DNA or RNA) to which an RNA polymerase binds. An RNA polymerase initiates and transcribes polynucleotides operably linked to the promoter. In particular embodiments, promoters operative in mammalian cells comprise an AT-rich region located approximately 25 to 30 bases upstream from the site where transcription is initiated and/or another sequence found 70 to 80 bases upstream from the start of transcription, a CNCAAT region where N may be any nucleotide. The term "enhancer" refers to a segment of DNA which contains sequences capable of providing enhanced transcription and in some instances can function independent of their orientation relative to another control sequence. An enhancer can function cooperatively or additively with promoters and/or other enhancer elements. The term "promoter/enhancer" refers to a segment of DNA which contains sequences capable of providing both promoter and enhancer functions.

The term "operably linked", refers to a juxtaposition wherein the components described are in a relationship permitting them to function in their intended manner. In one embodiment, the term refers to a functional linkage between an expression control sequence (such as a promoter, and/or enhancer) and a second polynucleotide sequence encoding a polypeptide, wherein the expression control sequence directs transcription of the nucleic acid corresponding to the second sequence.

Illustrative ubiquitous expression control sequences suitable for use in particular embodiments include, but are not limited to, a β-actin promoter, a cytomegalovirus (CMV) immediate early promoter, a simian virus 40 (SV40) (e.g., early or late) promoter, a Moloney murine leukemia virus (MoMLV) promoter, a Rous sarcoma virus (RSV) promoter, a herpes simplex virus (HSV) (thymidine kinase) promoter, an SV40/CD43 promoter, a spleen focus forming virus (SFFV) promoter, an elongation factor 1-alpha (EF1α) short promoter (intronless), an EF1α long promoter containing an intron, a Ubiquitin C (UBC) promoter, a phosphoglycerate kinase-1 (PGK) promoter, a cytomegalovirus enhancer/chicken β-actin (CAG) promoter, and a myeloproliferative sarcoma virus enhancer, negative control region deleted, dl587rev primer-binding site substituted (MND) U3 promoter (Haas et al., *Journal of Virology.* 2003; 77(17): 9439-9450).

Illustrative examples of ubiquitous expression control sequences suitable for use in particular embodiments contemplated herein include those comprising polynucleotide sequences set forth in Table 14.

TABLE 14

| SEQ ID NO: | NUCLEIC ACID SEQUENCE |
|---|---|
| 318 | GCGTTACATAACTTACGGTAAATGGCCCGCCTGGCTGACCGCCCAACGACCCCCGCCCATTGAC<br>GTCAATAATGACGTATGTTCCCATAGTAACGCCAATAGGGACTTTCCATTGACGTCAATGGGTG<br>GAGTATTTACGGTAAACTGCCCACTTGGCAGTACATCAAGTGTATCATATGCCAAGTACGCCCC<br>CTATTGACGTCAATGACGGTAAATGGCCCGCCTGGCATTATGCCCAGTACATGACCTTATGGGA<br>CTTTCCTACTTGGCAGTACATCTACGTATTAGTCATCGCTATTACCATGGTCGAGGTGAGCCCC<br>ACGTTCTGCTTCACTCTCCCCATCTCCCCCCCCTCCCCACCCCCAATTTTGTATTTATTTATTT<br>TTTAATTATTTTGTGCAGCGATGGGGGCGGGGGGGGGGGGGGGGCGCGCGCCAGGCGGGGCGGG<br>GCGGGGCGAGGGGCGGGGCGGGGCGAGGCGGAGAGGTGCGGCGGCAGCCAATCAGAGCGGCGCG<br>CTCCGAAAGTTTCCTTTTATGGCGAGGCGGCGGCGGCGGCGGCCCTATAAAAAGCGAAGCGCGC<br>GGCGGGCG |
| 319 | CGTGAGGCTCCGGTGCCCGTCAGTGGGCAGAGCGCACATCGCCCACAGTCCCCGAGAAGTTGGG<br>GGGAGGGGTCGGCAATTGAACCGGTGCCTAGAGAAGGTGGCGCGGGGTAAACTGGGAAAGTGAT<br>GTCGTGTACTGGCTCCGCCTTTTTCCCGAGGGTGGGGGAGAACCGTATATAAGTGCAGTAGTCG<br>CCGTGAACGTTCTTTTTCGCAACGGGTTTGCCGCCAGAACACAGGTAAGTGCCGTGTGTGGTTC<br>CCGCGGGCCTGGCCTCTTTACGGGTTATGGCCCTTGCGTGCCTTGAATTACTTCCACCTGGCTG<br>CAGTACGTGATTCTTGATCCCGAGCTTCGGGTTGGAAGTGGGTGGGAGAGTTCGAGGCCTTGCG<br>CTTAAGGAGCCCCTTCGCCTCGTGCTTGAGTTGAGGCCTGGCCTGGGCGCTGGGGCCGCCGCGT<br>GCGAATCTGGTGGCACCTTCGCGCCTGTCTCGCTGCTTTCGATAAGTCTCTAGCCATTTAAAAT<br>TTTTGATGACCTGCTGCGACGCTTTTTTTCTGGCAAGATAGTCTTGTAAATGCGGGCCAAGATC<br>TGCACACTGGTATTTCGGTTTTTGGGGCCGCGGGCGGCGACGGGGCCCGTGCGTCCCAGCGCAC<br>ATGTTCGGCGAGGCGGGGCCTGCGAGCGCGGCCACCGAGAATCGGACGGGGGTAGTCTCAAGCT<br>GGCCGGCCTGCTCTGGTGCCTGGCCTCGCGCCGCCGTGTATCGCCCCGCCCTGGGCGGCAAGGC<br>TGGCCCGGTCGGCACCAGTTGCGTGAGCGGAAAGATGGCCGCTTCCCGGCCCTGCTGCAGGGAG<br>CTCAAAATGGAGGACGCGGCGCTCGGGAGAGCGGGCGGGTGAGTCACCCACACAAAGGAAAAGG<br>GCCTTTCCGTCCTCAGCCGTCGCTTCATGTGACTCCACGGAGTACCGGGCGCCGTCCAGGCACC<br>TCGATTAGTTCTCGAGCTTTTGGAGTACGTCGTCTTTAGGTTGGGGGGAGGGGTTTTATGCGAT<br>GGAGTTTCCCCACACTGAGTGGGTGGAGACTGAAGTTAGGCCAGCTTGGCACTTGATGTAATTC<br>TCCTTGGAATTTGCCCTTTTTGAGTTTGGATCTTGGTTCATTCTCAAGCCTCAGACAGTGGTTC<br>AAAGTTTTTTTCTTCCATTTCAGGTGTCGTGA |
| 320 | AATGAAAGACCCCACCTGTAGGTTTGGCAAGCTAGGATCAAGGTTAGGAACAGAGAGACAGCAG<br>AATATGGGCCAAACAGGATATCTGTGGTAAGCAGTTCCTGCCCCGGCTCAGGGCCAAGAACAGT<br>TGGAACAGCAGAATATGGGCCAAACAGGATATCTGTGGTAAGCAGTTCCTGCCCCGGCTCAGGG<br>CCAAGAACAGATGGTCCCCAGATGCGGTCCCGCCCTCAGCAGTTTCTAGAGAACCATCAGATGT<br>TTCCAGGGTGCCCCAAGGACCTGAAATGACCCTGTGCCTTATTTGAACTAACCAATCAGTTCGC<br>TTCTCGCTTCTGTTCGCGCGCTTCTGCTCCCCGAGCTCAATAAAAGAGCCCACAACCCCTCACT<br>CGGC |
| 321 | GGGTAGGGGAGGCGCTTTTCCCAAGGCAGTCTGGAGCATGCGCTTTAGCAGCCCCGCTGGGCAC<br>TTGGCGCTACACAAGTGGCCTCTGGCCTCGCACACATTCCACATCCACCGGTAGGCGCCAACCG<br>GCTCCGTTCTTTGGTGGCCCCTTCGCGCCACCTTCTACTCCTCCCCTAGTCAGGAAGTTCCCCC<br>CCGCCCCGCAGCTCGCGTCGTGCAGGACGTGACAAATGGAAGTAGCACGTCTCACTAGTCTCGT<br>GCAGATGGACAGCACCGCTGAGCAATGGAAGCGGGTAGGCCTTTGGGGCAGCGGCCAATAGCAG<br>CTTTGCTCCTTCGCTTTCTGGGCTCAGAGGCTGGGAAGGGGTGGGTCCGGGGGCGGGCTCAGGG |

TABLE 14-continued

| SEQ ID NO: | NUCLEIC ACID SEQUENCE |
|---|---|
| | GCGGGCTCAGGGGCGGGGCGGGCGCCCGAAGGTCCTCCGGAGGCCCGGCATTCTGCACGCTTCA<br>AAAGCGCACGTCTGCCGCGCTGTTCTCCTCTTCCTCATCTCCGGGCCTTTCG |
| 322 | TGAAAGACCCCACCTGTAGGTTTGGCAAGATAGCTGCAGTAACGCCATTTTGCAAGGCATGGAA<br>AAATACCAAACCAAGAATAGAGAAGTTCAGATCAAGGGCGGGTACATGAAAATAGCTAACGTTG<br>GGCCAAACAGGATATCTGCGGTGAGCAGTTTCGGCCCCGGCCCGGGGCCAAGAACAGATGGTCA<br>CCGCAGTTTCGGCCCCGGCCCGAGGCCAAGAACAGATGGTCCCCAGATATGGCCCAACCCTCAG<br>CAGTTTCTTAAGACCCATCAGATGTTTCCAGGCTCCCCCAAGGACCTGAAATGACCCTGCGCCT<br>TATTTGAATTAACCAATCAGCCTGCTTCTCGCTTCTGTTCGCGCGCTTCTGCTTCCCGAGCTCT<br>ATAAAAGAGCTCACAACCCCTCACTCGGCGCGCCAGTCCTCCGATTGACTGAGTCGCCC |
| 323 | GGCCTCCGCGCCGGGTTTTGGCGCCTCCCGCGGGCGCCCCCCTCCTCACGGCGAGCGCTGCCAC<br>GTCAGACGAAGGGCGCAGCGAGCGTCCTGATCCTTCCGCCCGGACGCTCAGGACAGCGGCCCGC<br>TGCTCATAAGACTCGGCCTTAGAACCCCAGTATCAGCAGAAGGACATTTTAGGACGGGACTTGG<br>GTGACTCTAGGGCACTGGTTTTCTTTCCAGAGAGCGGAACAGGCGAGGAAAAGTAGTCCCTTCT<br>CGGCGATTCTGCGGAGGGATCTCCGTGGGGCGGTGAACGCCGATGATTATATAAGGACGCGCCG<br>GGTGTGGCACAGCTAGTTCCGTCGCAGCCGGGATTTGGGTCGCGGTTCTTGTTTGTGGATCGCT<br>GTGATCGTCACTTGGTGAGTAGCGGGCTGCTGGGCTGGCCGGGGCTTTCGTGGCCGCCGGGCCG<br>CTCGGTGGGACGGAAGCGTGTGGAGAGACCGCCAAGGGCTGTAGTCTGGGTCCGCGAGCAAGGT<br>TGCCCTGAACTGGGGGTTGGGGGGAGCGCAGCAAAATGGCGGCTGTTCCCGAGTCTTGAATGGA<br>AGACGCTTGTGAGGCGGGCTGTGAGGTCGTTGAAACAAGGTGGGGGGCATGGTGGGCGGCAAGA<br>ACCCAAGGTCTTGAGGCCTTCGCTAATGCGGGAAAGCTCTTATTCGGGTGAGATGGGCTGGGGC<br>ACCATCTGGGGACCCTGACGTGAAGTTTGTCACTGACTGGAGAACTCGGTTTGTCGTCTGTTGC<br>GGGGGCGGCAGTTATGGCGGTGCCGTTGGGCAGTGCACCCGTACCTTTGGGAGCGCGCGCCCTC<br>GTCGTGTCGTGACGTCACCCGTTCTGTTGGCTTATAATGCAGGGTGGGGCCACCTGCCGGTAGG<br>TGTGCGGTAGGCTTTTCTCCGTCGCAGGACGCAGGGTTCGGGCCTAGGGTAGGCTCTCCTGAAT<br>CGACAGGCGCCGGACCTCTGGTGAGGGGAGGGATAAGTGAGGCGTCAGTTTCTTTGGTCGGTTT<br>TATGTACCTATCTTCTTAAGTAGCTGAAGCTCCGGTTTTGAACTATGCGCTCGGGGTTGGCGAG<br>TGTGTTTTGTGAAGTTTTTTAGGCACCTTTTGAAATGTAATCATTTGGGTCAATATGTAATTTT<br>CAGTGTTAGACTAGTAAATTGTCCGCTAAATTCTGGCCGTTTTTGGCTTTTTTGTTAGAC |

In particular embodiments, a vector comprises a promoter comprising a polynucleotide sequence set forth in any one of SEQ ID NOs: 318, 319, 320, 321, 322, and 323 operably linked to a polynucleotide sequence encoding a CAR set forth in any one of SEQ ID NOs: 255, 256, 257, 258, 259, 260, 261, 262, 263, 264, 265, 266, 267, 268, 269, 270, 271, 272, 273, 274, 275, 276, 277, 278, 279, 280, 281, 282, and 283. In particular embodiments, a vector comprises a promoter comprising a polynucleotide sequence set forth in any one of SEQ ID NOs: 318, 319, 320, 321, 322, and 323 operably linked to a polynucleotide sequence encoding a signal peptide set forth in SEQ ID NO: 245 and a polynucleotide encoding a CAR set forth in any one of SEQ ID NOs: 259, 263, 266, 270, 273, and 277. In particular embodiments, a vector comprises a promoter comprising a polynucleotide sequence set forth in any one of SEQ ID NOs: 318, 319, 320, 321, 322, and 323 operably linked to a polynucleotide comprising a polynucleotide sequence set forth in any one of SEQ ID NOs: 295, 296, 297, 298, 299, 300, 301, 302, 303, 304, 305, 306, 307, 308, 309, 310, 311, 312, 313, and 314. In particular embodiments, a vector comprises a promoter comprising a polynucleotide sequence set forth in any one of SEQ ID NOs: 318, 319, 320, 321, 322, and 323 operably linked to a polynucleotide sequence set forth in SEQ ID NO: 294 and a polynucleotide sequence set forth in any one of SEQ ID NOs: 295, 296, 297, 298, 299, 300, 301, 302, 303, 304, 305, 306, 307, 308, 309, 310, 311, 312, 313, and 314.

In particular embodiments, a vector comprises a promoter comprising a polynucleotide sequence set forth in SEQ ID NO: 319 operably linked to a polynucleotide sequence encoding a CAR set forth in any one of SEQ ID NOs: 259, 263, 266, 270, 273 or 277. In particular embodiments, a vector comprises a promoter comprising a polynucleotide sequence set forth in SEQ ID NO: 319 operably linked to a polynucleotide comprising a polynucleotide sequence set forth in any one of SEQ ID NOs: 297, 299, 300, 302, 304, and 308. In particular embodiments, a vector comprises a promoter comprising a polynucleotide sequence set forth in SEQ ID NO: 319 operably linked to a polynucleotide sequence set forth in SEQ ID NO: 294 and a polynucleotide sequence set forth in any one of SEQ ID NOs: 297, 299, 300, 302, 304, and 308.

In particular embodiments, a vector comprises a promoter comprising a polynucleotide sequence set forth in SEQ ID NO: 320 operably linked to a polynucleotide sequence encoding a CAR set forth in any one of SEQ ID NOs: 259, 263, 266, 270, 273 or 277. In particular embodiments, a vector comprises a promoter comprising a polynucleotide sequence set forth in any one of SEQ ID NO: 320 operably linked to a polynucleotide comprising a polynucleotide sequence set forth in any one of SEQ ID NOs: 297, 299, 300, 302, 304, and 308. In particular embodiments, a vector comprises a promoter comprising a polynucleotide sequence set forth in SEQ ID NO: 320 operably linked to a polynucleotide sequence set forth in SEQ ID NO: 294 and a polynucleotide sequence set forth in any one of SEQ ID NOs: 297, 299, 300, 302, 304, and 308.

In particular embodiments, expression of polynucleotide sequences may be modulated by incorporating posttranscriptional regulatory elements into vectors. A variety of posttranscriptional regulatory elements may increase expression of a heterologous nucleic acid, e.g., woodchuck hepatitis virus posttranscriptional regulatory element (WPRE; Zufferey et al., 1999, *J. Virol.,* 73:2886); the posttranscriptional regulatory element present in hepatitis B vims (HPRE) (Huang et al., *Mol. Cell. Biol.,* 5:3864); and the like (Liu et al., 1995, *Genes Dev.,* 9:1766).

Illustrative examples of posttranscriptional control sequences suitable for use in particular embodiments contemplated herein include those comprising polynucleotide sequences set forth in Table 15.

encodes an MNDU3 promoter (e.g., SEQ ID NO: 320) operably linked to a polynucleotide sequence set forth in

TABLE 15

| SEQ ID NO: | NUCLEIC ACID SEQUENCE |
|---|---|
| 315 | AATCAACCTCTGGATTACAAAATTTGTGAAAGATTGACTGGTATTCTTAACTATGTTGCTC<br>CTTTTACGCTATGTGGATACGCTGCTTTAATGCCTTTGTATCATGCTATTGCTTCCCGTAT<br>GGCTTTCATTTTCTCCTCCTTGTATAAATCCTGGTTGCTGTCTCTTTATGAGGAGTTGTGG<br>CCCGTTGTCAGGCAACGTGGCGTGGTGTGCACTGTGTTTGCTGACGCAACCCCCACTGGTT<br>GGGGCATTGCCACCACCTGTCAGCTCCTTTCCGGGACTTTCGCTTTCCCCCTCCCTATTGC<br>CACGGCGGAACTCATCGCCGCCTGCCTTGCCCGCTGCTGGACAGGGGCTCGGCTGTTGGGC<br>ACTGACAATTCCGTGGTGTTGTCGGGGAAGCTGACGTCCTTTCCATGGCTGCTCGCCTGTG<br>TTGCCACCTGGATTCTGCGCGGGACGTCCTTCTGCTACGTCCCTTCGGCCCTCAATCCAGC<br>GGACCTTCCTTCCCGCGGCCTGCTGCCGGCTCTGCGGCCTCTTCCGCGTCTTCGCCTTCGC<br>CCTCAGACGAGTCGGATCTCCCTTTGGGCCGCCTCCCCGCCTG |
| 316 | AATCAACCTCTGGATTACAAAATTTGTGAAAGATTGACTGGTATTCTTAACTATGTTGCTC<br>CTTTTACGCTATGTGGATACGCTGCTTTAATGCCTTTGTATCATGCTATTGCTTCCCGTAT<br>GGCTTTCATTTTCTCCTCCTTGTATAAATCCTGGTTGCTGTCTCTTTATGAGGAGTTGTGG<br>CCCGTTGTCAGGCAACGTGGCGTGGTGTGCACTGTGTTTGCTGACGCAACCCCCACTGGTT<br>GGGGCATTGCCACCACCTGTCAGCTCCTTTCCGGGACTTTCGCTTTCCCCCTCCCTATTGC<br>CACGGCGGAACTCATCGCCGCCTGCCTTGCCCGCTGCTGGACAGGGGCTCGGCTGTTGGGC<br>ACTGACAATTCCGTGGTGTTGTCGGGGAAGGTCTGCTGAGACTCGGGGCTGCTCGCCTGTG<br>TTGCCACCTGGATTCTGCGCGGGACGTCCTTCTGCTACGTCCCTTCGGCCCTCAATCCAGC<br>GGACCTTCCTTCCCGCGGCCTGCTGCCGGCTCTGCGGCCTCTTCCGCGTCTTCGCCTTCGC<br>CCTCAGACGAGTCGGATCTCCCTTTGGGCCGCCTCCCCGCCTG |
| 317 | AATCAACCTCTGGATTACAAAATTTGTGAAAGATTGACTGATATTCTTAACTATGTTGCTC<br>CTTTTACGCTGTGTGGATATGCTGCTTTAATGCCTCTGTATCATGCTATTGCTTCCCGTAC<br>GGCTTTCGTTTTCTCCTCCTTGTATAAATCCTGGTTGCTGTCTCTTTATGAGGAGTTGTGG<br>CCCGTTGTCCGTCAACGTGGCGTGGTGTGCTCTGTGTTTGCTGACGCAACCCCCACTGGCT<br>GGGGCATTGCCACCACCTGTCAACTCCTTTCTGGGACTTTCGCTTTCCCCCTCCCGATCGC<br>CACGGCAGAACTCATCGCCGCCTGCCTTGCCCGCTGCTGGACAGGGGCTAGGTTGCTGGGC<br>ACTGATAATTCCGTGGTGTTGTC |

In particular embodiments, a vector comprises or encodes (in the case of an RNA vector, e.g., a retroviral vector) an MNDU3 promoter (e.g., SEQ ID NO: 320) operably linked to a polynucleotide encoding a chimeric antigen receptor comprising an amino acid set forth in any one of SEQ ID NOs: 259, 263, 266, 270, 273 or 277, and a polynucleotide comprising a posttranscriptional regulatory element set forth in any one of SEQ ID NOs: 315, 316, and 317. In particular embodiments, a vector comprises or encodes an MNDU3 promoter (e.g., SEQ ID NO: 320) operably linked to a polynucleotide sequence encoding a signal peptide set forth in SEQ ID NO: 245 and a polynucleotide encoding a chimeric antigen receptor comprising an amino acid set forth in any one of SEQ ID NOs: 259, 263, 266, 270, 273 or 277, and a polynucleotide comprising a posttranscriptional regulatory element set forth in any one of SEQ ID NOs: 315, 316, and 317. In particular embodiments, a vector comprises or encodes an MNDU3 promoter (e.g., SEQ ID NO: 320) operably linked to a polynucleotide sequence set forth in SEQ ID NO: 294, a polynucleotide encoding a chimeric antigen receptor comprising an amino acid set forth in any one of SEQ ID NOs: 259, 263, 266, 270, 273 or 277, and a polynucleotide comprising a posttranscriptional regulatory element set forth in any one of SEQ ID NOs: 315, 316, and 317.

In particular embodiments, a vector comprises or encodes an MNDU3 promoter (e.g., SEQ ID NO: 320) operably linked to a polynucleotide encoding a chimeric antigen receptor comprising a polynucleotide sequence set forth in any one of SEQ ID NOs: 297, 299, 300, 302, 304, and 308, and a polynucleotide comprising a posttranscriptional regulatory element set forth in any one of SEQ ID NOs: 315, 316, and 317. In particular embodiments, a vector comprises or SEQ ID NO: 294, a polynucleotide sequence set forth in any one of SEQ ID NOs: 297, 299, 300, 302, 304, and 308, and a polynucleotide comprising a posttranscriptional regulatory element set forth in any one of SEQ ID NOs: 315, 316, and 317.

In particular embodiments, a vector comprises or encodes (in the case of an RNA vector, e.g., a retroviral vector) an EF1α promoter (e.g., SEQ ID NO: 319) operably linked to a polynucleotide encoding a chimeric antigen receptor comprising an amino acid set forth in any one of SEQ ID NOs: 259, 263, 266, 270, 273 or 277, and a polynucleotide comprising a posttranscriptional regulatory element set forth in any one of SEQ ID NOs: 315, 316, and 317. In particular embodiments, a vector comprises or encodes an EF1α promoter (e.g., SEQ ID NO: 319) operably linked to a polynucleotide sequence encoding a signal peptide set forth in SEQ ID NO: 245 and a polynucleotide encoding a chimeric antigen receptor comprising an amino acid set forth in any one of SEQ ID NOs: 259, 263, 266, 270, 273 or 277, and a polynucleotide comprising a posttranscriptional regulatory element set forth in any one of SEQ ID NOs: 315, 316, and 317. In particular embodiments, a vector comprises or encodes an EF1α promoter (e.g., SEQ ID NO: 319) operably linked to a polynucleotide sequence set forth in SEQ ID NO: 294, a polynucleotide encoding a chimeric antigen receptor comprising an amino acid set forth in any one of SEQ ID NOs: 259, 263, 266, 270, 273 or 277, and a polynucleotide comprising a posttranscriptional regulatory element set forth in any one of SEQ ID NOs: 315, 316, and 317.

In particular embodiments, a vector comprises or encodes an EF1α promoter (e.g., SEQ ID NO: 319) operably linked to a polynucleotide encoding a chimeric antigen receptor comprising a polynucleotide sequence set forth in any one of SEQ ID NOs: 297, 299, 300, 302, 304, and 308, and a polynucleotide comprising a posttranscriptional regulatory element set forth in any one of SEQ ID NOs: 315, 316, and 317. In particular embodiments, a vector comprises or encodes an EF1α promoter (e.g., SEQ ID NO: 319) operably linked to a polynucleotide sequence set forth in SEQ ID NO: 294, a polynucleotide sequence set forth in any one of SEQ ID NOs: 297, 299, 300, 302, 304, and 308, and a polynucleotide comprising a posttranscriptional regulatory element set forth in any one of SEQ ID NOs: 315, 316, and 317.

Efficient expression of polynucleotides can also be increased in some embodiments, by using sequences that increase translational efficiency, e.g., through an increase in mRNA ribosomal binding or an increase in mRNA stability. In certain embodiments, polynucleotides encoding a chimeric antigen receptor comprise a short recognition sequence, i.e., a Kozak sequence, that greatly facilitates the initial binding of mRNA to the small subunit of the ribosome and increases translation. The consensus Kozak sequence is (GCC)RCCATGG, where R is a purine (A or G) (Kozak, Cell. 44:283-92(1986), and Kozak, Nucleic Acids Res. 15:8125-48 (1987)).

Elements directing the efficient termination and polyadenylation of heterologous nucleic acid transcripts may also increase heterologous gene expression. Transcription termination signals are generally found downstream of the polyadenylation signal. In particular embodiments, vectors comprise a polyadenylation sequence 3' to a sequence to be transcribed and/or expressed. The term "polyadenylation (or poly(A)) signal" refers to a DNA sequence which directs both the termination and polyadenylation of the nascent RNA transcript by RNA polymerase II. Polyadenylation signals can promote mRNA stability by addition of a poly (A) tail to the 3' end of the coding sequence and thus, contribute to increased translational efficiency. Cleavage and polyadenylation are directed by a poly(A) signal in the RNA. The core poly(A) signal for mammalian pre-mRNAs has two recognition elements flanking a cleavage-polyadenylation site. Typically, an almost invariant AAUAAA hexamer lies 20-50 nucleotides upstream of a more variable element rich in U or GU residues. Cleavage of the nascent transcript occurs between these two elements and is coupled to the addition of up to 250 adenosines to the 5' cleavage product. In particular embodiments, the core poly(A) signal is an ideal poly(A) signal (e.g., AATAAA, ATTAAA, AGTAAA). In particular embodiments, the poly(A) signal is an SV40 poly(A) signal, a bovine growth hormone poly(A) signal (BGHpA), a rabbit β-globin poly(A) signal (rBgpA), variants thereof, or another suitable heterologous or endogenous poly(A) signal known in the art. In particular embodiments, the poly(A) signal is synthetic.

In particular embodiments, a polynucleotide comprises or encodes a promoter operably a polynucleotide sequence encoding a chimeric antigen receptor comprising a signal peptide isolated from a polypeptide selected from the group consisting of CD8α, murine IgGκ, human IgGk, CD33, tPA, SEAP, hGM-CSF, gaussian luciferase, CSF2R, B2M, and CD80, wherein the signal peptide is subsequently cleaved from the translated chimeric antigen receptor. In particular embodiments, a polynucleotide comprises or encodes a promoter operably linked to a polynucleotide sequence encoding a chimeric antigen receptor comprising a signal peptide comprising an amino acid sequence set forth in any one of SEQ ID NOs: 245, 246, 247, 248, 249, 250, 251, 252, 253, and 254. An illustrative example of a polynucleotide encoding a signal peptide is set forth in SEQ ID NO: 294 (5' ATGGCTCTTCCCGTAACAGCCCTTTTGTTGCCCCTT GCACTCCTTCTGCATGCA GCACGACCG 3').

H. Vectors

Recombinant lentiviral particles contemplated in particular embodiments comprise (i) a viral envelope comprising (a) a mutated vesiculovirus envelope glycoprotein, e.g., VSIV-G, COCV-G, that does not bind its cognate receptor, e.g., LDLR, and (b) a non-viral membrane-bound tropism polypeptide that redirects the particle to immune effector cells; and (ii) a lentiviral vector comprising a polynucleotide encoding a promoter operably linked to a polynucleotide encoding an anti-BCMA chimeric antigen receptor comprising an amino acid sequence set forth in any one of SEQ ID NOs: 255, 256, 257, 258, 259, 260, 261, 262, 263, 264, 265, 266, 267, 268, 269, 270, 271, 272, 273, 274, 275, 276, 277, 278, 279, 280, 281, 282, and 283.

In various embodiments, a lentiviral vector (lentivector) is engineered or derived from a lentivirus genome selected from the group consisting of HIV-1, HIV-2, VMV, CAEV, EIAV, FIV, BIV, and SIV. In particular embodiments, lentiviral vectors are derived from HIV viral genomes, preferably HIV-1 or HIV-2 viral genomes and more preferably, HIV-1 viral genomes (i.e., HIV-1 cis-acting sequence elements are preferred).

In various embodiments, a recombinant lentiviral particle comprises (i) a viral envelope comprising (a) a mutated vesiculovirus envelope glycoprotein, e.g., VSIV-G, COCV-G, that does not bind its cognate receptor, e.g., LDLR, and (b) a non-viral membrane-bound tropism polypeptide that redirects the particle to immune effector cells that express CD3; and (ii) two copies of a lentiviral vector-based RNA genome comprising a 5' long terminal repeat (LTR) comprising R and U5 regions; a Psi (Ψ) packaging signal; a cPPT/FLAP, an export element; a polynucleotide comprising or encoding a promoter operably linked to a polynucleotide encoding an anti-BCMA CAR; optionally a WPRE or HPRE; a 3' LTR comprising U3 and R regions; a polyadenylation signal and a poly(A) tail.

In various embodiments, a recombinant lentiviral particle comprises (i) a viral envelope comprising (a) a mutated vesiculovirus envelope glycoprotein, e.g., VSIV-G, COCV-G, that does not bind its cognate receptor, e.g., LDLR, and (b) a non-viral membrane-bound tropism polypeptide that redirects the particle to immune effector cells that express CD3; and (ii) two copies of a lentiviral vector-based RNA genome comprising a 5' long terminal repeat (LTR) comprising R and U5 regions; a Psi (Ψ) packaging signal; a cPPT/FLAP, an export element; a polynucleotide comprising or encoding a promoter operably linked to a polynucleotide encoding an anti-BCMA CAR comprising an amino acid sequence set forth in any one of SEQ ID NOs: 259, 263, 266, 270, 273, and 277; optionally a WPRE or HPRE; a 3' LTR comprising U3 and R regions; a polyadenylation signal and a poly(A) tail.

The term "long terminal repeat (LTR)," as used herein, refers to elements located at the ends of lentiviral polynucleotides which, in their natural sequence context, are direct repeats and contain U3, R and U5 regions. LTRs generally provide functions fundamental to the expression of lentiviral genes (e.g., promotion, initiation and polyadenylation of gene transcripts) and to lentiviral replication. The LTR contains numerous regulatory signals including transcriptional control elements, polyadenylation signals and sequences needed for replication and integration of the lentiviral genome. The lentiviral LTR is divided into three regions called U3, R and U5. The U3 region contains the enhancer and promoter elements. The U5 region is the sequence between the primer binding site and the R region and contains the polyadenylation signal. The R (repeat) region is flanked by the U3 and U5 regions. A transfer plasmid, which is used to package a lentiviral vector genome comprises a 5' LTR comprising U3, R and/or U5 regions and a 3' LTR comprising U3, R and/or U5 regions. Adjacent to the 5' LTR are sequences necessary for reverse transcription of the genome (the tRNA primer binding site) and for efficient packaging of lentiviral RNA into particles (the Psi "Y" site). A lentiviral vector-based genome packaged in a particle comprises a 5' LTR comprising R and U5 regions and a 3' LTR comprising U3 and R regions. The lentiviral vector-based genome is reverse transcribed and integrated into the host cell genome as a provector. Through reverse transcription and second strand synthesis of the lentiviral vector genome, provectors comprise two copies of the 3' LTR, one copy that replaces the 5' LTR and the 3' LTR.

A "TAR" element as used herein, refers to the "trans-activation response" genetic element located in the R region of lentiviral vector LTRs. This element interacts with the lentiviral trans-activator (tat) genetic element to enhance lentiviral vector genome replication. In third generation lentiviral vectors, this element is not usually present because lentiviral vector transfer plasmids comprise a 5' LTR U3 region replaced by a heterologous promoter.

An "R region," as used herein, refers to the region within LTRs beginning at the start of the capping group (i.e., the start of transcription) and ending immediately prior to the start of the polyA signal. The R region is also defined as being flanked by the U3 and U5 regions. The R region plays a role during reverse transcription in permitting the transfer of nascent DNA from one end of the genome to the other.

As used herein, a "packaging signal" or "packaging sequence" refers to sequences located within the lentiviral genome which are required for insertion of the lentiviral RNA into the lentiviral capsid or particle, see e.g., Clever et al., 1995. *J. of Virology*, Vol. 69, No. 4; pp. 2101-2109. Several lentiviral vectors use the minimal packaging signal (also referred to as the psi [Ψ] or [Ψ+] sequence) needed for encapsidation of the lentiviral genome. Thus, as used herein, the terms "packaging sequence," "packaging signal," "psi" and the symbol "Ψ," are used in reference to the non-coding sequence required for encapsidation of lentiviral RNA strands during lentiviral particle formation.

A "FLAP element" or "cPPT/FLAP," as used herein refers to a nucleic acid whose sequence includes the central polypurine tract and central termination sequences (cPPT and CTS) of a lentivirus, e.g., HIV-1 or HIV-2. "FLAP element" and "cPPT/FLAP" may used interchangeably to refer to the foregoing FLAP element. Suitable FLAP elements are described in U.S. Pat. No. 6,682,907 and in Zennou, et al., 2000, *Cell,* 101:173. During HIV-1 reverse transcription, central initiation of the plus-strand DNA at the central polypurine tract (cPPT) and central termination at the central termination sequence (CTS) lead to the formation of a three-stranded DNA structure: the HIV-1 central DNA flap. While not wishing to be bound by any particular theory, the DNA flap may act as a cis-active determinant of lentiviral vector nuclear import and/or may increase lentiviral titer.

As used herein, an "export element" refers to a cis-acting post-transcriptional regulatory element which regulates the transport of an RNA transcript from the nucleus to the cytoplasm of a cell. Examples of RNA export elements include, but are not limited to, the human immunodeficiency virus (HIV) rev response element (RRE) (see e.g., Cullen et al., 1991. *J. Virol.* 65:1053; and Cullen et al., 1991. *Cell* 58:423), the woodchuck hepatitis virus posttranscriptional regulatory element (WPRE), and the hepatitis B virus post-transcriptional regulatory element (HPRE).

Lentiviral vectors may contain one or more safety enhancements to reduce the risk of replication, insertional mutagenesis, and off-target transduction and/or expression. In particular embodiments, a lentiviral vector comprises one or more or the following safety enhancements: one or more modifications of the 5' and 3' LTRs, cell or tissue specific expression control sequences, e.g., promoters, enhancers. A "modified LTR," as used herein, refers to one or more nucleotide additions, deletions or substitutions in the native HIV-1 5' LTR and/or 3' LTR. The skilled artisan would be able to determine whether an LTR is modified by comparison to a reference LTR.

"Self-inactivating" (SIN) vectors, as used herein, refer to replication-defective vectors, e.g., lentiviral vectors, in which the right (3') LTR enhancer-promoter region, known as the U3 region, has been modified (e.g., by deletion or substitution) to prevent viral transcription beyond the first round of lentiviral replication. Self-inactivation is achieved through a deletion in the U3 region of the 3' LTR of the lentiviral vector transfer plasmid that removes the LTR TATA box (e.g., deletions from −418 to −18), without significant reductions in titers.

An additional safety enhancement is provided by replacing the U3 region of the 5" LTR of the lentiviral vector transfer plasmid with a heterologous promoter to drive transcription of the lentiviral genome during production of recombinant lentiviral particles. Examples of heterologous promoters which can be used include, for example, viral simian virus 40 (SV40) (e.g., early or late), cytomegalovirus (CMV) (e.g., immediate early), Moloney murine leukemia virus (MoMLV), Rous sarcoma virus (RSV), and herpes simplex virus (HSV) (thymidine kinase) promoters.

In particular embodiments, a lentiviral vector is engineered to integrate into an immune effector cell genome.

In certain embodiments, a lentiviral vector is engineered to be integration defective, episomal, and not integrate in the cell genome. As used herein, the term "integration defective lentivirus" or "IDLV" refers to a lentivirus having an integrase that lacks the capacity to integrate the viral vector into the host cell genome. Integration-incompetent lentiviral vectors have been described in patent application WO 2006/010834, which is herein incorporated by reference in its entirety. Illustrative mutations in HIV-1 integrase suitable to reduce integrase activity include, but are not limited to: H12N, H12C, H16C, H16V, S81R, D41A, K42A, H51A, Q53C, D55V, D64E, D64V, E69A, K71A, E85A, E87A, D116N, D116I, D116A, N120G, N120I, N120E, E152G, E152A, K156E, K156A, E157A, K159E, K159A, K160A, R166A, D167A, E170A, H171A, K173A, K186Q, K186T, K188T, E198A, R199C, R199T, R199A, D202A, K211A, Q214L, Q216L, Q221L, W235F, W235E, K236S, K236A, K246A, G247W, D253A, R262A, R263A and K264H. In particular embodiments, an HIV-1 integration deficient integrase comprises a D64V, D1611, D116A, E152G, or E152A mutation; D64V, D116A, and E152G mutations; D64V, D116A, and E152A mutations; or a D64V mutation.

In particular embodiments, a recombinant lentiviral particle comprises (i) a viral envelope comprising (a) a mutated VSIV-G or COCV-G polypeptide comprising amino acid substitutions at positions 47 and 354 of the mature polypeptide and (b) a non-viral membrane-bound tropism polypeptide comprising an anti-CD3 scFv and a CD8α hinge and transmembrane domain; and (ii) two copies of an HIV-1 lentiviral vector-based RNA genome comprising a 5' LTR comprising R and U5 regions; a Psi (Ψ) packaging signal; a cPPT/FLAP, an RRE export element; a polynucleotide comprising or encoding an MNDU3 or EF1α promoter operably linked to a polynucleotide encoding a signal peptide, an anti-BCMA CAR, optionally a WPRE or HPRE; a 3' LTR comprising U3 and R regions; a polyadenylation signal and a poly(A) tail.

In particular embodiments, a recombinant lentiviral particle comprises (i) a viral envelope comprising (a) a fusogen comprising an amino acid sequence set forth in any one of SEQ ID NOs: 332, 333, 334, and 335 and (b) a non-viral membrane-bound tropism polypeptide comprising an amino acid sequence set forth in any one of SEQ ID NOs: 324, 325, 326, 327, 328, 329, 330, and 331; and (ii) two copies of an HIV-1 lentiviral vector-based RNA genome comprising a 5' LTR comprising R and U5 regions; a Psi (') packaging signal; a cPPT/FLAP, an RRE export element; a promoter comprising or encoding a polynucleotide sequence set forth in SEQ ID NO: 320 operably linked to a polynucleotide encoding a signal peptide comprising an amino acid sequence set forth in SEQ ID NO: 245 and an anti-BCMA CAR comprising an amino acid sequence set forth in any one of SEQ ID NOs: 259, 263, 266, 270, 273, and 277, and optionally, a polynucleotide comprising a posttranscriptional regulatory element set forth in any one of SEQ ID NOs: 315, 316, and 317; a 3' LTR comprising U3 and R regions; a polyadenylation signal and a poly(A) tail.

In particular embodiments, a recombinant lentiviral particle comprises (i) a viral envelope comprising (a) a fusogen comprising an amino acid sequence set forth in any one of SEQ ID NOs: 332, 333, 334, and 335 and (b) a non-viral membrane-bound tropism polypeptide comprising an amino acid sequence set forth in any one of SEQ ID NOs: 324, 325, 326, 327, 328, 329, 330, and 331; and (ii) two copies of an HIV-1 lentiviral vector-based RNA genome comprising a 5' LTR comprising R and U5 regions; a Psi (Ψ) packaging signal; a cPPT/FLAP, an RRE export element; a promoter comprising or encoding a polynucleotide sequence set forth in SEQ ID NO: 320 operably linked to a polynucleotide encoding a signal peptide comprising an amino acid sequence set forth in SEQ ID NO: 245 and an anti-BCMA CAR comprising an amino acid sequence set forth in any one of SEQ ID NOs: 259, 263, 266, and 270, and optionally, a polynucleotide comprising a posttranscriptional regulatory element set forth in any one of SEQ ID NOs: 315, 316, and 317; a 3' LTR comprising U3 and R regions; a polyadenylation signal and a poly(A) tail.

In particular embodiments, a recombinant lentiviral particle comprises (i) a viral envelope comprising (a) a fusogen comprising an amino acid sequence set forth in any one of SEQ ID NOs: 332, 333, 334, and 335 and (b) a non-viral membrane-bound tropism polypeptide comprising an amino acid sequence set forth in any one of SEQ ID NOs: 324, 325, 326, 327, 328, 329, 330, and 331; and (ii) two copies of an HIV-1 lentiviral vector-based RNA genome comprising a 5' LTR comprising R and U5 regions; a Psi (Ψ) packaging signal; a cPPT/FLAP, an RRE export element; a promoter comprising or encoding a polynucleotide sequence set forth in SEQ ID NO: 320 operably linked to a polynucleotide encoding a signal peptide encoded by a polynucleotide sequence set forth in SEQ ID NO: 294 and an anti-BCMA CAR encoded by a polynucleotide sequence set forth in any one of SEQ ID NOs: 297, 299, 300, 302, 304, and 308, and optionally, a polynucleotide comprising a posttranscriptional regulatory element set forth in any one of SEQ ID NOs: 315, 316, and 317; a 3' LTR comprising U3 and R regions; a polyadenylation signal and a poly(A) tail.

In particular embodiments, a recombinant lentiviral particle comprises (i) a viral envelope comprising (a) a fusogen comprising an amino acid sequence set forth in any one of SEQ ID NOs: 332, 333, 334, and 335 and (b) a non-viral membrane-bound tropism polypeptide comprising an amino acid sequence set forth in any one of SEQ ID NOs: 324, 325, 326, 327, 328, 329, 330, and 331; and (ii) two copies of an HIV-1 lentiviral vector-based RNA genome comprising a 5' LTR comprising R and U5 regions; a Psi (Ψ) packaging signal; a cPPT/FLAP, an RRE export element; a promoter comprising or encoding a polynucleotide sequence set forth in SEQ ID NO: 319 operably linked to a polynucleotide encoding a signal peptide comprising an amino acid sequence set forth in SEQ ID NO: 245 and an anti-BCMA CAR comprising an amino acid sequence set forth in any one of SEQ ID NOs: 259, 263, 266, 270, 273, and 277, and optionally, a polynucleotide comprising a posttranscriptional regulatory element set forth in any one of SEQ ID NOs: 315, 316, and 317; a 3' LTR comprising U3 and R regions; a polyadenylation signal and a poly(A) tail.

In particular embodiments, a recombinant lentiviral particle comprises (i) a viral envelope comprising (a) a fusogen comprising an amino acid sequence set forth in any one of SEQ ID NOs: 332, 333, 334, and 335 and (b) a non-viral membrane-bound tropism polypeptide comprising an amino acid sequence set forth in any one of SEQ ID NOs: 324, 325, 326, 327, 328, 329, 330, and 331; and (ii) two copies of an HIV-1 lentiviral vector-based RNA genome comprising a 5' LTR comprising R and U5 regions; a Psi (Ψ) packaging signal; a cPPT/FLAP, an RRE export element; a promoter comprising or encoding a polynucleotide sequence set forth in SEQ ID NO: 319 operably linked to a polynucleotide encoding a signal peptide comprising an amino acid sequence set forth in SEQ ID NO: 245 and an anti-BCMA CAR comprising an amino acid sequence set forth in any one of SEQ ID NOs: 259, 263, 266, and 270, and optionally, a polynucleotide comprising a posttranscriptional regulatory element set forth in any one of SEQ ID NOs: 315, 316, and 317; a 3' LTR comprising U3 and R regions; a polyadenylation signal and a poly(A) tail.

In particular embodiments, a recombinant lentiviral particle comprises (i) a viral envelope comprising (a) a fusogen comprising an amino acid sequence set forth in any one of SEQ ID NOs: 332, 333, 334, and 335 and (b) a non-viral membrane-bound tropism polypeptide comprising an amino acid sequence set forth in any one of SEQ ID NOs: 324, 325, 326, 327, 328, 329, 330, and 331; and (ii) two copies of an HIV-1 lentiviral vector-based RNA genome comprising a 5' LTR comprising R and U5 regions; a Psi (Ψ) packaging signal; a cPPT/FLAP, an RRE export element; a promoter comprising or encoding a polynucleotide sequence set forth in SEQ ID NO: 319 operably linked to a polynucleotide encoding a signal peptide encoded by a polynucleotide sequence set forth in SEQ ID NO: 294 and an anti-BCMA CAR encoded by a polynucleotide sequence set forth in any one of SEQ ID NOS: 297, 299, 300, 302, 304, and 308, and optionally, a polynucleotide comprising a posttranscriptional regulatory element set forth in any one of SEQ ID NOs: 315, 316, and 317; a 3' LTR comprising U3 and R regions; a polyadenylation signal and a poly(A) tail.

In particular embodiments, a recombinant lentiviral particle comprises (i) a viral envelope comprising (a) a fusogen comprising an amino acid sequence set forth in any one of SEQ ID NOs: 336, 337, 338, and 339 and (b) a non-viral membrane-bound tropism polypeptide comprising an amino acid sequence set forth in any one of SEQ ID NOs: 324, 325, 326, 327, 328, 329, 330, and 331; and (ii) two copies of an HIV-1 lentiviral vector-based RNA genome comprising a 5' LTR comprising R and U5 regions; a Psi (Ψ) packaging signal; a cPPT/FLAP, an RRE export element; a promoter comprising or encoding a polynucleotide sequence set forth in SEQ ID NO: 320 operably linked to a polynucleotide encoding a signal peptide encoded by a polynucleotide sequence set forth in SEQ ID NO: 294 and an anti-BCMA CAR encoded by a polynucleotide sequence set forth in any one of SEQ ID NOs: 297, 299, 300, 302, 304, and 308, and a polynucleotide comprising a posttranscriptional regulatory element set forth in any one of SEQ ID NOs: 315, 316, and 317; a 3' LTR comprising U3 and R regions; a polyadenylation signal and a poly(A) tail.

In particular embodiments, a recombinant lentiviral particle comprises (i) a viral envelope comprising (a) a fusogen comprising an amino acid sequence set forth in any one of SEQ ID NOs: 336, 337, 338, and 339 and (b) a non-viral membrane-bound tropism polypeptide comprising an amino acid sequence set forth in any one of SEQ ID NOs: 324, 325, 326, 327, 328, 329, 330, and 331; and (ii) two copies of an HIV-1 lentiviral vector-based RNA genome comprising a 5' LTR comprising R and U5 regions; a Psi (Ψ) packaging signal; a cPPT/FLAP, an RRE export element; a promoter comprising or encoding a polynucleotide sequence set forth in SEQ ID NO: 319 operably linked to a polynucleotide encoding a signal peptide encoded by a polynucleotide sequence set forth in SEQ ID NO: 294 and an anti-BCMA CAR encoded by a polynucleotide sequence set forth in any one of SEQ ID NOs: 297, 299, 300, 302, 304, and 308, and, a polynucleotide comprising a posttranscriptional regulatory element set forth in any one of SEQ ID NOs: 315, 316, and 317; a 3' LTR comprising U3 and R regions; a polyadenylation signal and a poly(A) tail.

I. Cells

Recombinant particles contemplated herein are engineered to bind and transduce an immune effector cell. In particular embodiments, a recombinant lentiviral particle engineered to bind and transduce and immune effector cell comprises a viral envelope comprising a mutated COCV-G polypeptide or a mutated VSIV-G polypeptide, wherein the mutated COCV-G or VSIV-G polypeptide comprises amino acid substitutions at positions 47 and 354; a non-viral membrane-bound tropism polypeptide comprising an anti-CD3ε scFv and a human CD8α hinge and transmembrane domain; and a recombinant lentiviral vector comprising a polynucleotide encoding a myeloproliferative sarcoma virus enhancer, negative control region deleted, dl587rev primer-binding site substituted (MND) U3 promoter or an EF1α promoter operably linked to a polynucleotide encoding an anti-BCMA chimeric antigen receptor comprising an anti-BCMA scFv or anti-BCMA VHH, a CD8α hinge and transmembrane domain, a CD137 costimulatory domain, a CD3ζ primary signaling domain.

An "immune effector cell" is any cell of the immune system that has one or more effector functions (e.g., cytotoxic cell killing activity, secretion of cytokines, induction of ADCC and/or CDC). Illustrative types of immune effector cells contemplated in particular embodiments include, without limitation, T lymphocytes, dendritic cells (DC), Treg cells, natural killer (NK) cells, natural killer T (NKT) cells, and macrophages. The terms "T cell" or "T lymphocyte" are art-recognized and are intended, in particular embodiments, to include thymocytes, immature T lymphocytes, mature T lymphocytes, resting T lymphocytes, and/or activated T lymphocytes. Illustrative examples of T lymphocytes suitable for use in particular embodiments, include but not limited to cytotoxic T cells (CTLs; $CD8^+$ T cells), TILs, helper T cells (HTLs; $CD4^+$ T cells), $CD4^+CD8^+$ T cells, $CD4^-$ $CD8^-$ T cells, or any other subset of T cells that has an effector function. In a particular embodiment, the cells comprise αβ T cells. In a particular embodiment, the cells comprise γδ T cells.

J. Compositions and Formulations

Compositions contemplated herein comprise a recombinant particle and/or an immune effector cell modified ex vivo formulated with a pharmaceutically acceptable or physiologically-acceptable carrier for administration to a cell, tissue, organ, or an animal, either alone, or in combination with one or more other modalities of therapy.

In particular embodiments, a composition comprises a recombinant lentiviral particle comprising a viral envelope comprising a mutated VSIV-G or COCV-G polypeptide comprising amino acid substitutions at positions 47 and 354 of the mature polypeptide and a non-viral membrane-bound tropism polypeptide comprising an anti-CD3 scFv and a CD8α hinge and transmembrane domain; and one or more copies of a lentiviral vector comprising a polynucleotide comprising or encoding an MNDU3 or EF1α promoter operably linked to a polynucleotide encoding an anti-BCMA CAR, and optionally a WPRE.

In particular embodiments, a composition comprises a recombinant lentiviral particle comprising a viral envelope comprising a mutated VSIV-G or COCV-G polypeptide comprising amino acid substitutions at positions 47 and 354 of the mature polypeptide and a non-viral membrane-bound tropism polypeptide comprising an anti-CD3 scFv and a CD8α hinge and transmembrane domain; and one or more copies of a recombinant lentiviral vector comprising a polynucleotide comprising or encoding an MNDU3 or EF1α promoter operably linked to a polynucleotide encoding a signal peptide, an anti-BCMA chimeric antigen receptor comprising an anti-BCMA scFv or anti-BCMA VHH, a CD8α hinge and transmembrane domain, a CD137 costimulatory domain, a CD3ζ primary signaling domain, and optionally a WPRE.

In particular embodiments, a composition comprises a recombinant lentiviral particle comprising a viral envelope comprising a fusogen comprising an amino acid sequence set forth in any one of SEQ ID NOs: 332, 333, 334, and 335 and a non-viral membrane-bound tropism polypeptide comprising an amino acid sequence set forth in any one of SEQ ID NOs: 324, 325, 326, 327, 328, 329, 330, and 331; and two copies of a lentiviral vector comprising a promoter comprising or encoding a polynucleotide sequence set forth in SEQ ID NO: 320 operably linked to a polynucleotide encoding a signal peptide comprising an amino acid sequence set forth in SEQ ID NO: 245 and an anti-BCMA CAR comprising an amino acid sequence set forth in any one of SEQ ID NOs: 259, 263, 266, 270, 273, and 277, and optionally, a polynucleotide comprising a posttranscriptional regulatory element set forth in any one of SEQ ID NOs: 315, 316, and 317.

In particular embodiments, a composition comprises a recombinant lentiviral particle comprising a viral envelope comprising a fusogen comprising an amino acid sequence set forth in any one of SEQ ID NOs: 332, 333, 334, and 335 and a non-viral membrane-bound tropism polypeptide comprising an amino acid sequence set forth in any one of SEQ ID NOs: 324, 325, 326, 327, 328, 329, 330, and 331; and two copies of a lentiviral vector comprising a promoter comprising or encoding a polynucleotide sequence set forth in SEQ ID NO: 320 operably linked to a polynucleotide encoding a signal peptide encoded by a polynucleotide sequence set forth in SEQ ID NO: 294 and an anti-BCMA CAR encoded by a polynucleotide sequence set forth in any one of SEQ ID NOs: 297, 299, 300, 302, 304, and 308, and optionally, a polynucleotide comprising a posttranscriptional regulatory element set forth in any one of SEQ ID NOs: 315, 316, and 317.

In particular embodiments, a composition comprises a recombinant lentiviral particle comprising a viral envelope comprising a fusogen comprising an amino acid sequence set forth in any one of SEQ ID NOs: 332, 333, 334, and 335 and a non-viral membrane-bound tropism polypeptide comprising an amino acid sequence set forth in any one of SEQ ID NOs: 324, 325, 326, 327, 328, 329, 330, and 331; and two copies of a lentiviral vector comprising a promoter comprising or encoding a polynucleotide sequence set forth in SEQ ID NO: 319 operably linked to a polynucleotide encoding a signal peptide comprising an amino acid sequence set forth in SEQ ID NO: 245 and an anti-BCMA CAR comprising an amino acid sequence set forth in any one of SEQ ID NOs: 259, 263, 266, 270, 273, and 277, and optionally, a polynucleotide comprising a posttranscriptional regulatory element set forth in any one of SEQ ID NOs: 315, 316, and 317.

In particular embodiments, a composition comprises a recombinant lentiviral particle comprising a viral envelope comprising a fusogen comprising an amino acid sequence set forth in any one of SEQ ID NOs: 332, 333, 334, and 335 and a non-viral membrane-bound tropism polypeptide comprising an amino acid sequence set forth in any one of SEQ ID NOs: 324, 325, 326, 327, 328, 329, 330, and 331; and two copies of a lentiviral vector comprising a promoter comprising or encoding a polynucleotide sequence set forth in SEQ ID NO: 319 operably linked to a polynucleotide encoding a signal peptide encoded by a polynucleotide sequence set forth in SEQ ID NO: 294 and an anti-BCMA CAR encoded by a polynucleotide sequence set forth in any one of SEQ ID NOs: 297, 299, 300, 302, 304, and 308, and optionally, a polynucleotide comprising a posttranscriptional regulatory element set forth in any one of SEQ ID NOs: 315, 316, and 317.

In particular embodiments, the composition is a pharmaceutical composition. A "pharmaceutical composition" refers to a composition formulated in a pharmaceutically-acceptable or physiologically-acceptable solution for administration to a cell or a subject, either alone, or in combination with one or more other modalities of therapy.

"Pharmaceutically acceptable" refers to molecular entities and compositions that do not produce excessive toxicity, irritation, allergic response, or other problems or complications, commensurate with a reasonable benefit/risk ratio when administered to a human.

In particular embodiments, a composition comprises a pharmaceutically acceptable carrier and a recombinant particle contemplated herein. The term "pharmaceutically acceptable carrier" refers to a diluent, adjuvant, excipient, vehicle and the like with which a recombinant particle, e.g., a recombinant retroviral or lentiviral particle, is physiologically compatible with administration to a human, including but not limited to pharmaceutically acceptable cell culture media, Dulbecco's phosphate buffered saline (PBS), Ringer's solution, 5% dextrose in water (D5W), and normal/physiologic saline (0.9% NaCl).

In particular embodiments, a composition comprises a pharmaceutically acceptable carrier and a recombinant lentiviral particle comprising a viral envelope comprising a mutated VSIV-G or COCV-G polypeptide comprising amino acid substitutions at positions 47 and 354 of the mature polypeptide and a non-viral membrane-bound tropism polypeptide comprising an anti-CD3 scFv and a CD8α hinge and transmembrane domain; and one or more copies of a lentiviral vector comprising a polynucleotide comprising or encoding an MNDU3 or EF1α promoter operably linked to a polynucleotide encoding an anti-BCMA CAR, and optionally a WPRE.

In particular embodiments, a composition comprises a pharmaceutically acceptable carrier and a recombinant lentiviral particle comprising a viral envelope comprising a mutated VSIV-G or COCV-G polypeptide comprising amino acid substitutions at positions 47 and 354 of the mature polypeptide and a non-viral membrane-bound tropism polypeptide comprising an anti-CD3 scFv and a CD8α hinge and transmembrane domain; and one or more copies of a recombinant lentiviral vector comprising a polynucleotide comprising or encoding an MNDU3 or EF1α promoter operably linked to a polynucleotide encoding a signal peptide, an anti-BCMA chimeric antigen receptor comprising an anti-BCMA scFv or anti-BCMA VHH, a CD8α hinge and transmembrane domain, a CD137 costimulatory domain, a CD32 primary signaling domain, and optionally a WPRE.

In particular embodiments, a composition comprises a pharmaceutically acceptable carrier and a recombinant lentiviral particle comprising a viral envelope comprising a fusogen comprising an amino acid sequence set forth in any one of SEQ ID NOs: 332, 333, 334, and 335 and a non-viral membrane-bound tropism polypeptide comprising an amino acid sequence set forth in any one of SEQ ID NOs: 324, 325, 326, 327, 328, 329, 330, and 331; and two copies of a lentiviral vector comprising a promoter comprising or encoding a polynucleotide sequence set forth in SEQ ID NO: 320 operably linked to a polynucleotide encoding a signal peptide comprising an amino acid sequence set forth in SEQ ID NO: 245 and an anti-BCMA CAR comprising an amino acid sequence set forth in any one of SEQ ID NOs: 259, 263, 266, 270, 273, and 277, and optionally, a polynucleotide comprising a posttranscriptional regulatory element set forth in any one of SEQ ID NOs: 315, 316, and 317.

In particular embodiments, a composition comprises a pharmaceutically acceptable carrier and a recombinant lentiviral particle comprising a viral envelope comprising a fusogen comprising an amino acid sequence set forth in any one of SEQ ID NOs: 332, 333, 334, and 335 and a non-viral membrane-bound tropism polypeptide comprising an amino acid sequence set forth in any one of SEQ ID NOs: 324, 325, 326, 327, 328, 329, 330, and 331; and two copies of a lentiviral vector comprising a promoter comprising or encoding a polynucleotide sequence set forth in SEQ ID NO: 320 operably linked to a polynucleotide encoding a signal peptide encoded by a polynucleotide sequence set forth in SEQ ID NO: 294 and an anti-BCMA CAR encoded by a polynucleotide sequence set forth in any one of SEQ ID NOs: 297, 299, 300, 302, 304, and 308, and optionally, a polynucleotide comprising a posttranscriptional regulatory element set forth in any one of SEQ ID NOs: 315, 316, and 317.

In particular embodiments, a composition comprises a pharmaceutically acceptable carrier and a recombinant lentiviral particle comprising a viral envelope comprising a fusogen comprising an amino acid sequence set forth in any one of SEQ ID NOs: 332, 333, 334, and 335 and a non-viral membrane-bound tropism polypeptide comprising an amino acid sequence set forth in any one of SEQ ID NOs: 324, 325, 326, 327, 328, 329, 330, and 331; and two copies of a lentiviral vector comprising a promoter comprising or encoding a polynucleotide sequence set forth in SEQ ID NO: 319 operably linked to a polynucleotide encoding a signal peptide comprising an amino acid sequence set forth in SEQ ID NO: 245 and an anti-BCMA CAR comprising an amino acid sequence set forth in any one of SEQ ID NOs: 259, 263, 266, 270, 273, and 277, and optionally, a polynucleotide comprising a posttranscriptional regulatory element set forth in any one of SEQ ID NOs: 315, 316, and 317.

In particular embodiments, a composition comprises a pharmaceutically acceptable carrier and a recombinant lentiviral particle comprising a viral envelope comprising a fusogen comprising an amino acid sequence set forth in any one of SEQ ID NOs: 332, 333, 334, and 335 and a non-viral membrane-bound tropism polypeptide comprising an amino acid sequence set forth in any one of SEQ ID NOs: 324, 325, 326, 327, 328, 329, 330, and 331; and two copies of a lentiviral vector comprising a promoter comprising or encoding a polynucleotide sequence set forth in SEQ ID NO: 319 operably linked to a polynucleotide encoding a signal peptide encoded by a polynucleotide sequence set forth in SEQ ID NO: 294 and an anti-BCMA CAR encoded by a polynucleotide sequence set forth in any one of SEQ ID NOs: 297, 299, 300, 302, 304, and 308, and optionally, a polynucleotide comprising a posttranscriptional regulatory element set forth in any one of SEQ ID NOs: 315, 316, and 317.

In particular embodiments, a composition comprises a recombinant particle and a pharmaceutically acceptable carrier suitable for enteral or parenteral, e.g., intravascular (intravenous or intraarterial), intraosseous, intraperitoneal, intraventricular, intracerebral, intracranial, intraspinal, intrathecal, intramuscular, and intramedullary, administration and formulation.

In particular embodiments, a composition is substantially free of *mycoplasma*, endotoxin, and microbial contamination. By "substantially free" with respect to endotoxin is meant that there is less endotoxin per dose of cells than is allowed by the FDA for a biologic, which is a total endotoxin of 5 EU/kg body weight per day, which for an average 70 kg person is 350 EU per total dose of cells. In particular embodiments, compositions contemplated herein contain about 0.5 EU/mL to about 5.0 EU/mL, or about 0.5 EU/mL, 1.0 EU/mL, 1.5 EU/mL, 2.0 EU/mL, 2.5 EU/mL, 3.0 EU/mL, 3.5 EU/mL, 4.0 EU/mL, 4.5 EU/mL, or 5.0 EU/mL.

In particular embodiments, compositions contemplated herein are used in the treatment of a cancer. In particular embodiments, a composition comprises a recombinant particle contemplated herein and one or more cytokines, growth factors, steroids, NSAIDs, DMARDs, anti-inflammatoires, chemotherapeutics, radiotherapeutics, therapeutic antibodies, or other active and ancillary agents, either alone or in combination.

It would be understood by the skilled artisan that particular embodiments contemplated herein may comprise other formulations, such as those that are well known in the pharmaceutical art, and are described, for example, in *Remington: The Science and Practice of Pharmacy*, Volume I and Volume II. 23rd Edition. Edited by Adeboye Adejare. Academic Press, 2020, which is incorporated by reference herein, in its entirety.

K. Methods of Making

The manufacturing processes contemplated herein comprise an upstream process that produces a recombinant lentiviral particle and a downstream process that purifies the recombinant lentiviral particle. Methods of manufacturing lentiviral particles are described in WO2023/003844, which is hereby incorporated by reference in its entirety. See, also Kutner et al., *BMC Biotechnol.* 2009; 9:10. doi: 10.1186/1472-6750-9-10 and Kutner et al. *Nat. Protoc.* 2009; 4(4): 495-505. doi: 10.1038/nprot.2009.22.

In particular embodiments, a method of manufacturing recombinant lentiviral particles comprises transfecting a host cell culture with packaging plasmids and a transfer plasmid, culturing transfected host cells to produce lentiviral particles; and collecting and processing the culture supernatant that contains the crude lentiviral particles to remove impurities and concentrate and formulate the particles for clinical use.

In particular embodiments, lentiviral particles are manufactured by transfecting host cells with a multi-plasmid system comprising (i) an envelope plasmid encoding a mutated VSIV-G or COCV-G polypeptide comprising amino acid substitutions at positions 47 and 354 of the mature polypeptide and a non-viral membrane-bound tropism polypeptide comprising an anti-CD3 scFv and a CD8α hinge and transmembrane domain, (ii) a packaging plasmid encoding lentiviral gag-pol, (iii) a packaging plasmid encoding lentiviral rev, and (iv) a transfer plasmid comprising a polynucleotide encoding a lentiviral vector contemplated herein.

In particular embodiments, lentiviral particles are manufactured by transfecting host cells with a multi-plasmid system comprising (i) an envelope plasmid encoding a mutated VSIV-G or COCV-G polypeptide comprising amino acid substitutions at positions 47 and 354 of the mature polypeptide and a non-viral membrane-bound tropism polypeptide comprising an anti-CD3 scFv and a CD8α hinge and transmembrane domain, (ii) a packaging plasmid encoding lentiviral gag-pol, (iii) a packaging plasmid encoding lentiviral rev, and (iv) a transfer plasmid comprising a polynucleotide encoding a lentiviral vector comprising or encoding an MNDU3 or EF1α promoter operably linked to a polynucleotide encoding a signal peptide, an anti-BCMA chimeric antigen receptor comprising an anti-BCMA scFv or anti-BCMA VHH, a CD8α hinge and transmembrane domain, a CD137 costimulatory domain, a CD3ζ primary signaling domain, and optionally a WPRE.

In particular embodiments, lentiviral particles are manufactured by transfecting host cells with a multi-plasmid system comprising (i) an envelope plasmid encoding a mutated VSIV-G or COCV-G polypeptide comprising amino acid substitutions at positions 47 and 354 of the mature polypeptide and a non-viral membrane-bound tropism polypeptide comprising an anti-CD3 scFv and a CD8α hinge and transmembrane domain, (ii) a packaging plasmid encoding lentiviral gag-pol, (iii) a packaging plasmid encoding lentiviral rev, and (iv) a transfer plasmid comprising a polynucleotide encoding a lentiviral vector comprising a promoter comprising or encoding a polynucleotide sequence set forth in SEQ ID NO: 320 operably linked to a polynucleotide encoding a signal peptide comprising an amino acid sequence set forth in SEQ ID NO: 245 and an anti-BCMA CAR comprising an amino acid sequence set forth in any one of SEQ ID NOs: 259, 263, 266, 270, 273, and 277, and optionally, a polynucleotide comprising a posttranscriptional regulatory element set forth in any one of SEQ ID NOs: 315, 316, and 317.

In particular embodiments, lentiviral particles are manufactured by transfecting host cells with a multi-plasmid system comprising (i) an envelope plasmid encoding a mutated VSIV-G or COCV-G polypeptide comprising amino acid substitutions at positions 47 and 354 of the mature polypeptide and a non-viral membrane-bound tropism polypeptide comprising an anti-CD3 scFv and a CD8α hinge and transmembrane domain, (ii) a packaging plasmid encoding lentiviral gag-pol, (iii) a packaging plasmid encoding lentiviral rev, and (iv) a transfer plasmid comprising a polynucleotide encoding a lentiviral vector comprising a promoter comprising or encoding a polynucleotide sequence set forth in SEQ ID NO: 320 operably linked to a polynucleotide encoding a signal peptide encoded by a polynucleotide sequence set forth in SEQ ID NO: 294 and an anti-BCMA CAR encoded by a polynucleotide sequence set forth in any one of SEQ ID NOs: 297, 299, 300, 302, 304, and 308, and optionally, a polynucleotide comprising a posttranscriptional regulatory element set forth in any one of SEQ ID NOs: 315, 316, and 317.

In particular embodiments, lentiviral particles are manufactured by transfecting host cells with a multi-plasmid system comprising (i) an envelope plasmid encoding a mutated VSIV-G or COCV-G polypeptide comprising amino acid substitutions at positions 47 and 354 of the mature polypeptide and a non-viral membrane-bound tropism polypeptide comprising an anti-CD3 scFv and a CD8α hinge and transmembrane domain, (ii) a packaging plasmid encoding lentiviral gag-pol, (iii) a packaging plasmid encoding lentiviral rev, and (iv) a transfer plasmid comprising a polynucleotide encoding a lentiviral vector comprising a promoter comprising or encoding a polynucleotide sequence set forth in SEQ ID NO: 319 operably linked to a polynucleotide encoding a signal peptide comprising an amino acid sequence set forth in SEQ ID NO: 245 and an anti-BCMA CAR comprising an amino acid sequence set forth in any one of SEQ ID NOs: 259, 263, 266, 270, 273, and 277, and optionally, a polynucleotide comprising a posttranscriptional regulatory element set forth in any one of SEQ ID NOs: 315, 316, and 317.

In particular embodiments, lentiviral particles are manufactured by transfecting host cells with a multi-plasmid system comprising (i) an envelope plasmid encoding a mutated VSIV-G or COCV-G polypeptide comprising amino acid substitutions at positions 47 and 354 of the mature polypeptide and a non-viral membrane-bound tropism polypeptide comprising an anti-CD3 scFv and a CD8α hinge and transmembrane domain, (ii) a packaging plasmid encoding lentiviral gag-pol, (iii) a packaging plasmid encoding lentiviral rev, and (iv) a transfer plasmid comprising a polynucleotide encoding a lentiviral vector comprising a promoter comprising or encoding a polynucleotide sequence set forth in SEQ ID NO: 319 operably linked to a polynucleotide encoding a signal peptide encoded by a polynucleotide sequence set forth in SEQ ID NO: 294 and an anti-BCMA CAR encoded by a polynucleotide sequence set forth in any one of SEQ ID NOs: 297, 299, 300, 302, 304, and 308, and optionally, a polynucleotide comprising a posttranscriptional regulatory element set forth in any one of SEQ ID NOs: 315, 316, and 317.

A "transfer plasmid" or "transfer vector" encodes a lentiviral genomic RNA modified to package a lentiviral vector that comprises a polynucleotide sequence delivered by recombinant lentiviral particle to a cell. In particular embodiments, a transfer plasmid comprises one or more polynucleotide sequences of interest flanked by LTR sequences, which facilitate packaging, reverse transcription and integration of the lentiviral vector and associated polynucleotide sequences into the host genome. Lentiviral vectors contemplated herein are replication incompetent, i.e., lack the genetic elements necessary for generation of infective particles in the host cell. For example, a lentiviral vector may comprise a deletion of the 3' LTR, rendering the virus "self-inactivating" (SIN).

Illustrative examples of host cells suitable for transfection with the aforementioned plasmid systems include but are not limited to HEK293 cells, HEK293S cells, HEK293T cells adapted for suspension culture (HEK293 Ts), HEK293F cells, HEK293FT cells, HEK293FTM cells, and HEK293E cells.

Once host cells are transfected and produce lentiviral particles, the cell culture is subjected to a downstream process that yields particles sufficient for clinical use, In particular embodiments, a downstream process comprises treating the contents of the bioreactor with a DNA endonuclease, e.g., benzonase; harvesting and clarifying the suspension culture supernatant by filtration; capturing and concentrating the lentiviral particles in the resultant filtrate using affinity chromatography or cation exchange chromatography; filtering the eluate comprising the lentiviral particles; ultrafiltering and diafiltering the lentiviral particles using tangential flow filtration (TFF); and formulating the lentiviral particles in a physiologically acceptable diluent to produce a formulated bulk lentiviral particles. In one embodiment, the formulated bulk lentiviral particles are sterile filtered, filled, and frozen; and subsequently thawed, sterile filtered, subjected to a final fill finish, and frozen. In another embodiment, the bulk lentiviral particles are sterile filtered, subjected to a final fill finish, and frozen.

L. Methods of Use

Recombinant particles contemplated herein are engineered to modify an immune cell that expresses CD3 in vivo to express an anti-BCMA CAR, which redirects the CD3-expressing immune cell to a target cell expressing BCMA, thereby preventing, treating, or ameliorating at least one symptom associated with a disease, disorder, or condition associated therewith.

In particular embodiments, a method of preventing, treating, or ameliorating at least one symptom of a cancer comprises administering the subject an amount of recombinant particle contemplated herein. The term "amount" as used herein, refers to "an amount effective" or "an effective amount" of a recombinant particle contemplated herein comprising a payload contemplated herein, etc., to achieve a beneficial or desired prophylactic or therapeutic result, including clinical results. A "prophylactically effective amount" refers to an amount of recombinant particle contemplated herein comprising payload contemplated herein, effective to achieve the desired prophylactic result. A "therapeutically effective amount" refers to an amount of recombinant particle contemplated herein comprising a lentiviral vector encoding an anti-BCMA CAR, that is effective to "treat" a subject (e.g., a patient). When a therapeutic amount is indicated, the precise amount of the compositions to be administered can be determined by a physician with consideration of individual differences in age, weight, tumor size, extent of infection or metastasis, and condition of the patient (subject).

In particular embodiments, a recombinant lentiviral particle comprising a viral envelope comprising a mutated VSIV-G or COCV-G polypeptide comprising amino acid substitutions at positions 47 and 354 of the mature polypeptide and a non-viral membrane-bound tropism polypeptide comprising an anti-CD3 scFv and a CD8α hinge and transmembrane domain; and one or more copies of a lentiviral vector comprising a polynucleotide comprising or encoding an MNDU3 or EF1α promoter operably linked to a polynucleotide encoding an anti-BCMA CAR, and optionally a WPRE, is administered to a subject to treat, prevent, or ameliorate at least one symptom of multiple myeloma in the subject.

In particular embodiments, a recombinant lentiviral particle comprising a viral envelope comprising a mutated VSIV-G or COCV-G polypeptide comprising amino acid substitutions at positions 47 and 354 of the mature polypeptide and a non-viral membrane-bound tropism polypeptide comprising an anti-CD3 scFv and a CD8α hinge and transmembrane domain; and one or more copies of a recombinant lentiviral vector comprising a polynucleotide comprising or encoding an MNDU3 or EF1α promoter operably linked to a polynucleotide encoding a signal peptide, an anti-BCMA chimeric antigen receptor comprising an anti-BCMA scFv or anti-BCMA VHH, a CD8α hinge and transmembrane domain, a CD137 costimulatory domain, a CD3ζ primary signaling domain, and optionally a WPRE, is administered to a subject to treat, prevent, or ameliorate at least one symptom of multiple myeloma in the subject.

In particular embodiments, a recombinant lentiviral particle comprising a viral envelope comprising a fusogen comprising an amino acid sequence set forth in any one of SEQ ID NOs: 332, 333, 334, and 335 and a non-viral membrane-bound tropism polypeptide comprising an amino acid sequence set forth in any one of SEQ ID NOS: 324, 325, 326, 327, 328, 329, 330, and 331; and two copies of a lentiviral vector comprising a promoter comprising or encoding a polynucleotide sequence set forth in SEQ ID NO: 320 operably linked to a polynucleotide encoding a signal peptide comprising an amino acid sequence set forth in SEQ ID NO: 245 and an anti-BCMA CAR comprising an amino acid sequence set forth in any one of SEQ ID NOs: 259, 263, 266, 270, 273, and 277, and optionally, a polynucleotide comprising a posttranscriptional regulatory element set forth in any one of SEQ ID NOs: 315, 316, and 317, is administered to a subject to treat, prevent, or ameliorate at least one symptom of multiple myeloma in the subject.

In particular embodiments, a recombinant lentiviral particle comprising a viral envelope comprising a fusogen comprising an amino acid sequence set forth in any one of SEQ ID NOs: 332, 333, 334, and 335 and a non-viral membrane-bound tropism polypeptide comprising an amino acid sequence set forth in any one of SEQ ID NOs: 324, 325, 326, 327, 328, 329, 330, and 331; and two copies of a lentiviral vector comprising a promoter comprising or encoding a polynucleotide sequence set forth in SEQ ID NO: 320 operably linked to a polynucleotide encoding a signal peptide encoded by a polynucleotide sequence set forth in SEQ ID NO: 294 and an anti-BCMA CAR encoded by a polynucleotide sequence set forth in any one of SEQ ID NOs: 297, 299, 300, 302, 304, and 308, and optionally, a polynucleotide comprising a posttranscriptional regulatory element set forth in any one of SEQ ID NOs: 315, 316, and 317, is administered to a subject to treat, prevent, or ameliorate at least one symptom of multiple myeloma in the subject.

In particular embodiments, a recombinant lentiviral particle comprising a viral envelope comprising a fusogen comprising an amino acid sequence set forth in any one of SEQ ID NOs: 332, 333, 334, and 335 and a non-viral membrane-bound tropism polypeptide comprising an amino acid sequence set forth in any one of SEQ ID NOS: 324, 325, 326, 327, 328, 329, 330, and 331; and two copies of a lentiviral vector comprising a promoter comprising or encoding a polynucleotide sequence set forth in SEQ ID NO: 319 operably linked to a polynucleotide encoding a signal peptide comprising an amino acid sequence set forth in SEQ ID NO: 245 and an anti-BCMA CAR comprising an amino acid sequence set forth in any one of SEQ ID NOs: 259, 263, 266, 270, 273, and 277, and optionally, a polynucleotide comprising a posttranscriptional regulatory element set forth in any one of SEQ ID NOs: 315, 316, and 317, is administered to a subject to treat, prevent, or ameliorate at least one symptom of multiple myeloma in the subject.

In particular embodiments, a recombinant lentiviral particle comprising a viral envelope comprising a fusogen comprising an amino acid sequence set forth in any one of SEQ ID NOs: 332, 333, 334, and 335 and a non-viral membrane-bound tropism polypeptide comprising an amino acid sequence set forth in any one of SEQ ID NOs: 324, 325, 326, 327, 328, 329, 330, and 331; and two copies of a lentiviral vector comprising a promoter comprising or encoding a polynucleotide sequence set forth in SEQ ID NO: 319 operably linked to a polynucleotide encoding a signal peptide encoded by a polynucleotide sequence set forth in SEQ ID NO: 294 and an anti-BCMA CAR encoded by a polynucleotide sequence set forth in any one of SEQ ID NOs: 297, 299, 300, 302, 304, and 308, and optionally, a polynucleotide comprising a posttranscriptional regulatory element set forth in any one of SEQ ID NOs: 315, 316, and 317, is administered to a subject to treat, prevent, or ameliorate at least one symptom of multiple myeloma in the subject.

In particular embodiments, a recombinant lentiviral particle contemplated herein is administered to a subject to treat, prevent, or ameliorate at least one symptom of a multiple myeloma or precursor thereof selected from the group consisting of: monoclonal gammopathy of undetermined significance (MGUS), active multiple myeloma, smoldering multiple myeloma, light chain myeloma, nonsecretory myeloma, IgD myeloma, IgE myeloma, osteosclerotic myeloma, solitary plasmacytoma of bone, and extramedullary plasmacytoma.

In particular embodiments, a recombinant lentiviral particle is administered to a subject in combination with one or more anti-cancer therapies including, but not limited to, an autologous stem cell transplant (ASCT), radiation, surgery, a chemotherapeutic agent, an immunomodulatory agent and a targeted cancer therapy.

In particular embodiments, the one or more anti-cancer therapies is selected from the group consisting of 6-mercaptopurine, abiraterone, alemtuzumab, all-trans retinoic acid, anastrozole, aprepitant, arsenic trioxide, atezolizumab, avelumab, azacytidine, bafetinib, bavituximab, bevacizumab, bivatuzumab, bleomycin, blinatumomab, bortezomib, bosutinib, cabazitaxel, capecitabine, carboplatin, carfilzomib, cetuximab, cisplatin, cladribine, conatumumab, corticosteroid, crizotinib, cyclophosphamide, cytarabine, dacetuzumab, dalotuzumab, daratumumab, dasatinib, daunorubicin, danusertib, decitabine, denosumab, dexamethasone, docetaxel, doxorubicin, duligotumab, durvalumab, elotozumab, eribulin, erlotinib, etoposide, everolimus, exemestane, filgrastim, fludarabine, fluorouracil, fulvestrant, gemcitabine, gemtuzumab, hydroxyurca, ibritumomab, idarubicin, imatinib, imiquimod, indatuximab, inotuzumab, ipilimumab, ixabepilone, ixazomib, lapatinib, lenalidomide, letrozole, leuprolide, lorvotuzumab, lucatumumab, melphalan, methotrexate, milatuzumab, mitoxantrone, moxetumomab, nilotinib, nivolumab, ocaratuzumab, ofatumumab, oxaliplatin, paclitaxel, palonosctron, pembrolizumab, pemetrexed, pomalidomide, ponatinib, prednisone, radium-223, rituximab, saracatinib, siltuximab, sipuleucel-T, sorafenib, sunitinib, tamoxifen, temozolomide, temsirolimus, teprotumumab, thalidomide, tinorelbine, topotecan, tozasertib, trastuzumab, ublituximab, vincristine, and zoledronic acid.

M. Enumerated Embodiments

Embodiment 1: A recombinant lentiviral particle comprising:

(a) a viral envelope comprising (i) a mutated cocal virus envelope glycoprotein (COCV-G) or a mutated vesicular stomatitis Indiana virus envelope glycoprotein (VSIV-G), wherein the mutated COCV-G or VSIV-G comprises amino acid substitutions at positions 47 and 354; and (ii) a non-viral membrane-bound tropism polypeptide comprising an anti-CD3ε scFv and a human CD8α hinge and transmembrane domain; and (b) a recombinant lentiviral vector comprising a polynucleotide encoding a myeloproliferative sarcoma virus enhancer, negative control region deleted, dl587rev primer-binding site substituted (MND) U3 promoter or an EF1α promoter operably linked to a polynucleotide encoding an anti-BCMA chimeric antigen receptor comprising an anti-BCMA scFv or anti-BCMA VHH, a CD8α hinge and transmembrane domain, a CD137 costimulatory domain, a CD3 primary signaling domain.

Embodiment 2: The particle of embodiment 1, wherein the mutated COCV-G or the mutated VSIV-G comprises amino acid substitutions selected from the group consisting of: K47A and R354A; K47A and R354Q; K47Q and R354A; and K47Q and R354Q.

Embodiment 3: The particle of embodiment 1 or embodiment 2, wherein the mutated COCV-G or the mutated VSIV-G comprises the amino acid substitutions K47A and R354A.

Embodiment 4: The particle of embodiment 1 or embodiment 2, wherein the mutated COCV-G or the mutated VSIV-G comprises the amino acid substitutions K47A and R354Q.

Embodiment 5: The particle of embodiment 1 or embodiment 2, wherein the mutated COCV-G or the mutated VSIV-G comprises the amino acid substitutions K47Q and R354A.

Embodiment 6: The particle of embodiment 1 or embodiment 2, wherein the mutated COCV-G or the mutated VSIV-G comprises the amino acid substitutions K47Q and R354Q.

Embodiment 7: The particle of any one of embodiments 1 to 6, wherein the mutated COCV-G or the mutated VSIV-G comprises the amino acid sequence set forth in any one of SEQ ID NOs: 332, 333, 334, 335, 336, 337, 338, and 339.

Embodiment 8: The particle of any one of embodiments 1 to 7, wherein the mutated COCV-G or the mutated VSIV-G comprises the amino acid sequence set forth in any one of SEQ ID NOs: 332, 333, 334, and 335.

Embodiment 9: The particle of any one of embodiments 1 to 7, wherein the mutated COCV-G or the mutated VSIV-G comprises the amino acid sequence set forth in any one of SEQ ID NOs: 336, 337, 338, and 339.

Embodiment 10: The particle of any one of embodiments 1 to 9, wherein the anti-CD38 scFv is isolated from an antibody selected from the group consisting of: OKT3, UCHT1, YTH12.5, TR66, and variants thereof.

Embodiment 11: The particle of any one of embodiments 1 to 10, wherein the anti-CD38 scFv is isolated from OKT3.

Embodiment 12: The particle of any one of embodiments 1 to 10, wherein the anti-CD3E scFv is isolated from UCHT1.

Embodiment 13: The particle of any one of embodiments 1 to 10, wherein the anti-CD3ε scFv is isolated from YTH12.5.

Embodiment 14: The particle of any one of embodiments 1 to 10, wherein the anti-CD38 scFv is isolated from TR66.

Embodiment 15: The particle of any one of embodiments 1 to 10, wherein the anti-CD3ε scFv comprises an amino acid sequence set forth in any one of SEQ ID NOs: 153, 154, 163, 164, 173, 174, 183, 184, 193, 194, 203, 204, 213, 214, 223, and 224.

Embodiment 16: The particle of any one of embodiments 1 to 10, wherein the non-viral membrane-bound tropism polypeptide comprises an amino acid sequence set forth in any one of SEQ ID NOs: 324, 325, 326, 327, 328, 329, 330, and 331.

Embodiment 17: The particle of any one of embodiments 1 to 16, wherein the MND U3 promoter comprises the polynucleotide sequence set forth in SEQ ID NO: 320.

Embodiment 18: The particle of any one of embodiments 1 to 16, wherein the EF1α promoter comprises the polynucleotide sequence set forth in SEQ ID NO: 319.

Embodiment 19: The particle of any one of embodiments 1 to 18, wherein the anti-BCMA CAR comprises an anti-BCMA scFv comprising an amino acid sequence selected from the group consisting of: 19, 20, 29, 30, 39, 40, 49, 50, 59, 60, 69, 70, 79, 80, 89, 90, 99, and 100.

Embodiment 20: The particle of any one of embodiments 1 to 19, wherein the anti-BCMA CAR comprises an anti-BCMA scFv comprising an amino acid sequence selected from the group consisting of: 20, 30, 39, 50, 59, 70, 80, 90, and 100.

Embodiment 21: The particle of any one of embodiments 1 to 20, wherein the anti-BCMA CAR comprises an anti-BCMA scFv comprising an amino acid sequence selected from the group consisting of: 39, 59, 70, and 90.

Embodiment 22: The particle of any one of embodiments 1 to 18, wherein the anti-BCMA CAR comprises an anti-BCMA VHH comprising an amino acid sequence selected from the group consisting of: 101, 105, 109, 113, 117, 121, 125, 129, 133, 137, and 141.

Embodiment 23: The particle of any one of embodiments 1 to 18, wherein the anti-BCMA CAR comprises an anti-BCMA VHH comprising an amino acid sequence selected from the group consisting of: 101 and 117.

Embodiment 24: The particle of any one of embodiments 1 to 23, wherein the anti-BCMA CAR comprises the amino acid sequence set forth in any one of SEQ ID NOs: 259, 263, 266, 270, 273 and 277.

Embodiment 25: The particle of any one of embodiments 1 to 24, wherein the polynucleotide encoding the anti-BCMA CAR comprises the polynucleotide sequence set forth in any one of SEQ ID NOs: 297, 299, 300, 302, 304, and 308.

Embodiment 26: The particle of any one of embodiments 1 to 25, wherein the polynucleotide encoding the anti-BCMA CAR further comprises a polynucleotide sequence encoding a signal peptide.

Embodiment 27: The particle of any one of embodiments 1 to 25, wherein the polynucleotide encoding the anti-BCMA CAR further comprises a polynucleotide sequence encoding a signal peptide isolated from a polypeptide selected from the group consisting of: CD8α, mIgGκ, hIgGk, CD33, tPA, SEAP, hGM-CSF, CSF2R, and B2M.

Embodiment 28: The particle of any one of embodiments 1 to 27, wherein the polynucleotide encoding the anti-BCMA CAR further comprises a polynucleotide sequence encoding a signal peptide comprising an amino acid sequence set forth in any one of SEQ ID NOs: 245, 246, 247, 248, 249, 250, 251, 252, 253, and 254.

Embodiment 29: The particle of any one of embodiments 21 to 23, wherein the polynucleotide encoding the signal peptide comprises the polynucleotide sequence set forth in SEQ ID NO: 294.

Embodiment 30: The particle of any one of embodiments 1 to 24, wherein the lentiviral vector further comprises a WPRE operably linked to the 3' end of the polynucleotide encoding the anti-BCMA CAR.

Embodiment 31: The particle of any one of embodiments 1 to 25, wherein the lentiviral vector further comprises a WPRE that comprises, consists essentially of, or consists of a polynucleotide sequence set forth in any one of SEQ ID NOs: 315, 316, and 317.

Embodiment 32: A recombinant lentiviral particle comprising:

(a) a viral envelope comprising (i) a mutated viral envelope glycoprotein comprising an amino acid sequence set forth in any one of SEQ ID NOs: 332, 333, 334, and 335 and (ii) a non-viral membrane-bound tropism polypeptide comprising an amino acid sequence set forth in any one of SEQ ID NOs: 324, 325, 326, 327, 328, 329, 330, and 331; and (b) a recombinant lentiviral vector comprising a 5' long terminal repeat (LTR) comprising R and U5 regions; a Psi (Ψ) packaging signal, a cPPT/FLAP, a rev response element (RRE); a polynucleotide encoding an MND promoter or an EF1α promoter operably linked to a polynucleotide encoding an anti-BCMA chimeric antigen receptor (CAR) comprising an amino acid sequence set forth in any one of SEQ ID NOs: 259, 263, 266, 270, 273, and 277 or an amino acid sequence at least 95%, at least 96%, at least 97%, at least 98%, at least 99% identical thereto; optionally a WPRE; a 3' LTR comprising U3 and R regions; a polyadenylation signal and a poly(A) tail.

Embodiment 33: The particle of embodiment 32, wherein the mutated viral envelope glycoprotein comprises an amino acid sequence set forth in SEQ ID NO: 332.

Embodiment 34: The particle of embodiment 32, wherein the mutated viral envelope glycoprotein comprises an amino acid sequence set forth in SEQ ID NO: 333.

Embodiment 35: The particle of embodiment 32, wherein the mutated viral envelope glycoprotein comprises an amino acid sequence set forth in SEQ ID NO: 334.

Embodiment 36: The particle of embodiment 32, wherein the mutated viral envelope glycoprotein comprises an amino acid sequence set forth in SEQ ID NO: 335.

Embodiment 37: A recombinant lentiviral particle comprising:

(a) a viral envelope comprising (i) a mutated viral envelope glycoprotein comprising an amino acid sequence set forth in any one of SEQ ID NOs: 336, 337, 338, and 339 and (ii) a non-viral membrane-bound tropism polypeptide comprising an amino acid sequence set forth in any one of SEQ ID NOs: 324, 325, 326, 327, 328, 329, 330, and 331; and (b) a recombinant lentiviral vector comprising a 5' long terminal repeat (LTR) comprising R and U5 regions; a Psi (Ψ) packaging signal, a cPPT/FLAP, a rev response element (RRE); a polynucleotide encoding an MND promoter or an EF1α promoter operably linked to a polynucleotide encoding an anti-BCMA chimeric antigen receptor (CAR) comprising an amino acid sequence set forth in any one of SEQ ID NOs: 259, 263, 266, 270, 273, and 277 or an amino acid sequence at least 95%, at least 96%, at least 97%, at least 98%, at least 99% identical thereto; optionally a WPRE; a 3' LTR comprising U3 and R regions; a polyadenylation signal and a poly(A) tail.

Embodiment 38: The particle of embodiment 37, wherein the mutated viral envelope glycoprotein comprises an amino acid sequence set forth in SEQ ID NO: 336.

Embodiment 39: The particle of embodiment 37, wherein the mutated viral envelope glycoprotein comprises an amino acid sequence set forth in SEQ ID NO: 337.

Embodiment 40: The particle of embodiment 37, wherein the mutated viral envelope glycoprotein comprises an amino acid sequence set forth in SEQ ID NO: 338.

Embodiment 41: The particle of embodiment 37, wherein the mutated viral envelope glycoprotein comprises an amino acid sequence set forth in SEQ ID NO: 339.

Embodiment 42: The particle of any one of embodiments 32 to 41, wherein the non-viral membrane-bound tropism polypeptide comprises an amino acid sequence set forth in SEQ ID NO: 324.

Embodiment 43: The particle of any one of embodiments 32 to 41, wherein the non-viral membrane-bound tropism polypeptide comprises an amino acid sequence set forth in SEQ ID NO: 325.

Embodiment 44: The particle of any one of embodiments 32 to 41, wherein the non-viral membrane-bound tropism polypeptide comprises an amino acid sequence set forth in SEQ ID NO: 326.

Embodiment 45: The particle of any one of embodiments 32 to 41, wherein the non-viral membrane-bound tropism polypeptide comprises an amino acid sequence set forth in SEQ ID NO: 327.

Embodiment 46: The particle of any one of embodiments 32 to 41, wherein the non-viral membrane-bound tropism polypeptide comprises an amino acid sequence set forth in SEQ ID NO: 328.

Embodiment 47: The particle of any one of embodiments 32 to 41, wherein the non-viral membrane-bound tropism polypeptide comprises an amino acid sequence set forth in SEQ ID NO: 329.

Embodiment 48: The particle of any one of embodiments 32 to 41, wherein the non-viral membrane-bound tropism polypeptide comprises an amino acid sequence set forth in SEQ ID NO: 330.

Embodiment 49: The particle of any one of embodiments 32 to 41, wherein the non-viral membrane-bound tropism polypeptide comprises an amino acid sequence set forth in SEQ ID NO: 331.

Embodiment 50: The particle of any one of embodiments 32 to 49, wherein the recombinant lentiviral vector is derived from HIV-1 or HIV-2.

Embodiment 51: The particle of any one of embodiments 32 to 50, wherein the MND U3 promoter comprises the polynucleotide sequence set forth in SEQ ID NO: 320.

Embodiment 52: The particle of any one of embodiments 32 to 50, wherein the EF1α promoter comprises the polynucleotide sequence set forth in SEQ ID NO: 319.

Embodiment 53: The particle of any one of embodiments 32 to 52, wherein the polynucleotide encoding the anti-BCMA CAR comprises the polynucleotide sequence set forth in any one of SEQ ID NOs: 297, 299, 300, 302, 304, and 308.

Embodiment 54: The particle of any one of embodiments 32 to 53, wherein the polynucleotide encoding the anti-BCMA CAR further comprises a polynucleotide sequence encoding a signal peptide.

Embodiment 55: The particle of any one of embodiments 32 to 54, wherein the polynucleotide encoding the anti-BCMA CAR further comprises a polynucleotide sequence encoding a signal peptide isolated from a polypeptide selected from the group consisting of: CD8α, mIgGκ, hIgGk, CD33, tPA, SEAP, hGM-CSF, CSF2R, and B2M.

Embodiment 56: The particle of any one of embodiments 32 to 55, wherein the polynucleotide encoding the anti-BCMA CAR further comprises a polynucleotide sequence encoding a signal peptide comprising an amino acid sequence set forth in any one of SEQ ID NOs: 245, 246, 247, 248, 249, 250, 251, 252, 253, and 254.

Embodiment 57: The particle of any one of embodiments 32 to 56, wherein the lentiviral vector further comprises a WPRE operably linked to the 3' end of the polynucleotide encoding the anti-BCMA CAR.

Embodiment 58: The particle of any one of embodiments 32 to 56, wherein the lentiviral vector further comprises a WPRE operably linked to the 3' end of the polynucleotide encoding the anti-BCMA CAR, wherein the WPRE comprises, consists essentially of, or consists of the polynucleotide sequence set forth in any one of SEQ ID NOs: 315, 316, and 317.

Embodiment 59: A recombinant lentiviral particle comprising:

(a) a viral envelope comprising (i) a mutated viral envelope glycoprotein comprising an amino acid sequence set forth in SEQ ID NO: 335 and (ii) a non-viral membrane-bound tropism polypeptide comprising an amino acid sequence set forth in SEQ ID NO: 324; and (b) a recombinant lentiviral vector comprising a 5' long terminal repeat (LTR) comprising R and U5 regions; a Psi (Ψ) packaging signal, a cPPT/FLAP, a rev response element (RRE); a polynucleotide encoding an EF1α promoter operably linked to a polynucleotide encoding an anti-BCMA chimeric antigen receptor (CAR) comprising an amino acid sequence set forth in SEQ ID NO: 266 or an amino acid sequence at least 95%, at least 96%, at least 97%, at least 98%, at least 99% identical thereto; optionally a WPRE; a 3' LTR comprising U3 and R regions; a polyadenylation signal and a poly(A) tail.

Embodiment 60: A cell transduced with the particle of any one of embodiments 1 to 59.

Embodiment 61: The cell of embodiment 60, wherein the cell is an immune effector cell.

Embodiment 62: The cell of embodiment 60 or embodiment 61, wherein the cell is a T cell or a natural killer T (NKT) cell.

Embodiment 63: A composition comprising the particle of any one of embodiments 1 to 58 or the cell of any one of embodiments 60 to 62.

Embodiment 64: A pharmaceutical composition comprising a pharmaceutically acceptable carrier and the particle of any one of embodiments 1 to 59, the cell of any one of embodiments 60 to 62, or the composition of embodiment 63.

Embodiment 65: A method of treating, preventing, or ameliorating at least one symptom of a disease, disorder or condition associated therewith in a subject, comprising administering to the subject an effective amount of the particle of any one of embodiments 1 to 59, the cell of any one of embodiments 60 to 62, the composition of embodiment 63, or the pharmaceutical composition of embodiment 64.

Embodiment 66: The method of embodiment 65, wherein the disease, disorder, or condition is a cancer.

Embodiment 67: The method of embodiment 65 or embodiment 66, wherein the cancer is a multiple myeloma (MM).

Embodiment 68: The method of embodiment 66 or embodiment 67, wherein the cancer is MM selected from the group consisting of: active multiple myeloma, smoldering multiple myeloma, light chain myeloma, non-secretory myeloma, IgD myeloma, IgE myeloma, osteosclerotic myeloma, solitary plasmacytoma of bone, and extramedullary plasmacytoma.

Embodiment 69: The method of any one of embodiments 66 to 68, wherein the cancer is relapsed and/or refractory.

Embodiment 70: A method of treating a subject that has, or has been diagnosed with, a multiple myeloma, comprising administering the subject an effective amount of the particle of any one of embodiments 1 to 59, the cell of any one of embodiments 60 to 62, the composition of embodiment 63, or the pharmaceutical composition of embodiment 64.

Embodiment 71: The method of embodiment 70, wherein the administration is parenteral administration.

Embodiment 72: The methods of embodiment 70 or embodiment 71, wherein the administration is intravenous.

Embodiment 73: A method of transducing an immune effector cell in vivo, comprising administering to a subject a pharmaceutical composition comprising a pharmaceutically acceptable carrier and an effective amount of the particle of any one of embodiments 1 to 59, the cell of any one of embodiments 60 to 62, the composition of embodiment 63, or the pharmaceutical composition of embodiment 64.

Embodiment 74: A method of making a recombinant lentivirus comprising (a) transfecting a host cell with four polynucleotides: a first polynucleotide that encodes lentiviral gag-pol, a second polynucleotide that encodes lentiviral rev, a third polynucleotide that encodes the mutated viral envelope glycoprotein set forth in any one of embodiments 1 to 59 and the non-viral membrane-bound tropism polypeptide set forth in any one of embodiments 1 to 59, and a fourth polynucleotide that is a transfer plasmid encoding the recombinant lentiviral vector of any one of embodiments 1 to 59; and b) culturing the transduced cell for about 1 to 3 days to produce the recombinant lentivirus.

Embodiment 75: A kit comprising the particle of any one of embodiments 1 to 59, a pharmaceutically acceptable carrier, and instructions for use.

All publications, patent applications, and issued patents cited in this specification are herein incorporated by reference as if each individual publication, patent application, or issued patent were specifically and individually indicated to be incorporated by reference.

Although the foregoing embodiments have been described in some detail by way of illustration and example for purposes of clarity of understanding, it will be readily apparent to one of ordinary skill in the art in light of the teachings contemplated herein that certain changes and modifications may be made thereto without departing from the spirit or scope of the appended claims. The following examples are provided by way of illustration only and not by way of limitation. Those of skill in the art will readily recognize a variety of noncritical parameters that could be changed or modified to yield essentially similar results.

N. Examples

Example 1

Recombinant Lentivirus Delivers Functional Anti-BCMA Cars to T Cells

Figure 1:
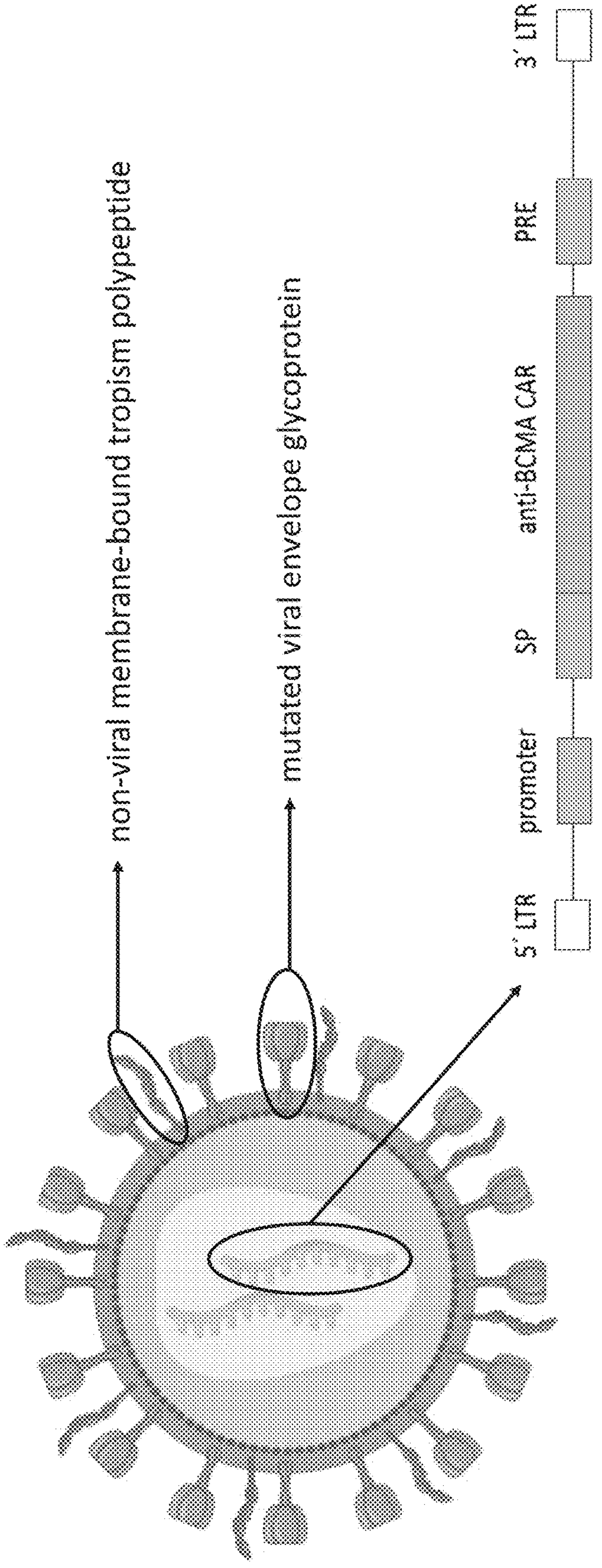
FIG. 1 is a cartoon of a recombinant lentiviral particle comprising a viral envelope expressing a mutated viral envelope glycoprotein and non-viral membrane-bound tropism polypeptide and two copies of a lentiviral vector encoding a promoter operably linked to a polynucleotide encoding an anti-BCMA CAR and an optional post-transcriptional response element (PRE) operably linked to the 3' prime end of the polynucleotide encoding the anti-BCMA CAR.

Recombinant T cell specific lentiviral particles with a viral envelope expressing a mutated viral envelope glycoprotein (fusogen) and a non-viral membrane bound tropism molecule and harboring a lentiviral vector encoding an anti-BCMA CAR were generated. FIG. 1.

HEK293T cells were transfected with plasmids encoding a non-viral membrane bound tropism molecule comprising an anti-CD3 scFv fused to a CD8α hinge and transmembrane domain (e.g., SEQ ID NO: 324); a mutant VSIV-G fusogen (e.g., SEQ ID NOs: 335); lentiviral GAG/POL; lentiviral REV; and a transfer plasmid encoding a lentiviral vector comprising an MNDU3 promoter operably linked to a polynucleotide encoding a CD8α signal peptide and an anti-BCMA CAR and a WPRE element operably linked to the 3' end of the polynucleotide encoding the anti-BCMA CAR.

Table 16 lists the recombinant lentivirus (LV) reference number and the corresponding SEQ ID NOs of the amino acid sequences of the anti-BCMA CARs and their CARchitectures.

TABLE 16

| LV Ref. | SEQ ID NO. | anti-BCMA binding domain | Hinge | TM | Costim | Primary |
|---|---|---|---|---|---|---|
| LV 1 | 256 | scFv | CD8α | CD8α | CD137 | CD3ζ |
| LV 2 | 258 | scFv | CD8α | CD8α | CD137 | CD3ζ |
| LV 3 | 259 | scFv | CD8α | CD8α | CD137 | CD3ζ |
| LV 4 | 262 | scFv | CD8α | CD8α | CD137 | CD3ζ |
| LV 5 | 263 | scFv | CD8α | CD8α | CD137 | CD3ζ |
| LV 6 | 266 | scFv | CD8α | CD8α | CD137 | CD3ζ |
| LV 7 | 268 | scFv | CD8α | CD8α | CD137 | CD3ζ |
| LV 8 | 270 | scFv | CD8α | CD8α | CD137 | CD3ζ |
| LV 9 | 273 | VHH | CD8α | CD8α | CD137 | CD3ζ |
| LV 10 | 274 | VHH | CD8α | CD8α | CD137 | CD3ζ |
| LV 11 | 275 | VHH | CD8α | CD8α | CD137 | CD3ζ |
| LV 12 | 276 | VHH | CD8α | CD8α | CD137 | CD3ζ |
| LV 13 | 277 | VHH | CD8α | CD8α | CD137 | CD3ζ |
| LV 14 | 278 | VHH | CD8α | CD8α | CD137 | CD3ζ |
| LV 15 | 279 | VHH | CD8α | CD8α | CD137 | CD3ζ |
| LV 16 | 281 | VHH | CD8α | CD8α | CD137 | CD3ζ |
| LV 17 | 282 | VHH | CD8α | CD8α | CD137 | CD3ζ |
| LV 18 | 283 | VHH | CD8α | CD8α | CD137 | CD3ζ |
| LV 19 | NA | scFv | CD8α | CD8α | CD137 | CD3ζ |

Figure 2A:
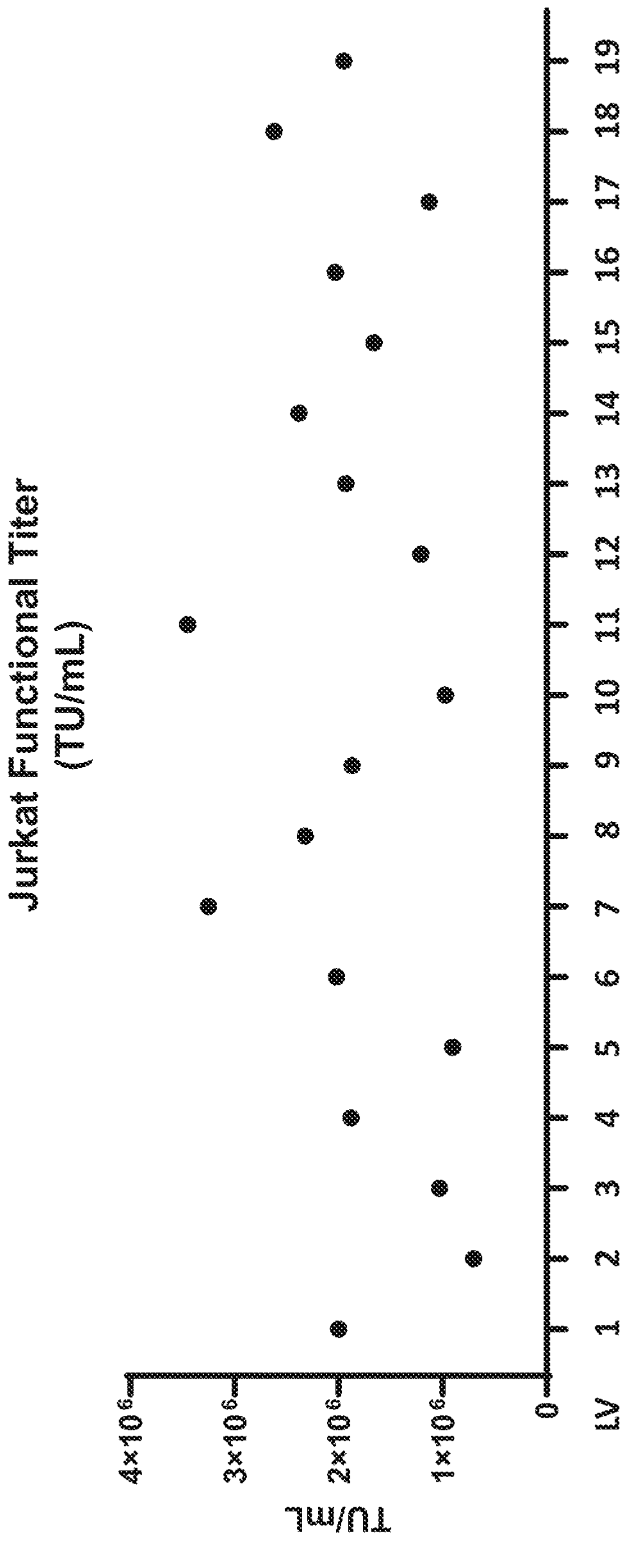
FIG. 2A shows Jurkat cell titer of recombinant lentiviruses comprising a viral envelope expressing a mutated vesicular stomatitis Indiana virus envelope glycoprotein G (VSIV-G) and a non-viral membrane-bound tropism polypeptide that binds CD3 and a lentiviral vector encoding an MNDU3 promoter operably linked to a polynucleotide encoding a CD8α signal peptide and an anti-BCMA CAR and a WPRE operably linked to the 3' prime end of the polynucleotide encoding the anti-BCMA CAR (18 anti-BCMA CARs were evaluated).

Jurkat Functional Titer $1\times10^5$ Jurkat cells were plated in each well of a 96-well plate. Cells were transduced with recombinant lentiviruses LV 1 to LV 18 that harbor novel anti-BCMA CARs and LV 19, which harbors a control anti-BCMA CAR obtained from the literature. Seven days post-transduction, Jurkat cells were harvested and stained with a recombinant, phycoerythrin (PE) labeled, BCMA extracellular domain-FC fusion protein (BCMA-PE) and analyzed by flow cytometry. Functional titer, expressed as the number of transducing units (TU) per mL, was determined by measuring the number of transduced Jurkat cells. FIG. 2A.

Figure 2B:
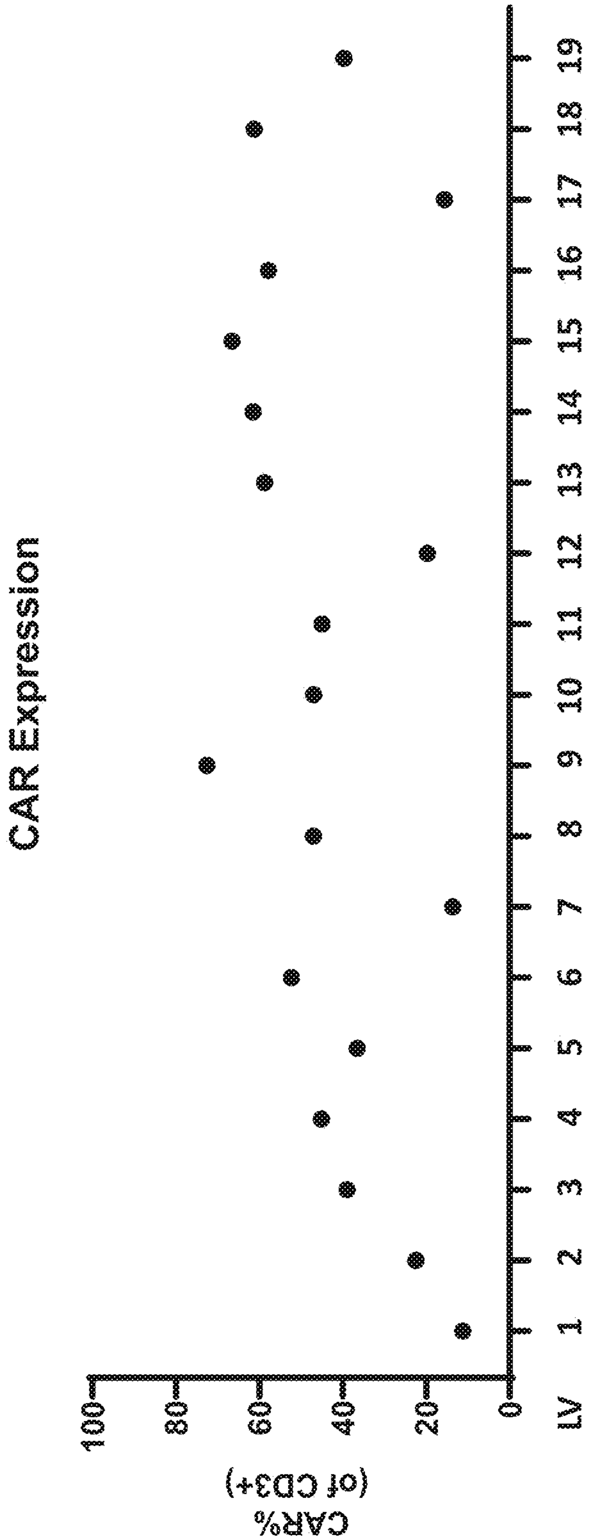
FIG. 2B shows anti-BCMA CAR expression on PBMCs transduced with recombinant lentiviral particles comprising a viral envelope expressing a mutated VSIV-G and a non-viral membrane-bound tropism polypeptide that binds CD3 and a lentiviral vector encoding an MNDU3 promoter operably linked to a polynucleotide encoding a CD8α signal peptide and an anti-BCMA CAR and a WPRE operably linked to the 3' prime end of the polynucleotide encoding the anti-BCMA CAR (18 anti-BCMA CARs were evaluated).
Figure 2C:
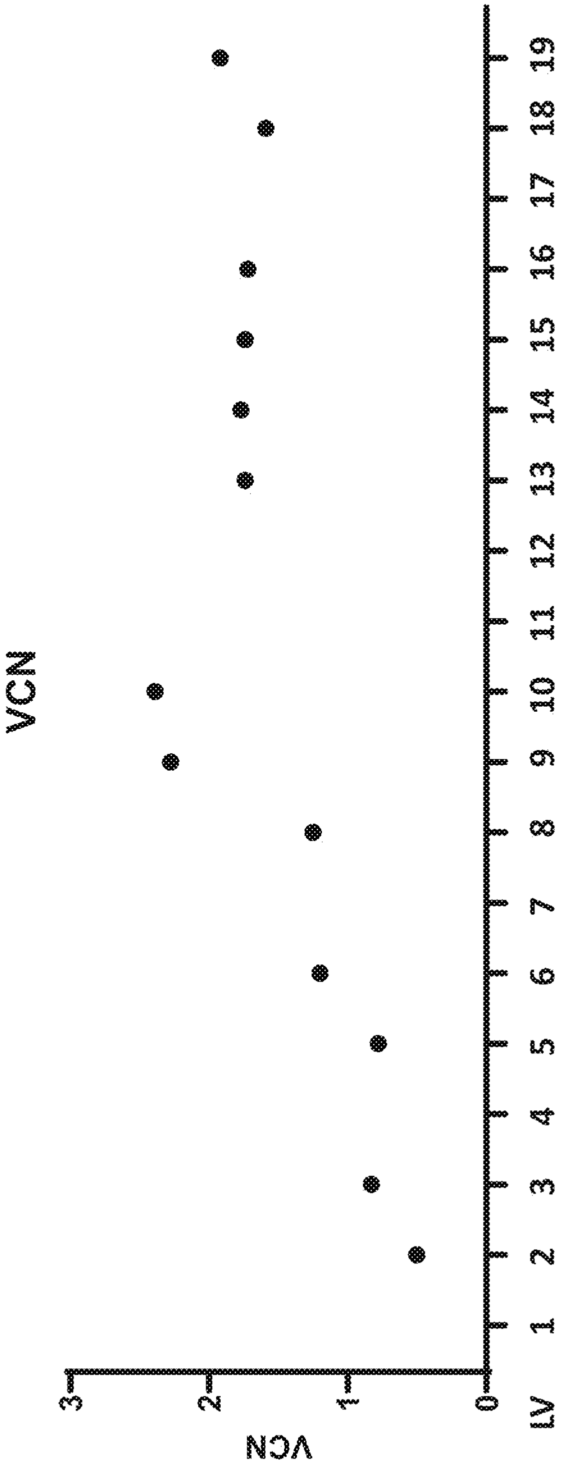
FIG. 2C shows the vector copy number (VCN) in PBMCs transduced with recombinant lentiviral particles comprising a viral envelope expressing a mutated VSIV-G and a non-viral membrane-bound tropism polypeptide that binds CD3 and a lentiviral vector encoding an MNDU3 promoter operably linked to a polynucleotide encoding a CD8α signal peptide and an anti-BCMA CAR and a WPRE operably linked to the 3' prime end of the polynucleotide encoding the anti-BCMA CAR (18 anti-BCMA CARs were evaluated).

Anti-BCMA CAR Expression $5\times10^5$ human PBMCs were plated in each well of a 24-well plate. Cells were transduced with recombinant lentiviruses LV 1 to LV 19 at a MOI 2 based on the Jurkat functional titer, or a 0.5 mL volumetric transduction if MOI 2 was not achievable. Seven days post-transduction, PBMCs were harvested and stained with BCMA-PE and analyzed by flow cytometry to assess the percentage of anti-BCMA CAR expressing cells. FIG. 2B.

Figure 2D:
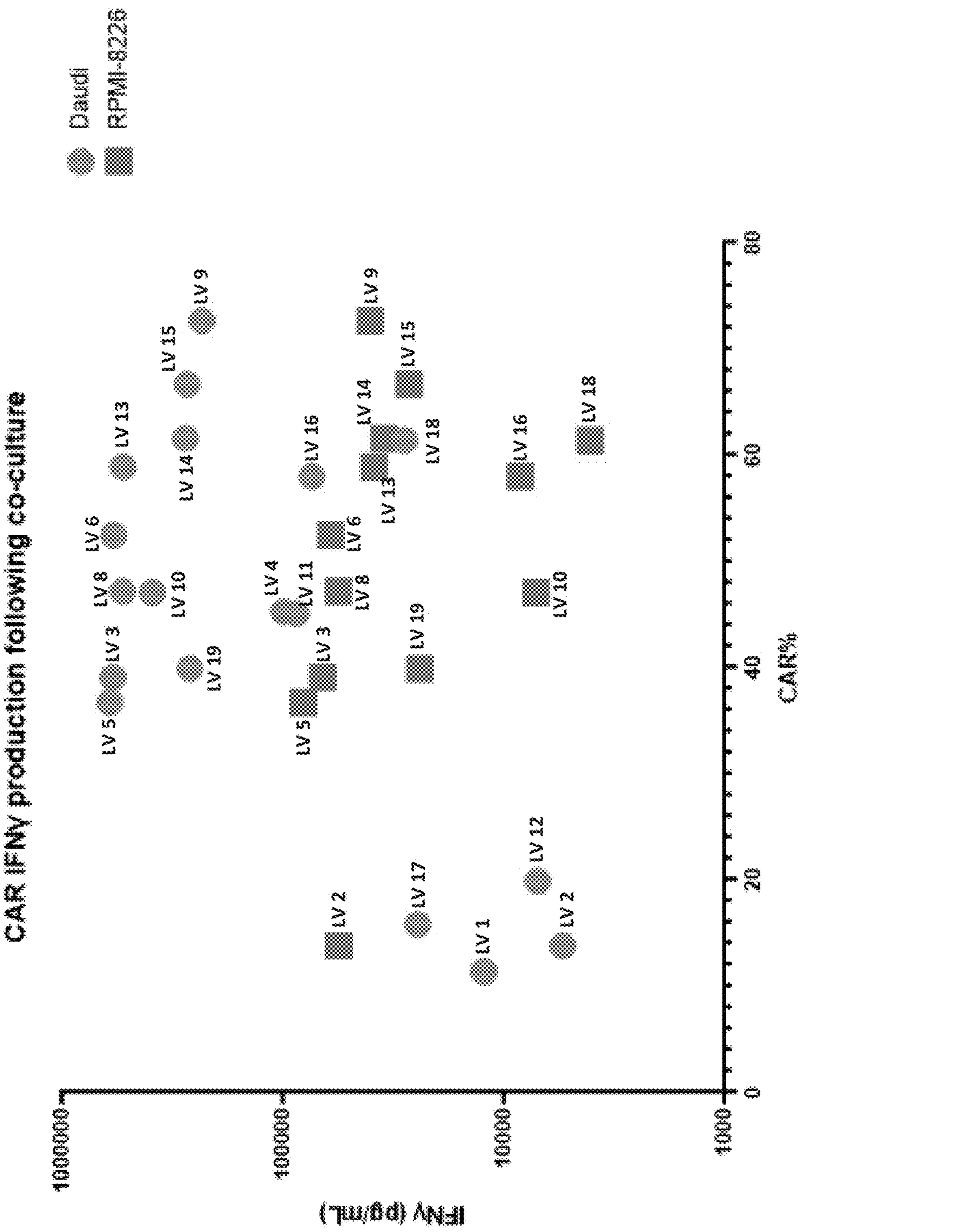
FIG. 2D shows the anti-BCMA CAR activity measured as the amount of IFNγ produced in a co-culture assay. PBMCs transduced with recombinant lentiviral particles comprising a viral envelope expressing a mutated VSIV-G and a non-viral membrane-bound tropism polypeptide that binds CD3 and a lentiviral vector encoding an MNDU3 promoter operably linked to a polynucleotide encoding a CD8α signal peptide and an anti-BCMA CAR and a WPRE operably linked to the 3' prime end of the polynucleotide encoding the anti-BCMA CAR (18 anti-BCMA CARs were evaluated) were co-cultured with Daudi cells (low BCMA expression) or RPMI-8226 cells (high BCMA expression) for 24 hours. After 24 hours, IFNγ levels in co-culture supernatant were measured and plotted as a function of % anti-BCMA CAR positive cells in the co-culture.

Anti-BCMA CAR Activity $5\times10^4$ PBMCs transduced with recombinant lentiviruses LV 1 to LV 19 were co-cultured with $5\times10^4$ high BCMA-expressing tumor cells (RPMI-8226) or $5\times10^4$ low BCMA-expressing tumor cells (Daudi) for 24 hours. Anti-BCMA CAR activity was assessed by harvesting co-culture supernatants and measuring IFNγ levels using a Meso Scale Discovery (MSD®) assay. The percentage of anti-BCMA CAR positive cells was plotted against IFNγ levels produced in co-culture. FIG. 2D.

SUMMARY

These data indicate that the recombinant T cell specific lentiviral particles harboring anti-BCMA CARs (LV 1 to LV 18) are able to transduce CD3 expressing cells, that anti-BCMA CARs are expressed on PBMCs transduced with LV 1 to LV 18 and that the transduced PBMCs express anti-BCMA CARs that recognize high or low BCMA-expressing cells and produce IFNγ in response to binding antigen.

Example 2

Lentiviral Vector Architecture and Anti-BCMA Car Expression and Function

Recombinant T cell specific lentiviral particles with a viral envelope expressing a mutated viral envelope glycoprotein (fusogen) and a non-viral membrane bound tropism molecule and harboring a lentiviral vector encoding various promoters, anti-BCMA CARs, and either no posttranscriptional response element (PRE) or a wild-type WPRE, or a mutated WPRE.

HEK293T cells were transfected with plasmids encoding a non-viral membrane bound tropism molecule comprising an anti-CD3 scFv fused to a CD8α hinge and transmembrane domain (e.g., SEQ ID NO: 324); a mutant VSIV-G fusogen (e.g., SEQ ID NOs: 335); lentiviral GAG/POL; lentiviral REV; and a transfer plasmid encoding a lentiviral vector comprising either an MNDU3 promoter (SEQ ID NO: 319), an SFFV promoter (SEQ ID NO: 322), or an EF1α promoter (SEQ ID NO: 320) operably linked to a polynucleotide encoding a CD8α signal peptide and an anti-BCMA CAR and either no posttranscriptional response element or a wild-type WPRE (SEQ ID NO: 315) or a mutated WPRE (SEQ ID NO: 316) operably linked to the 3' end of the polynucleotide encoding the anti-BCMA CAR.

Table 17 lists the recombinant lentivirus reference number and the corresponding SEQ ID NOs of the amino acid sequences of the anti-BCMA CARs and the different lentiviral vector architectures.

TABLE 17

| Ref. | SEQ ID NO. | Promoter | WPRE |
|---|---|---|---|
| LV 3.1 | 259 | MNDU3 | wild-type |
| LV 3.2 | 259 | MNDU3 | no PRE |
| LV 3.3 | 259 | MNDU3 | mutant WPRE |
| LV 3.4 | 259 | SFFV | wild-type |
| LV 3.5 | 259 | SFFV | no PRE |
| LV 3.6 | 259 | SFFV | mutant WPRE |
| LV 3.7 | 259 | EF1α | wild-type |
| LV 3.8 | 259 | EF1α | no PRE |

TABLE 17-continued

| Ref. | SEQ ID NO. | Promoter | WPRE |
|---|---|---|---|
| LV 3.9 | 259 | EF1α | mutant WPRE |
| LV 5.1 | 263 | MNDU3 | wild-type |
| LV 5.2 | 263 | MNDU3 | no PRE |
| LV 5.3 | 263 | MNDU3 | mutant WPRE |
| LV 5.4 | 263 | SFFV | wild-type |
| LV 5.5 | 263 | SFFV | no PRE |
| LV 5.6 | 263 | SFFV | mutant WPRE |
| LV 5.7 | 263 | EF1α | wild-type |
| LV 5.8 | 263 | EF1α | no PRE |
| LV 5.9 | 263 | EF1α | mutant WPRE |
| LV 6.1 | 266 | MNDU3 | wild-type |
| LV 6.2 | 266 | MNDU3 | no PRE |
| LV 6.3 | 266 | MNDU3 | mutant WPRE |
| LV 6.4 | 266 | SFFV | wild-type |
| LV 6.5 | 266 | SFFV | no PRE |
| LV 6.6 | 266 | SFFV | mutant WPRE |
| LV 6.7 | 266 | EF1α | wild-type |
| LV 6.8 | 266 | EF1α | no PRE |
| LV 6.9 | 266 | EF1α | mutant WPRE |
| LV 8.1 | 270 | MNDU3 | wild-type |
| LV 8.2 | 270 | MNDU3 | no PRE |
| LV 8.3 | 270 | MNDU3 | mutant WPRE |
| LV 8.4 | 270 | SFFV | wild-type |
| LV 8.5 | 270 | SFFV | no PRE |
| LV 8.6 | 270 | SFFV | mutant WPRE |
| LV 8.7 | 270 | EF1α | wild-type |
| LV 8.8 | 270 | EF1α | no PRE |
| LV 8.9 | 270 | EF1α | mutant WPRE |
| LV 9.1 | 273 | MNDU3 | wild-type |
| LV 9.2 | 273 | MNDU3 | no PRE |
| LV 9.3 | 273 | MNDU3 | mutant WPRE |
| LV 9.4 | 273 | SFFV | wild-type |
| LV 9.5 | 273 | SFFV | no PRE |
| LV 9.6 | 273 | SFFV | mutant WPRE |
| LV 9.7 | 273 | EF1α | wild-type |
| LV 9.8 | 273 | EF1α | no PRE |
| LV 9.9 | 273 | EF1α | mutant WPRE |
| LV 13.1 | 277 | MNDU3 | wild-type |
| LV 13.2 | 277 | MNDU3 | no PRE |
| LV 13.3 | 277 | MNDU3 | mutant WPRE |
| LV 13.4 | 277 | SFFV | wild-type |
| LV 13.5 | 277 | SFFV | no PRE |
| LV 13.6 | 277 | SFFV | mutant WPRE |
| LV 13.7 | 277 | EF1α | wild-type |
| LV 13.8 | 277 | EF1α | no PRE |
| LV 13.9 | 277 | EF1α | mutant WPRE |
| LV19 | | MNDU3 | no PRE |

Figure 3A:
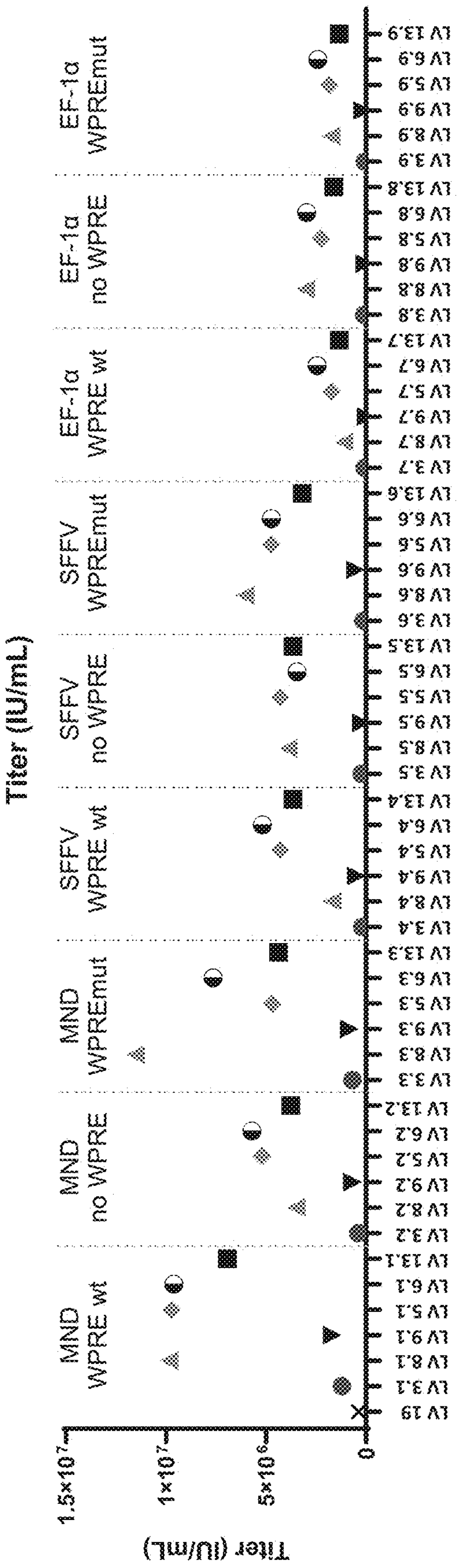
FIG. 3A shows Jurkat cell functional titer of recombinant lentivirus comprising a viral envelope expressing a mutated VSIV-G and a non-viral membrane-bound tropism polypeptide that binds CD3 and a lentiviral vector encoding either an MNDU3 promoter, an SFFV promoter, or an EF1α promoter operably linked to a polynucleotide encoding a CD8α signal peptide and an anti-BCMA CAR (6 anti-BCMA CARs were evaluated) and either no PRE or a wild-type or mutated WPRE operably linked to the 3' prime end of the polynucleotide encoding the anti-BCMA CAR.

Infectious Titer $1\times10^5$ Jurkat cells were plated in each well of a 96-well plate and transduced with the recombinant lentiviruses listed in Table 17 including LV 19, which harbors a lentiviral vector encoding a control anti-BCMA CAR obtained from the literature. Three days post-transduction, the cells were passaged. Seven days post-transduction the cells were harvested. Genomic DNA was isolated and purified from the harvested cells and used in a quantitative PCR (qPCR) assay to determine vector copy number (VCN) and subsequently, IU/mL. FIG. 3A.

All lentiviral vector architectures examined produced infectious titers and were subsequently used to transduce PBMCs.

VCN and Anti-BCMA CAR Expression $5\times10^5$ human PBMCs were plated in each well of a 24-well plate and transduced with volume matched recombinant lentiviruses listed in Table 17.

Figure 3B:
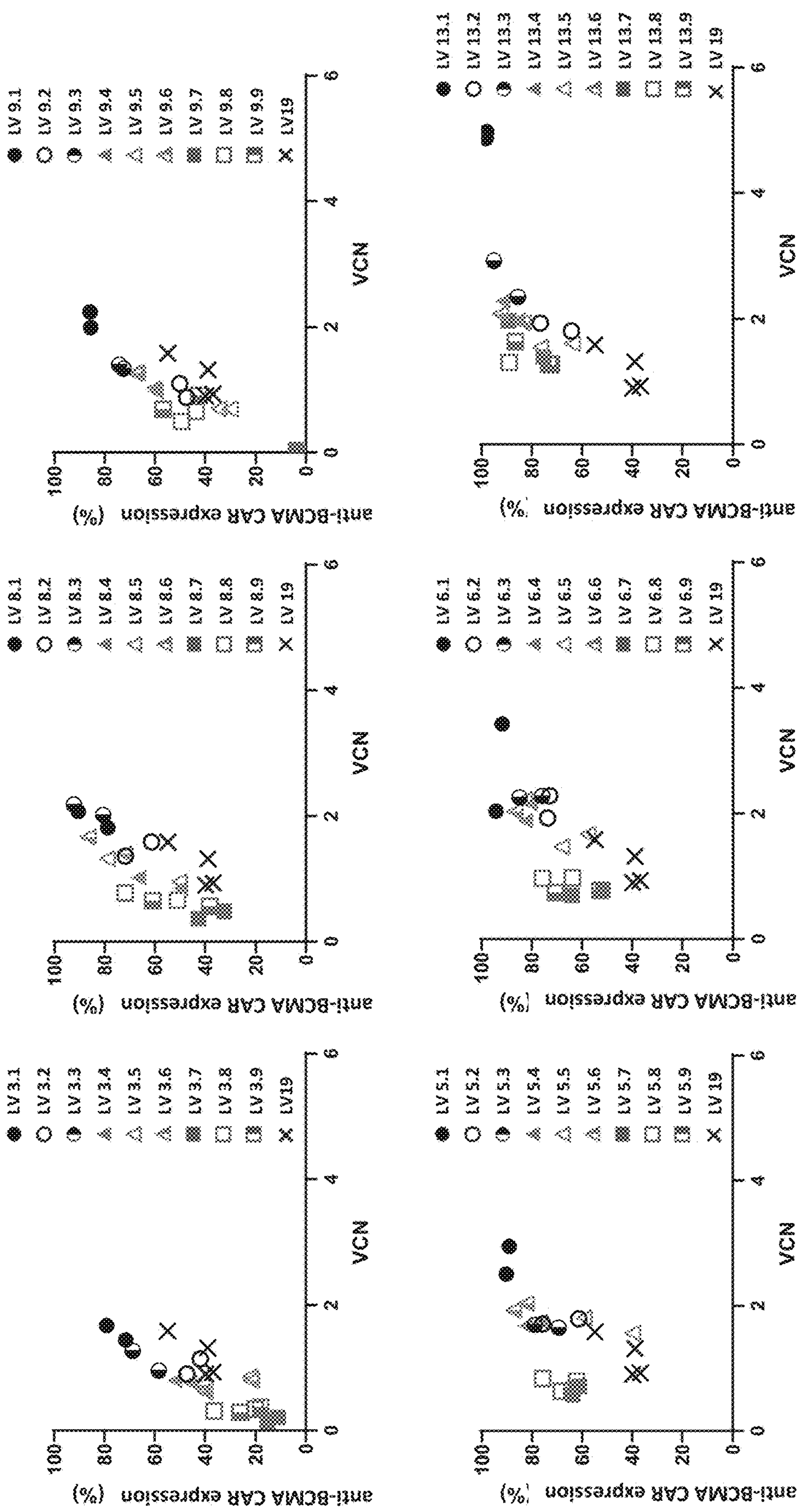
FIG. 3B shows the VCN in transduced PBMCs as a function of the percentage of PBMCs expressing an anti-BCMA CAR. Human PBMCs were transduced with a recombinant lentivirus comprising a viral envelope expressing a mutated VSIV-G and a non-viral membrane-bound tropism polypeptide that binds CD3 and a lentiviral vector encoding either an MNDU3 promoter, an SFFV promoter, or an EF1α promoter operably linked to a polynucleotide encoding a CD8α signal peptide and an anti-BCMA CAR (6 anti-BCMA CARs were evaluated) and either no PRE or a wild-type or mutated WPRE operably linked to the 3' prime end of the polynucleotide encoding the anti-BCMA CAR.

Four days post-transduction, PBMCs were passaged to a 24-well GREX plate. Seven days post-transduction, PBMCs were harvested, one aliquot of cells was stained with 5 BCMA-PE and analyzed by flow cytometry to assess the percentage of anti-BCMA CAR expressing cells and another aliquot was used to isolate and purify genomic DNA for a quantitative PCR (qPCR) assay to determine vector copy number (VCN). FIG. 3B.

These data show that different lentiviral vector architectures tested in combination with different anti-BCMA CARs result in a spectrum of transduction and anti-BCMA CAR expression.

Anti-BCMA CAR Activity $5\times10^5$ human PBMCs were plated in each well of a 24-well plate and transduced with recombinant lentiviruses listed in Table 17 that have the following lentiviral vector architectures: MNDU3 promoter and wild-type WPRE, MNDU3 promoter and a mutated WPRE, SFFV promoter and a mutated WPRE, and EF1α promoter and no WPRE. PBMCs were transduced at an MOI of 1 (based on IU/mL determined in Jurkat cells), except for LV 3.6, LV 3.8, LV 9.8, and LV 13.8, in which volume matched lentivirus was used. Four days post-transduction, PBMCs were passaged to a 24-well GREX plate. Seven days post-transduction, PBMCs were harvested, one aliquot of cells was stained with BCMA-PE and analyzed by flow cytometry to assess the number of anti-BCMA CAR expressing cells and another aliquot was used in co-culture assays to assess anti-BCMA CAR function.

Figure 3C:
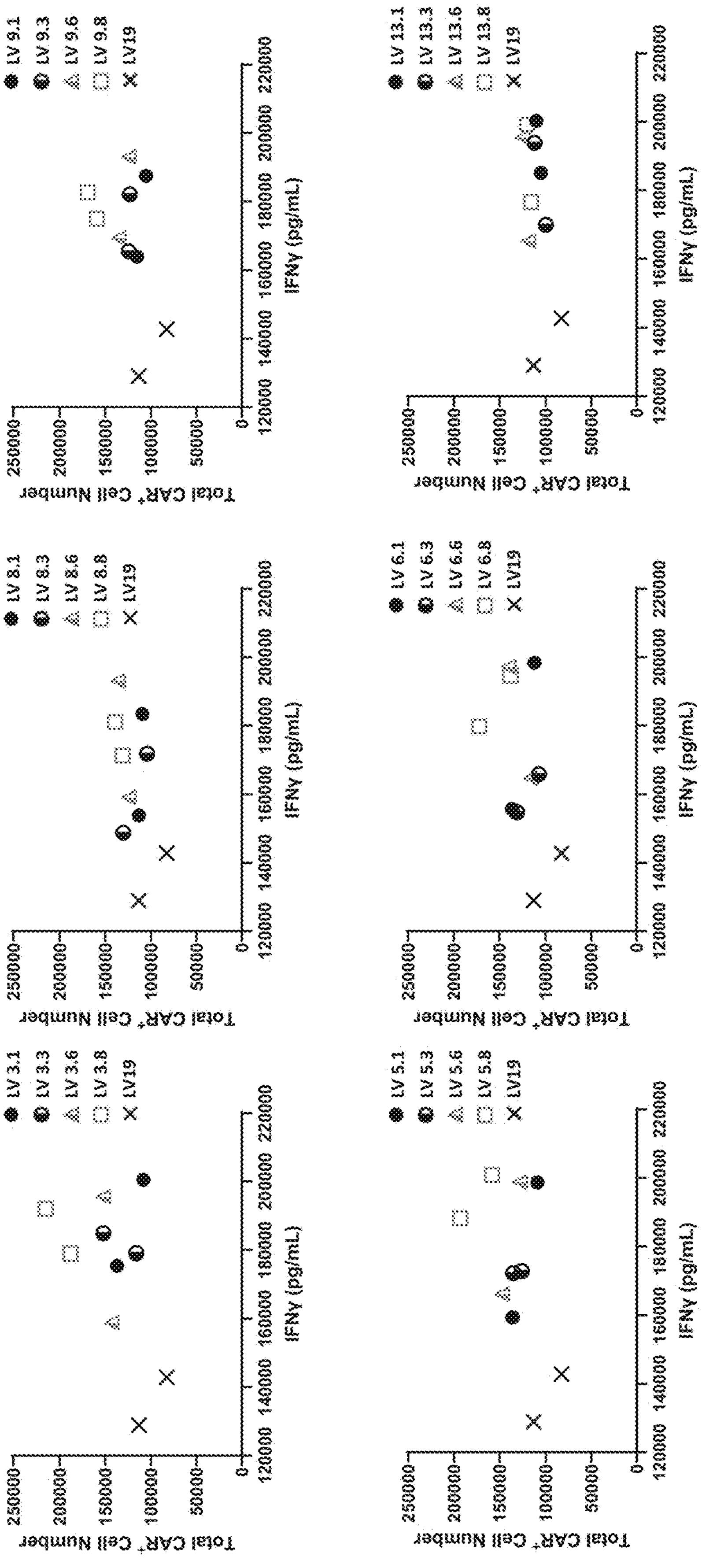
FIG. 3C shows the amount of IFNγ secreted from PBMCs expressing an anti-BCMA CAR co-cultured with RPMI-8226 cells (BCMA expressing cells) for 24 hours as a function of the CAR-expressing cells in the co-culture.
Figure 3D:
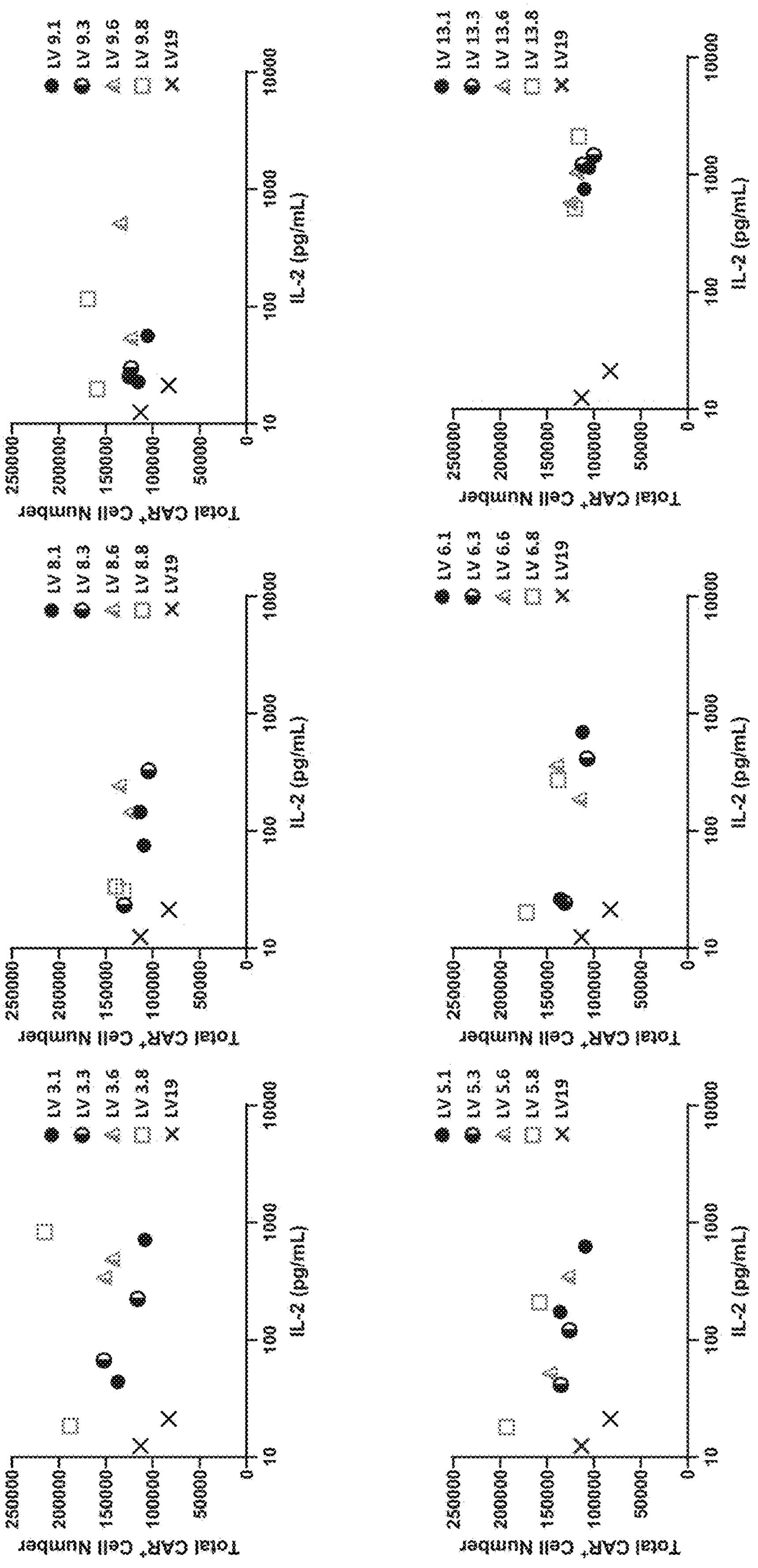
FIG. 3D shows the amount of IL-2 secreted from PBMCs expressing an anti-BCMA CAR co-cultured with RPMI-8226 cells (BCMA expressing cells) for 24 hours as a function of the CAR-expressing cells in the co-culture.

$5\times10^4$ transduced PBMCs were co-cultured with $5\times10^4$ RPMI-8226 cells for 24 hours. Anti-BCMA CAR activity was assessed by harvesting PBMC/RPMI-8226 cell co-culture supernatants and measuring IFNγ and IL-2 levels using an MSD assay. IFNγ and IL-2 levels produced in co-culture were plotted against the percentage of anti-BCMA CAR positive cells. FIGS. 3C and 3D.

Figure 3E:
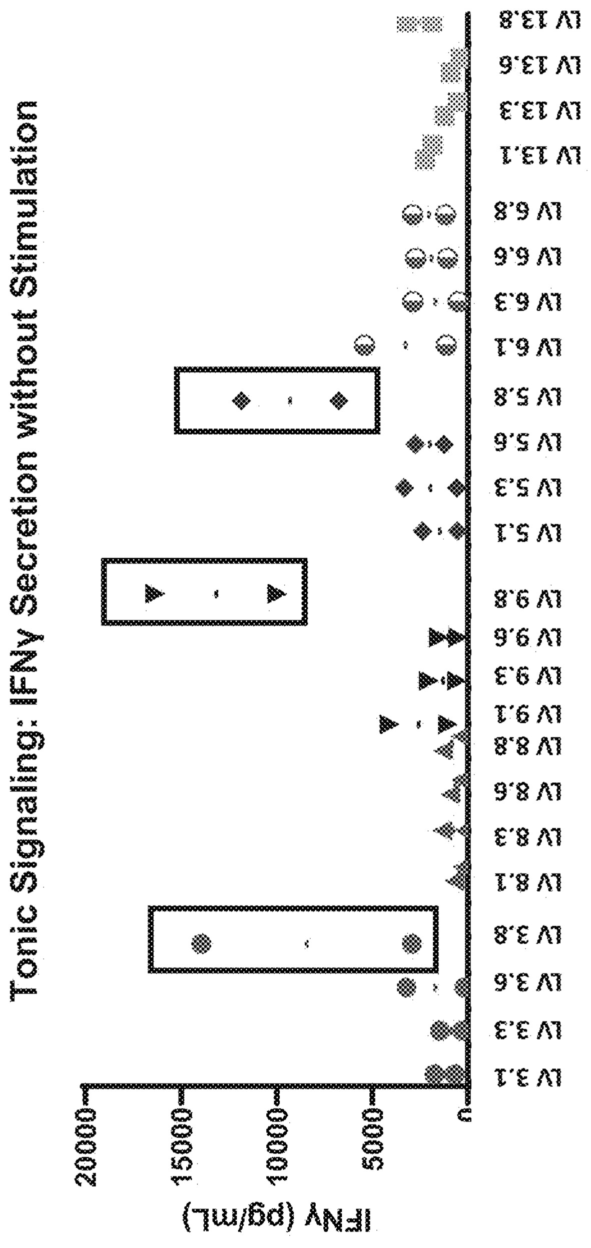
FIG. 3E shows the amount of IFNγ secreted from PBMCs expressing an anti-BCMA CAR in the absence of target cells. Human PBMCs were transduced with a recombinant lentivirus comprising a viral envelope expressing a mutated VSIV-G and a non-viral membrane-bound tropism polypeptide that binds CD3 and a lentiviral vector comprising one of the following lentiviral vector architectures, MNDU3 promoter and wild-type WPRE, MNDU3 promoter and a mutated WPRE, SFFV promoter and a mutated WPRE, and EF1α promoter and no WPRE and encoding an anti-BCMA CAR (6 anti-BCMA CARs were evaluated).

Antigen independent anti-BCMA CAR activity was assessed by culturing $5\times10^4$ transduced PBMCs in the absence of target cells for 24 hours. After 24 hours, the supernatants were harvested and IFNγ levels measured using an MSD assay. IFNγ levels were plotted against lentiviral architectures used to express the anti-BCMA CARs. FIG. 3E.

These data indicate that combinations of different lentiviral architectures and anti-BCMA CARs can be selected to modulate anti-BCMA CAR expression and activity. Further, the data show that PBMCs expressing the anti-BCMA CARs set forth in SEQ ID NOs: 259, 263, 266, 270, 273, and 277 show comparable or increased cell expansion and comparable or increased activity compared to the control anti-BCMA CAR and that only three combinations showed high levels of antigen independent (tonic) signaling.

Off-Target Transduction

Off-target transduction of multiple myeloma cells was evaluated in two BCMA-expressing multiple myeloma cell lines, RPMI-8226 cells and KMS-11 cells. $1\times10^5$ RPMI-8226 or $1\times10^5$ KMS-11 cells were plated in each well of a 96-well plate and treated at an MOI of 1 with recombinant lentiviruses listed in Table 17 that have the following lentiviral vector architectures, MNDU3 promoter and wild-type WPRE, MNDU3 promoter and a mutated WPRE, SFFV promoter and a mutated WPRE, and EF1α promoter and no WPRE; LV 19; and with LV 20. LV 20 is a recombinant lentiviral particle comprising a viral envelope that expresses a non-viral membrane bound tropism molecule comprising an anti-CD3 scFv fused to a CD8α hinge and transmembrane domain (e.g., SEQ ID NO: 324); a mutant VSIV-G fusogen (e.g., SEQ ID NOs: 335); and a lentiviral vector comprising an MNDU3 promoter (SEQ ID NO: 319), operably linked to a polynucleotide encoding a CD8α signal peptide and GFP and a wild-type WPRE (SEQ ID NO: 315) operably linked to the 3' end of the polynucleotide encoding GFP.

Three days post-treatment, the cells were passaged. Seven days post-treatment, the cells were harvested and genomic DNA was isolated and purified for a qPCR assay to determine vector integration using VCN. VCN values for anti-BCMA CARs were normalized to VCN for LV 20, which expresses GFP rather than an anti-BCMA CAR.

Figure 3F:
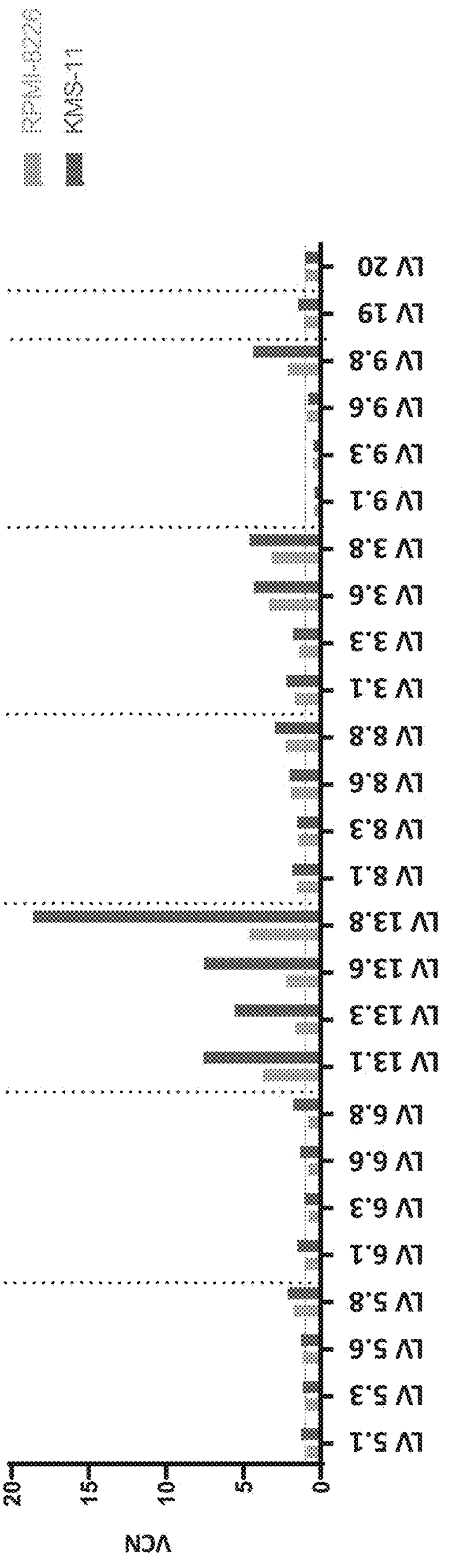
FIG. 3F shows the levels of off-target transduction in BCMA expressing cells (RPMI-8226 and KMS-11) of recombinant lentiviruses comprising a viral envelope expressing a mutated VSIV-G and a non-viral membrane-bound tropism polypeptide that binds CD3 and a lentiviral vector comprising one of the following lentiviral vector architectures, MNDU3 promoter and wild-type WPRE, MNDU3 promoter and a mutated WPRE, SFFV promoter and a mutated WPRE, and EF1α promoter and no WPRE and encoding an anti-BCMA CAR (6 anti-BCMA CARs were evaluated). Transduction was normalized to VCN in cells transduced with a recombinant lentivirus encoding GFP in place of an anti-BCMA CAR.

The data show that differences in off-target multiple myeloma transduction were largely driven by the particular anti-BCMA CAR being expressed, rather than any particular lentiviral vector architecture. Several architectures used to express the anti-BCMA CARs in LV 3, LV 5, LV 6, LV 8, and LV 9 showed low levels of off-target transduction that were comparable to or less than LV 19, which expresses a control anti-BCMA CAR. In contrast, LV 13 exhibited the highest rates of off-target transduction compared to other LVs. FIG. 3F.

Example 3

In Vivo Administered Lentivirus Demonstrates Anti-Tumor Efficacy in a Multiple Myeloma Mouse Model The anti-tumor efficacy of in vivo administered recombinant lentiviral particles comprising an envelope that expresses an anti-CD3-based tropism molecule and a mutant VSIV-G fusogen and a lentiviral vector encoding an anti-BCMA CAR was investigated in multiple myeloma mouse models.

Recombinant lentivirus for in vivo administration was produced by transient transfection of HEK293T cells with plasmids encoding an anti-CD3-based tropism molecule (SEQ ID NO: 324); a mutant VSIV-G fusogen (e.g., SEQ ID NO: 335); lentiviral GAG/POL; lentiviral REV; and a transfer plasmid encoding a lentiviral vector comprising: (i) an MNDU3 promoter (SEQ ID NO: 319) operably linked to a polynucleotide encoding a CD8α signal peptide and an anti-BCMA CAR, and a wild-type WPRE (SEQ ID NO: 315) operably linked to the 3' end of the polynucleotide encoding the anti-BCMA CAR; (ii) an MNDU3 promoter (SEQ ID NO: 319) operably linked to a polynucleotide encoding a CD8α signal peptide and an anti-BCMA CAR, and a mutated WPRE (SEQ ID NO: 316) operably linked to the 3' end of the polynucleotide encoding the anti-BCMA CAR; (iii) an SFFV promoter (SEQ ID NO: 322) operably linked to a polynucleotide encoding a CD8α signal peptide and an anti-BCMA CAR, and a mutated WPRE (SEQ ID NO: 316) operably linked to the 3' end of the polynucleotide encoding the anti-BCMA CAR; or (iv) an EF1α promoter (SEQ ID NO: 320) operably linked to a polynucleotide encoding a CD8α signal peptide and an anti-BCMA CAR without a PRE.

The recombinant lentivirus reference number, the SEQ ID NO of the anti-BCMA CAR polypeptide and the corresponding lentiviral architectures shown in Table 18 were used in this Example.

TABLE 18

| Ref. | SEQ ID NO. | Promoter | WPRE |
|---|---|---|---|
| LV 3.1 | 259 | MNDU3 | wild-type |
| LV 3.3 | 259 | MNDU3 | mutant WPRE |
| LV 3.6 | 259 | SFFV | mutant WPRE |
| LV 3.8 | 259 | EF1α | no PRE |
| LV 5.1 | 263 | MNDU3 | wild-type |

TABLE 18-continued

| Ref. | SEQ ID NO. | Promoter | WPRE |
|---|---|---|---|
| LV 5.3 | 263 | MNDU3 | mutant WPRE |
| LV 5.6 | 263 | SFFV | mutant WPRE |
| LV 5.8 | 263 | EF1α | no PRE |
| LV 6.1 | 266 | MNDU3 | wild-type |
| LV 6.3 | 266 | MNDU3 | mutant WPRE |
| LV 6.6 | 266 | SFFV | mutant WPRE |
| LV 6.8 | 266 | EF1α | no PRE |
| LV 8.1 | 270 | MNDU3 | wild-type |
| LV 8.3 | 270 | MNDU3 | mutant WPRE |
| LV 8.6 | 270 | SFFV | mutant WPRE |
| LV 8.8 | 270 | EF1α | no PRE |
| LV 9.1 | 273 | MNDU3 | wild-type |
| LV 9.3 | 273 | MNDU3 | mutant WPRE |
| LV 9.6 | 273 | SFFV | mutant WPRE |
| LV 9.8 | 273 | EF1α | no PRE |
| LV 13.1 | 277 | MNDU3 | wild-type |
| LV 13.3 | 277 | MNDU3 | mutant WPRE |
| LV 13.6 | 277 | SFFV | mutant WPRE |
| LV 13.8 | 277 | EF1α | no PRE |

Ex vivo anti-BCMA CAR T cells were also prepared. Briefly, HEK293T cells were transiently transfected with plasmids encoding a wild-type VSIV-G fusogen; lentiviral GAG/POL; lentiviral REV; and a transfer plasmid encoding a lentiviral vector comprising an MNDU3 promoter operable linked to a CD8α signal peptide and a control anti-BCMA CAR obtained from the literature, and a wild-type WPRE (SEQ ID NO: 315) operably linked to the 3' end of the polynucleotide encoding the anti-BCMA CAR. PBMCs were then transduced with the recombinant lentivirus and cultured for 7 days to generate anti-BCMA CAR T cells.

First Daudi Model Study

NSG mice were intravenously injected with $2\times10^6$ Daudi cells labeled with firefly luciferase. After four days, four out of five groups of mice were intravenously administered $1\times10^6$ human PBMCs. The next day mice that received the $1\times10^6$ human PBMCs were administered vehicle control (DMEM); or $2.2\times10^8$ IU of LV 3.1, LV 6.1, LV 8.1, or LV 13.1. Mice that were not administered PBMCs were administered $5\times10^6$ ex vivo anti-BCMA CAR T cells. All groups of mice then received three doses of $2\times10^5$ IU recombinant human IL-2 at 6, 24, and 48 hours post LV administration. Tumor volume was measured by using a bioluminescence imaging system.

Tumor size increased in mice treated with vehicle. Mice treated with ex vivo anti-BCMA CAR T cells and in vivo with LV anti-BCMA CAR experienced tumor regression. FIG. 4A.

Second Daudi Model Study

NSG mice were intravenously injected with $2\times10^6$ Daudi cells labeled with firefly luciferase. After four days, eight out of nine groups of mice were intravenously administered $1\times10^6$ human PBMCs. The next day mice that received the $1\times10^6$ human PBMCs were administered vehicle control (DMEM); $1.25\times10^8$ IU of LV 3.1, LV 6.1, LV 6.3, LV 8.1, LV 9.3, LV 9.6, or LV 13.8; or $5.6\times10^7$ IU of LV 6.8. Mice that were not administered PBMCs were administered $5\times10^6$ ex vivo anti-BCMA CAR T cells. All groups of mice then received three doses of $2\times10^5$ IU recombinant human IL-2 at 6, 24, and 48 hours post LV administration. Tumor volume was measured by using a bioluminescence imaging system.

Tumor size increased in mice treated with vehicle. Mice treated with ex vivo anti-BCMA CAR T cells and in vivo with some LV anti-BCMA CARs experienced mild control of tumor growth, whereas LV 6.8 and LV 13.8 experienced durable tumor regression. FIG. 4B.

Third Daudi Model Study

NSG mice were intravenously injected with $2\times10^6$ Daudi cells labeled with firefly luciferase. After four days, eight out of nine groups of mice were intravenously administered $1\times10^6$ human PBMCs. The next day mice that received the $1\times10^6$ human PBMCs were administered vehicle control (DMEM); $1.25\times10^8$ IU of LV 3.3, LV 3.6, LV 8.3, LV 8.6, LV 8.8, LV 13.3, or LV 13.6; or $5.6\times10^7$ IU of LV 6.8. Mice that were not administered PBMCs were administered $5\times10^6$ ex vivo anti-BCMA CAR T cells. All groups of mice then received three doses of $2\times10^5$ IU recombinant human IL-2 at 6, 24, and 48 hours post LV administration. Tumor volume was measured by using a bioluminescence imaging system.

Tumor size increased in mice treated with vehicle. Mice treated with ex vivo anti-BCMA CAR T cells and in vivo with some LV anti-BCMA CARs experienced mild control of tumor growth, whereas LV 6.8 and LV 8.8 experienced durable tumor regression. FIG. 4C.

First RPMI Model Study

NOD scid gamma (NSG) mice were subcutaneously injected with $1\times10^6$ RPMI-8226 cells (a BCMA positive tumor cell line). Tumors were allowed to grow to a size of about 110 $mm^3$ to 140 $mm^3$ (about two and a half weeks).

Five out of six groups of mice were then intravenously administered $1\times10^6$ human PBMCs. The next day, mice that received the $1\times10^6$ human PBMCs were administered vehicle control (DMEM); $5.0\times10^7$ IU of LV 6.3, LV 6.8, LV 8.3, or LV 8.8. The sixth group of mice was administered $2\times10^6$ unmodified ex vivo anti-BCMA CAR T cells. All groups of mice then received three doses of $2\times10^5$ IU recombinant human IL-2 at 6, 24, and 48 hours post LV administration. Tumor volume was measured externally using calipers and mice were euthanized at pre-determined humane endpoints based on tumor size and body condition.

Tumor size increased in mice treated with vehicle control. Mice treated with LV 6.3 experienced moderate tumor regression, whereas mice treated with ex vivo anti-BCMA CAR T cells or in vivo with LV 6.8, LV 8.3, or LV 8.8 experienced complete and durable tumor regression. FIG. 4D.

Mice that were not administered PBMCs were administered $5\times10^6$ ex vivo anti-BCMA CAR T cells. All groups of mice then received three doses of $2\times10^5$ IU recombinant human IL-2 at 6, 24, and 48 hours post LV administration.

Second RPMI Model Study

NOD scid gamma (NSG) mice were subcutaneously injected with $1\times10^6$ RPMI-8226 cells (a BCMA positive tumor cell line). Tumors were allowed to grow to a size of about 110 $mm^3$ to 140 $mm^3$ (about two and a half weeks).

Four out of five groups of mice were then intravenously administered $1\times10^6$ human PBMCs. The next day, mice that received the $1\times10^6$ human PBMCs were administered vehicle control (DMEM); $1.25\times10^7$ IU of LV 6.8, $5.0\times10^7$ IU of LV 6.8, or $1.25\times10^8$ IU of LV 6.8. The fifth group of mice was administered $2\times10^6$ unmodified ex vivo anti-BCMA CAR T cells. All groups of mice then received three doses of $2\times10^5$ IU recombinant human IL-2 at 6, 24, and 48 hours post LV administration. Tumor volume was measured externally using calipers and mice were euthanized at pre-determined humane endpoints based on tumor size and body condition.

Tumor size increased in mice treated with vehicle control. Mice treated with all three doses of LV 6.8 experienced dose-dependent but complete and durable tumor regression. Mice treated with ex vivo anti-BCMA CAR T cells also experienced complete and durable tumor regression. FIG. 4E.

Third RPMI Model Study

NOD scid gamma (NSG) mice were subcutaneously injected with $1\times10^6$ RPMI-8226 cells (a BCMA positive tumor cell line). Tumors were allowed to grow to a size of about 110 $mm^3$ to 140 $mm^3$ (about two and a half weeks).

Three out of four groups of mice were then intravenously administered $1\times10^6$ human PBMCs. The next day, mice that received the $1\times10^6$ human PBMCs were administered vehicle control (DMEM); $5.0\times10^7$ IU of LV 6.3 or $1.25\times10^8$ IU of LV 6.3. The fourth group of mice was administered $2\times10^6$ unmodified ex vivo anti-BCMA CAR T cells. All groups of mice then received three doses of $2\times10^5$ IU recombinant human IL-2 at 6, 24, and 48 hours post LV administration. Tumor volume was measured externally using calipers and mice were euthanized at pre-determined humane endpoints based on tumor size and body condition.

Tumor size increased in mice treated with vehicle control. Mice treated with both doses of LV 6.3 experienced dose-dependent tumor regression. Mice treated with ex vivo anti-BCMA CAR T cells experienced complete and durable tumor regression. FIG. 4F.

Fourth Daudi Model Study

NSG mice were intravenously injected with $2\times10^6$ Daudi cells labeled with firefly luciferase. After four days, four out of five groups of mice were intravenously administered $1\times10^6$ human PBMCs. The next day mice that received the $1\times10^6$ human PBMCs were administered vehicle control (DMEM); $1.25\times10^8$ IU of LV 6.1 or LV6.3; or $5.6\times10^7$ IU of LV 6.8. Mice that were not administered PBMCs were administered $5\times10^6$ ex vivo anti-BCMA CAR T cells. All groups of mice then received three doses of $2\times10^5$ IU recombinant human IL-2 at 6, 24, and 48 hours post LV administration. Tumor volume was measured by using a bioluminescence imaging system.

Tumor size increased in mice treated with vehicle. Mice treated with ex vivo anti-BCMA CAR T cells and in vivo with LV 6.1 and LV 6.3 experienced mild control of tumor growth, whereas LV 6.8 experienced complete and durable tumor regression. FIG. 4G.

Example 4

Comparative Anti-Tumor Efficacy in a Multiple Myeloma Mouse Model in Both in Vivo and Ex Vivo Formats The anti-tumor efficacy of recombinant lentiviral particles comprising an envelope that expresses an anti-CD3-based tropism molecule and a mutant VSIV-G fusogen and a lentiviral vector encoding various anti-BCMA CARs was investigated in multiple myeloma mouse models. The recombinant lentiviruses were formulated as in vivo administered lentiviral particles and were also used to manufacture ex vivo anti-BCMA CAR T cells.

Recombinant lentivirus was produced by transient transfection of HEK293T cells with plasmids encoding a non-viral membrane bound tropism molecule comprising an anti-CD3 scFv fused to a CD8α hinge and transmembrane domain; a mutant VSIV-G fusogen comprising K47Q and R354A amino acid substitutions; lentiviral GAG/POL; lentiviral REV; and a transfer plasmid encoding a lentiviral vector encoding an anti-BCMA CAR set forth in SEQ ID NO: 266, SEQ ID NO: 340, or SEQ ID NO: 341 or a GFP control.

TABLE 19

| SEQ ID NO: | NUCLEIC ACID SEQUENCE |
|---|---|
| 340 | DIVLTQSPPSLAMSLGKRATISCRASESVTILGSHLIHWYQQKPGQPPTLLIQLASNVQTG<br>VPARFSGSGSRTDFTLTIDPVEEDDVAVYYCLQSRTIPRTFGGGTKLEIKGSTSGSGKPGS<br>GEGSTKGQIQLVQSGPELKKPGETVKISCKASGYTFTDYSINWVKRAPGKGLKWMGWINTE<br>TREPAYAYDERGRFAFSLETSASTAYLQINNLKYEDTATYFCALDYSYAMDYWGQGTSVTV<br>SSAAATTTPAPRPPTPAPTIASQPLSLRPEACRPAAGGAVHTRGLDFACDIYIWAPLAGTC<br>GVLLLSLVITLYCKRGRKKLLYIFKQPFMRPVQTTQEEDGCSCRFPEEEEGGCELRVKFSR<br>SADAPAYQQGQNQLYNELNLGRREEYDVLDKRRGRDPEMGGKPRRKNPQEGLYNELQKDKM<br>AEAYSEIGMKGERRRGKGHDGLYQGLSTATKDTYDALHMQALPPR |
| 341 | QVKLEESGGGLVQAGRSLRLSCAASEHTFSSHVMGWFRQAPGKERESVAVIGWRDISTSYA<br>DSVKGRFTISRDNAKKTLYLQMNSLKPEDTAVYYCAARRIDAADFDSWGQGTQVTVSSGGG<br>GSEVQLVESGGGLVQAGGSLRLSCAASGRTFTMGWFRQAPGKEREFVAAISLSPTLAYYAE<br>SVKGRFTISRDNAKNTVVLQMNSLKPEDTALYYCAADRKSVMSIRPDYWGQGTQVTVSSTS<br>TTTPAPRPPTPAPTIASQPLSLRPEACRPAAGGAVHTRGLDFACDIYIWAPLAGTCGVLLL<br>SLVITLYCKRGRKKLLYIFKQPFMRPVQTTQEEDGCSCRFPEEEEGGCELRVKFSRSADAP<br>AYQQGQNQLYNELNLGRREEYDVLDKRRGRDPEMGGKPRRKNPQEGLYNELQKDKMAEAYS<br>EIGMKGERRRGKGHDGLYQGLSTATKDTYDALHMQALPPR |

The recombinant lentivirus reference number, the SEQ ID NO of the anti-BCMA CAR polypeptide and the corresponding lentiviral architectures shown in Table 12 were used in this Example.

TABLE 20

| Ref. | SEQ ID NO. | Promoter | WPRE |
|---|---|---|---|
| LV 6.8 | 266 | EF1α | none |
| LV A | 340 | MNDU3 | WT WPRE |
| LV B | 341 | EF1α | none |
| LV19 | GFP | MNDU3 | none |

Ex vivo anti-BCMA CAR T cells were also prepared by transducing PBMCs with the recombinant lentivirus and culturing the transduced cell for 7 days to generate anti-BCMA CAR T cells.

In Vivo Daudi Model Study

NSG mice were intravenously injected with $2\times10^6$ Daudi cells labeled with firefly luciferase. After four days, four out of five groups of mice were intravenously administered $1\times10^6$ human PBMCs. The next day, mice that did not receive PBMCs were administered vehicle control (DMEM) and mice that received the PBMCs were administered $5.0\times10^7$ IU of LV 6.8, LV A, LV B, or LV 19 (GFP control). Tumor volume was measured by using a bioluminescence imaging system.

Tumor size increased in mice treated with vehicle, mice treated with the GFP control, and mice treated with a lentivirus expressing an anti-BCMA CAR comprising the binding domain used in idecabtagene vicleucel. Mice treated with a lentivirus expressing an anti-BCMA CAR comprising the binding domains like those used in ciltacabtagene autoleucel experienced suppression of tumor growth. Only mice treated with an anti-BCMA CAR comprising SEQ ID NO: 266 experienced tumor regression. FIG. 5A.

Ex Vivo Daudi Model Study

NSG mice were intravenously injected with $2\times10^6$ Daudi cells labeled with firefly luciferase. After five days, three out of five groups of mice were intravenously administered $2\times10^6$ human anti-BCMA CAR T cells. Mice that did not receive anti-BCMA CAR T cells were administered vehicle control (DMEM) or $2\times10^6$ untransduced control human T cells (UTD) and mice that received the anti-BCMA CAR T cells were administered $2\times10^6$ anti-BCMA CAR T cells expressing the CAR encoded by SEQ ID NO: 266, SEQ ID NO: 340 or SEQ ID NO: 341. Tumor volume was measured by using a bioluminescence imaging system.

Tumor size increased in mice treated with vehicle and with untransduced control T cells. Mice treated with CAR T cells expressing an anti-BCMA CAR comprising the binding domain used in idecabtagene vicleucel showed a transient decrease in tumor burden whereas mice treated with CAR T cells expressing an anti-BCMA CAR comprising SEQ ID NO: 266 or an anti-BCMA CAR comprising the binding domains like those used in ciltacabtagene autoleucel experienced comparable and complete tumor regression. FIG. 5B.

In general, in the following claims, the terms used should not be construed to limit the claims to the specific embodiments disclosed in the specification and the claims, but should be construed to include all possible embodiments along with the full scope of equivalents to which such claims are entitled. Accordingly, the claims are not limited by the disclosure.

What is claimed is:

1. A recombinant lentiviral particle comprising:

(a) a viral envelope comprising (i) a vesicular stomatitis Indiana virus envelope glycoprotein (VSIV-G) comprising amino acid substitutions selected from the group consisting of: K47A and R354A; K47A and R354Q; K47Q and R354A; and K47Q and R354Q; and (ii) a non-viral membrane-bound tropism polypeptide comprising an anti-CD38 scFv and a human CD8α hinge and transmembrane domain; and (b) a recombinant lentiviral vector comprising a polynucleotide encoding a myeloproliferative sarcoma virus enhancer, negative control region deleted, dl587rev primer-binding site substituted (MND) U3 promoter or an EF1α promoter, the promoter operably linked to a polynucleotide encoding (i) a signal peptide and (ii) an anti-BCMA chimeric antigen receptor comprising an anti-BCMA scFv comprising a heavy chain variable region (VH) comprising a CDRH1, a CDRH2, and a CDRH3 comprising the amino acid sequences set forth in SEQ ID NOs: 62, 63, and 64, and a light chain variable region (VL) comprising a CDRL1, a CDRL2, and a CDRL3 comprising the amino acid sequences set forth in SEQ ID NOs: 66, 67, and 68; a CD8a hinge and transmembrane domain; a CD137 costimulatory domain; and a CD3 primary signaling domain.

2. The particle of claim 1, wherein the anti-CD38 scFv is isolated from TR66 or variants thereof.

3. The particle of claim 1, wherein the anti-CD38 scFv comprises an amino acid sequence set forth in any one of SEQ ID NOs: 153, 154, 163, 164, 173, 174, 183, 184, 193, 194, 203, 204, 213, 214, 223, and 224.

4. An immune effector cell transduced with the particle of claim 1.

5. A composition comprising the immune effector cell of claim 4.

6. A composition comprising the particle of claim 1.

7. A pharmaceutical composition comprising a pharmaceutically acceptable carrier and the particle of claim 1.

8. A kit comprising the particle of claim 1, a pharmaceutically acceptable carrier, and instructions for use.

9. A recombinant lentiviral particle comprising:

(a) a viral envelope comprising (i) a mutated viral envelope glycoprotein comprising an amino acid sequence set forth in any one of SEQ ID NOs: 332, 333, 334, and 335 and (ii) a non-viral membrane-bound tropism polypeptide comprising an amino acid sequence set forth in any one of SEQ ID NOs: 324, 325, 326, 327, 328, 329, 330, and 331; and (b) a recombinant lentiviral vector comprising a 5' long terminal repeat (LTR) comprising R and U5 regions; a Psi (Ψ) packaging signal; a cPPT/FLAP; a rev response element (RRE); a polynucleotide encoding an MND promoter or an EF1α promoter, the promoter operably linked to a polynucleotide encoding (i) a signal peptide and (ii) an anti-BCMA chimeric antigen receptor (CAR) comprising an amino acid sequence set forth in SEQ ID NO: 266; optionally a woodchuck hepatitis virus posttranscriptional regulatory element (WPRE); a 3' LTR comprising U3 and R regions; a polyadenylation signal; and a poly(A) tail.

10. The particle of claim 9, wherein the mutated viral envelope glycoprotein comprises an amino acid sequence set forth in SEQ ID NO: 335.

11. The particle of claim 9, wherein the non-viral membrane-bound tropism polypeptide comprises an amino acid sequence set forth in SEQ ID NO: 324.

12. An immune effector cell transduced with the particle of claim 9.

13. A composition comprising the particle of claim 9.

14. A pharmaceutical composition comprising a pharmaceutically acceptable carrier and the particle of claim 9.

15. A kit comprising the particle of claim 9, a pharmaceutically acceptable carrier, and instructions for use.

16. A recombinant lentiviral particle comprising:

(a) a viral envelope comprising (i) a mutated viral envelope glycoprotein comprising an amino acid sequence set forth in SEQ ID NO: 335 and (ii) a non-viral membrane-bound tropism polypeptide comprising an amino acid sequence set forth in SEQ ID NO: 324; and (b) a recombinant lentiviral vector comprising a 5' long terminal repeat (LTR) comprising R and U5 regions; a Psi (Ψ) packaging signal; a cPPT/FLAP; a rev response element (RRE); a polynucleotide encoding an EF1α promoter operably linked to a polynucleotide encoding (i) a signal peptide and (ii) an anti-BCMA chimeric antigen receptor (CAR) comprising an amino acid sequence set forth in SEQ ID NO: 266; optionally a WPRE; a 3' LTR comprising U3 and R regions;

a polyadenylation signal; and a poly(A) tail.

17. The particle of claim 16, wherein the EF1α promoter comprises the polynucleotide sequence set forth in SEQ ID NO: 319.

18. The particle of claim 16, wherein the recombinant lentiviral vector is a recombinant HIV-1 lentiviral vector or a recombinant HIV-2 lentiviral vector.

19. The particle of claim 16, wherein the polynucleotide encoding the anti-BCMA CAR comprises the polynucleotide sequence set forth in SEQ ID NO: 300.

20. The particle of claim 16, wherein the signal peptide is isolated from a polypeptide selected from the group consisting of: CD8α, mIgGκ, hIgGk, CD33, tPA, SEAP, hGM-CSF, CSF2R, and B2M.

21. The particle of claim 16, wherein the lentiviral vector further comprises a WPRE operably linked to the 3' end of the polynucleotide encoding the anti-BCMA CAR.

22. An immune effector cell transduced with the particle of claim 16.

23. The immune effector cell of claim 22, wherein the immune effector cell is a T cell or natural killer (NK) cell.

24. A composition comprising the particle of claim 16.

25. A pharmaceutical composition comprising a pharmaceutically acceptable carrier and the particle of claim 16.

* * * * *